(12) United States Patent
Turner et al.

(10) Patent No.: US 10,100,048 B2
(45) Date of Patent: Oct. 16, 2018

(54) HETEROCYCLIC COMPOUNDS AND THEIR USE AS GLYCOGEN SYNTHASE KINASE-3 INHIBITORS

(71) Applicant: AbbVie Deutschland GmbH & Co. KG, Wiesbaden (DE)

(72) Inventors: Sean Colm Turner, Ludwigshafen (DE); Margaretha Henrica Maria Bakker, Ludwigshafen (DE); Marcel van Gaalen, Ludwigshafen (DE); Falko Ernst Wolter, Ludwigshafen (DE); Wilfried Hornberger, Ludwigshafen (DE); Marjoleen Nijsen, Ludwigshafen (DE)

(73) Assignee: ABBVIE DEUTSCHLAND GMBH & CO. KG, Wiesbaden (DE)

( * ) Notice: Subject to any disclaimer, the term of this patent is extended or adjusted under 35 U.S.C. 154(b) by 0 days.

(21) Appl. No.: 14/870,566

(22) Filed: Sep. 30, 2015

(65) Prior Publication Data

US 2016/0016932 A1   Jan. 21, 2016

Related U.S. Application Data

(62) Division of application No. 13/245,123, filed on Sep. 26, 2011, now Pat. No. 9,266,855.

(60) Provisional application No. 61/386,849, filed on Sep. 27, 2010.

(51) Int. Cl.
C07D 471/04 (2006.01)
C07D 401/04 (2006.01)

(52) U.S. Cl.
CPC ......... *C07D 471/04* (2013.01); *C07D 401/04* (2013.01)

(58) Field of Classification Search
CPC .......................... C07D 215/38; C07D 217/26
USPC ................................................ 546/175, 145
See application file for complete search history.

(56) References Cited

U.S. PATENT DOCUMENTS

| | | | |
|---|---|---|---|
| 7,037,918 B2 | 5/2006 | Nuss et al. | |
| 7,205,314 B2 | 4/2007 | Berg et al. | |
| 7,399,780 B2 | 7/2008 | Berg et al. | |
| 7,572,914 B2 | 8/2009 | Gangloff et al. | |
| 8,158,661 B2 | 4/2012 | Medina et al. | |
| 8,207,216 B2 | 6/2012 | Kozikowski et al. | |
| 8,236,858 B2 | 8/2012 | Peleg-Shulman et al. | |
| 8,318,793 B2 | 11/2012 | Turner et al. | |
| 8,426,425 B2 | 4/2013 | Jimenez et al. | |
| 8,592,437 B2 | 11/2013 | Lochead et al. | |
| 8,686,042 B2 | 4/2014 | Gil et al. | |
| 9,090,592 B2 | 7/2015 | Turner et al. | |
| 2002/0177556 A1 | 11/2002 | Engel et al. | |
| 2003/0199526 A1 | 10/2003 | Choquette et al. | |
| 2004/0186288 A1 | 9/2004 | Kruger et al. | |
| 2005/0153966 A1* | 7/2005 | Gangloff ............ C07D 401/04 514/243 |
| 2006/0009460 A1 | 1/2006 | Dickson et al. | |
| 2007/0281949 A1 | 12/2007 | Bacon et al. | |
| 2008/0153869 A1 | 6/2008 | Bressi et al. | |

FOREIGN PATENT DOCUMENTS

| | | |
|---|---|---|
| EP | 1256578 A1 | 11/2002 |
| WO | WO-9921835 A1 | 5/1999 |
| WO | WO-0112188 A1 | 2/2001 |
| WO | WO-0210141 A1 | 2/2002 |
| WO | WO-0218346 A1 | 3/2002 |
| WO | WO-0222601 A1 | 3/2002 |
| WO | WO-03004472 A1 | 1/2003 |
| WO | WO-03035065 A1 | 5/2003 |
| WO | WO-03053330 A2 | 7/2003 |
| WO | WO-03053444 A1 | 7/2003 |
| WO | WO-03055492 A1 | 7/2003 |
| WO | WO-03055877 A1 | 7/2003 |
| WO | WO-03082853 A1 | 10/2003 |
| WO | WO-2004072029 A2 | 8/2004 |
| WO | WO-2005012256 A1 | 2/2005 |
| WO | WO-2005019190 A2 | 3/2005 |
| WO | WO-2005061516 A1 | 7/2005 |
| WO | WO-2005061519 A1 | 7/2005 |
| WO | WO-2005120509 A1 | 12/2005 |
| WO | WO-2005123672 A2 | 12/2005 |
| WO | WO-2006003440 A1 | 1/2006 |
| WO | WO-2006091737 A1 | 8/2006 |
| WO | WO-2007003525 A2 | 1/2007 |
| WO | WO-2007017145 A2 | 2/2007 |
| WO | WO-2007040438 A2 | 4/2007 |
| WO | WO-2007083978 A1 | 7/2007 |
| WO | WO-2007089192 A1 | 8/2007 |
| WO | WO-2007120102 A1 | 10/2007 |
| WO | WO-2007125110 A1 | 11/2007 |

(Continued)

OTHER PUBLICATIONS

Aho L., et al., "Systematic Appraisal using Immunohistochemistry of Brain Pathology in Aged and Demented Subjects.," Dementia and Geriatric Cognitive Disorders, 2008, vol. 25 (5), pp. 423-432.
Anderson M.O., et al., "Parallel Synthesis of Diarylureas and their Evaluation as Inhibitors of Insulin-like Growth Factor Receptor," Journal of Combinatorial Chemistry, 2006, vol. 8 (5), pp. 784-790.
Barth et al., "Pyridaiino[3,4-b][1,5]benzoxazepin-5(6H)-ones: synthesis and biological evaluation, CODEN: ACCHEH; ISSN: 0956-3202, XP009074718," Antiviral Chemistry and Chemotherapy, vol. 7 (6), pp. 300-312, 1996.
Calabresi P. et al., "Section IX Chemotherapy of Neoplastic Diseases—Introduction," in: Goodman & Gilman's The Pharmacological Basis of Therapeutics, 10th Edition, Hardman J.G. et al., eds, 2001, McGraw-Hill, New York, pp. 1381-1388.

(Continued)

*Primary Examiner* — Jeffrey S Lundgren
*Assistant Examiner* — Meghan Finn
(74) *Attorney, Agent, or Firm* — Neal, Gerber & Eisenberg LLP

(57) ABSTRACT

The present invention relates to novel heterocyclic compounds which are useful for inhibiting glycogen synthase kinase 3 (GSK-3), methods of making the compounds, compositions containing the compounds, and methods of treatment using the compounds.

25 Claims, No Drawings

(56) References Cited

FOREIGN PATENT DOCUMENTS

| WO | WO-2008046919 A2 | 4/2008 |
|---|---|---|
| WO | WO-2008130312 A1 | 10/2008 |
| WO | WO-2009130317 A1 | 10/2009 |

OTHER PUBLICATIONS

Cole A.R., et al., "GSK-3 Phosphorylation of the Alzheimer Epitope Within Collapsin Response Mediator Proteins Regulates Axon Elongation in Primary Neurons.," The Journal of Biological Chemistry, 2004, vol. 279 (48), pp. 50176-50180.
Cotter D., et al., "Abnormalities of Wnt Signalling in Schizophrenia—Evidence for Neurodevelopmental Abnormality," NeuroReport, 1998, vol. 9 (7), pp. 1261-1265.
Cowper-Smith C.D., et al., "Delayed Administration of a Potent Cyclin Dependent Kinase and Glycogen Synthase Kinase 3 Beta Inhibitor Produces Long-Term Neuroprotection in a Hypoxia-Ischemia Model of Brain Injury.," Neuroscience, 2008, vol. 155 (3), pp. 864-875.
De Sarno P., et al., "Lithium Prevents and Ameliorates Experimental Autoimmune Encephalomyelitis.," Journal of Immunology (Baltimore, Md. : 1950), 2008, vol. 181 (1), pp. 338-345.
Elchebly M., et al., "Increased Insulin Sensitivity and Obesity Resistance in Mice Lacking the Protein Tyrosine Phosphatase-1B Gene," Science, 1999, vol. 283 (5407), pp. 1544-1548.
Engel T., et al., "Chronic Lithium Administration to Ftdp-17 Tau and GSK-3Beta Overexpressing Mice Prevents Tau Hyperphosphorylation and Neurofibrillary Tangle Formation, But Pre-Formed Neurofibrillary Tangles Do Not Revert.," Journal of Neurochemistry, 2006, vol. 99 (6), pp. 1445-1455.
Engel T., et al., "Full Reversal of Alzheimer's Disease-Like Phenotype in a Mouse Model with Conditional Overexpression of Glycogen Synthase Kinase-3.," The Journal of Neuroscience : the Official Journal of the Society for Neuroscience, 2006, vol. 26 (19), pp. 5083-5090.
Engel T., et al., "Hippocampal Neuronal Subpopulations are Differentially Affected in Double Transgenic Mice Overexpressing Frontotemporal Dementia and Parkinsonism Linked to Chromosome 17 Tau and Glycogen Synthase Kinase-3Beta," Neuroscience, 2008, vol. 157 (4), pp. 772-780.
Gould T.D., et al., "Ar-A014418, a Selective GSK-3 Inhibitor, Produces Antidepressant-Like Effects in the Forced Swim Test.," The International Journal of Neuropsychopharmacology, 2004, vol. 7 (4), pp. 387-390.
Hanger D.P., et al., "Glycogen Synthase Kinase-3 Induces Alzheimer's Disease-Like Phosphorylation of Tau: Generation of Paired Helical Filament Epitopes and Neuronal Localisation of the Kinase.," Neuroscience Letters, 1992, vol. 147 (1), pp. 58-62.
Heinisch et al., "Pyridazines. 81. A novel 1,2-diazine containing tricyclic system: synthesis of pyridazinol[3,4-b][1,5]benzodiazepin-5-ones as potential HIV-1 reverse transcriptase inhibitors, CODEN: HTCYAM; ISSN: 0385-5414, 1997, XP00124802," HETEROCYC.
Heinisch G., et al., "Synthesis of Pyridazino[3,4-b][1,5]Benzodiazepin-5-ones and their Biological Evaluation as Non-Nucleoside HIV Reverse Transcriptase Inhibitors," Archives of Pharmacology, 1997, vol. 330, pp. 29-34.
Heinisch G., et al., "Synthesis of Substituted Tri- and Tetracyclic Compounds Bearing a Pyridazine Core and their Biological Evaluation as Antimycobacterial Agents," Archives of Pharmacology, 2000, vol. 333, pp. 231-240.
Honma T., et al., "Structure-Based Generation of a New Class of Potent Cdk4 Inhibitors: New de Novo Design Strategy and Library Design," Journal of Medicinal Chemistry, 2001, vol. 44, pp. 4615-4627.
Imazu M., et al., "Phosphorylation and Inactivation of Liver Glycogen Synthase by Liver Protein Kinases," The Journal of Biological Chemistry, 1984, vol. 259 (3), pp. 1813-1821.

Infante J., et al., "Synergistic Effect of Two Oxidative Stress-Related Genes (Heme Oxygenase-1 and Gsk3B) on the Risk of Parkinson S Disease," European Journal of Neurology, 2010, vol. 17 (5), pp. 760-762.
Intelihealth, "Alzheimer's disease," [online] [Retrieved on Jun. 30, 2008] Retrieved from the Internet:< URL: http://www.intelihealth.com/IH/intlh/WSIHW000/8303/9117/195703.html?d=d mtHealthAZ >.
Intelihealth, "Dementia" [online] [Retrieved on Sep. 22, 2009] Retrieved from the Internet:< URL: http://www.intelihealth.com/IH/ihtlH/WSIHW000/24479/11184.html>.
Intelihealth, "Parkinson's disease," [online] [Retrieved on Sep. 22, 2009] Retrieved from the Internet:< URL: http://www.intelihealth.com/IH/ihtiH?d=dmtHealthAZ&c=201957>.
Ishiguro K., et al., "Glycogen Synthase Kinase 3 Beta Is Identical to Tau Protein Kinase I Generating Several Epitopes of Paired Helical Filaments.," Febs Letters, 1993, vol. 325 (3), pp. 167-172.
Kaytor M.D., et al., "The GSK3Beta Signaling Cascade and Neurodegenerative Disease," Current Opinion in Neurobiology, 2002, vol. 12 (3), pp. 275-278.
King F.D., Ed., "Bioisosteres, Conformational Restriction and Pro-Drugs-Case History: An Example of a Conformational Restriction Approach," Medical Chemistry: Principles and Practice, 1994, Chapter 14, pp. 206-209.
Koh S-H., et al., "Inhibition of Glycogen Synthase Kinase-3 Suppresses the Onset of Symptoms and Disease Progression of G93A-Sod1 Mouse Model of Als," Experimental Neurology, 2007, vol. 205 (2), pp. 336-346.
Koh S.H., et al., "Role of Glycogen Synthase Kinase-3 in I-DOPA Induced neurotoxicity," Expert Opinion on Drug Metabolism & Toxicology, 2009, vol. 5 (11), pp. 1359-1368.
Koros E., et al., "The Role of Glycogen Synthase Kinase-3Beta in Schizophrenia.," Drug News &Amp; Perspectives, 2007, vol. 20 (7), pp. 437-445.
Kwok J.B.J., et al., "GSK3B Polymorphisms Alter Transcription and Splicing in Parkinson's Disease," Annals of Neurology, 2005, vol. 58 (6), pp. 829-839.
Kypta R.M., . et al, "GSK-3 Inhibitors and Their Potential in the Treatment of Alzheimer's Disease," Expert Opinion on Therapeutic Patents, 2005, vol. 15 (10), pp. 1315-1331.
Leroy K., et al., "Increased Level of Active GSK-3Beta in Alzheimer's Disease and Accumulation in Argyrophilic Grains and in Neurones at Different Stages of Neurofibrillary Degeneration.," Neuropathology and Applied Neurobiology, 2007, vol. 33 (1), pp. 43-55.
Lijam N., et al., "Social Interaction and Sensorimotor Gating Abnormalities in Mice Lacking Dvl1," Cell, 1997, vol. 90 (5), pp. 895-905.
Intelihealth, "Schizophrenia" [online] Retrieved on [Apr. 10, 2011] Retrieved from the Internet:< URL: http://www. intelihealth.com/1 H/ihtlH!WSIHW000/8271/8694/1 88010.html?d= dmtHealthAZ@prevent>.
Intelihealth, "Obesity" [online] [Retrieved on Apr. 10, 2011] Retrieved from the Internet:< URl: http://www.intelihealth.com/IH/ihtlH? t=23671&p=br, IHWI-st,82711-r, WSIHWOOOI-b, *l>.
Lucas J.J., et al., "Decreased Nuclear Beta-Catenin, Tau Hyperphosphorylation and Neurodegeneration in GSK-3Beta Conditional Transgenic Mice.," The Embo Journal, 2001, vol. 20 (1-2), pp. 27-39.
Luna-Munoz J., et al., "Earliest Stages of Tau Conformational Changes are Related to the Appearance of a Sequence of Specific Phospho-Dependent Tau Epitopes in Alzheimer's Disease.," Journal of Alzheimer's Disease 2007, vol. 12 (4), pp. 365-375.
Mandelkow E.M., et al., "Glycogen Synthase Kinase-3 and the Alzheimer-Like State of Microtubule-Associated Protein Tau.," FEBS Letters, 1992, vol. 314 (3), pp. 315-321.
Martin M., et al., "Toll-Like Receptor-Mediated Cytokine Production is Differentially Regulated by Glycogen Synthase Kinase 3.," Nature Immunology, 2005, vol. 6 (8), pp. 777-784.
Martins D.F., et al., "The Antinociceptive Effects of Ar-A014418, a Selective Inhibitor of Glycogen Synthase Kinase-3 Beta, in Mice.," The Journal of Pain : Official Journal of the American Pain Society, 2011, vol. 12 (3), pp. 315-322.

(56) References Cited

OTHER PUBLICATIONS

McCubrey J.A., et al., "Gsk-3 as Potential Target for Therapeutic Intervention in Cancer," Oncotarget, 2014, vol. 5 (10), pp. 2881-2911.

Medina., et al., "Medina et al., Frontiers in Molecular Neuroscience, 2011, vol. 4 (24), pp. 1-10.," Frontiers in Molecular Neuroscience, 2011, vol. 4 (24), pp. 1-10.

Medina M., et al., "Glycogen Synthase Kinase-3 (GSK-3) Inhibitors for the Treatment of Alzheimer's Disease," Current Pharmaceutical Design, 2010, vol. 16 (25), pp. 2790-2798.

Noble W., et al., "Inhibition of Glycogen Synthase Kinase-3 by Lithium Correlates with Reduced Tauopathy and Degeneration in Vivo.," Proceedings of the National Academy of Sciences of the United States of America, 2005, vol. 102 (19), pp. 6990-6995.

Onishi T., et al., "A Novel Glycogen Synthase Kinase-3 Inhibitor 2-Methyl-5-(3-{4-[(S)-Methylsulfinyl]Phenyl}-1-Benzofuran-5-Yi)-1,3,4-Oxadiazole Decreases Tau Phosphorylation and Ameliorates Cognitive Deficits in a Transgenic Model of Alzheimer's Disease.," Journal of Neurochemistry, 2011, vol. 119 (6), pp. 1330-1340.

Ott, Ingo et al., "Substituted Pyridazino[3,4-b][1,5]benzoxazepin-5(6H)on es as Multidrug-Resistance Modulating Agents," Journal of Medicinal Chemistry, vol. 47 (18), pp. 4627-4630, 2004.

Pei J.J., et al., "Distribution, Levels, and Activity of Glycogen Synthase Kinase-3 in the Alzheimer Disease Brain.," Journal of Neuropathology and Experimental Neurology, 1997, vol. 56 (1), pp. 70-78.

Peineau S., et al., "Ltp Inhibits Ltd in the Hippocampus Via Regulation of GSK3Beta.," Neuron, 2007, vol. 53 (5), pp. 703-717.

Rockenstein E., et al., "Neuroprotective Effects of Regulators of the Glycogen Synthase Kinase-3Beta Signaling Pathway in a Transgenic Model of Alzheimer's Disease are Associated with Reduced Amyloid Precursor Protein Phosphorylation," The Journal of Neuroscience, 2007, vol. 27 (8), pp. 1981-1991.

Rubinfeld B., et al., "Binding of GSK3Beta to the Apc-Beta-Catenin Complex and Regulation of Complex Assembly.," Science (New York, N.Y.), 1996, vol. 272 (5264), pp. 1023-1026.

Shaw J.T., et al., "The Preparation of 2,6-Diaminopyrazine,2,6-Diazidopyrazine and Some of their Derivatives," Journal of Heterocyclic Chemistry, 1980, vol. 17 (1), pp. 11-16.

Soos T.J., et al., "Cdk/GSK-3 Inhibitors as a New Approach for the Treatment of Proliferative Renal Diseases.," Drug News &Amp; Perspectives, 2006, vol. 19 (6), pp. 325-328.

Spillantini M.G., et al., "Tau Protein Pathology in Neurodegenerative Diseases," Trends in Neurosciences, 1998, vol. 21 (10), pp. 428-433.

Szczepankiewicz A., et al., "Association Analysis of the GSK-3Beta T-50C Gene Polymorphism with Schizophrenia and Bipolar Disorder.," Neuropsychobiology, 2006, vol. 53 (1), pp. 51-56.

Takada Y., et al., "Genetic Deletion of Glycogen Synthase Kinase-3Beta Abrogates Activation of kappa alpha Kinase, Jnk, Akt, and P44/P42 Mapk But Potentiates Apoptosis Induced by Tumor Necrosis Factor.," The Journal of Biological Chemistry, 2004, vol. 279 (38), pp. 39541-39554.

Waterbeemd Van De H., et al., "Property-based Design: Optimization of Drug Absorption and Pharmacokinetics," Journal of Medicinal Chemistry, 2001, vol. 44 (9), pp. 1313-1333.

Whittle B.J., et al., "Reduction of Experimental Colitis in the Rat by Inhibitors of Glycogen Synthase Kinase-3Beta.," British Journal of Pharmacology, 2006, vol. 147 (5), pp. 575-582.

Zhang J., et al., "Tau Protein is Hyperphosphorylated in a Site-Specific Manner in Apoptotic Neuronal Pc12 Cells.," Journal of Neurochemistry, 2000, vol. 75 (6), pp. 2346-2357.

International Search Report and Written Opinion for Application No. PCT/EP2011/066684, dated Dec. 23, 2011, 10 pages.

* cited by examiner

HETEROCYCLIC COMPOUNDS AND THEIR USE AS GLYCOGEN SYNTHASE KINASE-3 INHIBITORS

CROSS-REFERENCE TO RELATED APPLICATION(S)

This is a divisional of U.S. patent application Ser. No. 13/245,123, filed on Sep. 26, 2011, which claims priority to U.S. Provisional Patent Application No. 61/386,849, filed on Sep. 27, 2010, the entire contents of all of which are fully incorporated herein by reference.

TECHNICAL FIELD

The present invention relates to novel heterocyclic compounds which are useful for inhibiting glycogen synthase kinase 3 (GSK-3), methods of making the compounds, compositions containing the compounds, and methods of treatment using the compounds.

BACKGROUND OF THE INVENTION

Glycogen synthase kinase-3 (GSK-3) is a serine/threonine kinase encoded by two isoforms, GSK-3α and GSK-3β, with molecular weights of 51 and 47 kDa, respectively. These share 97% sequence similarity in their kinase catalytic domains. The GSK-3α isoform has an extended glycine-rich N-terminal tail. A minor splice variant of GSK-3β has been identified (expressed at ~15% of total) with a 13 amino acid insert within the kinase domain. This variant had a reduced activity towards tau. GSK-3 is highly conserved throughout evolution, and found in all mammalians thus far with high homology in the kinase domain. Both isoforms are ubiquitously expressed in mammalian tissues, including the brain. Pharmacological GSK-3 inhibitors are not able to selectively inhibit one of the isoforms.

GSK-3β plays an important role in the control of metabolism, differentiation and survival. It was initially identified as an enzyme able to phosphorylate and hence inhibit glycogen synthase. Subsequently, it was recognised that GSK-3β was identical to tau protein kinase 1 (TPK1), an enzyme that phosphorylates tau protein in epitopes that are also found to be hyperphosphorylated in Alzheimer's disease and in several tauopathies.

Interestingly, protein kinase B (AKT) phosphorylation of GSK-3β results in a loss of kinase activity, and it has been proposed that this inhibition may mediate some of the effects of neurotrophic factors. Moreover, phosphorylation of β-catenin (a protein involved in cell survival) by GSK-3β, results in its degradation by an ubiquitinilation dependent proteasome pathway.

Therefore it appears that inhibition of GSK-3β activity may result in neurotrophic activity. There is evidence that lithium, an uncompetitive inhibitor of GSK-3β, enhances neuritogenesis in some models and can also increase neuronal survival, through the induction of survival factors such as Bcl-2 and the inhibition of the expression of proapoptotic factors such as P53 and Bax.

Further studies have shown that β-amyloid increases GSK-3β activity and tau protein phosphorylation. Moreover, this hyperphosphorylation as well as the neurotoxic effects of β-amyloid are blocked by lithium chloride and by a GSK-3β antisense mRNA. These observations taken together suggest that GSK-3β may be the link between the two major pathological processes in Alzheimer's disease: abnormal APP (Amyloid Precursor Protein) processing and tau protein hyperphosphorylation.

These experimental observations indicate that compounds which modulate the GSK-3β activity may find application in the treatment of the neuropathological consequences and the cognitive and attention deficits associated with Alzheimer's disease, as well as other acute and chronic neurodegenerative diseases. These include, but are not limited to: Parkinson's disease, tauopathies (e.g. frontotemporoparietal dementia, corticobasal degeneration, Pick's disease, progressive supranuclear palsy, argyophilic grain disease) and other dementia including vascular dementia; acute stroke and others traumatic injuries; cerebrovascular accidents (e.g. age related macular degeneration); brain and spinal cord trauma; peripheral neuropathies; bipolar disorders, retinopathies and glaucoma.

GSK-3β may further have utility in the treatment of inflammatory diseases, such as rheumatoid arthritis and osteoarthritis.

GSK-3β may also have utility in the treatment of other diseases such as: Non-insulin dependent diabetes and obesity; osteoporosis; manic depressive illness; schizophrenia; alopecia; cancers such as breast cancer, non-small cell lung carcinoma, thyroid cancer, T or B-cell leukemia and several virus-induced tumors.

A review on GSK-3, its functions, its therapeutic potential and its possible inhibitors is given in "Glycogen Synthase Kinase 3 (GSK-3) and its inhibitors: Drug Discovery and Developments" by A. Martinez et al. (editors), John Wiley and Sons, 2006.

WO 03/053330 describes 2-oxindoles substituted in the 3-position with a bicyclic hetaryl group and their use for treating conditions related to glycogen synthase kinase-3. WO 03/082853 describes substituted 2-oxindoles substituted in the 3-position with a monocyclic hetaryl group and their use for treating conditions related to glycogen synthase kinase-3. WO 2005/123672 relates to 2-hydroxyindoles carrying in the 3-position an optionally fused pyrid-2-yl ring and their use for inhibiting kinases. WO 2005/061519 relates to 2-hydroxyindoles carrying in the 3-position a pyrid-2-yl ring fused to an aromatic or heteroaromatic ring and their use for inhibiting kinases.

SUMMARY OF THE INVENTION

The object of the present invention is to provide compounds which modulate the GSK-3β activity, in particular compounds which have an inhibitory activity on GSK-3β and which thus are useful as an active ingredient of a composition for preventive and/or therapeutic treatment of a disease caused by abnormal GSK-3β activity, especially of neurodegenerative and/or inflammatory diseases. More specifically, the goal is to provide novel compounds useful as an active ingredient of a composition that enables prevention and/or treatment of neurodegenerative diseases such as Alzheimer's disease.

It was surprisingly found that the problem is solved by providing a heterocyclic compound of the general formulae IA and IB (IA)

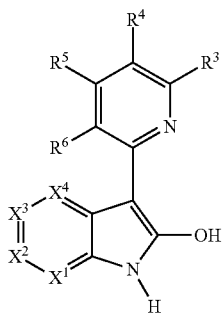

(IB)

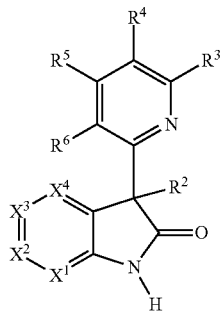

the stereoisomers, N-oxides, prodrugs, tautomers and/or physiologically tolerated acid addition salts thereof; and the compounds of the general formulae IA and IB, wherein at least one of the atoms has been replaced by its stable, non-radioactive isotope, wherein $X^1$, $X^2$, $X^3$ and $X^4$ are independently of each other selected from the group consisting of $CR^1$ and N;

each $R^1$ is independently selected from the group consisting of hydrogen, cyano, $NR^aR^b$, OH, halogen, $C_1$-$C_6$-alkyl, $C_1$-$C_6$-haloalkyl, $C_3$-$C_7$-cycloalkyl, $C_3$-$C_7$-halocycloalkyl, $C_2$-$C_4$-alkenyl, $C_2$-$C_4$-haloalkenyl, $C_1$-$C_6$-alkoxy, $C_1$-$C_6$-haloalkoxy, formyl, $C_1$-$C_6$-alkylcarbonyl, $C_1$-$C_6$-haloalkylcarbonyl, COOH, $C_1$-$C_6$-alkoxycarbonyl, $C_1$-$C_6$-haloalkoxycarbonyl, $C_1$-$C_6$-alkyl-$NR^aR^b$, CO—$NR^aR^b$, an aromatic radical Ar, which is selected from the group consisting of phenyl and a 5- or 6-membered N- or C-bound heteroaromatic radical comprising 1, 2 or 3 heteroatoms independently selected from O, S and N as ring members, wherein Ar is unsubstituted or carries one or two radicals $R^7$ and wherein Ar may also be bonded via a $CH_2$ group, and saturated or partially unsaturated 3-, 4-, 5-, 6- or 7-membered heterocyclic radical comprising 1, 2 or 3 heteroatoms selected from O, S and N as ring members, wherein the heterocyclic radical is unsubstituted or substituted by 1, 2, 3 or 4 radicals independently selected from halogen, cyano, $C_1$-$C_4$-alkyl, $C_1$-$C_4$-haloalkyl, $C_1$-$C_4$-alkoxy and $C_1$-$C_4$-haloalkoxy;

$R^2$ is hydrogen, $C_1$-$C_4$-alkyl, $C_1$-$C_4$-haloalkyl, $C_2$-$C_4$-alkenyl, $C_2$-$C_4$-haloalkenyl, OH or F;

$R^3$ and $R^4$; or $R^4$ and $R^5$; or $R^5$ and $R^6$ form together a bridging group —$(CH_2)_m$—, wherein m is 3, 4 or 5, where 1, 2 or 3 of the $CH_2$ groups may be replaced by a group or a heteroatom selected from CO, O, S, SO, $SO_2$, $NR^c$ and NO, and where 1, 2 or 3 hydrogen atoms of the bridging group may be replaced by a radical $R^8$;

where the radicals $R^3$, $R^4$, $R^5$ and $R^6$, which are not part of the bridging group, are independently selected from the group consisting of hydrogen, halogen, cyano, $C_1$-$C_4$-alkyl, $C_1$-$C_4$-haloalkyl, $C_1$-$C_4$-alkoxy, $C_1$-$C_4$-haloalkoxy and $NR^aR^b$;

each $R^7$ is independently selected from the group consisting of halogen, OH, CN, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $NR^aR^b$, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, CO—$NR^aR^b$, a phenyl group and a saturated, partially unsaturated or aromatic 5- or 6-membered heterocyclic radical comprising 1, 2 or 3 heteroatoms selected from O, S and N as ring members, wherein phenyl and the heterocyclic radical are, independently of each other, unsubstituted or substituted by 1, 2, 3 or 4 radicals independently selected from halogen, cyano, $C_1$-$C_4$-alkyl, $C_1$-$C_4$-haloalkyl, $C_1$-$C_4$-alkoxy and $C_1$-$C_4$-haloalkoxy, or in the heterocyclic ring two geminally bound radicals may together form a group =O;

each $R^8$ is independently selected from the group consisting of halogen, OH, CN, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $NR^aR^b$, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, CO—$NR^aR^b$, a phenyl group and a saturated, partially unsaturated or aromatic 3-, 4-, 5-, 6- or 7-membered heterocyclic radical comprising 1, 2 or 3 heteroatoms selected from O, S and N as ring members, wherein phenyl and the heterocyclic radical are, independently of each other, unsubstituted or substituted by 1, 2, 3 or 4 radicals independently selected from halogen, cyano, $C_1$-$C_4$-alkyl, $C_1$-$C_4$-haloalkyl, $C_1$-$C_4$-alkoxy and $C_1$-$C_4$-haloalkoxy;

$R^a$ and $R^b$ are independently of each other selected from the group consisting of hydrogen, $C_1$-$C_6$-alkyl, $C_1$-$C_4$-haloalkyl, $C_1$-$C_4$-alkoxy, $C_1$-$C_4$-haloalkoxy, $C_1$-$C_4$-alkylcarbonyl, $C_1$-$C_4$-haloalkylcarbonyl, $C_1$-$C_6$-alkoxycarbonyl and $C_1$-$C_6$-haloalkoxycarbonyl; or $R^a$ and $R^b$ form, together with the nitrogen atom to which they are bonded, a 3-, 4-, 5-, 6- or 7-membered saturated or aromatic or non-aromatic N-heterocyclic ring, which may contain 1 further heteroatom or heteroatom-containing group selected from N, O, S, SO and $SO_2$ as a ring member, where the N-heterocyclic ring may carry 1 or 2 radicals selected from halogen, cyano, $C_1$-$C_4$-alkyl, $C_1$-$C_4$-haloalkyl, $C_1$-$C_4$-alkoxy and $C_1$-$C_4$-haloalkoxy; and each $R^c$ is independently selected from the group consisting of hydrogen, $C_1$-$C_6$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_6$-alkoxycarbonyl and $C_1$-$C_6$-haloalkoxycarbonyl.

Thus, the present invention relates to compounds of the formulae IA and IB as defined herein and in the claims, to the stereoisomers, tautomers, prodrugs and/or physiologically tolerated acid addition salts thereof.

According to a further aspect, the present invention relates to a pharmaceutical composition comprising at least one compound of the formula IA and/or IB as defined herein, a stereoisomer, a tautomer, a prodrug and/or a physiologically tolerated acid addition salt thereof or comprising at least one heterocyclic compound as defined above, wherein at least one of the atoms has been replaced by its stable, non-radioactive isotope, optionally together with at least one physiologically acceptable carrier and/or auxiliary substance.

According to a further aspect, the present invention relates to the use of at least one compound of the formula IA and/or IB as defined herein, the stereoisomers, tautomers, prodrugs and/or physiologically tolerated acid addition salts thereof, for the preparation of a medicament for the treatment of a medical disorder susceptible to treatment with a compound that modulates glycogen synthase kinase 3β activity.

According to a further aspect, the present invention relates to a method for treating a medical disorder susceptible to treatment with a compound that modulates glycogen synthase kinase 3β activity, said method comprising administering an effective amount of at least one compound of the formula IA and/or IB as defined herein, a stereoisomer, a tautomer, a prodrug and/or a physiologically tolerated acid addition salt thereof, to a subject in need thereof.

DETAILED DESCRIPTION OF THE INVENTION

Provided the compounds of the formulae IA and IB of a given constitution may exist in different spatial arrangements, for example if they possess one or more centers of asymmetry, polysubstituted rings or double bonds, or as different tautomers, it is also possible to use enantiomeric mixtures, in particular racemates, diastereomeric mixtures and tautomeric mixtures, preferably, however, the respective essentially pure enantiomers, diastereomers and tautomers of the compounds of formulae IA and IB and/or of their salts.

In case $R^2$ in compound IB is hydrogen, this compound IB is a tautomer of the respective compound IA wherein the remaining variables have the same meaning.

It is likewise possible to use physiologically tolerated salts of the compounds of the formulae IA and/or IB, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 et seq., Birkhäuser Verlag, Basel and Stuttgart, 1966.

In the terms of the present invention, "prodrugs" are compounds which are metabolized in vivo to give the compounds of the invention of formulae IA or IB. Typical examples for prodrugs are for example described in C. G. Wermeth (editor): The Practice of Medicinal Chemistry, Academic Press, San Diego, 1996, pages 671-715. Examples are phosphates, carbamates, aminoacids, esters, amides, peptides, urea and the like. In the present case, suitable prodrugs can be compounds of formula IA or IB wherein an external nitrogen atom, for example a secondary nitrogen ring atom of the ring fused to the pyridyl ring (i.e. in the group —$(CH_2)_m$— formed by $R^3$ together with $R^4$ or $R^4$ together with $R^5$ or $R^5$ together with $R^6$, at least one $CH_2$ group is replaced by a group $NR^c$ and at least one $R^c$ is hydrogen) or a nitrogen atom of a primary or secondary amino group being a substituent $R^1$, $R^3$, $R^4$, $R^5$, $R^6$, $R^7$ and/or $R^8$ (=at least one of $R^1$, $R^3$, $R^4$, $R^5$, $R^6$, $R^7$ and $R^8$ is $NR^aR^b$, wherein at least one of $R^a$ and $R^b$ is H), forms an amide/peptide bond in that this nitrogen atom is substituted by a $C_1$-$C_4$-alkylcarbonyl group, e.g. by acetyl, propionyl, n-propylcarbonyl, isopropylcarbonyl, n-butylcarbonyl or tert-butylcarbonyl (pivaloyl), by benzoyl, or by an aminoacid group bonded via CO, e.g. glycine, alanine, serine, phenylalanine and the like bonded via CO. Suitable prodrugs are furthermore alkylcarbonyloxyalkylcarbamates, wherein said nitrogen atom carries a group —C(=O)—O—CHR$^x$—O—C(=O)—R$^y$, wherein R$^x$ and R$^y$ independently of each other are $C_1$-$C_4$-alkyl. These carbamate compounds are for example described in J. Alexander, R. Cargill, S. R. Michelson, H. Schwam, J. Medicinal Chem. 1988, 31(2), 318-322. These groups can be removed under metabolic conditions and result in compounds IA/IB wherein said nitrogen atom carries a hydrogen atom instead. Also, $R^1$ may be chosen so as to be hydrolysable under metabolic conditions and thus to be one of the above-listed groups (i.a. a $C_1$-$C_4$-alkylcarbonyl group, an aminoacid group bonded via CO or a group —C(=O)—O—CHR$^x$—O—C(=O)—R$^y$). Another prodrug is e.g. a compound IB, wherein $R^2$ is F.

The compounds of formulae IA or IB may also be present in the form of the respective tautomers. Apart the tautomery already mentioned above of formulae IA and IB, where in formula IB $R^2$ is H, tautomery may also be present in compounds IA and IB wherein $R^1$ is OH and this substituent is bonded to a carbon atom which is in α-position to a nitrogen ring atom. This results for example in following tautomeric formulae (the examples are only given for formula IA, but are analogous for formula IB):

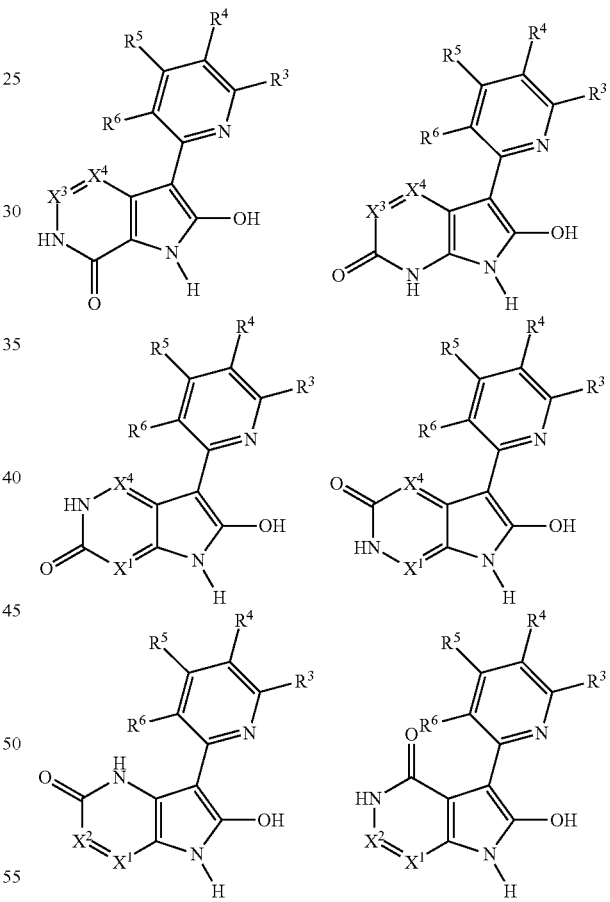

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

$C_1$-$C_2$-Alkyl is methyl or ethyl; $C_1$-$C_3$-alkyl is additionally n-propyl or isopropyl.

$C_1$-$C_4$-Alkyl is a straight-chain or branched alkyl group having from 1 to 4 carbon atoms. Examples are methyl, ethyl, n-propyl, isopropyl, n-butyl, 2-butyl (sec-butyl), isobutyl and tert-butyl.

$C_1$-$C_6$-Alkyl is a straight-chain or branched alkyl group having from 1 to 6 carbon atoms. Examples include the residues mentioned above for $C_1$-$C_4$-alkyl and also pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

$C_1$-$C_2$-Haloalkyl is an alkyl group having 1 or 2 carbon atoms (as mentioned above), where at least one of the hydrogen atoms, e.g. 1, 2, 3, 4 or 5 hydrogen atoms in these groups are replaced by halogen atoms as mentioned above, such as chloromethyl, dichloromethyl, trichloromethyl, fluoromethyl, difluoromethyl, trifluoromethyl, bromomethyl, chlorofluoromethyl, dichlorofluoromethyl, chlorodifluoromethyl, 1-chloroethyl, 1-bromoethyl, 1-fluoroethyl, 2-chloroethyl, 2-bromoethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

$C_1$-$C_4$-Haloalkyl is a straight-chain or branched alkyl group having 1 to 4 carbon atoms (as mentioned above), where at least one of the hydrogen atoms, e.g. 1, 2, 3, 4 or 5 hydrogen atoms in these groups are replaced by halogen atoms as mentioned above. Examples are, apart those listed above for $C_1$-$C_2$-haloalkyl, 1-chloropropyl, 1-bromopropyl, 1-fluoropropyl, 2-chloropropyl, 2-bromopropyl, 2-fluoropropyl, 3-chloropropyl, 3-bromopropyl, 3-fluoropropyl, 1,1-dichloropropyl, 1,1-difluoropropyl, 2,2-dichloropropyl, 2,2-difluoropropyl, 2,3-dichloropropyl, 2,3-difluoropropyl, 1,3-dichloropropyl, 1,3-difluoropropyl, 3,3-dichloropropyl, 3,3-difluoropropyl, 1,1,2-trichloropropyl, 1,1,2-trifluoropropyl, 1,2,2-trichloropropyl, 1,2,2-trifluoropropyl, 1,2,3-trichloropropyl, 1,2,3-trifluoropropyl, 2,2,3-trichloropropyl, 2,2,3-trifluoropropyl, 3,3,3-trichloropropyl, 3,3,3-trifluoropropyl, 1,1,1-trifluoroprop-2-yl, 1-chlorobutyl, 1-bromobutyl, 1-fluorobutyl, 2-chlorobutyl, 2-bromobutyl, 2-fluorobutyl, 3-chlorobutyl, 3-bromobutyl, 3-fluorobutyl, 4-chlorobutyl, 4-bromobutyl, 4-fluorobutyl, and the like.

$C_1$-$C_6$-Haloalkyl is a straight-chain or branched alkyl group having 1 to 6 carbon atoms (as mentioned above), where at least one of the hydrogen atoms in these groups is replaced by halogen atoms as mentioned above. Examples are, apart those listed above for $C_1$-$C_4$-haloalkyl, chloropentyl, bromopentyl, fluoropentyl, chlorohexyl, bromohexyl, fluorohexyl, and the like.

$C_1$-$C_2$-Fluoroalkyl (=fluorinated $C_1$-$C_2$-alkyl) is an alkyl group having 1 or 2 carbon atoms (as mentioned above), where at least one of the hydrogen atoms, e.g. 1, 2, 3, 4 or 5 hydrogen atoms in these groups are replaced by fluorine atoms, such as difluoromethyl, trifluoromethyl, 1-fluoroethyl, (R)-1-fluoroethyl, (S)-1-fluoroethyl, 2-fluoroethyl, 2,2-difluoroethyl, 2,2,2-trifluoroethyl, or pentafluoroethyl.

$C_1$-$C_4$-Fluoroalkyl (=fluorinated $C_1$-$C_4$-alkyl) is a straight-chain or branched alkyl group having 1 to 4 carbon atoms (as mentioned above), where at least one of the hydrogen atoms, e.g. 1, 2, 3, 4 or 5 hydrogen atoms in these groups are replaced by fluorine atoms. Examples are, apart those listed above for $C_1$-$C_2$-fluoroalkyl, 1-fluoropropyl, (R)-1-fluoropropyl, (S)-1-fluoropropyl, 2-fluoropropyl, (R)-2-fluoropropyl, (S)-2-fluoropropyl, 3-fluoropropyl, 1,1-difluoropropyl, 2,2-difluoropropyl, 1,2-difluoropropyl, 2,3-difluoropropyl, 1,3-difluoropropyl, 3,3-difluoropropyl, 1,1,2-trifluoropropyl, 1,2,2-trifluoropropyl, 1,2,3-trifluoropropyl, 2,2,3-trifluoropropyl, 3,3,3-trifluoropropyl, 1,1,1-trifluoroprop-2-yl, 2-fluoro-1-methylethyl, (R)-2-fluoro-1-methylethyl, (S)-2-fluoro-1-methylethyl, 2,2-difluoro-1-methylethyl, (R)-2,2-difluoro-1-methylethyl, (S)-2,2-difluoro-1-methylethyl, 1,2-difluoro-1-methylethyl, (R)-1,2-difluoro-1-methylethyl, (S)-1,2-difluoro-1-methylethyl, 2,2,2-trifluoro-1-methylethyl, (R)-2,2,2-trifluoro-1-methylethyl, (S)-2,2,2-trifluoro-1-methylethyl, 2-fluoro-1-(fluoromethyl)ethyl, 1-(difluoromethyl)-2,2-difluoroethyl, 1-(trifluoromethyl)-2,2,2-trifluoroethyl, 1-(trifluoromethyl)-1,2,2,2-tetrafluoroethyl, 1-fluorobutyl, (R)-1-fluorobutyl, (S)-1-fluorobutyl, 2-fluorobutyl, (R)-2-fluorobutyl, (S)-2-fluorobutyl, 3-fluorobutyl, (R)-3-fluorobutyl, (S)-3-fluorobutyl, 4-fluorobutyl, 1,1-difluorobutyl, 2,2-difluorobutyl, 3,3-difluorobutyl, 4,4-difluorobutyl, 4,4,4-trifluorobutyl and the like.

$C_1$-$C_6$-Fluoroalkyl (=fluorinated $C_1$-$C_6$-alkyl) is a straight-chain or branched alkyl group having 1 to 6 carbon atoms (as mentioned above), where at least one of the hydrogen atoms, e.g. 1, 2, 3, 4 or 5 hydrogen atoms in these groups are replaced by fluorine atoms. Examples are, apart those listed above for $C_1$-$C_4$-fluoroalkyl, 1-fluoropentyl, (R)-1-fluoropentyl, (S)-1-fluoropentyl, 2-fluoropentyl, (R)-2-fluoropentyl, (S)-2-fluoropentyl, 3-fluoropentyl, (R)-3-fluoropentyl, (S)-3-fluoropentyl, 4-fluoropentyl, (R)-4-fluoropentyl, (S)-4-fluoropentyl, 5-fluoropentyl, (R)-5-fluoropentyl, (S)-5-fluoropentyl, 1-fluorohexyl, (R)-1-fluorohexyl, (S)-1-fluorohexyl, 2-fluorohexyl, (R)-2-fluorohexyl, (S)-2-fluorohexyl, 3-fluorohexyl, (R)-3-fluorohexyl, (S)-3-fluorohexyl, 4-fluorohexyl, (R)-4-fluorohexyl, (S)-4-fluorohexyl, 5-fluorohexyl, (R)-5-fluorohexyl, (S)-5-fluorohexyl, 65-fluorohexyl, (R)-6-fluorohexyl, (S)-6-fluorohexyl, and the like.

$C_1$-$C_4$-Alkoxy is a straight-chain or branched alkyl group having from 1 to 4 carbon atoms, which is bound to the remainder of the molecule via an oxygen atom. Examples include methoxy, ethoxy, n-propoxy, isopropoxy, n-butoxy, 2-butoxy, isobutoxy and tert-butoxy.

$C_1$-$C_6$-Alkoxy is a straight-chain or branched alkyl group having from 1 to 6 carbon atoms, which is bound to the remainder of the molecule via an oxygen atom. Examples include, apart those listed above for $C_1$-$C_4$-alkoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutyloxy, 1,2-dimethylbutyloxy, 1,3-dimethylbutyloxy, 2,2-dimethylbutyloxy, 2,3-dimethylbutyloxy, 3,3-dimethylbutyloxy, 1-ethylbutyloxy, 2-ethylbutyloxy, 1,1,2-trimethylpropoxy, 1,2,2-trimethylpropoxy, 1-ethyl-1-methylpropoxy and 1-ethyl-2-methylpropoxy.

Halogenated $C_1$-$C_6$-alkoxy (which is also termed $C_1$-$C_6$-haloalkoxy), in particular fluorinated $C_1$-$C_6$-alkoxy (also termed $C_1$-$C_6$-fluoroalkoxy) is a straight-chain or branched alkoxy group having from 1 to 6, in particular 1 to 4 carbon atoms (=fluorinated $C_1$-$C_4$-alkoxy), wherein at least one, e.g. 1, 2, 3, 4 or all of the hydrogen atoms are replaced by a halogen atoms, in particular fluorine atoms such as in fluoromethoxy, difluoromethoxy, trifluoromethoxy, (R)-1-fluoroethoxy, (S)-1-fluoroethoxy, 2-fluoroethoxy, 1,1-difluoroethoxy, 2,2-difluoroethoxy, 2,2,2-trifluoroethoxy, 1,1,2,2-tetrafluoroethoxy, (R)-1-fluoropropoxy, (S)-1-fluoropropoxy, (R)-2-fluoropropoxy, (S)-2-fluoropropoxy, 3-fluoropropoxy, 1,1-difluoropropoxy, 2,2-difluoropropoxy, 3,3-difluoropropoxy, 3,3,3-trifluoropropoxy, (R)-2-fluoro-1-methylethoxy, (S)-2-fluoro-1-methylethoxy, (R)-2,2-difluoro-1-methylethoxy, (S)-2,2-difluoro-1-methylethoxy, (R)-1,2-difluoro-1-methylethoxy, (S)-1,2-difluoro-1-methylethoxy, (R)-2,2,2-trifluoro-1-methylethoxy, (S)-2,2,2-trifluoro-1-methylethoxy, 2-fluoro-1-(fluoromethyl)ethoxy, 1-(difluoromethyl)-2,2-difluoroethoxy, (R)-1-fluorobutoxy, (S)-1-fluorobutoxy, 2-fluorobutoxy, 3-fluorobutoxy, 4-fluorobutoxy, 1,1-difluorobutoxy, 2,2-difluorobutoxy, 3,3-difluorobutoxy, 4,4-difluorobutoxy, 4,4,4-trifluorobutoxy, and the like.

$C_1$-$C_4$-Alkylcarbonyl is a straight-chain or branched alkyl group having from 1 to 4 carbon atoms), which is bound to the remainder of the molecule via a carbonyl group (CO), such as in acetyl, propionyl, isopropylcarbonyl, butylcarbonyl, sec-butylcarbonyl, isobutylcarbonyl, and tert-butylcarbonyl.

$C_1$-$C_6$-Alkylcarbonyl is a straight-chain or branched alkyl group having from 1 to 6 carbon atoms, which is bound to the remainder of the molecule via a carbonyl group (CO). Examples include, apart those listed above for $C_1$-$C_4$-alkylcarbonyl, pentylcarbonyl, hexylcarbonyl and the constitutional isomers thereof.

$C_1$-$C_4$-Haloalkylcarbonyl is a straight-chain or branched haloalkyl group having from 1 to 4 carbon atoms as defined above, which is bound to the remainder of the molecule via a carbonyl group (CO)

$C_1$-$C_6$-Haloalkylcarbonyl is a straight-chain or branched haloalkyl group having from 1 to 6 carbon atoms as defined above, which is bound to the remainder of the molecule via a carbonyl group (CO)

$C_1$-$C_4$-Fluoroalkylcarbonyl is a straight-chain or branched fluoroalkyl group having from 1 to 4 carbon atoms as defined above, which is bound to the remainder of the molecule via a carbonyl group (CO)

$C_1$-$C_6$-fluoroalkylcarbonyl is a straight-chain or branched fluoroalkyl group having from 1 to 6 carbon atoms as defined above, which is bound to the remainder of the molecule via a carbonyl group (CO)

$C_1$-$C_6$-Alkoxycarbonyl is a straight-chain or branched alkoxy group having from 1 to 6, especially 1 to 4 carbon atoms (=$C_1$-$C_4$-alkoxycarbonyl), in particular 1 to 3 carbon atoms (=$C_1$-$C_3$-alkoxycarbonyl), which is bound to the remainder of the molecule via a carbonyl group (CO), such as in methoxycarbonyl, ethoxycarbonyl, propyloxycarbonyl, and isopropyloxycarbonyl.

$C_1$-$C_6$-Haloalkoxycarbonyl is a straight-chain or branched haloalkoxy group having from 1 to 6, especially 1 to 4 carbon atoms (=$C_1$-$C_4$-haloalkoxycarbonyl), in particular 1 to 3 carbon atoms (=$C_1$-$C_3$-haloalkoxycarbonyl) as defined above, which is bound to the remainder of the molecule via a carbonyl group (CO).

$C_1$-$C_6$-Fluoroalkoxycarbonyl is a straight-chain or branched fluorooalkoxy group having from 1 to 6, especially 1 to 4 carbon atoms (=$C_1$-$C_4$-fluoroalkoxycarbonyl), in particular 1 to 3 carbon atoms (=$C_1$-$C_3$-fluoroalkoxycarbonyl) as defined above, which is bound to the remainder of the molecule via a carbonyl group (CO).

$C_3$-$C_6$-Cycloalkyl is a cycloaliphatic radical having from 3 to 6 C atoms, such as cyclopropyl, cyclobutyl, cyclopentyl and cyclohexyl. $C_3$-$C_4$-cycloalkyl is a cycloaliphatic radical having from 3 to 4 C atoms, such as cyclopropyl and cyclobutyl.

$C_3$-$C_7$-Cycloalkyl is a cycloaliphatic radical having from 3 to 7 C atoms, such as cyclopropyl, cyclobutyl, cyclopentyl, cyclohexyl and cycloheptyl.

$C_3$-$C_6$-Halocycloalkyl is a cycloaliphatic radical having from 3 to 6 C atoms, such as cyclopropyl, cyclobutyl, cyclopentyl and cyclohexyl, wherein at least one, e.g. 1, 2, 3, 4 or all of the hydrogen atoms are replaced by a halogen atoms, preferably by fluorine atoms such as in 1-fluorocyclopropyl, 2-fluorocyclopropyl, (S)- and (R)-2,2-difluorocyclopropyl, 1,2-difluorocyclopropyl, 2,3-difluorocyclopropyl, pentafluorocyclopropyl, 1-fluorocyclobutyl, 2-fluorocyclobutyl, 3-fluorocyclobutyl, 2,2-difluorocyclobutyl, 3,3-difluorocyclobutyl, 1,2-difluorocyclobutyl, 1,3-difluorocyclobutyl, 2,3-difluorocyclobutyl, 2,4-difluorocyclobutyl, or 1,2,2-trifluorocyclobutyl.

$C_3$-$C_7$-Halocycloalkyl is a cycloaliphatic radical having from 3 to 7 C atoms, such as cyclopropyl, cyclobutyl, cyclopentyl, cyclohexyl and cycloheptyl, wherein at least one, e.g. 1, 2, 3, 4 or all of the hydrogen atoms are replaced by a halogen atoms, preferably by fluorine atoms. Examples include, apart those listed above for $C_3$-$C_6$-fluorocycloalkyl, 1-fluorocycloheptyl, 2-fluorocycloheptyl, 3-fluorocycloheptyl, 4-fluorocycloheptyl, 1,2-difluorocycloheptyl, 1,3-difluorocycloheptyl, 1,4-difluorocycloheptyl, 2,2-difluorocycloheptyl, 2,3-difluorocycloheptyl, 2,4-difluorocycloheptyl, 2,5-difluorocycloheptyl, 2,6-difluorocycloheptyl, 2,7-difluorocycloheptyl, 3,3-difluorocycloheptyl, 3,4-difluorocycloheptyl, 3,5-difluorocycloheptyl, 3,6-difluorocycloheptyl, 4,4-difluorocycloheptyl, 4,5-difluorocycloheptyl, and the like.

$C_2$-$C_4$-Alkenyl is a singly unsaturated hydrocarbon radical having 2, 3 or 4 C-atoms and one C—C double bond, e.g. vinyl, allyl (2-propen-1-yl), 1-propen-1-yl, 2-propen-2-yl, buten-1-yl, buten-2-yl, buten-3-yl, methallyl (2-methylprop-2-en-1-yl) and the like.

$C_2$-$C_4$-Haloalkenyl is a singly unsaturated hydrocarbon radical having 2, 3 or 4 C-atoms, wherein at least one, e.g. 1, 2, 3, 4 or all of the hydrogen atoms are replaced by halogen atoms, preferably by fluorine atoms such as in 1-fluorovinyl, 2-fluorovinyl, 2,2-fluorovinyl, 3,3,3-fluoropropenyl, 1,1-difluoro-2-propenyl, 1-fluoro-2-propenyl and the like.

Examples for 5- or 6-membered N— or C-bound heteroaromatic radicals comprising one nitrogen atom and optionally 1, 2 or 3 further heteroatoms independently selected from O, S and N as ring members are pyrrol-1-yl, pyrrol-2-yl, pyrrol-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, [1,2,3]-1H-triazol-1-yl, [1,2,3]-1H-triazol-4-yl, [1,2,3]-1H-triazol-5-yl, [1,2,3]-2H-triazol-2-yl, [1,2,3]-2H-triazol-4-yl, [1,2,3]-2H-triazol-5-yl, [1,2,4]-1H-triazol-1-yl, [1,2,4]-1H-triazol-3-yl, [1,2,4]-1H-triazol-5-yl, [1,2,4]-4H-triazol-3-yl, [1,2,4]-4H-triazol-4-yl, oxadiazolyl, thiadiazolyl, [1,2,3,4]-1H-tetrazol-1-yl, [1,2,3,4]-1H-tetrazol-5-yl, [1,2,3,4]-2H-tetrazol-2-yl, [1,2,3,4]-2H-tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and triazin-2-yl.

Examples for 5- or 6-membered N— or C-bound heteroaromatic radicals comprising 1, 2 or 3 heteroatoms independently selected from O, S and N as ring members are furan-2-yl, furan-3-yl, thien-2-yl, thien-3-yl, pyrrol-1-yl, pyrrol-2-yl, pyrrol-3-yl, pyrazol-1-yl, pyrazol-3-yl, pyrazol-4-yl, pyrazol-5-yl, imidazol-1-yl, imidazol-2-yl, imidazol-4-yl, imidazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, [1,2,3]-1H-triazol-1-yl, [1,2,3]-1H-triazol-4-yl, [1,2,3]-1H-triazol-5-yl, [1,2,3]-2H-triazol-2-yl, [1,2,3]-2H-triazol-4-yl, [1,2,3]-2H-triazol-5-yl, [1,2,4]-1H-triazol-1-yl, [1,2,4]-1H-triazol-3-yl, [1,2,4]-1H-triazol-5-yl, [1,2,4]-4H-triazol-3-yl, [1,2,4]-4H-triazol-4-yl, oxadiazolyl, thiadiazolyl, [1,2,3,4]-1H-tetrazol-1-yl, [1,2,3,4]-1H-tetrazol-5-yl, [1,2,3,4]-2H-tetrazol-2-yl, [1,2,3,4]-2H-tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl and triazin-2-yl.

Examples for N-bound 3-, 4-, 5-, 6- or 7-membered saturated or unsaturated aromatic or non-aromatic N-heterocyclic rings, which may contain 1 further heteroatom or heteroatom-containing group selected from the group consisting of O, S, SO, $SO_2$ and N as a ring member (thus as rings formed by $R^a$ and $R^b$ together with the nitrogen atom to which they are bound), are aziridin-1-yl, azetidin-1-yl, pyrrolidin-1-yl, pyrazolidin-1-yl, imidazolidin-1-yl, oxazolidin-3-yl, isoxazolidin-2-yl, thiazolidin-3-yl, isothiazolidin-1-yl, [1,2,3]-triazolidin-1-yl, [1,2,3]-triazolidin-2-yl, [1,2,4]-triazolidin-1-yl, [1,2,4]-triazolidin-4-yl, piperidin-1-yl, piperazin-1-yl, morpholin-4-yl, thiomorpholin-1-yl, 1-oxohiomorpholin-1-yl, 1,1-dioxothiomorpholin-1-yl, azepan-1-yl, azirin-1-yl, azetin-1-yl, pyrrolin-1-yl, pyrazolin-1-yl, imidazolin-1-yl, oxazolin-3-yl, isoxazolin-2-yl, thiazolin-3-yl, isothiazolin-1-yl, 1,2-dihydropyridin-1-yl, 1,2,3,4-tetrahydropyridin-1-yl, 1,2,5,6-tetrahydropyridin-1-yl, 1,2-dihydropyridazin, 1,6-dihydropyridazin, 1,2,3,4-tetrahydropyridazin-1-yl, 1,2,5,6-tetrahydropyridazin-1-yl, 1,2-dihydropyrimidin, 1,6-dihydropyrimidin, 1,2,3,4-tetrahydropyrimidin-1-yl, 1,2,5,6-tetrahydropyrimidin-1-yl, 1,2-dihydropyrazin-1-yl, 1,2,3,4-tetrahydropyrazin-1-yl, 1,2,5,6-tetrahydropyrazin-1-yl, pyrrol-1-yl, pyrazol-1-yl, imidazol-1-yl, [1,2,3]-1H-triazol-1-yl, [1,2,3]-2H-triazol-2-yl, [1,2,4]-1H-triazol-1-yl and [1,2,4]-4H-triazol-4-yl.

Examples for saturated, partially unsaturated or aromatic 3-, 4-, 5-, 6- or 7-membered heterocyclic radicals comprising 1, 2 or 3 heteroatoms selected from O, S and N as ring members, wherein two geminally bound substituents may together form a group $=O$ are the above-listed examples for 5- or 6-membered N— or C-bound heteroaromatic radicals and further 2-oxiranyl, 2-thiiranyl, 1- or 2-aziridinyl, 1-, 2- or 3-azetidinyl, 2-tetrahydrofuranyl, 3-tetrahydrofuranyl, 3-tetrahydrofuran-2-onyl, 4-tetrahydrofuran-2-onyl, 5-tetrahydrofuran-2-onyl, 2-tetrahydrofuran-3-onyl, 4-tetrahydrofuran-3-onyl, 5-tetrahydrofuran-3-onyl, 2-tetrahydrothienyl, 3-tetrahydrothienyl, 3-tetrahydrothien-2-onyl, 4-tetrahydrothien-2-onyl, 5-tetrahydrothien-2-onyl, 2-tetrahydrothien-3-onyl, 4-tetrahydrothien-3-onyl, 5-tetrahydrothien-3-onyl, 2-pyrrolidinyl, 3-pyrrolidinyl, 1-pyrrolidin-2-onyl, 3-pyrrolidin-2-onyl, 4-pyrrolidin-2-onyl, 5-pyrrolidin-2-onyl, 1-pyrrolidin-3-onyl, 2-pyrrolidin-3-onyl, 4-pyrrolidin-3-onyl, 5-pyrrolidin-3-onyl, 1-pyrrolidin-2,5-dionyl, 3-pyrrolidin-2,5-dionyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl. For further examples see also the non-aromatic rings A listed below.

The remarks made above and in the following with respect to preferred aspects of the invention, e.g. to preferred meanings of the variables $X^1$, $X^2$, $X^3$, $X^4$, $R^1$, $R^2$, $R^3$, $R^4$, $R^5$, $R^6$, $R^7$, $R^8$, $R^a$, $R^b$, $R^c$ of compounds IA and IB, to preferred compounds IA and IB and to preferred embodiments of the method or the use according to the invention, apply in each case on their own or in particular to combinations thereof.

Preferably, each $R^1$ is independently selected from hydrogen, halogen, CN, $C_1$-$C_6$-alkyl, $C_1$-$C_6$-haloalkyl, $C_1$-$C_6$-alkoxy, $C_1$-$C_6$-haloalkoxy and COOH. More preferably, each $R^1$ is independently selected from hydrogen, halogen, COOH and cyano. Preferably, at most one of $R^1$ is different from hydrogen. In particular, all radicals $R^1$ are hydrogen or one radical $R^1$ is different from hydrogen and is preferably halogen, COOH or cyano and the remaining radicals $R^1$ are hydrogen. Specifically, one $R^1$ is cyano and the others are hydrogen.

Preferably, $R^2$ is hydrogen.

In an alternatively preferred embodiment, $R^2$ is $C_1$-$C_4$-alkyl, $C_1$-$C_4$-haloalkyl, $C_2$-$C_4$-alkenyl or fluorine.

Specifically, $R^2$ is hydrogen, $C_1$-$C_4$-haloalkyl, especially $C_1$-$C_4$-fluoroalkyl, or allyl and very specifically hydrogen.

In one preferred embodiment of the invention, $R^3$ and $R^4$; or $R^4$ and $R^5$; or $R^5$ and $R^6$ form together a bridging group —$(CH_2)_m$—, wherein m is 3, 4 or 5, where 1, 2 or 3 of the $CH_2$ groups may be replaced by a group or a heteroatom selected from CO, O, S, SO, $SO_2$, $NR^c$ and NO, and where 1, 2 or 3 hydrogen atoms of the bridging group may be replaced by a radical $R^8$;

with the proviso that in case $R^3$ and $R^4$ form together a bridging group —$(CH_2)_m$—, the $CH_2$ unit bound in the position of $R^3$ is not replaced by an $NR^c$ group (in other words, the fused pyridyl moiety is not

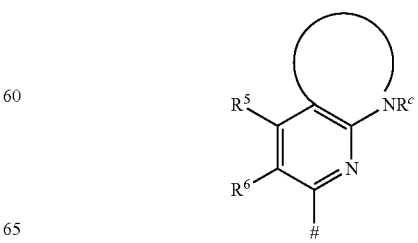

wherein the bow stands for —$(CH_2)_{m-1}$—, wherein 1 or 2 of the $CH_2$ groups may be replaced by a group or a heteroatom selected from CO, O, S, SO, $SO_2$, $NR^c$ and NO, and where 1, 2 or 3 hydrogen atoms of the bridging group may be replaced by a radical $R^8$; and # is the attachment point to the remainder of the molecule);

and with the proviso that $R^3$, when not being part of the bridging group, is not $NR^aR^b$ (in other words: where the radicals $R^3$, $R^4$, $R^5$ and $R^6$, which are not part of the bridging group, are independently selected from the group consisting of hydrogen, halogen, cyano, $C_1$-$C_4$-alkyl, $C_1$-$C_4$-haloalkyl, $C_1$-$C_4$-alkoxy and $C_1$-$C_4$-haloalkoxy, and where $R^4$, $R^5$ and $R^6$ may independently also be selected from $NR^aR^b$).

In an alternatively preferred embodiment, $R^3$ and $R^4$; or $R^4$ and $R^5$; or $R^5$ and $R^6$ form together a bridging group —$(CH_2)_m$—, wherein m is 3, 4 or 5, where 1 or 2 of the $CH_2$ groups may be replaced by a group or a heteroatom selected from CO, O and $NR^c$, and where 1 or 2 or 3 hydrogen atoms of the bridging group may be replaced by a radical $R^8$, where $R^c$ and $R^8$ have one of the above-given general or, in particular, one of the below-given preferred meanings. Preferably, the above two provisos (i.e. in case $R^3$ and $R^4$ form together a bridging group —$(CH_2)_m$—, the $CH_2$ unit bound in the position of $R^3$ is not replaced by an $NR^c$ group; and $R^3$, when not being part of the bridging group, is not $NR^aR^b$) apply here, too.

Preferably, m is 3 or 4.

More preferably, the bridging group is selected from —$CH_2CH_2CH_2$—, —$OCH_2CH_2$—, —$CH_2CH_2O$—, —$CH_2OCH_2$—, —$NR^cCH_2CH_2$—, —$CH_2CH_2NR^c$—, —$CH_2NR^cCH_2$—, —$CH_2CH_2CH_2CH_2$—, —$OCH_2CH_2CH_2$—, —$CH_2OCH_2CH_2$—, —$CH_2CH_2OCH_2$—, —$CH_2CH_2CH_2O$—, —$NR^cCH_2CH_2CH_2$—, —$CH_2NR^cCH_2CH_2$—, —$CH_2CH_2NR^cCH_2$—, —$CH_2CH_2CH_2NR^c$—, —$C(=O)CH_2CH_2CH_2$—, —$CH_2C(=O)CH_2CH_2$—, —$CH_2CH_2C(=O)CH_2$— and —$CH_2CH_2CH_2C(=O)$—, where the hydrogen atoms of the above groups may be replaced by 1 or 2 radicals $R^8$, where $R^c$ and $R^8$ have one of the above-given general or, in particular, one of the below-given preferred meanings. Preferably, the above two provisos (i.e. in case $R^3$ and $R^4$ form together a bridging group —$(CH_2)_m$—, the $CH_2$ unit bound in the position of $R^3$ is not replaced by an $NR^c$ group; and $R^3$, when not being part of the bridging group, is not $NR^aR^b$) apply here, too. Thus, even more preferably, the bridging group is selected from —$CH_2CH_2CH_2$—, —$OCH_2CH_2$—, —$CH_2CH_2O$—, —$CH_2OCH_2$—, —$CH_2NR^cCH_2$—, —$CH_2CH_2CH_2CH_2$—, —$OCH_2CH_2CH_2$—, —$CH_2OCH_2CH_2$—, —$CH_2CH_2OCH_2$—, —$CH_2CH_2CH_2O$—, —$CH_2NR^cCH_2CH_2$—, —$CH_2CH_2NR^cCH_2$—, —$C(=O)CH_2CH_2CH_2$—, —$CH_2C(=O)CH_2CH_2$—, —$CH_2CH_2C(=O)CH_2$— and —$CH_2CH_2CH_2C(=O)$—, where the hydrogen atoms of the above groups may be replaced by 1 or 2 radicals $R^8$, where $R^c$ and $R^8$ have one of the above-given general or, in particular, one of the below-given preferred meanings.

In particular, the bridging group is selected from —$CH_2CH_2CH_2$—, —$CH_2NR^cCH_2$—, —$NR^cCH_2CH_2$—, —$CH_2CH_2NR^c$—, —$CH_2OCH_2$—, —$CH_2CH_2CH_2CH_2$—, —$CH_2NR^cCH_2CH_2$—, —$CH_2CH_2NR^cCH_2$—, —$C(=O)CH_2CH_2CH_2$—, —$CH_2OCH_2CH_2$—, —$CH_2CH_2OCH_2$—, —$CH_2C(=O)CH_2CH_2$—, —$CH_2CH_2C(=O)CH_2$— and —$CH_2CH_2CH_2C(=O)$—, and more particularly from —$CH_2CH_2CH_2$—, —$CH_2NR^cCH_2$—, —$CH_2OCH_2$—, —$CH_2CH_2CH_2CH_2$—, —$CH_2NR^cCH_2CH_2$—, —$CH_2CH_2NR^cCH_2$—, —$C(=O)CH_2CH_2CH_2$—, —$CH_2OCH_2CH_2$—, —$CH_2CH_2OCH_2$—, —$CH_2C(=O)CH_2CH_2$—, —$CH_2CH_2C(=O)CH_2$— and —$CH_2CH_2CH_2C(=O)$—, where the hydrogen atoms of the above groups may be replaced by 1 or 2 radicals $R^8$, where $R^c$ and $R^8$ have one of the above-given general or, in particular, one of the below-given preferred meanings.

Specifically, the bridging group is selected from —$CH_2CH_2CH_2$—, —$CH_2NR^cCH_2$—, —$CH_2CH_2CH_2CH_2$—, —$CH_2NR^cCH_2CH_2$—, —$CH_2CH_2NR^cCH_2$—, —$C(=O)CH_2CH_2CH_2$—, —$CH_2C(=O)CH_2CH_2$—, —$CH_2CH_2C(=O)CH_2$— and —$CH_2CH_2CH_2C(=O)$—, where the hydrogen atoms of the above groups may be replaced by 1 or 2 radicals $R^8$, where $R^c$ and $R^8$ have one of the above-given general or, in particular, one of the below-given preferred meanings.

Preferably, the radicals $R^3$, $R^4$, $R^5$ and $R^6$, which are not part of the bridging group, are selected from hydrogen, halogen, cyano, $C_1$-$C_4$-alkyl, $C_1$-$C_4$-haloalkyl, $C_1$-$C_4$-alkoxy and $C_1$-$C_4$-haloalkoxy, more preferably from hydrogen, halogen, $C_1$-$C_2$-alkyl and $C_1$-$C_2$-haloalkyl, and are in particular hydrogen.

Preferably, $R^3$ and $R^4$; or $R^4$ and $R^5$ (and not $R^5$ and $R^6$) form together a bridging group as defined above. More preferably, $R^3$ and $R^4$ (and not $R^4$ and $R^5$ or $R^5$ and $R^6$) form together a bridging group as defined above.

Preferably, each $R^7$ is independently selected from halogen, CN, $C_1$-$C_6$-alkyl, $C_1$-$C_6$-haloalkyl, $C_1$-$C_6$-alkoxy and $C_1$-$C_6$-haloalkoxy. And more preferably from CN, $C_1$-$C_4$-alkyl, $C_1$-$C_4$-haloalkyl, $C_1$-$C_4$-alkoxy and $C_1$-$C_4$-haloalkoxy.

Preferably, each $R^8$ is independently selected from the group consisting of halogen, OH, $C_1$-$C_4$-alkyl, $C_1$-$C_4$-haloalkyl, $C_1$-$C_4$-alkoxy, $C_1$-$C_4$-haloalkoxy, $NR^aR^b$, $C_1$-$C_6$-alkylcarbonyl, $C_1$-$C_6$-haloalkylcarbonyl, $C_1$-$C_6$-alkoxycarbonyl and $C_1$-$C_6$-haloalkoxycarbonyl, more preferably from halogen, OH, $C_1$-$C_4$-alkyl, $C_1$-$C_4$-haloalkyl, $C_1$-$C_4$-alkoxy, $C_1$-$C_4$-haloalkoxy, $NR^aR^b$, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl, where preferably $R^a$ and $R^b$ are independently selected from hydrogen and $C_1$-$C_4$-alkyl, and specifically from OH, halogen, especially fluorine, $C_1$-$C_4$-alkoxy, especially methoxy, $C_1$-$C_4$-haloalkoxy, especially trifluoromethoxy, and $NR^aR^b$, where preferably $R^a$ and $R^b$ are independently selected from hydrogen and $C_1$-$C_4$-alkyl. Very specifically, each $R^8$ is independently selected from the group consisting of OH, $C_1$-$C_4$-alkoxy and $C_1$-$C_4$-haloalkoxy.

$R^a$ and $R^b$ are, independently of each other, preferably selected from hydrogen, $C_1$-$C_6$-alkyl, $C_1$-$C_4$-haloalkyl, $C_1$-$C_4$-alkylcarbonyl, $C_1$-$C_4$-haloalkylcarbonyl, $C_1$-$C_6$-alkoxycarbonyl and $C_1$-$C_6$-haloalkoxycarbonyl or form together with the nitrogen atom to which they are bound an N-bound 3-, 4-, 5-, 6- or 7-membered saturated or unsaturated aromatic or non-aromatic N-heterocyclic ring, which may contain 1 further heteroatom or heteroatom-containing group selected from N, O, S, SO and $SO_2$ as a ring member, where the N-heterocyclic ring may carry 1 or 2 radicals selected from halogen, cyano, $C_1$-$C_4$-alkyl, $C_1$-$C_4$-haloalkyl, $C_1$-$C_4$-alkoxy and $C_1$-$C_4$-haloalkoxy, and are more preferably selected from hydrogen, $C_1$-$C_4$-alkyl, $C_1$-$C_4$-haloalkyl, $C_1$-$C_6$-alkoxycarbonyl and $C_1$-$C_6$-haloalkoxycarbonyl or form together with the nitrogen atom to which they are bound an N-bound 5- or 6-membered saturated or unsaturated aromatic or non-aromatic N-heterocyclic ring, which may contain 1 further heteroatom or heteroatom-containing group selected from N and O as a ring member, where the N-heterocyclic ring may carry 1 or 2 radicals selected from halogen, cyano, $C_1$-$C_4$-alkyl, $C_1$-$C_4$-haloalkyl, $C_1$-$C_4$-alkoxy and $C_1$-$C_4$-haloalkoxy.

Preferably, each $R^c$ is independently selected from hydrogen, $C_1$-$C_6$-alkyl, $C_1$-$C_4$-haloalkyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_6$-alkoxycarbonyl and $C_1$-$C_6$-haloalkoxycarbonyl, more preferably from hydrogen, $C_1$-$C_6$-alkyl, $C_1$-$C_4$-haloalkyl, $C_1$-$C_4$-alkoxy-$C_1$-$C_4$-alkyl, $C_1$-$C_6$-alkoxycarbonyl and $C_1$-$C_6$-haloalkoxycarbonyl, even more preferably from hydrogen, $C_1$-$C_4$-alkyl, $C_1$-$C_4$-haloalkyl, $C_1$-$C_4$-alkoxy-$C_1$-$C_4$-alkyl, $C_1$-$C_6$-alkoxycarbonyl and $C_1$-$C_4$-haloalkoxycarbonyl, and in particular from hydrogen, $C_1$-$C_4$-alkyl, $C_1$-$C_4$-haloalkyl, $C_1$-$C_4$-alkoxy-$C_1$-$C_4$-alkyl and $C_1$-$C_6$-alkoxycarbonyl. Specifically, each $R^c$ is independently selected from hydrogen and $C_1$-$C_6$-alkoxycarbonyl.

Preferably, all of $X^1$, $X^2$, $X^3$ and $X^4$ are $CR^1$ or one of $X^1$, $X^2$, $X^3$ and $X^4$ is N and the others are $CR^1$. More preferably, all of $X^1$, $X^2$, $X^3$ and $X^4$ are $CR^1$. Even more preferably, $X^1$, $X^2$ and $X^4$ are CH and $X^3$ is $CR^1$, wherein $R^1$ has one of the above-given general or preferred definitions and is preferably H, COOH or CN. Specifically, $X^1$, $X^2$ and $X^4$ are CH and $X^3$ is $CR^1$, wherein $R^1$ is different from H and is preferably COOH or CN. In particular, $X^1$, $X^2$ and $X^4$ are CH and $X^3$ is $CR^1$, wherein $R^1$ is CN.

A particularly preferred embodiment of the invention relates to compounds of the formulae IA-1 and IB-1

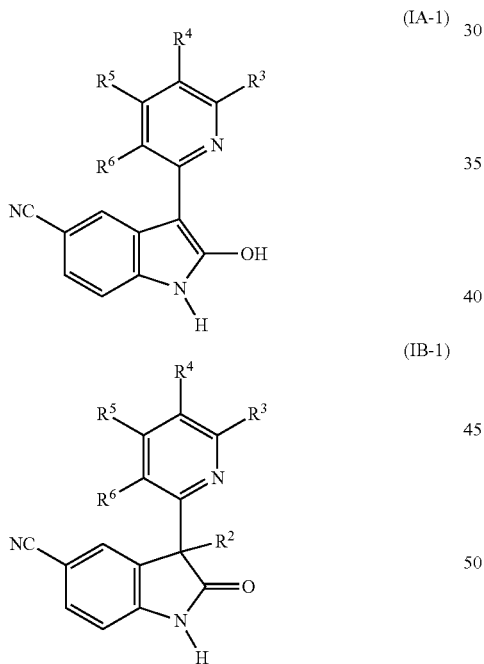

wherein $R^2$, $R^3$, $R^4$, $R^5$ and $R^6$ have one of the general meanings or, in particular, one of the preferred meanings given above.

Compounds IA-1 and compounds IB-1 wherein $R^2$ is H are tautomers and thus the formulae can be used interchangeably.

Suitable compounds IA and IB are those of formulae I.1 to I.144, the stereoisomers, prodrugs, tautomers and/or physiologically tolerated acid addition salts thereof, wherein $R^1$, $R^2$ and $R^c$ have the above-defined general or preferred meanings and $R^{81}$ is hydrogen or has one of the above-defined general or preferred meanings given for $R^8$. Particularly preferred meanings of $R^1$, $R^2$, $R^{81}$ and $R^c$ specifically in compounds of formulae I.1 to I.144 are as defined below.

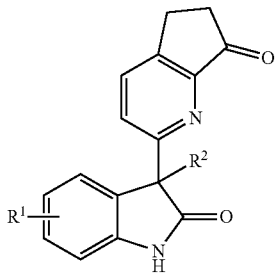

I.1

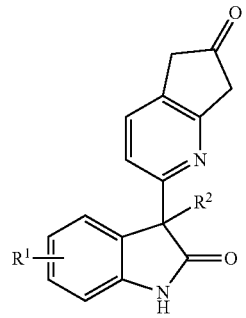

I.2

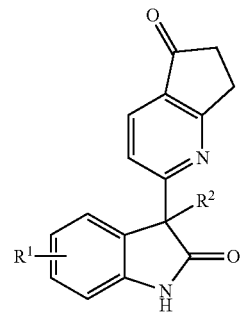

I.3

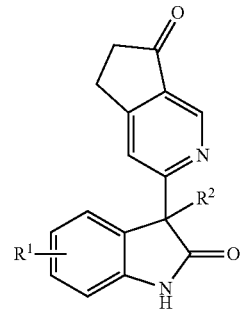

I.4

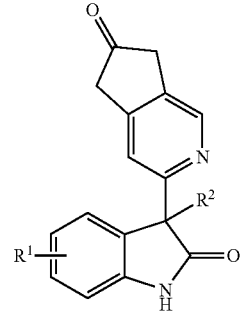

I.5

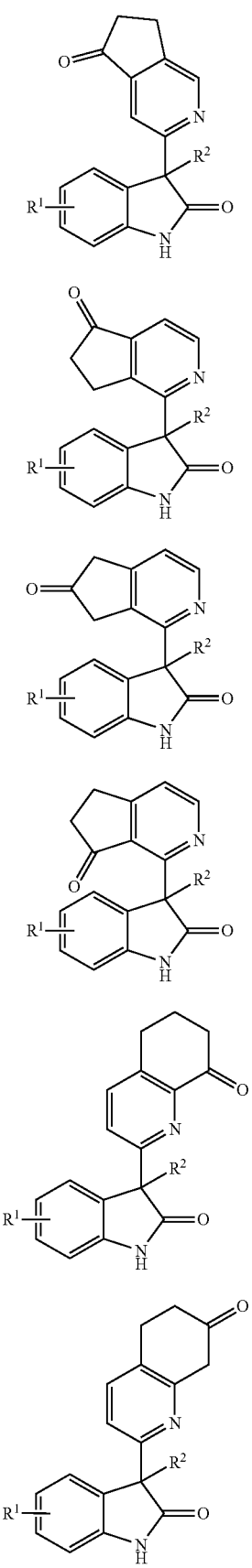
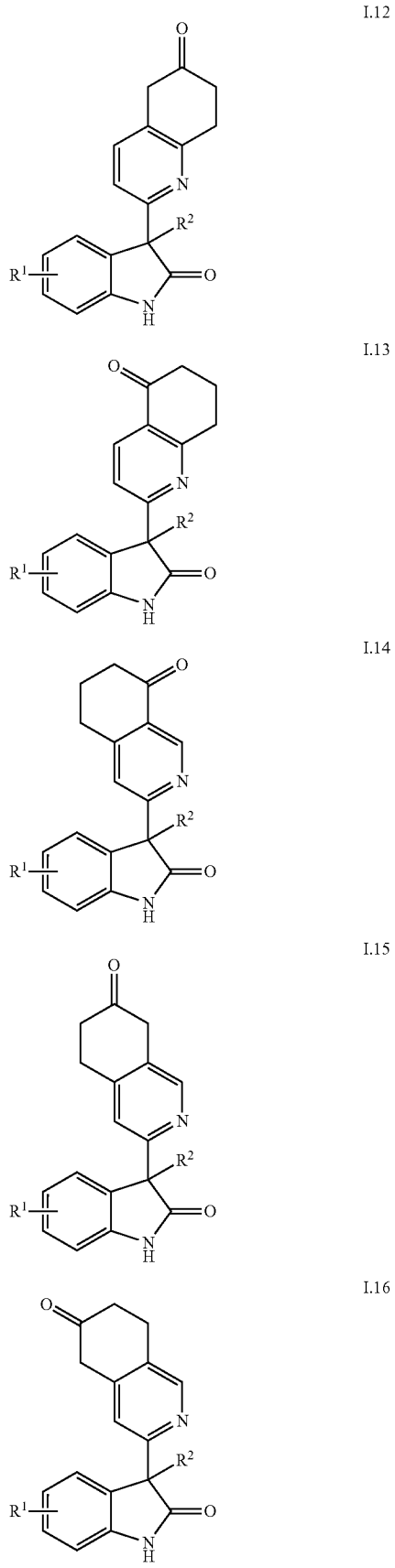

I.17
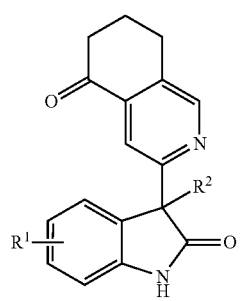
I.18
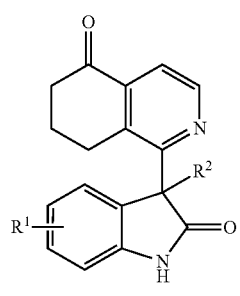
I.19
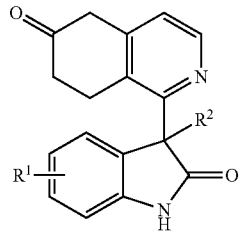
I.20
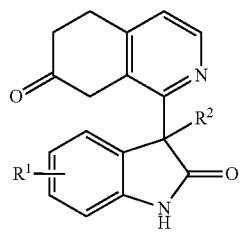
I.21
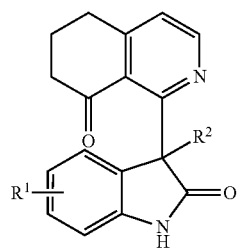
I.22
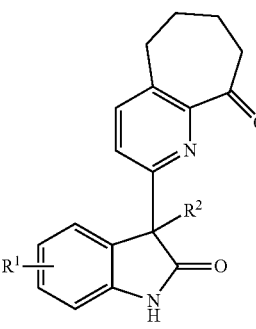
I.23
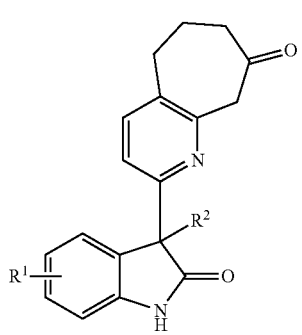
I.24
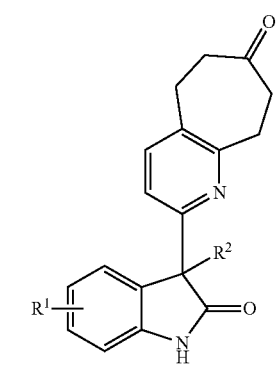
I.25
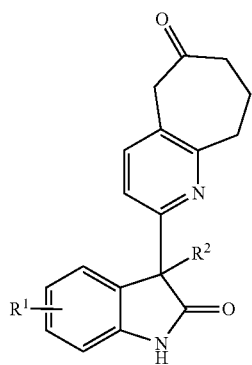
I.26
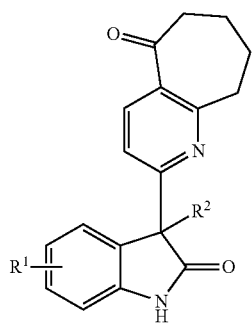

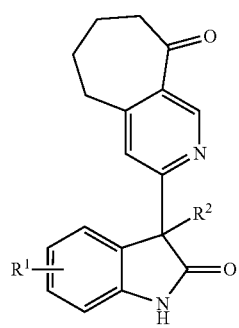
I.27
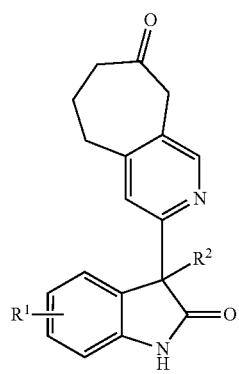
I.28
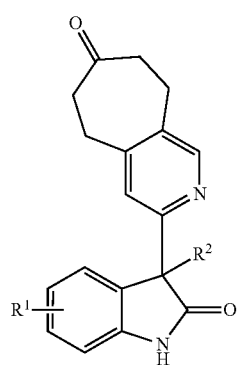
I.29
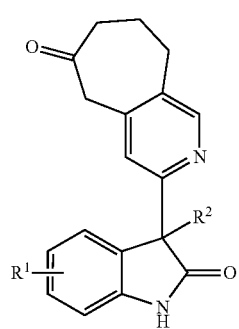
I.30
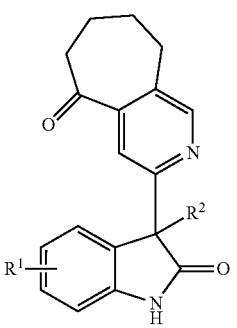
I.31
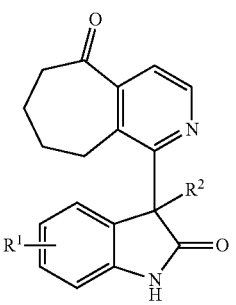
I.32
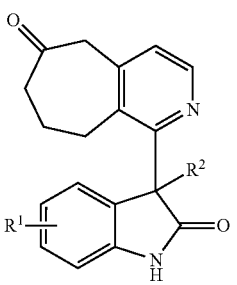
I.33
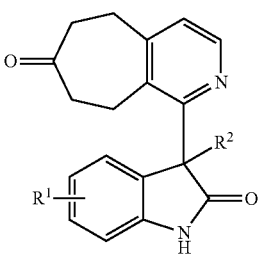
I.34
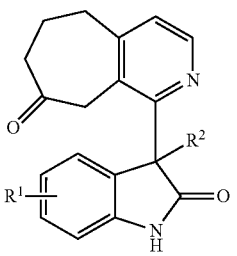
I.35

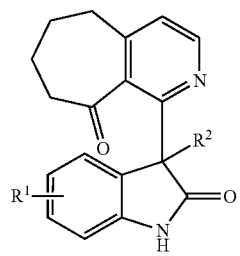 I.36
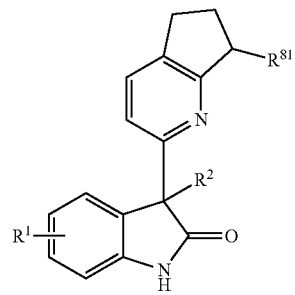 I.37
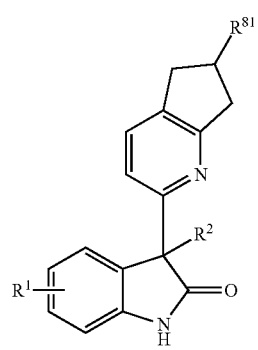 I.38
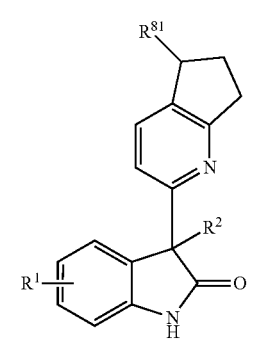 I.39
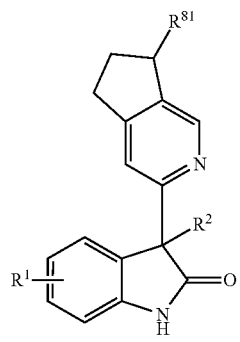 I.40
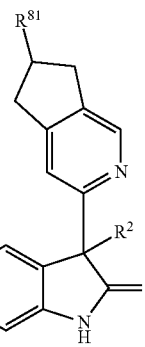 I.41
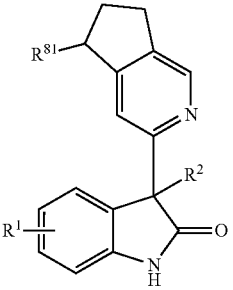 I.42
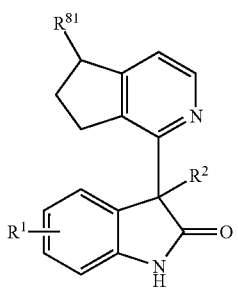 I.43
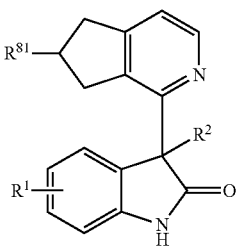 I.44
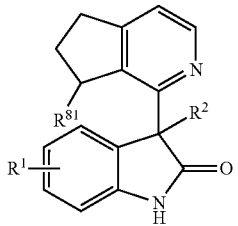 I.45

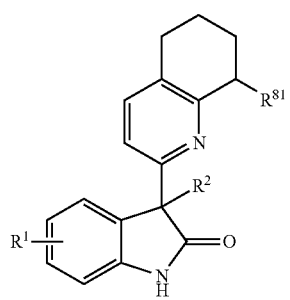
I.46
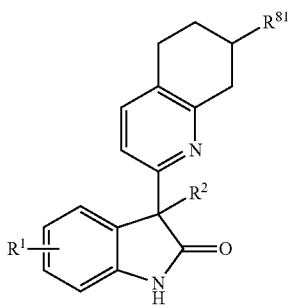
I.47
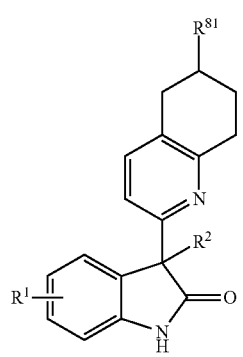
I.48
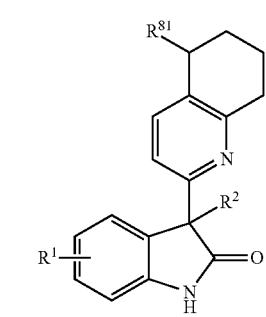
I.49
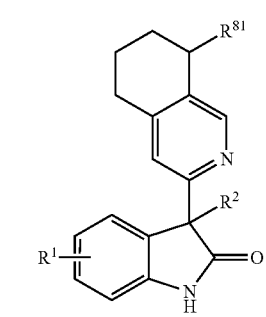
I.50
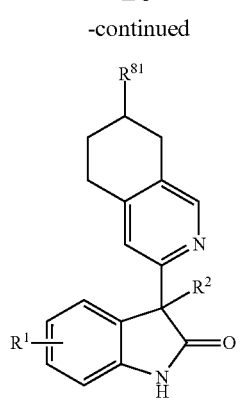
I.51
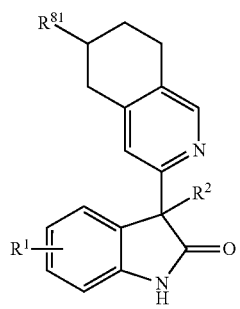
I.52
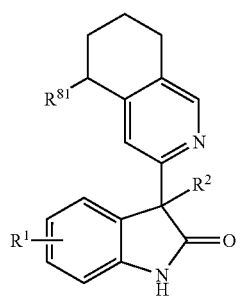
I.53
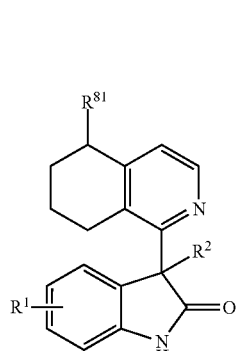
I.54
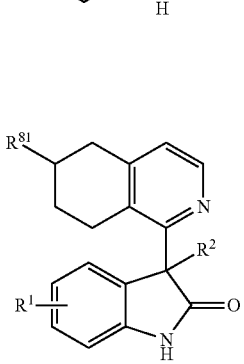
I.55

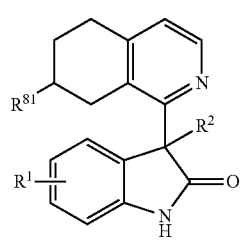 I.56
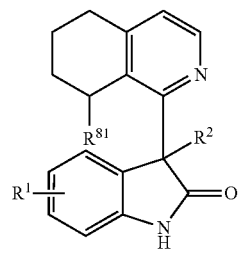 I.57
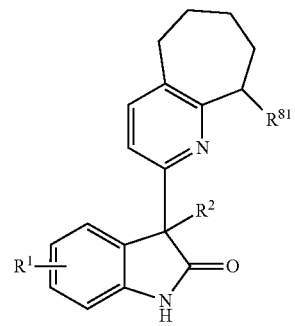 I.58
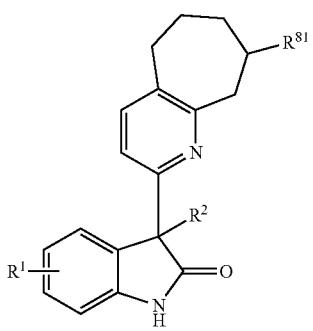 I.59
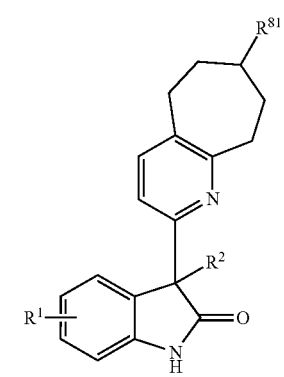 I.60
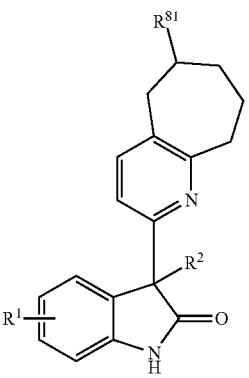 I.61
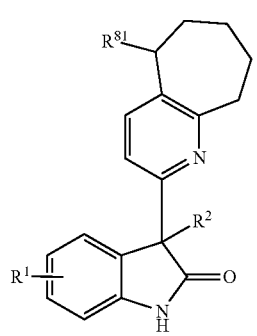 I.62
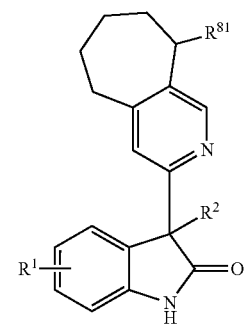 I.63
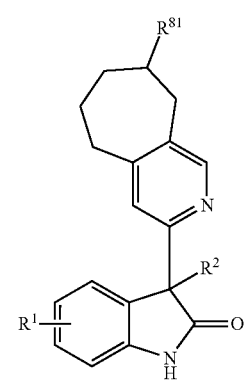 I.64

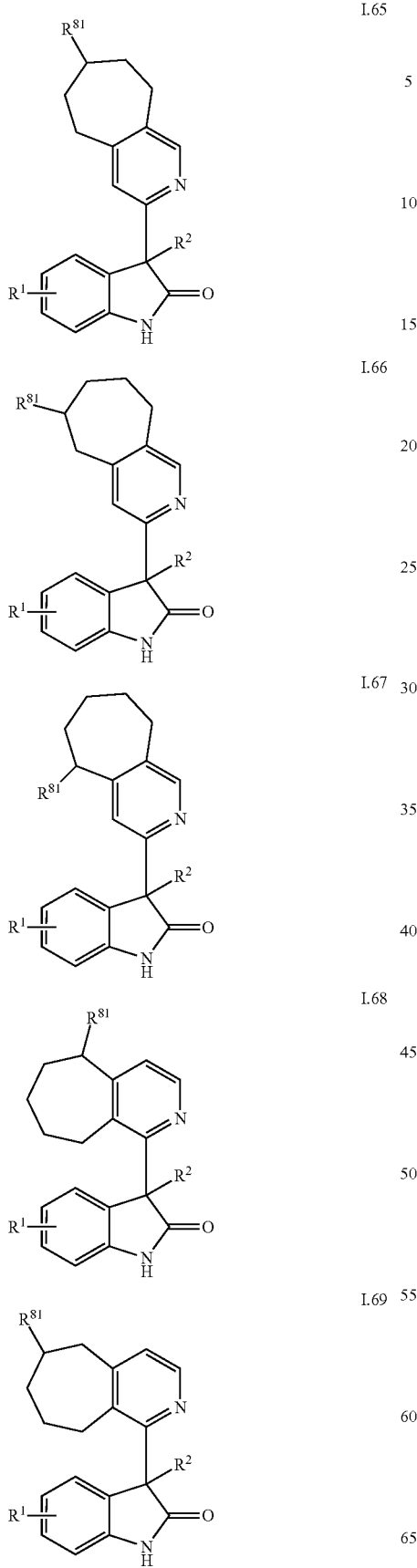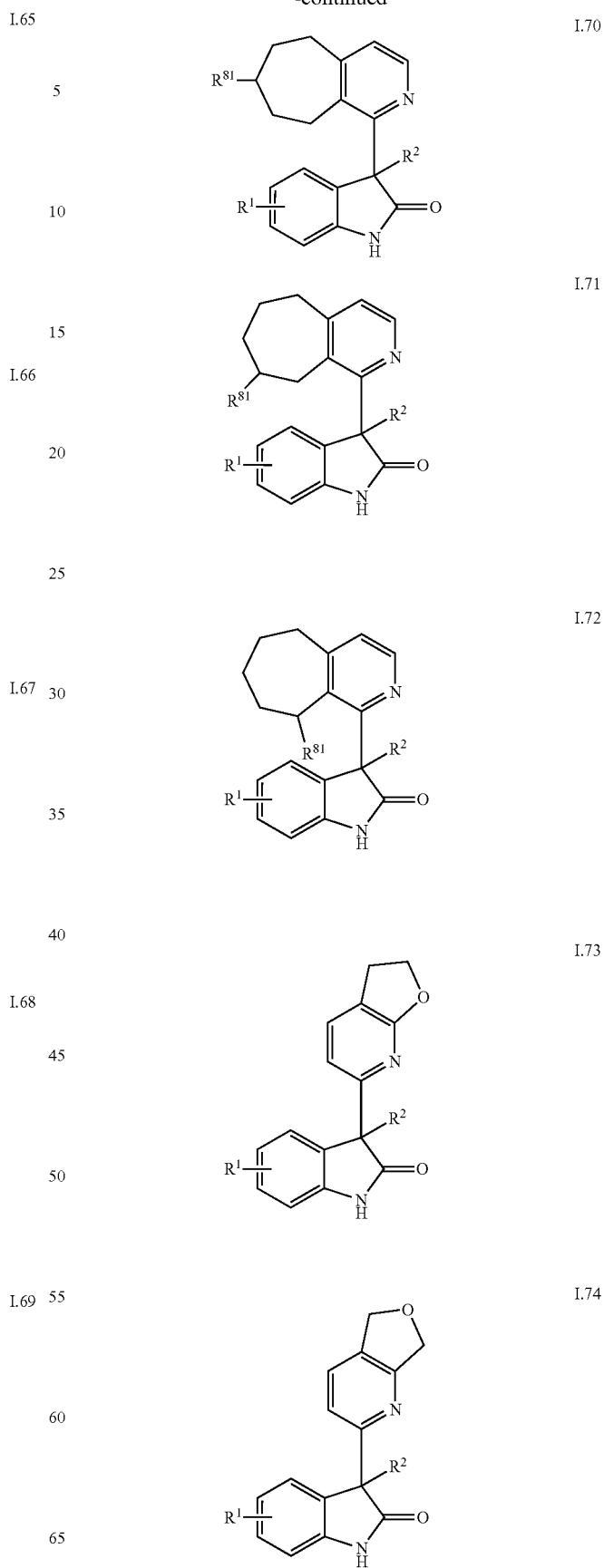

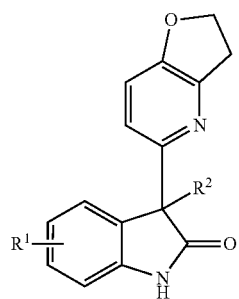 I.75
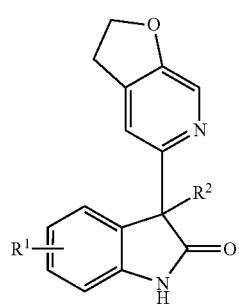 I.76
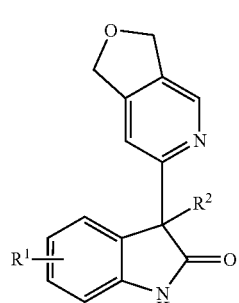 I.77
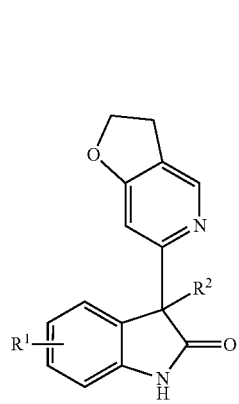 I.78
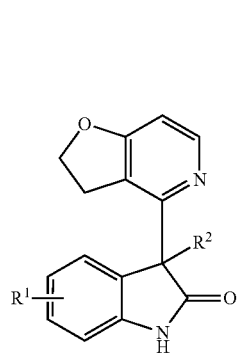 I.79
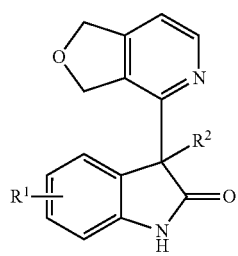 I.80
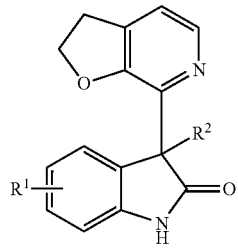 I.81
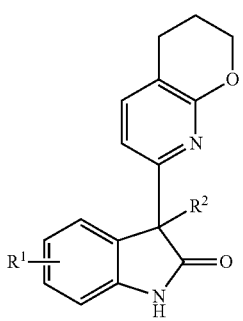 I.82
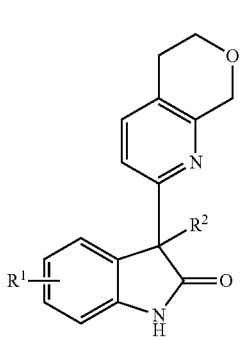 I.83
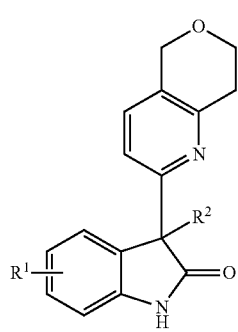 I.84

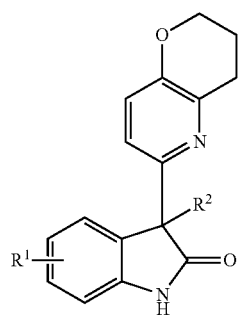
I.85
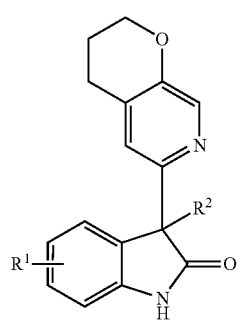
I.86
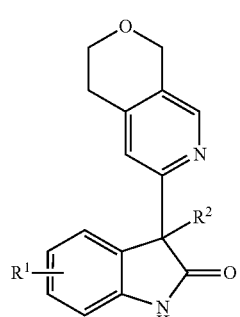
I.87
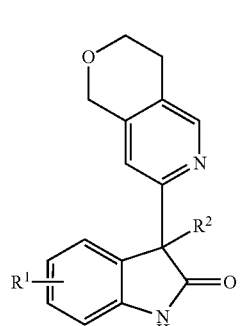
I.88
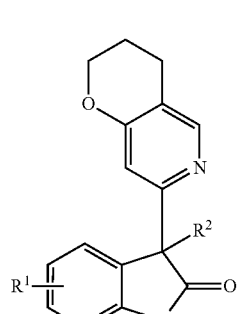
I.89
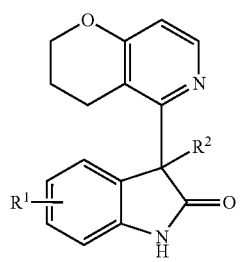
I.90
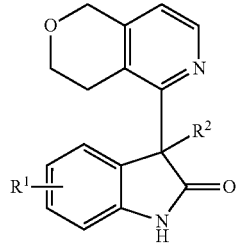
I.91
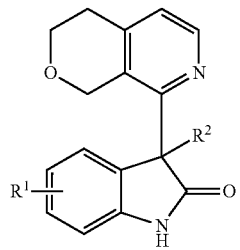
I.92
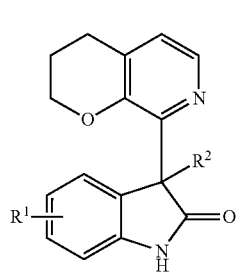
I.93
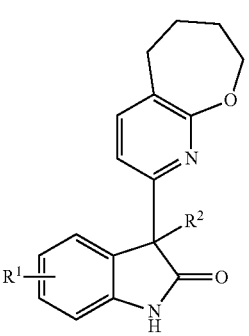
I.94

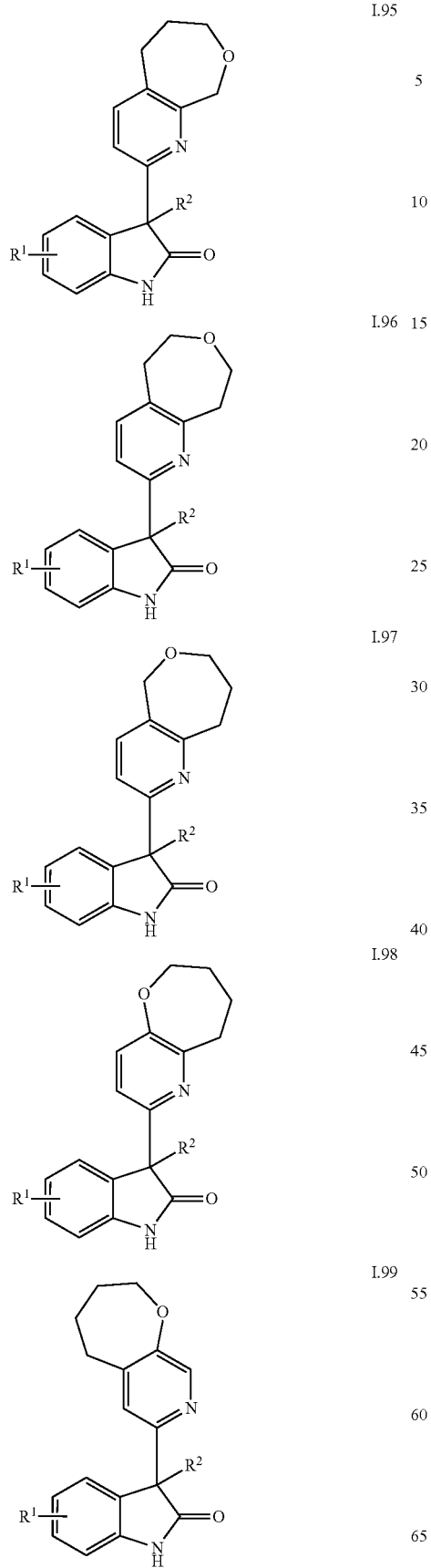
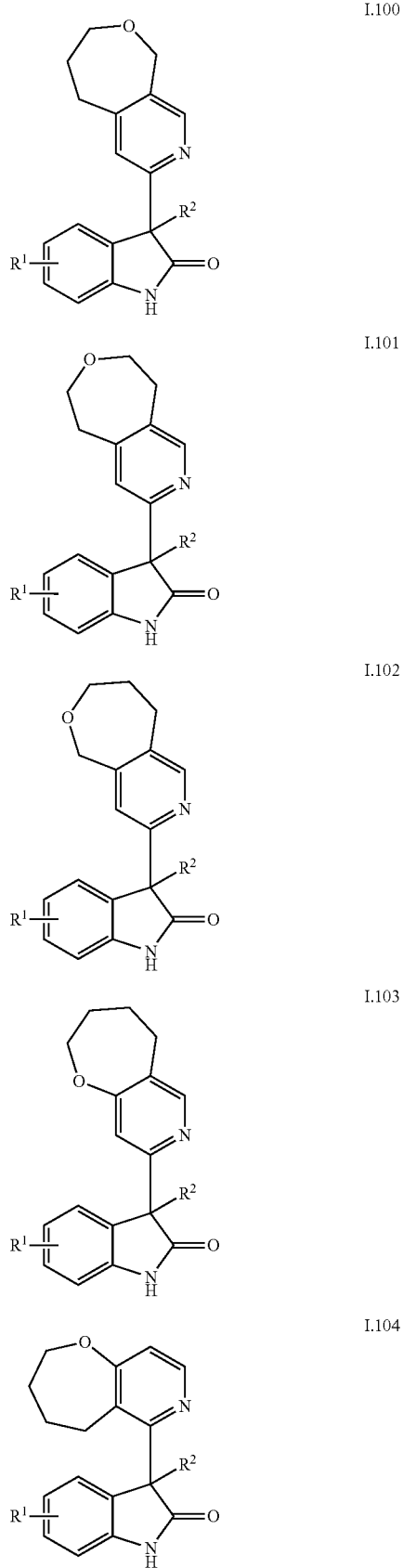

-continued
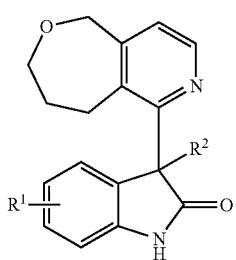
I.105
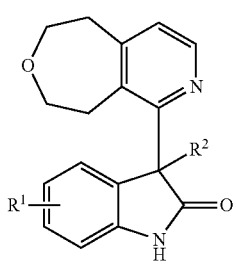
I.106
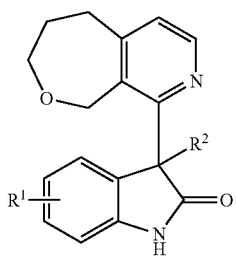
I.107
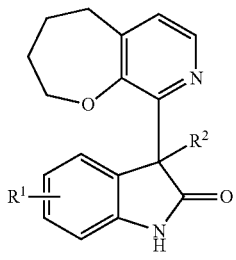
I.108
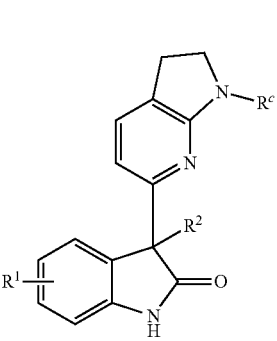
I.109
-continued
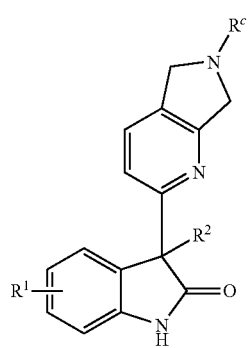
I.110
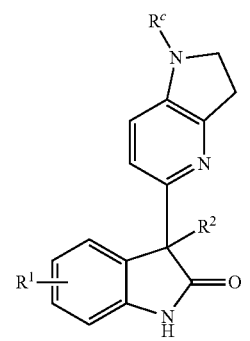
I.111
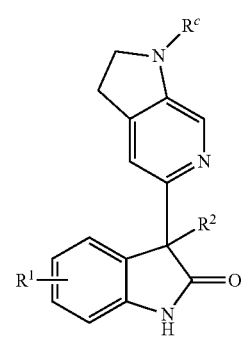
I.112
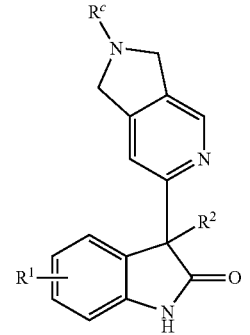
I.113

I.114 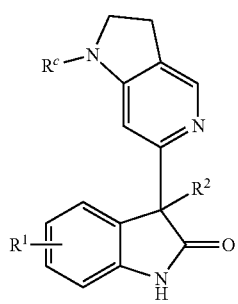
I.115 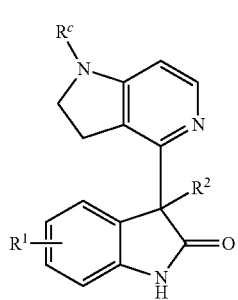
I.116 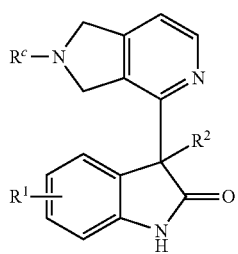
I.117 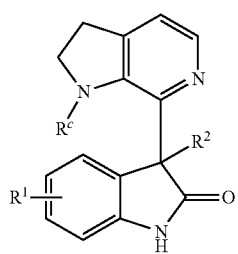
I.118 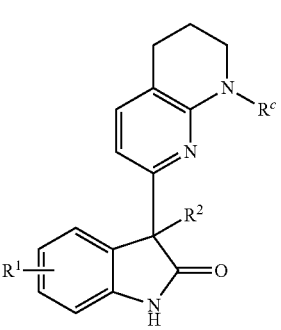
I.119 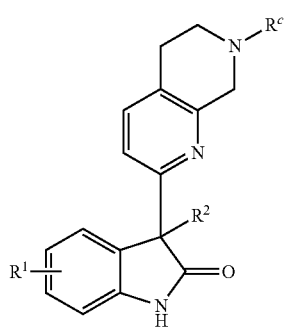
I.120 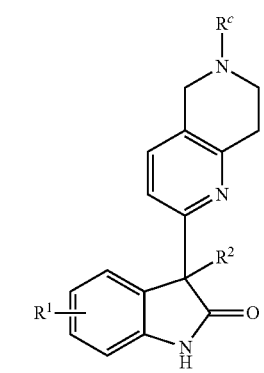
I.121 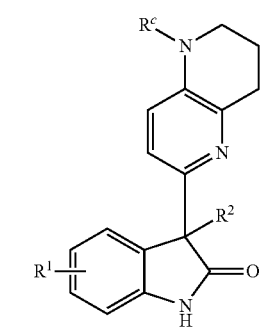
I.122 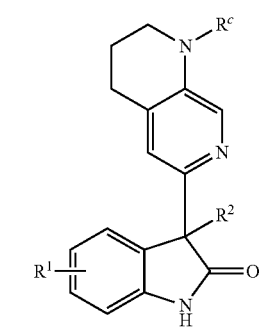

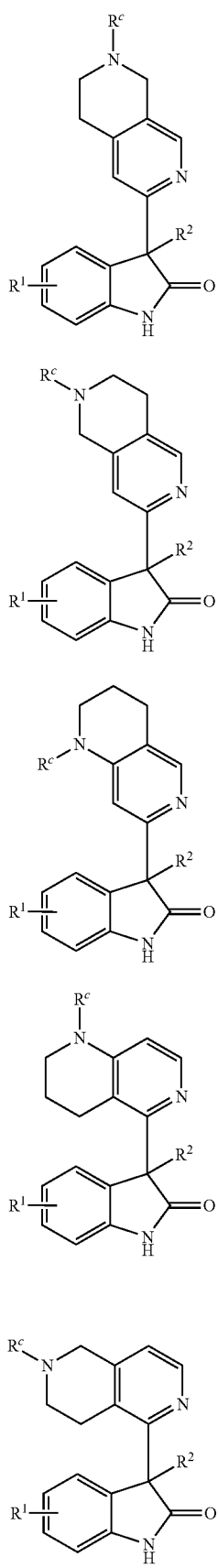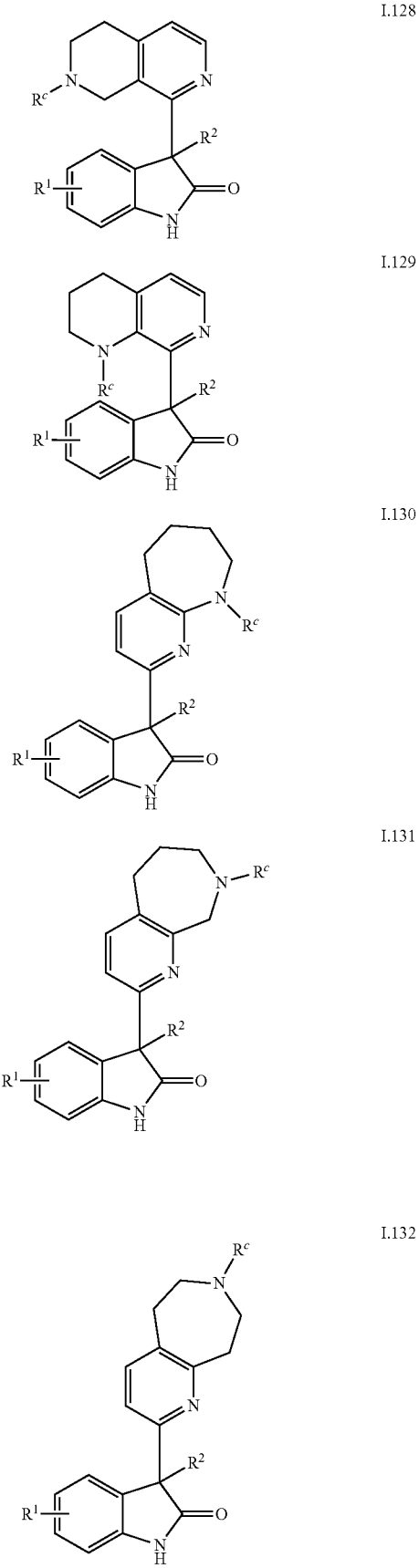

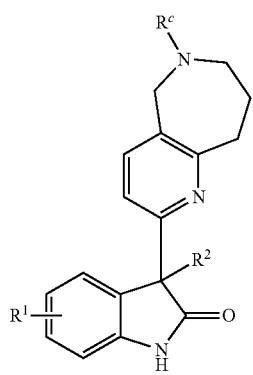 I.133
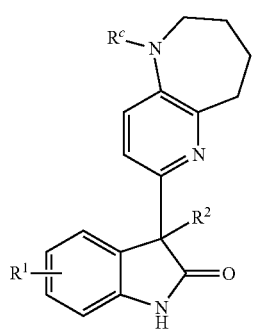 I.134
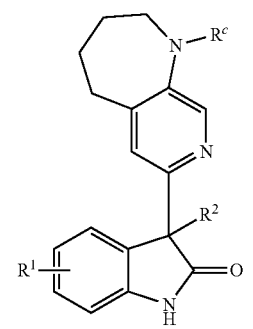 I.135
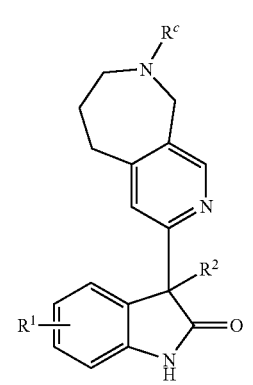 I.136
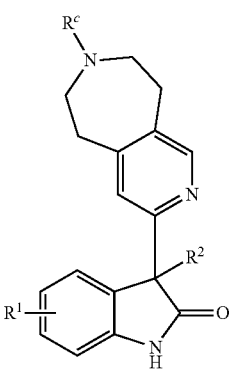 I.137
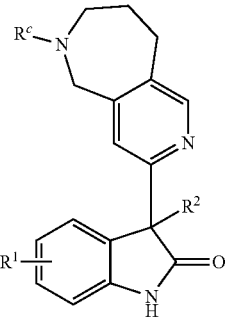 I.138
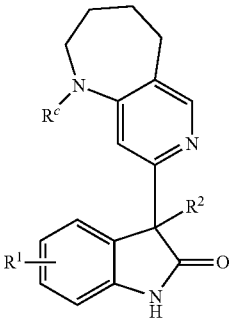 I.139
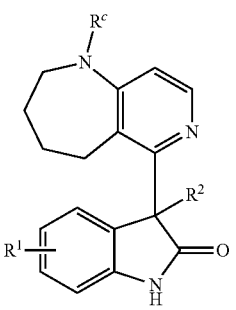 I.140
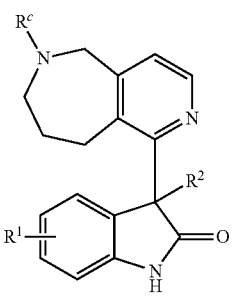 I.141

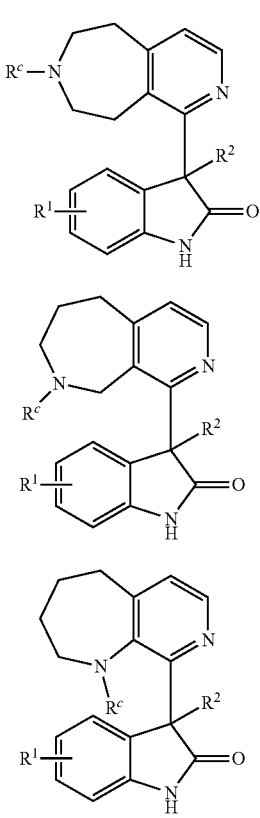

I.142

I.143

I.144

Examples of preferred compounds which are represented by the formulae I.1 to I.144 are the individual compounds compiled in the tables 1 to 6192 below, where the variables $R^1$ and $R^2$ have the meanings given in one row of Table A. Moreover, the meanings mentioned for the individual variables in the tables are per se, independently of the combination in which they are mentioned, a particularly preferred embodiment of the substituents in question. Rings A-1 to A-111 mentioned in the tables are defined below.

Table 1
Compounds of the formula I.1 in which the combination of $R^1$ and $R^2$ for a compound corresponds in each case to one row of Table A.

Table 2
Compounds of the formula I.2 in which the combination of $R^1$ and $R^2$ for a compound corresponds in each case to one row of Table A.

Table 3
Compounds of the formula I.3 in which the combination of $R^1$ and $R^2$ for a compound corresponds in each case to one row of Table A.

Table 4
Compounds of the formula I.4 in which the combination of $R^1$ and $R^2$ for a compound corresponds in each case to one row of Table A.

Table 5
Compounds of the formula I.5 in which the combination of $R^1$ and $R^2$ for a compound corresponds in each case to one row of Table A.

Table 6
Compounds of the formula I.6 in which the combination of $R^1$ and $R^2$ for a compound corresponds in each case to one row of Table A.

Table 7
Compounds of the formula I.7 in which the combination of $R^1$ and $R^2$ for a compound corresponds in each case to one row of Table A.

Table 8
Compounds of the formula I.8 in which the combination of $R^1$ and $R^2$ for a compound corresponds in each case to one row of Table A.

Table 9
Compounds of the formula I.9 in which the combination of $R^1$ and $R^2$ for a compound corresponds in each case to one row of Table A.

Table 10
Compounds of the formula I.10 in which the combination of $R^1$ and $R^2$ for a compound corresponds in each case to one row of Table A.

Table 11
Compounds of the formula I.11 in which the combination of $R^1$ and $R^2$ for a compound corresponds in each case to one row of Table A.

Table 12
Compounds of the formula I.12 in which the combination of $R^1$ and $R^2$ for a compound corresponds in each case to one row of Table A.

Table 13
Compounds of the formula I.13 in which the combination of $R^1$ and $R^2$ for a compound corresponds in each case to one row of Table A.

Table 14
Compounds of the formula I.14 in which the combination of $R^1$ and $R^2$ for a compound corresponds in each case to one row of Table A.

Table 15
Compounds of the formula I.15 in which the combination of $R^1$ and $R^2$ for a compound corresponds in each case to one row of Table A.

Table 16
Compounds of the formula I.16 in which the combination of $R^1$ and $R^2$ for a compound corresponds in each case to one row of Table A.

Table 17
Compounds of the formula I.17 in which the combination of $R^1$ and $R^2$ for a compound corresponds in each case to one row of Table A.

Table 18
Compounds of the formula I.18 in which the combination of $R^1$ and $R^2$ for a compound corresponds in each case to one row of Table A.

Table 19
Compounds of the formula I.19 in which the combination of $R^1$ and $R^2$ for a compound corresponds in each case to one row of Table A.

Table 20
Compounds of the formula I.20 in which the combination of $R^1$ and $R^2$ for a compound corresponds in each case to one row of Table A.

Table 21
Compounds of the formula I.21 in which the combination of $R^1$ and $R^2$ for a compound corresponds in each case to one row of Table A.

Table 22
Compounds of the formula I.22 in which the combination of $R^1$ and $R^2$ for a compound corresponds in each case to one row of Table A.

Table 23
Compounds of the formula I.23 in which the combination of $R^1$ and $R^2$ for a compound corresponds in each case to one row of Table A.

Table 24
Compounds of the formula I.24 in which the combination of $R^1$ and $R^2$ for a compound corresponds in each case to one row of Table A.

Table 25
Compounds of the formula I.25 in which the combination of $R^1$ and $R^2$ for a compound corresponds in each case to one row of Table A.

Table 26
Compounds of the formula I.26 in which the combination of $R^1$ and $R^2$ for a compound corresponds in each case to one row of Table A.

Table 27
Compounds of the formula I.27 in which the combination of $R^1$ and $R^2$ for a compound corresponds in each case to one row of Table A.

Table 28
Compounds of the formula I.28 in which the combination of $R^1$ and $R^2$ for a compound corresponds in each case to one row of Table A.

Table 29
Compounds of the formula I.29 in which the combination of $R^1$ and $R^2$ for a compound corresponds in each case to one row of Table A.

Table 30
Compounds of the formula I.30 in which the combination of $R^1$ and $R^2$ for a compound corresponds in each case to one row of Table A.

Table 31
Compounds of the formula I.31 in which the combination of $R^1$ and $R^2$ for a compound corresponds in each case to one row of Table A.

Table 32
Compounds of the formula I.32 in which the combination of $R^1$ and $R^2$ for a compound corresponds in each case to one row of Table A.

Table 33
Compounds of the formula I.33 in which the combination of $R^1$ and $R^2$ for a compound corresponds in each case to one row of Table A.

Table 34
Compounds of the formula I.34 in which the combination of $R^1$ and $R^2$ for a compound corresponds in each case to one row of Table A.

Table 35
Compounds of the formula I.35 in which the combination of $R^1$ and $R^2$ for a compound corresponds in each case to one row of Table A.

Table 36
Compounds of the formula I.36 in which the combination of $R^1$ and $R^2$ for a compound corresponds in each case to one row of Table A.

Table 37
Compounds of the formula I.37 in which $R^{81}$ is hydrogen and the combination of $R^1$ and $R^2$ for a compound corresponds in each case to one row of Table A.

Table 38
Compounds of the formula I.37 in which $R^{81}$ is methyl and the combination of $R^1$ and $R^2$ for a compound corresponds in each case to one row of Table A.

Table 39
Compounds of the formula I.37 in which $R^{81}$ is ethyl and the combination of $R^1$ and $R^2$ for a compound corresponds in each case to one row of Table A.

Table 40
Compounds of the formula I.37 in which $R^{81}$ is propyl and the combination of $R^1$ and $R^2$ for a compound corresponds in each case to one row of Table A.

Table 41
Compounds of the formula I.37 in which $R^{81}$ is isopropyl and the combination of $R^1$ and $R^2$ for a compound corresponds in each case to one row of Table A.

Table 42
Compounds of the formula I.37 in which $R^{81}$ is $CH_2F$ and the combination of $R^1$ and $R^2$ for a compound corresponds in each case to one row of Table A.

Table 43
Compounds of the formula I.37 in which $R^{81}$ is $CHF_2$ and the combination of $R^1$ and $R^2$ for a compound corresponds in each case to one row of Table A.

Table 44
Compounds of the formula I.37 in which $R^{81}$ is $CF_3$ and the combination of $R^1$ and $R^2$ for a compound corresponds in each case to one row of Table A.

Table 45
Compounds of the formula I.37 in which $R^{81}$ is $CH_2CHF_2$ and the combination of $R^1$ and $R^2$ for a compound corresponds in each case to one row of Table A.

Table 46
Compounds of the formula I.37 in which $R^{81}$ is $CH_2CF_3$ and the combination of $R^1$ and $R^2$ for a compound corresponds in each case to one row of Table A.

Table 47
Compounds of the formula I.37 in which $R^{81}$ is F and the combination of $R^1$ and $R^2$ for a compound corresponds in each case to one row of Table A.

Table 48
Compounds of the formula I.37 in which $R^{81}$ is Cl and the combination of $R^1$ and $R^2$ for a compound corresponds in each case to one row of Table A.

Table 49
Compounds of the formula I.37 in which $R^{81}$ is Br and the combination of $R^1$ and $R^2$ for a compound corresponds in each case to one row of Table A.

Table 50
Compounds of the formula I.37 in which $R^{81}$ is OH and the combination of $R^1$ and $R^2$ for a compound corresponds in each case to one row of Table A.

Table 51
Compounds of the formula I.37 in which $R^{81}$ is methoxy and the combination of $R^1$ and $R^2$ for a compound corresponds in each case to one row of Table A.

Table 52
Compounds of the formula I.37 in which $R^{81}$ is ethoxy and the combination of $R^1$ and $R^2$ for a compound corresponds in each case to one row of Table A.

Table 53
Compounds of the formula I.37 in which $R^{81}$ is propoxy and the combination of $R^1$ and $R^2$ for a compound corresponds in each case to one row of Table A.

Table 54
Compounds of the formula I.37 in which $R^{81}$ is isopropoxy and the combination of $R^1$ and $R^2$ for a compound corresponds in each case to one row of Table A.

Table 55
Compounds of the formula I.37 in which $R^{81}$ is $OCHF_2$ and the combination of $R^1$ and $R^2$ for a compound corresponds in each case to one row of Table A.
Table 56
Compounds of the formula I.37 in which $R^{81}$ is $OCF_3$ and the combination of $R^1$ and $R^2$ for a compound corresponds in each case to one row of Table A.
Table 57
Compounds of the formula I.37 in which $R^{81}$ is $OCH_2CHF_2$ and the combination of $R^1$ and $R^2$ for a compound corresponds in each case to one row of Table A.
Table 58
Compounds of the formula I.37 in which $R^{81}$ is $OCH_2CF_3$ and the combination of $R^1$ and $R^2$ for a compound corresponds in each case to one row of Table A.
Table 59
Compounds of the formula I.37 in which $R^{81}$ is $NH_2$ and the combination of $R^1$ and $R^2$ for a compound corresponds in each case to one row of Table A.
Table 60
Compounds of the formula I.37 in which $R^{81}$ is methylamino and the combination of $R^1$ and $R^2$ for a compound corresponds in each case to one row of Table A.
Table 61
Compounds of the formula I.37 in which $R^{81}$ is dimethylamino and the combination of $R^1$ and $R^2$ for a compound corresponds in each case to one row of Table A.
Table 62
Compounds of the formula I.37 in which $R^{81}$ is ethylamino and the combination of $R^1$ and $R^2$ for a compound corresponds in each case to one row of Table A.
Table 63
Compounds of the formula I.37 in which $R^{81}$ is diethylamino and the combination of $R^1$ and $R^2$ for a compound corresponds in each case to one row of Table A.
Table 64
Compounds of the formula I.37 in which $R^{81}$ is propylamino and the combination of $R^1$ and $R^2$ for a compound corresponds in each case to one row of Table A.
Table 65
Compounds of the formula I.37 in which $R^{81}$ is dipropylamino and the combination of $R^1$ and $R^2$ for a compound corresponds in each case to one row of Table A.
Table 66
Compounds of the formula I.37 in which $R^{81}$ is $NHC(O)CH_3$ and the combination of $R^1$ and $R^2$ for a compound corresponds in each case to one row of Table A.
Table 67
Compounds of the formula I.37 in which $R^{81}$ is $NHC(O)CF_3$ and the combination of $R^1$ and $R^2$ for a compound corresponds in each case to one row of Table A.
Table 68
Compounds of the formula I.37 in which $R^{81}$ is $NHC(O)OCH_3$ and the combination of $R^1$ and $R^2$ for a compound corresponds in each case to one row of Table A.
Table 69
Compounds of the formula I.37 in which $R^{81}$ is $NHC(O)OCF_3$ and the combination of $R^1$ and $R^2$ for a compound corresponds in each case to one row of Table A.
Table 70
Compounds of the formula I.37 in which $R^{81}$ is $NHC(O)OC(CH_3)_3$ and the combination of $R^1$ and $R^2$ for a compound corresponds in each case to one row of Table A.
Table 71
Compounds of the formula I.37 in which $R^{81}$ is cyclopropyl and the combination of $R^1$ and $R^2$ for a compound corresponds in each case to one row of Table A.
Table 72
Compounds of the formula I.37 in which $R^{81}$ is cyclobutyl and the combination of $R^1$ and $R^2$ for a compound corresponds in each case to one row of Table A.
Table 73
Compounds of the formula I.37 in which $R^{81}$ is cyclopentyl and the combination of $R^1$ and $R^2$ for a compound corresponds in each case to one row of Table A.
Table 74
Compounds of the formula I.37 in which $R^{81}$ is cyclohexyl and the combination of $R^1$ and $R^2$ for a compound corresponds in each case to one row of Table A.
Table 75
Compounds of the formula I.37 in which $R^{81}$ is cycloheptyl and the combination of $R^1$ and $R^2$ for a compound corresponds in each case to one row of Table A.
Table 76
Compounds of the formula I.37 in which $R^{81}$ is A-1 and the combination of $R^1$ and $R^2$ for a compound corresponds in each case to one row of Table A.
Table 77
Compounds of the formula I.37 in which $R^{81}$ is A-2 and the combination of $R^1$ and $R^2$ for a compound corresponds in each case to one row of Table A.
Table 78
Compounds of the formula I.37 in which $R^{81}$ is A-3 and the combination of $R^1$ and $R^2$ for a compound corresponds in each case to one row of Table A.
Table 79
Compounds of the formula I.37 in which $R^{81}$ is A-4 and the combination of $R^1$ and $R^2$ for a compound corresponds in each case to one row of Table A.
Table 80
Compounds of the formula I.37 in which $R^{81}$ is A-5 and the combination of $R^1$ and $R^2$ for a compound corresponds in each case to one row of Table A.
Table 81
Compounds of the formula I.37 in which $R^{81}$ is A-6 and the combination of $R^1$ and $R^2$ for a compound corresponds in each case to one row of Table A.
Table 82
Compounds of the formula I.37 in which $R^{81}$ is A-7 and the combination of $R^1$ and $R^2$ for a compound corresponds in each case to one row of Table A.
Table 83
Compounds of the formula I.37 in which $R^{81}$ is A-8 and the combination of $R^1$ and $R^2$ for a compound corresponds in each case to one row of Table A.
Table 84
Compounds of the formula I.37 in which $R^{81}$ is A-9 and the combination of $R^1$ and $R^2$ for a compound corresponds in each case to one row of Table A.
Table 85
Compounds of the formula I.37 in which $R^{81}$ is A-10 and the combination of $R^1$ and $R^2$ for a compound corresponds in each case to one row of Table A.
Table 86
Compounds of the formula I.37 in which $R^{81}$ is A-11 and the combination of $R^1$ and $R^2$ for a compound corresponds in each case to one row of Table A.
Table 87
Compounds of the formula I.37 in which $R^{81}$ is A-12 and the combination of $R^1$ and $R^2$ for a compound corresponds in each case to one row of Table A.

Table 88
Compounds of the formula I.37 in which $R^{81}$ is A-13 and the combination of $R^1$ and $R^2$ for a compound corresponds in each case to one row of Table A.

Table 89
Compounds of the formula I.37 in which $R^{81}$ is A-14 and the combination of $R^1$ and $R^2$ for a compound corresponds in each case to one row of Table A.

Table 90
Compounds of the formula I.37 in which $R^{81}$ is A-15 and the combination of $R^1$ and $R^2$ for a compound corresponds in each case to one row of Table A.

Table 91
Compounds of the formula I.37 in which $R^{81}$ is A-16 and the combination of $R^1$ and $R^2$ for a compound corresponds in each case to one row of Table A.

Table 92
Compounds of the formula I.37 in which $R^{81}$ is A-17 and the combination of $R^1$ and $R^2$ for a compound corresponds in each case to one row of Table A.

Table 93
Compounds of the formula I.37 in which $R^{81}$ is A-18 and the combination of $R^1$ and $R^2$ for a compound corresponds in each case to one row of Table A.

Table 94
Compounds of the formula I.37 in which $R^{81}$ is A-19 and the combination of $R^1$ and $R^2$ for a compound corresponds in each case to one row of Table A.

Table 95
Compounds of the formula I.37 in which $R^{81}$ is A-20 and the combination of $R^1$ and $R^2$ for a compound corresponds in each case to one row of Table A.

Table 96
Compounds of the formula I.37 in which $R^{81}$ is A-21 and the combination of $R^1$ and $R^2$ for a compound corresponds in each case to one row of Table A.

Table 97
Compounds of the formula I.37 in which $R^{81}$ is A-22 and the combination of $R^1$ and $R^2$ for a compound corresponds in each case to one row of Table A.

Table 98
Compounds of the formula I.37 in which $R^{81}$ is A-23 and the combination of $R^1$ and $R^2$ for a compound corresponds in each case to one row of Table A.

Table 99
Compounds of the formula I.37 in which $R^{81}$ is A-24 and the combination of $R^1$ and $R^2$ for a compound corresponds in each case to one row of Table A.

Table 100
Compounds of the formula I.37 in which $R^{81}$ is A-25 and the combination of $R^1$ and $R^2$ for a compound corresponds in each case to one row of Table A.

Table 101
Compounds of the formula I.37 in which $R^{81}$ is A-26 and the combination of $R^1$ and $R^2$ for a compound corresponds in each case to one row of Table A.

Table 102
Compounds of the formula I.37 in which $R^{81}$ is A-27 and the combination of $R^1$ and $R^2$ for a compound corresponds in each case to one row of Table A.

Table 103
Compounds of the formula I.37 in which $R^{81}$ is A-28 and the combination of $R^1$ and $R^2$ for a compound corresponds in each case to one row of Table A.

Table 104
Compounds of the formula I.37 in which $R^{81}$ is A-29 and the combination of $R^1$ and $R^2$ for a compound corresponds in each case to one row of Table A.

Table 105
Compounds of the formula I.37 in which $R^{81}$ is A-30 and the combination of $R^1$ and $R^2$ for a compound corresponds in each case to one row of Table A.

Table 106
Compounds of the formula I.37 in which $R^{81}$ is A-31 and the combination of $R^1$ and $R^2$ for a compound corresponds in each case to one row of Table A.

Table 107
Compounds of the formula I.37 in which $R^{81}$ is A-32 and the combination of $R^1$ and $R^2$ for a compound corresponds in each case to one row of Table A.

Table 108
Compounds of the formula I.37 in which $R^{81}$ is A-33 and the combination of $R^1$ and $R^2$ for a compound corresponds in each case to one row of Table A.

Table 109
Compounds of the formula I.37 in which $R^{81}$ is A-34 and the combination of $R^1$ and $R^2$ for a compound corresponds in each case to one row of Table A.

Table 110
Compounds of the formula I.37 in which $R^{81}$ is A-35 and the combination of $R^1$ and $R^2$ for a compound corresponds in each case to one row of Table A.

Table 111
Compounds of the formula I.37 in which $R^{81}$ is A-36 and the combination of $R^1$ and $R^2$ for a compound corresponds in each case to one row of Table A.

Table 112
Compounds of the formula I.37 in which $R^{81}$ is A-37 and the combination of $R^1$ and $R^2$ for a compound corresponds in each case to one row of Table A.

Table 113
Compounds of the formula I.37 in which $R^{81}$ is A-38 and the combination of $R^1$ and $R^2$ for a compound corresponds in each case to one row of Table A.

Table 114
Compounds of the formula I.37 in which $R^{81}$ is A-39 and the combination of $R^1$ and $R^2$ for a compound corresponds in each case to one row of Table A.

Table 115
Compounds of the formula I.37 in which $R^{81}$ is A-40 and the combination of $R^1$ and $R^2$ for a compound corresponds in each case to one row of Table A.

Table 116
Compounds of the formula I.37 in which $R^{81}$ is A-41 and the combination of $R^1$ and $R^2$ for a compound corresponds in each case to one row of Table A.

Table 117
Compounds of the formula I.37 in which $R^{81}$ is A-42 and the combination of $R^1$ and $R^2$ for a compound corresponds in each case to one row of Table A.

Table 118
Compounds of the formula I.37 in which $R^{81}$ is A-43 and the combination of $R^1$ and $R^2$ for a compound corresponds in each case to one row of Table A.

Table 119
Compounds of the formula I.37 in which $R^{81}$ is A-44 and the combination of $R^1$ and $R^2$ for a compound corresponds in each case to one row of Table A.

Table 120
Compounds of the formula I.37 in which $R^{81}$ is A-45 and the combination of $R^1$ and $R^2$ for a compound corresponds in each case to one row of Table A.

Table 121
Compounds of the formula I.37 in which $R^{81}$ is A-46 and the combination of $R^1$ and $R^2$ for a compound corresponds in each case to one row of Table A.

Table 122
Compounds of the formula I.37 in which $R^{81}$ is A-47 and the combination of $R^1$ and $R^2$ for a compound corresponds in each case to one row of Table A.

Table 123
Compounds of the formula I.37 in which $R^{81}$ is A-48 and the combination of $R^1$ and $R^2$ for a compound corresponds in each case to one row of Table A.

Table 124
Compounds of the formula I.37 in which $R^{81}$ is A-49 and the combination of $R^1$ and $R^2$ for a compound corresponds in each case to one row of Table A.

Table 125
Compounds of the formula I.37 in which $R^{81}$ is A-50 and the combination of $R^1$ and $R^2$ for a compound corresponds in each case to one row of Table A.

Table 126
Compounds of the formula I.37 in which $R^{81}$ is A-51 and the combination of $R^1$ and $R^2$ for a compound corresponds in each case to one row of Table A.

Table 127
Compounds of the formula I.37 in which $R^{81}$ is A-52 and the combination of $R^1$ and $R^2$ for a compound corresponds in each case to one row of Table A.

Table 128
Compounds of the formula I.37 in which $R^{81}$ is A-53 and the combination of $R^1$ and $R^2$ for a compound corresponds in each case to one row of Table A.

Table 129
Compounds of the formula I.37 in which $R^{81}$ is A-54 and the combination of $R^1$ and $R^2$ for a compound corresponds in each case to one row of Table A.

Table 130
Compounds of the formula I.37 in which $R^{81}$ is A-55 and the combination of $R^1$ and $R^2$ for a compound corresponds in each case to one row of Table A.

Table 131
Compounds of the formula I.37 in which $R^{81}$ is A-56 and the combination of $R^1$ and $R^2$ for a compound corresponds in each case to one row of Table A.

Table 132
Compounds of the formula I.37 in which $R^{81}$ is A-57 and the combination of $R^1$ and $R^2$ for a compound corresponds in each case to one row of Table A.

Table 133
Compounds of the formula I.37 in which $R^{81}$ is A-58 and the combination of $R^1$ and $R^2$ for a compound corresponds in each case to one row of Table A.

Table 134
Compounds of the formula I.37 in which $R^{81}$ is A-59 and the combination of $R^1$ and $R^2$ for a compound corresponds in each case to one row of Table A.

Table 135
Compounds of the formula I.37 in which $R^{81}$ is A-60 and the combination of $R^1$ and $R^2$ for a compound corresponds in each case to one row of Table A.

Table 136
Compounds of the formula I.37 in which $R^{81}$ is A-61 and the combination of $R^1$ and $R^2$ for a compound corresponds in each case to one row of Table A.

Table 137
Compounds of the formula I.37 in which $R^{81}$ is A-62 and the combination of $R^1$ and $R^2$ for a compound corresponds in each case to one row of Table A.

Table 138
Compounds of the formula I.37 in which $R^{81}$ is A-63 and the combination of $R^1$ and $R^2$ for a compound corresponds in each case to one row of Table A.

Table 139
Compounds of the formula I.37 in which $R^{81}$ is A-64 and the combination of $R^1$ and $R^2$ for a compound corresponds in each case to one row of Table A.

Table 140
Compounds of the formula I.37 in which $R^{81}$ is A-65 and the combination of $R^1$ and $R^2$ for a compound corresponds in each case to one row of Table A.

Table 141
Compounds of the formula I.37 in which $R^{81}$ is A-66 and the combination of $R^1$ and $R^2$ for a compound corresponds in each case to one row of Table A.

Table 142
Compounds of the formula I.37 in which $R^{81}$ is A-67 and the combination of $R^1$ and $R^2$ for a compound corresponds in each case to one row of Table A.

Table 143
Compounds of the formula I.37 in which $R^{81}$ is A-68 and the combination of $R^1$ and $R^2$ for a compound corresponds in each case to one row of Table A.

Table 144
Compounds of the formula I.37 in which $R^{81}$ is A-69 and the combination of $R^1$ and $R^2$ for a compound corresponds in each case to one row of Table A.

Table 145
Compounds of the formula I.37 in which $R^{81}$ is A-70 and the combination of $R^1$ and $R^2$ for a compound corresponds in each case to one row of Table A.

Table 146
Compounds of the formula I.37 in which $R^{81}$ is A-71 and the combination of $R^1$ and $R^2$ for a compound corresponds in each case to one row of Table A.

Table 147
Compounds of the formula I.37 in which $R^{81}$ is A-72 and the combination of $R^1$ and $R^2$ for a compound corresponds in each case to one row of Table A.

Table 148
Compounds of the formula I.37 in which $R^{81}$ is A-73 and the combination of $R^1$ and $R^2$ for a compound corresponds in each case to one row of Table A.

Table 149
Compounds of the formula I.37 in which $R^{81}$ is A-74 and the combination of $R^1$ and $R^2$ for a compound corresponds in each case to one row of Table A.

Table 150
Compounds of the formula I.37 in which $R^{81}$ is A-75 and the combination of $R^1$ and $R^2$ for a compound corresponds in each case to one row of Table A.

Table 151
Compounds of the formula I.37 in which $R^{81}$ is A-76 and the combination of $R^1$ and $R^2$ for a compound corresponds in each case to one row of Table A.

Table 152
Compounds of the formula I.37 in which $R^{81}$ is A-77 and the combination of $R^1$ and $R^2$ for a compound corresponds in each case to one row of Table A.

Table 153
Compounds of the formula I.37 in which $R^{81}$ is A-78 and the combination of $R^1$ and $R^2$ for a compound corresponds in each case to one row of Table A.

Table 154
Compounds of the formula I.37 in which $R^{81}$ is A-79 and the combination of $R^1$ and $R^2$ for a compound corresponds in each case to one row of Table A.

Table 155
Compounds of the formula I.37 in which $R^{81}$ is A-80 and the combination of $R^1$ and $R^2$ for a compound corresponds in each case to one row of Table A.

Table 156
Compounds of the formula I.37 in which $R^{81}$ is A-81 and the combination of $R^1$ and $R^2$ for a compound corresponds in each case to one row of Table A.

Table 157
Compounds of the formula I.37 in which $R^{81}$ is A-82 and the combination of $R^1$ and $R^2$ for a compound corresponds in each case to one row of Table A.

Table 158
Compounds of the formula I.37 in which $R^{81}$ is A-83 and the combination of $R^1$ and $R^2$ for a compound corresponds in each case to one row of Table A.

Table 159
Compounds of the formula I.37 in which $R^{81}$ is A-84 and the combination of $R^1$ and $R^2$ for a compound corresponds in each case to one row of Table A.

Table 160
Compounds of the formula I.37 in which $R^{81}$ is A-85 and the combination of $R^1$ and $R^2$ for a compound corresponds in each case to one row of Table A.

Table 161
Compounds of the formula I.37 in which $R^{81}$ is A-86 and the combination of $R^1$ and $R^2$ for a compound corresponds in each case to one row of Table A.

Table 162
Compounds of the formula I.37 in which $R^{81}$ is A-87 and the combination of $R^1$ and $R^2$ for a compound corresponds in each case to one row of Table A.

Table 163
Compounds of the formula I.37 in which $R^{81}$ is A-88 and the combination of $R^1$ and $R^2$ for a compound corresponds in each case to one row of Table A.

Table 164
Compounds of the formula I.37 in which $R^{81}$ is A-89 and the combination of $R^1$ and $R^2$ for a compound corresponds in each case to one row of Table A.

Table 165
Compounds of the formula I.37 in which $R^{81}$ is A-90 and the combination of $R^1$ and $R^2$ for a compound corresponds in each case to one row of Table A.

Table 166
Compounds of the formula I.37 in which $R^{81}$ is A-91 and the combination of $R^1$ and $R^2$ for a compound corresponds in each case to one row of Table A.

Table 167
Compounds of the formula I.37 in which $R^{81}$ is A-92 and the combination of $R^1$ and $R^2$ for a compound corresponds in each case to one row of Table A.

Table 168
Compounds of the formula I.37 in which $R^{81}$ is A-93 and the combination of $R^1$ and $R^2$ for a compound corresponds in each case to one row of Table A.

Table 169
Compounds of the formula I.37 in which $R^{81}$ is A-94 and the combination of $R^1$ and $R^2$ for a compound corresponds in each case to one row of Table A.

Table 170
Compounds of the formula I.37 in which $R^{81}$ is A-95 and the combination of $R^1$ and $R^2$ for a compound corresponds in each case to one row of Table A.

Table 171
Compounds of the formula I.37 in which $R^{81}$ is A-96 and the combination of $R^1$ and $R^2$ for a compound corresponds in each case to one row of Table A.

Table 172
Compounds of the formula I.37 in which $R^{81}$ is A-97 and the combination of $R^1$ and $R^2$ for a compound corresponds in each case to one row of Table A.

Table 173
Compounds of the formula I.37 in which $R^{81}$ is A-98 and the combination of $R^1$ and $R^2$ for a compound corresponds in each case to one row of Table A.

Table 174
Compounds of the formula I.37 in which $R^{81}$ is A-99 and the combination of $R^1$ and $R^2$ for a compound corresponds in each case to one row of Table A.

Table 175
Compounds of the formula I.37 in which $R^{81}$ is A-100 and the combination of $R^1$ and $R^2$ for a compound corresponds in each case to one row of Table A.

Table 176
Compounds of the formula I.37 in which $R^{81}$ is A-101 and the combination of $R^1$ and $R^2$ for a compound corresponds in each case to one row of Table A.

Table 177
Compounds of the formula I.37 in which $R^{81}$ is A-102 and the combination of $R^1$ and $R^2$ for a compound corresponds in each case to one row of Table A.

Table 178
Compounds of the formula I.37 in which $R^{81}$ is A-103 and the combination of $R^1$ and $R^2$ for a compound corresponds in each case to one row of Table A.

Table 179
Compounds of the formula I.37 in which $R^{81}$ is A-104 and the combination of $R^1$ and $R^2$ for a compound corresponds in each case to one row of Table A.

Table 180
Compounds of the formula I.37 in which $R^{81}$ is A-105 and the combination of $R^1$ and $R^2$ for a compound corresponds in each case to one row of Table A.

Table 181
Compounds of the formula I.37 in which $R^{81}$ is A-106 and the combination of $R^1$ and $R^2$ for a compound corresponds in each case to one row of Table A.

Table 182
Compounds of the formula I.37 in which $R^{81}$ is A-107 and the combination of $R^1$ and $R^2$ for a compound corresponds in each case to one row of Table A.

Table 183
Compounds of the formula I.37 in which $R^{81}$ is A-108 and the combination of $R^1$ and $R^2$ for a compound corresponds in each case to one row of Table A.

Table 184
Compounds of the formula I.37 in which $R^{81}$ is A-109 and the combination of $R^1$ and $R^2$ for a compound corresponds in each case to one row of Table A.

Table 185
Compounds of the formula I.37 in which $R^{81}$ is A-110 and the combination of $R^1$ and $R^2$ for a compound corresponds in each case to one row of Table A.

Table 186
Compounds of the formula I.37 in which $R^{81}$ is A-111 and the combination of $R^1$ and $R^2$ for a compound corresponds in each case to one row of Table A.

Tables 37 to 336

Compounds of the formula I.38 in which $R^{81}$ is as defined in tables 37 to 186 and the combination of $R^1$ and $R^2$ for a compound corresponds in each case to one row of Table A. Tables 337 to 486

Compounds of the formula I.39 in which $R^{81}$ is as defined in Tables 37 to 186 and the combination of $R^1$ and $R^2$ for a compound corresponds in each case to one row of Table A. Tables 487 to 636

Compounds of the formula I.40 in which $R^{81}$ is as defined in Tables 37 to 186 and the combination of $R^1$ and $R^2$ for a compound corresponds in each case to one row of Table A. Tables 637 to 786

Compounds of the formula I.41 in which $R^{81}$ is as defined in Tables 37 to 186 and the combination of $R^1$ and $R^2$ for a compound corresponds in each case to one row of Table A. Tables 787 to 936

Compounds of the formula I.42 in which $R^{81}$ is as defined in Tables 37 to 186 and the combination of $R^1$ and $R^2$ for a compound corresponds in each case to one row of Table A. Tables 937 to 1086

Compounds of the formula I.43 in which $R^{81}$ is as defined in Tables 37 to 186 and the combination of $R^1$ and $R^2$ for a compound corresponds in each case to one row of Table A. Tables 1087 to 1236

Compounds of the formula I.44 in which $R^{81}$ is as defined in Tables 37 to 186 and the combination of $R^1$ and $R^2$ for a compound corresponds in each case to one row of Table A. Tables 1237 to 1386

Compounds of the formula I.45 in which $R^{81}$ is as defined in Tables 37 to 186 and the combination of $R^1$ and $R^2$ for a compound corresponds in each case to one row of Table A. Tables 1387 to 1536

Compounds of the formula I.46 in which $R^{81}$ is as defined in Tables 37 to 186 and the combination of $R^1$ and $R^2$ for a compound corresponds in each case to one row of Table A. Tables 1537 to 1686

Compounds of the formula I.47 in which $R^{81}$ is as defined in Tables 37 to 186 and the combination of $R^1$ and $R^2$ for a compound corresponds in each case to one row of Table A. Tables 1687 to 1836

Compounds of the formula I.48 in which $R^{81}$ is as defined in Tables 37 to 186 and the combination of $R^1$ and $R^2$ for a compound corresponds in each case to one row of Table A. Tables 1837 to 1986

Compounds of the formula I.49 in which $R^{81}$ is as defined in Tables 37 to 186 and the combination of $R^1$ and $R^2$ for a compound corresponds in each case to one row of Table A. Tables 1987 to 2136

Compounds of the formula I.50 in which $R^{81}$ is as defined in Tables 37 to 186 and the combination of $R^1$ and $R^2$ for a compound corresponds in each case to one row of Table A. Tables 2137 to 2286

Compounds of the formula I.51 in which $R^{81}$ is as defined in Tables 37 to 186 and the combination of $R^1$ and $R^2$ for a compound corresponds in each case to one row of Table A. Tables 2287 to 2436

Compounds of the formula I.52 in which $R^{81}$ is as defined in Tables 37 to 186 and the combination of $R^1$ and $R^2$ for a compound corresponds in each case to one row of Table A. Tables 2437 to 2586

Compounds of the formula I.53 in which $R^{81}$ is as defined in Tables 37 to 186 and the combination of $R^1$ and $R^2$ for a compound corresponds in each case to one row of Table A. Tables 2587 to 2736

Compounds of the formula I.54 in which $R^{81}$ is as defined in Tables 37 to 186 and the combination of $R^1$ and $R^2$ for a compound corresponds in each case to one row of Table A. Tables 2737 to 2886

Compounds of the formula I.55 in which $R^{81}$ is as defined in Tables 37 to 186 and the combination of $R^1$ and $R^2$ for a compound corresponds in each case to one row of Table A. Tables 2887 to 3036

Compounds of the formula I.56 in which $R^{81}$ is as defined in Tables 37 to 186 and the combination of $R^1$ and $R^2$ for a compound corresponds in each case to one row of Table A. Tables 3037 to 3186

Compounds of the formula I.57 in which $R^{81}$ is as defined in Tables 37 to 186 and the combination of $R^1$ and $R^2$ for a compound corresponds in each case to one row of Table A. Tables 3187 to 3336

Compounds of the formula I.58 in which $R^{81}$ is as defined in Tables 37 to 186 and the combination of $R^1$ and $R^2$ for a compound corresponds in each case to one row of Table A. Tables 3337 to 3486

Compounds of the formula I.59 in which $R^{81}$ is as defined in Tables 37 to 186 and the combination of $R^1$ and $R^2$ for a compound corresponds in each case to one row of Table A. Tables 3487 to 3636

Compounds of the formula I.60 in which $R^{81}$ is as defined in Tables 37 to 186 and the combination of $R^1$ and $R^2$ for a compound corresponds in each case to one row of Table A. Tables 3637 to 3786

Compounds of the formula I.61 in which $R^{81}$ is as defined in Tables 37 to 186 and the combination of $R^1$ and $R^2$ for a compound corresponds in each case to one row of Table A. Tables 3787 to 3936

Compounds of the formula I.62 in which $R^{81}$ is as defined in Tables 37 to 186 and the combination of $R^1$ and $R^2$ for a compound corresponds in each case to one row of Table A. Tables 3937 to 4086

Compounds of the formula I.63 in which $R^{81}$ is as defined in Tables 37 to 186 and the combination of $R^1$ and $R^2$ for a compound corresponds in each case to one row of Table A. Tables 4087 to 4236

Compounds of the formula I.64 in which $R^{81}$ is as defined in Tables 37 to 186 and the combination of $R^1$ and $R^2$ for a compound corresponds in each case to one row of Table A. Tables 4237 to 4386

Compounds of the formula I.65 in which $R^{81}$ is as defined in Tables 37 to 186 and the combination of $R^1$ and $R^2$ for a compound corresponds in each case to one row of Table A. Tables 4387 to 4536

Compounds of the formula I.66 in which $R^{81}$ is as defined in Tables 37 to 186 and the combination of $R^1$ and $R^2$ for a compound corresponds in each case to one row of Table A. Tables 4537 to 4686

Compounds of the formula I.67 in which $R^{81}$ is as defined in Tables 37 to 186 and the combination of $R^1$ and $R^2$ for a compound corresponds in each case to one row of Table A. Tables 4687 to 4836

Compounds of the formula I.68 in which $R^{81}$ is as defined in Tables 37 to 186 and the combination of $R^1$ and $R^2$ for a compound corresponds in each case to one row of Table A. Tables 4837 to 4986

Compounds of the formula I.69 in which $R^{81}$ is as defined in Tables 37 to 186 and the combination of $R^1$ and $R^2$ for a compound corresponds in each case to one row of Table A. Tables 4987 to 5136

Compounds of the formula I.70 in which $R^{81}$ is as defined in Tables 37 to 186 and the combination of $R^1$ and $R^2$ for a compound corresponds in each case to one row of Table A.

Tables 5137 to 5286
Compounds of the formula I.71 in which $R^{81}$ is as defined in Tables 37 to 186 and the combination of $R^1$ and $R^2$ for a compound corresponds in each case to one row of Table A.

Tables 5287 to 5436
Compounds of the formula I.72 in which $R^{81}$ is as defined in Tables 37 to 186 and the combination of $R^1$ and $R^2$ for a compound corresponds in each case to one row of Table A.

Table 5437
Compounds of the formula I.73 in which the combination of $R^1$ and $R^2$ for a compound corresponds in each case to one row of Table A.

Table 5438
Compounds of the formula I.74 in which the combination of $R^1$ and $R^2$ for a compound corresponds in each case to one row of Table A.

Table 5439
Compounds of the formula I.75 in which the combination of $R^1$ and $R^2$ for a compound corresponds in each case to one row of Table A.

Table 5440
Compounds of the formula I.76 in which the combination of $R^1$ and $R^2$ for a compound corresponds in each case to one row of Table A.

Table 5441
Compounds of the formula I.77 in which the combination of $R^1$ and $R^2$ for a compound corresponds in each case to one row of Table A.

Table 5442
Compounds of the formula I.78 in which the combination of $R^1$ and $R^2$ for a compound corresponds in each case to one row of Table A.

Table 5443
Compounds of the formula I.79 in which the combination of $R^1$ and $R^2$ for a compound corresponds in each case to one row of Table A.

Table 5444
Compounds of the formula I.80 in which the combination of $R^1$ and $R^2$ for a compound corresponds in each case to one row of Table A.

Table 5445
Compounds of the formula I.81 in which the combination of $R^1$ and $R^2$ for a compound corresponds in each case to one row of Table A.

Table 5446
Compounds of the formula I.82 in which the combination of $R^1$ and $R^2$ for a compound corresponds in each case to one row of Table A.

Table 5447
Compounds of the formula I.83 in which the combination of $R^1$ and $R^2$ for a compound corresponds in each case to one row of Table A.

Table 5448
Compounds of the formula I.84 in which the combination of $R^1$ and $R^2$ for a compound corresponds in each case to one row of Table A.

Table 5449
Compounds of the formula I.85 in which the combination of $R^1$ and $R^2$ for a compound corresponds in each case to one row of Table A.

Table 5450
Compounds of the formula I.86 in which the combination of $R^1$ and $R^2$ for a compound corresponds in each case to one row of Table A.

Table 5451
Compounds of the formula I.87 in which the combination of $R^1$ and $R^2$ for a compound corresponds in each case to one row of Table A.

Table 5452
Compounds of the formula I.88 in which the combination of $R^1$ and $R^2$ for a compound corresponds in each case to one row of Table A.

Table 5453
Compounds of the formula I.89 in which the combination of $R^1$ and $R^2$ for a compound corresponds in each case to one row of Table A.

Table 5454
Compounds of the formula I.90 in which the combination of $R^1$ and $R^2$ for a compound corresponds in each case to one row of Table A.

Table 5455
Compounds of the formula I.91 in which the combination of $R^1$ and $R^2$ for a compound corresponds in each case to one row of Table A.

Table 5456
Compounds of the formula I.92 in which the combination of $R^1$ and $R^2$ for a compound corresponds in each case to one row of Table A.

Table 5457
Compounds of the formula I.93 in which the combination of $R^1$ and $R^2$ for a compound corresponds in each case to one row of Table A.

Table 5458
Compounds of the formula I.94 in which the combination of $R^1$ and $R^2$ for a compound corresponds in each case to one row of Table A.

Table 5459
Compounds of the formula I.95 in which the combination of $R^1$ and $R^2$ for a compound corresponds in each case to one row of Table A.

Table 5460
Compounds of the formula I.96 in which the combination of $R^1$ and $R^2$ for a compound corresponds in each case to one row of Table A.

Table 5461
Compounds of the formula I.97 in which the combination of $R^1$ and $R^2$ for a compound corresponds in each case to one row of Table A.

Table 5462
Compounds of the formula I.98 in which the combination of $R^1$ and $R^2$ for a compound corresponds in each case to one row of Table A.

Table 5463
Compounds of the formula I.99 in which the combination of $R^1$ and $R^2$ for a compound corresponds in each case to one row of Table A.

Table 5464
Compounds of the formula I.100 in which the combination of $R^1$ and $R^2$ for a compound corresponds in each case to one row of Table A.

Table 5465
Compounds of the formula I.101 in which the combination of $R^1$ and $R^2$ for a compound corresponds in each case to one row of Table A.

Table 5466
Compounds of the formula I.102 in which the combination of $R^1$ and $R^2$ for a compound corresponds in each case to one row of Table A.

Table 5467
Compounds of the formula I.103 in which the combination of $R^1$ and $R^2$ for a compound corresponds in each case to one row of Table A.

Table 5468
Compounds of the formula I.104 in which the combination of $R^1$ and $R^2$ for a compound corresponds in each case to one row of Table A.
Table 5469
Compounds of the formula I.105 in which the combination of $R^1$ and $R^2$ for a compound corresponds in each case to one row of Table A.
Table 5470
Compounds of the formula I.106 in which the combination of $R^1$ and $R^2$ for a compound corresponds in each case to one row of Table A.
Table 5471
Compounds of the formula I.107 in which the combination of $R^1$ and $R^2$ for a compound corresponds in each case to one row of Table A.
Table 5472
Compounds of the formula I.108 in which the combination of $R^1$ and $R^2$ for a compound corresponds in each case to one row of Table A.
Table 5473
Compounds of the formula I.109 in which $R^c$ is hydrogen and the combination of $R^1$ and $R^2$ for a compound corresponds in each case to one row of Table A.
Table 5474
Compounds of the formula I.109 in which $R^c$ is methyl and the combination of $R^1$ and $R^2$ for a compound corresponds in each case to one row of Table A.
Table 5475
Compounds of the formula I.109 in which $R^c$ is ethyl and the combination of $R^1$ and $R^2$ for a compound corresponds in each case to one row of Table A.
Table 5476
Compounds of the formula I.109 in which $R^c$ is propyl and the combination of $R^1$ and $R^2$ for a compound corresponds in each case to one row of Table A.
Table 5477
Compounds of the formula I.109 in which $R^c$ is isopropyl and the combination of $R^1$ and $R^2$ for a compound corresponds in each case to one row of Table A.
Table 5478
Compounds of the formula I.109 in which $R^c$ is $CH_2OCH_3$ and the combination of $R^1$ and $R^2$ for a compound corresponds in each case to one row of Table A.
Table 5479
Compounds of the formula I.109 in which $R^c$ is $CH_2CH_2OCH_3$ and the combination of $R^1$ and $R^2$ for a compound corresponds in each case to one row of Table A.
Table 5480
Compounds of the formula I.109 in which $R^c$ is $CH_2CH_2OCH_2CH_3$ and the combination of $R^1$ and $R^2$ for a compound corresponds in each case to one row of Table A.
Table 5481
Compounds of the formula I.109 in which $R^c$ is $CHF_2$ and the combination of $R^1$ and $R^2$ for a compound corresponds in each case to one row of Table A.
Table 5482
Compounds of the formula I.109 in which $R^c$ is $CF_3$ and the combination of $R^1$ and $R^2$ for a compound corresponds in each case to one row of Table A.
Table 5483
Compounds of the formula I.109 in which $R^c$ is $CH_2CHF_2$ and the combination of $R^1$ and $R^2$ for a compound corresponds in each case to one row of Table A.
Table 5484
Compounds of the formula I.109 in which $R^c$ is $CH_2CF_3$ and the combination of $R^1$ and $R^2$ for a compound corresponds in each case to one row of Table A.
Table 5485
Compounds of the formula I.109 in which $R^c$ is $CF_2CF_3$ and the combination of $R^1$ and $R^2$ for a compound corresponds in each case to one row of Table A.
Table 5486
Compounds of the formula I.109 in which $R^c$ is $C(O)CH_3$ and the combination of $R^1$ and $R^2$ for a compound corresponds in each case to one row of Table A.
Table 5487
Compounds of the formula I.109 in which $R^c$ is $C(O)OCH_3$ and the combination of $R^1$ and $R^2$ for a compound corresponds in each case to one row of Table A.
Table 5488
Compounds of the formula I.109 in which $R^c$ is $C(O)OCF_3$ and the combination of $R^1$ and $R^2$ for a compound corresponds in each case to one row of Table A.
Table 5489
Compounds of the formula I.109 in which $R^c$ is $C(O)OC(CH_3)_3$ and the combination of $R^1$ and $R^2$ for a compound corresponds in each case to one row of Table A.
Table 5490
Compounds of the formula I.109 in which $R^c$ is $C(O)NH_2$ and the combination of $R^1$ and $R^2$ for a compound corresponds in each case to one row of Table A.
Table 5491
Compounds of the formula I.109 in which $R^c$ is $C(O)NHCH_3$ and the combination of $R^1$ and $R^2$ for a compound corresponds in each case to one row of Table A.
Table 5492
Compounds of the formula I.109 in which $R^c$ is $C(O)N(CH_3)_2$ and the combination of $R^1$ and $R^2$ for a compound corresponds in each case to one row of Table A.
Tables 5493 to 5512
Compounds of the formula I.110 in which $R^c$ is as defined in Tables 5472 to 5492 and the combination of $R^1$ and $R^2$ for a compound corresponds in each case to one row of Table A.
Tables 5513 to 5532
Compounds of the formula I.111 in which $R^c$ is as defined in Tables 5472 to 5492 and the combination of $R^1$ and $R^2$ for a compound corresponds in each case to one row of Table A.
Tables 5533 to 5552
Compounds of the formula I.112 in which $R^c$ is as defined in Tables 5472 to 5492 and the combination of $R^1$ and $R^2$ for a compound corresponds in each case to one row of Table A.
Tables 5553 to 5572
Compounds of the formula I.113 in which $R^c$ is as defined in Tables 5472 to 5492 and the combination of $R^1$ and $R^2$ for a compound corresponds in each case to one row of Table A.
Tables 5573 to 5592
Compounds of the formula I.114 in which $R^c$ is as defined in Tables 5472 to 5492 and the combination of $R^1$ and $R^2$ for a compound corresponds in each case to one row of Table A.
Tables 5593 to 5612
Compounds of the formula I.115 in which $R^c$ is as defined in Tables 5472 to 5492 and the combination of $R^1$ and $R^2$ for a compound corresponds in each case to one row of Table A.
Tables 5613 to 5632
Compounds of the formula I.116 in which $R^c$ is as defined in Tables 5472 to 5492 and the combination of $R^1$ and $R^2$ for a compound corresponds in each case to one row of Table A.
Tables 5633 to 5652
Compounds of the formula I.117 in which $R^c$ is as defined in Tables 5472 to 5492 and the combination of $R^1$ and $R^2$ for a compound corresponds in each case to one row of Table A.

Tables 5653 to 5672
Compounds of the formula I.118 in which $R^c$ is as defined in Tables 5472 to 5492 and the combination of $R^1$ and $R^2$ for a compound corresponds in each case to one row of Table A.
Tables 5673 to 5692
Compounds of the formula I.119 in which $R^c$ is as defined in Tables 5472 to 5492 and the combination of $R^1$ and $R^2$ for a compound corresponds in each case to one row of Table A.
Tables 5693 to 5712
Compounds of the formula I.120 in which $R^c$ is as defined in Tables 5472 to 5492 and the combination of $R^1$ and $R^2$ for a compound corresponds in each case to one row of Table A.
Tables 5713 to 5732
Compounds of the formula I.121 in which $R^c$ is as defined in Tables 5472 to 5492 and the combination of $R^1$ and $R^2$ for a compound corresponds in each case to one row of Table A.
Tables 5733 to 5752
Compounds of the formula I.122 in which $R^c$ is as defined in Tables 5472 to 5492 and the combination of $R^1$ and $R^2$ for a compound corresponds in each case to one row of Table A.
Tables 5753 to 5772
Compounds of the formula I.123 in which $R^c$ is as defined in Tables 5472 to 5492 and the combination of $R^1$ and $R^2$ for a compound corresponds in each case to one row of Table A.
Tables 5773 to 5792
Compounds of the formula I.124 in which $R^c$ is as defined in Tables 5472 to 5492 and the combination of $R^1$ and $R^2$ for a compound corresponds in each case to one row of Table A.
Tables 5793 to 5812
Compounds of the formula I.125 in which $R^c$ is as defined in Tables 5472 to 5492 and the combination of $R^1$ and $R^2$ for a compound corresponds in each case to one row of Table A.
Tables 5813 to 5832
Compounds of the formula I.126 in which $R^c$ is as defined in Tables 5472 to 5492 and the combination of $R^1$ and $R^2$ for a compound corresponds in each case to one row of Table A.
Tables 5833 to 5852
Compounds of the formula I.127 in which $R^c$ is as defined in Tables 5472 to 5492 and the combination of $R^1$ and $R^2$ for a compound corresponds in each case to one row of Table A.
Tables 5853 to 5872
Compounds of the formula I.128 in which $R^c$ is as defined in Tables 5472 to 5492 and the combination of $R^1$ and $R^2$ for a compound corresponds in each case to one row of Table A.
Tables 5873 to 5892
Compounds of the formula I.129 in which $R^c$ is as defined in Tables 5472 to 5492 and the combination of $R^1$ and $R^2$ for a compound corresponds in each case to one row of Table A.
Tables 5893 to 5912
Compounds of the formula I.130 in which $R^c$ is as defined in Tables 5472 to 5492 and the combination of $R^1$ and $R^2$ for a compound corresponds in each case to one row of Table A.
Tables 5913 to 5932
Compounds of the formula I.131 in which $R^c$ is as defined in Tables 5472 to 5492 and the combination of $R^1$ and $R^2$ for a compound corresponds in each case to one row of Table A.
Tables 5933 to 5952
Compounds of the formula I.132 in which $R^c$ is as defined in Tables 5472 to 5492 and the combination of $R^1$ and $R^2$ for a compound corresponds in each case to one row of Table A.
Tables 5953 to 5972
Compounds of the formula I.133 in which $R^c$ is as defined in Tables 5472 to 5492 and the combination of $R^1$ and $R^2$ for a compound corresponds in each case to one row of Table A.
Tables 5973 to 5992
Compounds of the formula I.134 in which $R^c$ is as defined in Tables 5472 to 5492 and the combination of $R^1$ and $R^2$ for a compound corresponds in each case to one row of Table A.
Tables 5993 to 6012
Compounds of the formula I.135 in which $R^c$ is as defined in Tables 5472 to 5492 and the combination of $R^1$ and $R^2$ for a compound corresponds in each case to one row of Table A.
Tables 6013 to 6032
Compounds of the formula I.136 in which $R^c$ is as defined in Tables 5472 to 5492 and the combination of $R^1$ and $R^2$ for a compound corresponds in each case to one row of Table A.
Tables 6033 to 6052
Compounds of the formula I.137 in which $R^c$ is as defined in Tables 5472 to 5492 and the combination of $R^1$ and $R^2$ for a compound corresponds in each case to one row of Table A.
Tables 6053 to 6072
Compounds of the formula I.138 in which $R^c$ is as defined in Tables 5472 to 5492 and the combination of $R^1$ and $R^2$ for a compound corresponds in each case to one row of Table A.
Tables 6073 to 6092
Compounds of the formula I.139 in which $R^c$ is as defined in Tables 5472 to 5492 and the combination of $R^1$ and $R^2$ for a compound corresponds in each case to one row of Table A.
Tables 6093 to 6112
Compounds of the formula I.140 in which $R^c$ is as defined in Tables 5472 to 5492 and the combination of $R^1$ and $R^2$ for a compound corresponds in each case to one row of Table A.
Tables 6113 to 6132
Compounds of the formula I.141 in which $R^c$ is as defined in Tables 5472 to 5492 and the combination of $R^1$ and $R^2$ for a compound corresponds in each case to one row of Table A.
Tables 6133 to 6152
Compounds of the formula I.142 in which $R^c$ is as defined in Tables 5472 to 5492 and the combination of $R^1$ and $R^2$ for a compound corresponds in each case to one row of Table A.
Tables 6153 to 6172
Compounds of the formula I.143 in which $R^c$ is as defined in Tables 5472 to 5492 and the combination of $R^1$ and $R^2$ for a compound corresponds in each case to one row of Table A.
Tables 6173 to 6192
Compounds of the formula I.144 in which $R^c$ is as defined in Tables 5472 to 5492 and the combination of $R^1$ and $R^2$ for a compound corresponds in each case to one row of Table A.

Rings A

"#" marks the attachment point to the remainder of the molecule

-continued
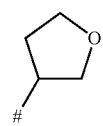
A-5
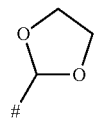
A-6
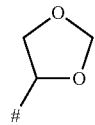
A-7
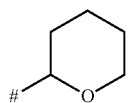
A-8
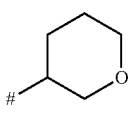
A-9
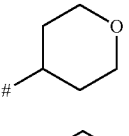
A-10
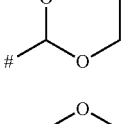
A-11
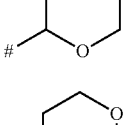
A-12
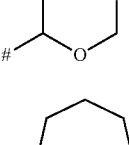
A-13
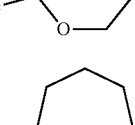
A-14
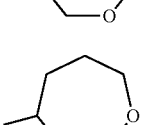
A-15
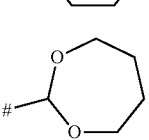
A-16
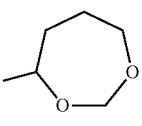
A-17
-continued
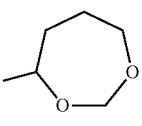
A-18
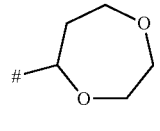
A-19
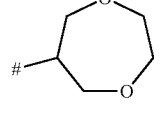
A-20
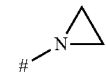
A-21
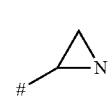
A-22
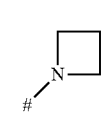
A-23
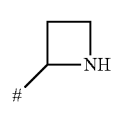
A-24
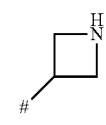
A-25
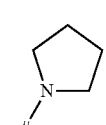
A-26
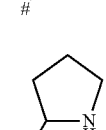
A-27
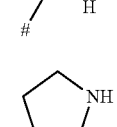
A-28
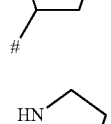
A-29
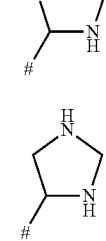
A-30

-continued

| | |
|---|---|
| A-31 | A-43 |
| A-32 | A-44 |
| A-33 | A-45 |
| A-34 | A-46 |
| A-35 | A-47 |
| A-36 | A-48 |
| A-37 | A-49 |
| A-38 | A-50 |
| A-39 | A-51 |
| A-40 | A-52 |
| A-41 | A-53 |
| A-42 | A-54 |

A-55 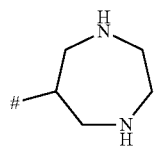
A-56 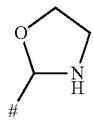
A-57 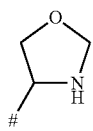
A-58 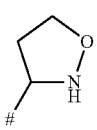
A-59 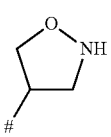
A-60 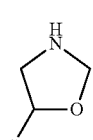
A-61 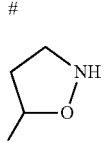
A-62 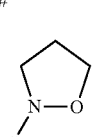
A-63 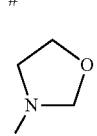
A-64 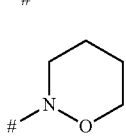
A-65 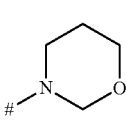
A-66 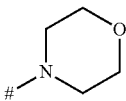
A-67 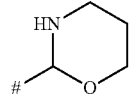
A-68 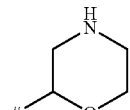
A-69 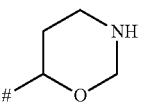
A-70 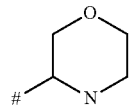
A-71 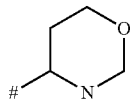
A-72 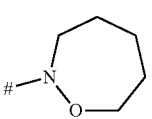
A-73 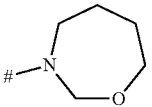
A-74 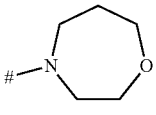
A-75 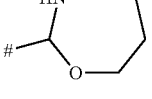
A-76 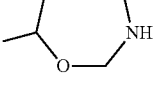
A-77 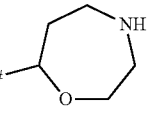
A-78 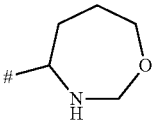

-continued
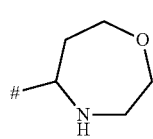
A-79
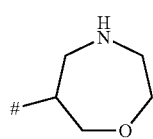
A-80
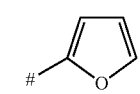
A-81
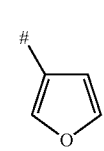
A-82
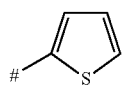
A-83
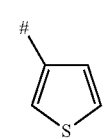
A-84
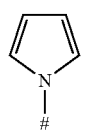
A-85
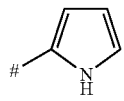
A-86
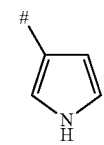
A-87
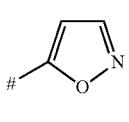
A-88
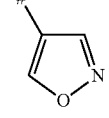
A-89
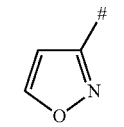
A-90
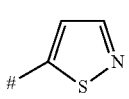
A-91
-continued
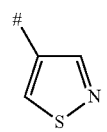
A-92
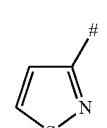
A-93
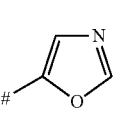
A-94
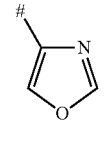
A-95
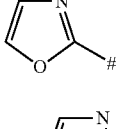
A-96
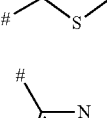
A-97
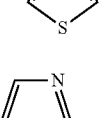
A-98
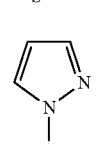
A-99
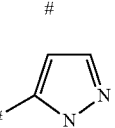
A-100
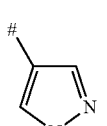
A-101
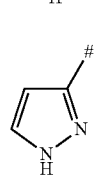
A-102
A-103

-continued

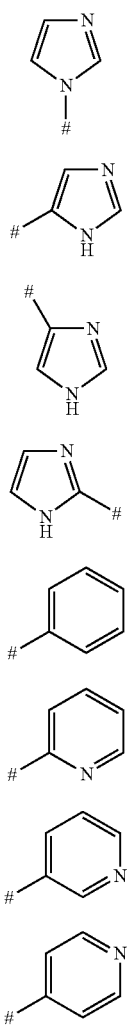

| | A-104 |
| | A-105 |
| | A-106 |
| | A-107 |
| | A-108 |
| | A-109 |
| | A-110 |
| | A-111 |

In Table A, the position of $R^1$ is characterized as follows:

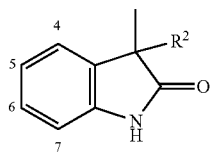

TABLE A

| No. | $R^2$ | $R^1$ |
| --- | --- | --- |
| A-1 | H | H |
| A-2 | H | 4-Cl |
| A-3 | H | 5-Cl |
| A-4 | H | 6-Cl |
| A-5 | H | 7-Cl |
| A-6 | H | 4-Br |
| A-7 | H | 5-Br |
| A-8 | H | 6-Br |
| A-9 | H | 7-Br |
| A-10 | H | 4-CN |
| A-11 | H | 5-CN |
| A-12 | H | 6-CN |

TABLE A-continued

| No. | $R^2$ | $R^1$ |
| --- | --- | --- |
| A-13 | H | 7-CN |
| A-14 | H | 4-OH |
| A-15 | H | 5-OH |
| A-16 | H | 6-OH |
| A-17 | H | 7-OH |
| A-18 | H | 4-methyl |
| A-19 | H | 5-methyl |
| A-20 | H | 6-methyl |
| A-21 | H | 7-methyl |
| A-22 | H | 4-ethyl |
| A-23 | H | 5-ethyl |
| A-24 | H | 6-ethyl |
| A-25 | H | 7-ethyl |
| A-26 | H | 4-propyl |
| A-27 | H | 5-propyl |
| A-28 | H | 6-propyl |
| A-29 | H | 7-propyl |
| A-30 | H | 4-isopropyl |
| A-31 | H | 5-isopropyl |
| A-32 | H | 6-isopropyl |
| A-33 | H | 7-isopropyl |
| A-34 | H | 4-hydroxymethyl |
| A-35 | H | 5-hydroxymethyl |
| A-36 | H | 6-hydroxymethyl |
| A-37 | H | 7-hydroxymethyl |
| A-38 | H | 4-(2-hydroxyethyl) |
| A-39 | H | 5-(2-hydroxyethyl) |
| A-40 | H | 6-(2-hydroxyethyl) |
| A-41 | H | 7-(2-hydroxyethyl) |
| A-42 | H | 4-(1-hydroxyethyl) |
| A-43 | H | 5-(1-hydroxyethyl) |
| A-44 | H | 6-(1-hydroxyethyl) |
| A-45 | H | 7-(1-hydroxyethyl) |
| A-46 | H | 4-(3-hydroxypropyl) |
| A-47 | H | 5-(3-hydroxypropyl) |
| A-48 | H | 6-(3-hydroxypropyl) |
| A-49 | H | 7-(3-hydroxypropyl) |
| A-50 | H | 4-(2-hydroxypropyl) |
| A-51 | H | 5-(2-hydroxypropyl) |
| A-52 | H | 6-(2-hydroxypropyl) |
| A-53 | H | 7-(2-hydroxypropyl) |
| A-54 | H | 4-(1-hydroxypropyl) |
| A-55 | H | 5-(1-hydroxypropyl) |
| A-56 | H | 6-(1-hydroxypropyl) |
| A-57 | H | 7-(1-hydroxypropyl) |
| A-58 | H | 4-aminomethyl |
| A-59 | H | 5-aminomethyl |
| A-60 | H | 6-aminomethyl |
| A-61 | H | 7-aminomethyl |
| A-62 | H | 4-(2-aminoethyl) |
| A-63 | H | 5-(2-aminoethyl) |
| A-64 | H | 6-(2-aminoethyl) |
| A-65 | H | 7-(2-aminoethyl) |
| A-66 | H | 4-(1-aminoethyl) |
| A-67 | H | 5-(1-aminoethyl) |
| A-68 | H | 6-(1-aminoethyl) |
| A-69 | H | 7-(1-aminoethyl) |
| A-70 | H | 4-(3-aminopropyl) |
| A-71 | H | 5-(3-aminopropyl) |
| A-72 | H | 6-(3-aminopropyl) |
| A-73 | H | 7-(3-aminopropyl) |
| A-74 | H | 4-(2-aminopropyl) |
| A-75 | H | 5-(2-aminopropyl) |
| A-76 | H | 6-(2-aminopropyl) |
| A-77 | H | 7-(2-aminopropyl) |
| A-78 | H | 4-(1-aminopropyl) |
| A-79 | H | 5-(1-aminopropyl) |
| A-80 | H | 6-(1-aminopropyl) |
| A-81 | H | 7-(1-aminopropyl) |
| A-82 | H | 4-COOH |
| A-83 | H | 5-COOH |
| A-84 | H | 6-COOH |
| A-85 | H | 7-COOH |
| A-86 | H | 4-COOCH$_3$ |
| A-87 | H | 5-COOCH$_3$ |
| A-88 | H | 6-COOCH$_3$ |
| A-89 | H | 7-COOCH$_3$ |
| A-90 | H | 4-COOCH$_2$CH$_3$ |

TABLE A-continued

| No. | R² | R¹ |
|---|---|---|
| A-91 | H | 5-COOCH₂CH₃ |
| A-92 | H | 6-COOCH₂CH₃ |
| A-93 | H | 7-COOCH₂CH₃ |
| A-94 | H | 4-COOCF₃ |
| A-95 | H | 5-COOCF₃ |
| A-96 | H | 6-COOCF₃ |
| A-97 | H | 7-COOCF₃ |
| A-98 | H | 4-CONH₂ |
| A-99 | H | 5-CONH₂ |
| A-100 | H | 6-CONH₂ |
| A-101 | H | 7-CONH₂ |
| A-102 | H | 4-CONHCH₃ |
| A-103 | H | 5-CONHCH₃ |
| A-104 | H | 6-CONHCH₃ |
| A-105 | H | 7-CONHCH₃ |
| A-106 | H | 4-CON(CH₃)₂ |
| A-107 | H | 5-CON(CH₃)₂ |
| A-108 | H | 6-CON(CH₃)₂ |
| A-109 | H | 7-CON(CH₃)₂ |
| A-110 | H | 4-CONHCH₂CH₃ |
| A-111 | H | 5-CONHCH₂CH₃ |
| A-112 | H | 6-CONHCH₂CH₃ |
| A-113 | H | 7-CONHCH₂CH₃ |
| A-114 | H | 4-CON(CH₂CH₃)₂ |
| A-115 | H | 5-CON(CH₂CH₃)₂ |
| A-116 | H | 6-CON(CH₂CH₃)₂ |
| A-117 | H | 7-CON(CH₂CH₃)₂ |
| A-118 | H | 4-A-1 |
| A-119 | H | 5-A-1 |
| A-120 | H | 6-A-1 |
| A-121 | H | 7-A-1 |
| A-122 | H | 4-A-2 |
| A-123 | H | 5-A-2 |
| A-124 | H | 6-A-2 |
| A-125 | H | 7-A-2 |
| A-126 | H | 4-A-3 |
| A-127 | H | 5-A-3 |
| A-128 | H | 6-A-3 |
| A-129 | H | 7-A-3 |
| A-130 | H | 4-A-4 |
| A-131 | H | 5-A-4 |
| A-132 | H | 6-A-4 |
| A-133 | H | 7-A-4 |
| A-134 | H | 4-A-5 |
| A-135 | H | 5-A-5 |
| A-136 | H | 6-A-5 |
| A-137 | H | 7-A-5 |
| A-138 | H | 4-A-6 |
| A-139 | H | 5-A-6 |
| A-140 | H | 6-A-6 |
| A-141 | H | 7-A-6 |
| A-142 | H | 4-A-7 |
| A-143 | H | 5-A-7 |
| A-144 | H | 6-A-7 |
| A-145 | H | 7-A-7 |
| A-146 | H | 4-A-8 |
| A-147 | H | 5-A-8 |
| A-148 | H | 6-A-8 |
| A-149 | H | 7-A-8 |
| A-150 | H | 4-A-9 |
| A-151 | H | 5-A-9 |
| A-152 | H | 6-A-9 |
| A-153 | H | 7-A-9 |
| A-154 | H | 4-A-10 |
| A-155 | H | 5-A-10 |
| A-156 | H | 6-A-10 |
| A-157 | H | 7-A-10 |
| A-158 | H | 4-A-11 |
| A-159 | H | 5-A-11 |
| A-160 | H | 6-A-11 |
| A-161 | H | 7-A-11 |
| A-162 | H | 4-A-12 |
| A-163 | H | 5-A-12 |
| A-164 | H | 6-A-12 |
| A-165 | H | 7-A-12 |
| A-166 | H | 4-A-13 |
| A-167 | H | 5-A-13 |
| A-168 | H | 6-A-13 |
| A-169 | H | 7-A-13 |
| A-170 | H | 4-A-14 |
| A-171 | H | 5-A-14 |
| A-172 | H | 6-A-14 |
| A-173 | H | 7-A-14 |
| A-174 | H | 4-A-15 |
| A-175 | H | 5-A-15 |
| A-176 | H | 6-A-15 |
| A-177 | H | 7-A-15 |
| A-178 | H | 4-A-16 |
| A-179 | H | 5-A-16 |
| A-180 | H | 6-A-16 |
| A-181 | H | 7-A-16 |
| A-182 | H | 4-A-17 |
| A-183 | H | 5-A-17 |
| A-184 | H | 6-A-17 |
| A-185 | H | 7-A-17 |
| A-186 | H | 4-A-18 |
| A-187 | H | 5-A-18 |
| A-188 | H | 6-A-18 |
| A-189 | H | 7-A-18 |
| A-190 | H | 4-A-19 |
| A-191 | H | 5-A-19 |
| A-192 | H | 6-A-19 |
| A-193 | H | 7-A-19 |
| A-194 | H | 4-A-20 |
| A-195 | H | 5-A-20 |
| A-196 | H | 6-A-20 |
| A-197 | H | 7-A-20 |
| A-198 | H | 4-A-21 |
| A-199 | H | 5-A-21 |
| A-200 | H | 6-A-21 |
| A-201 | H | 7-A-21 |
| A-202 | H | 4-A-22 |
| A-203 | H | 5-A-22 |
| A-204 | H | 6-A-22 |
| A-205 | H | 7-A-22 |
| A-206 | H | 4-A-23 |
| A-207 | H | 5-A-23 |
| A-208 | H | 6-A-23 |
| A-209 | H | 7-A-23 |
| A-210 | H | 4-A-24 |
| A-211 | H | 5-A-24 |
| A-212 | H | 6-A-24 |
| A-213 | H | 7-A-24 |
| A-214 | H | 4-A-25 |
| A-215 | H | 5-A-25 |
| A-216 | H | 6-A-25 |
| A-217 | H | 7-A-25 |
| A-218 | H | 4-A-26 |
| A-219 | H | 5-A-26 |
| A-220 | H | 6-A-26 |
| A-221 | H | 7-A-26 |
| A-222 | H | 4-A-27 |
| A-223 | H | 5-A-27 |
| A-224 | H | 6-A-27 |
| A-225 | H | 7-A-27 |
| A-226 | H | 4-A-28 |
| A-227 | H | 5-A-28 |
| A-228 | H | 6-A-28 |
| A-229 | H | 7-A-28 |
| A-230 | H | 4-A-29 |
| A-231 | H | 5-A-29 |
| A-232 | H | 6-A-29 |
| A-233 | H | 7-A-29 |
| A-234 | H | 4-A-30 |
| A-235 | H | 5-A-30 |
| A-236 | H | 6-A-30 |
| A-237 | H | 7-A-30 |
| A-238 | H | 4-A-31 |
| A-239 | H | 5-A-31 |
| A-240 | H | 6-A-31 |
| A-241 | H | 7-A-31 |
| A-242 | H | 4-A-32 |
| A-243 | H | 5-A-32 |
| A-244 | H | 6-A-32 |
| A-245 | H | 7-A-32 |
| A-246 | H | 4-A-33 |

TABLE A-continued

| No. | R² | R¹ |
|---|---|---|
| A-247 | H | 5-A-33 |
| A-248 | H | 6-A-33 |
| A-249 | H | 7-A-33 |
| A-250 | H | 4-A-34 |
| A-251 | H | 5-A-34 |
| A-252 | H | 6-A-34 |
| A-253 | H | 7-A-34 |
| A-254 | H | 4-A-35 |
| A-255 | H | 5-A-35 |
| A-256 | H | 6-A-35 |
| A-257 | H | 7-A-35 |
| A-258 | H | 4-A-36 |
| A-259 | H | 5-A-36 |
| A-260 | H | 6-A-36 |
| A-261 | H | 7-A-36 |
| A-262 | H | 4-A-37 |
| A-263 | H | 5-A-37 |
| A-264 | H | 6-A-37 |
| A-265 | H | 7-A-37 |
| A-266 | H | 4-A-38 |
| A-267 | H | 5-A-38 |
| A-268 | H | 6-A-38 |
| A-269 | H | 7-A-38 |
| A-270 | H | 4-A-39 |
| A-271 | H | 5-A-39 |
| A-272 | H | 6-A-39 |
| A-273 | H | 7-A-39 |
| A-274 | H | 4-A-40 |
| A-275 | H | 5-A-40 |
| A-276 | H | 6-A-40 |
| A-277 | H | 7-A-40 |
| A-278 | H | 4-A-41 |
| A-279 | H | 5-A-41 |
| A-280 | H | 6-A-41 |
| A-281 | H | 7-A-41 |
| A-282 | H | 4-A-42 |
| A-283 | H | 5-A-42 |
| A-284 | H | 6-A-42 |
| A-285 | H | 7-A-42 |
| A-286 | H | 4-A-43 |
| A-287 | H | 5-A-43 |
| A-288 | H | 6-A-43 |
| A-289 | H | 7-A-43 |
| A-290 | H | 4-A-44 |
| A-291 | H | 5-A-44 |
| A-292 | H | 6-A-44 |
| A-293 | H | 7-A-44 |
| A-294 | H | 4-A-45 |
| A-295 | H | 5-A-45 |
| A-296 | H | 6-A-45 |
| A-297 | H | 7-A-45 |
| A-298 | H | 4-A-46 |
| A-299 | H | 5-A-46 |
| A-300 | H | 6-A-46 |
| A-301 | H | 7-A-46 |
| A-302 | H | 4-A-47 |
| A-303 | H | 5-A-47 |
| A-304 | H | 6-A-47 |
| A-305 | H | 7-A-47 |
| A-306 | H | 4-A-48 |
| A-307 | H | 5-A-48 |
| A-308 | H | 6-A-48 |
| A-309 | H | 7-A-48 |
| A-310 | H | 4-A-49 |
| A-311 | H | 5-A-49 |
| A-312 | H | 6-A-49 |
| A-313 | H | 7-A-49 |
| A-314 | H | 4-A-50 |
| A-315 | H | 5-A-50 |
| A-316 | H | 6-A-50 |
| A-317 | H | 7-A-50 |
| A-318 | H | 4-A-51 |
| A-319 | H | 5-A-51 |
| A-320 | H | 6-A-51 |
| A-321 | H | 7-A-51 |
| A-322 | H | 4-A-52 |
| A-323 | H | 5-A-52 |
| A-324 | H | 6-A-52 |
| A-325 | H | 7-A-52 |
| A-326 | H | 4-A-53 |
| A-327 | H | 5-A-53 |
| A-328 | H | 6-A-53 |
| A-329 | H | 7-A-53 |
| A-330 | H | 4-A-54 |
| A-331 | H | 5-A-54 |
| A-332 | H | 6-A-54 |
| A-333 | H | 7-A-54 |
| A-334 | H | 4-A-55 |
| A-335 | H | 5-A-55 |
| A-336 | H | 6-A-55 |
| A-337 | H | 7-A-55 |
| A-338 | H | 4-A-56 |
| A-339 | H | 5-A-56 |
| A-340 | H | 6-A-56 |
| A-341 | H | 7-A-56 |
| A-342 | H | 4-A-57 |
| A-343 | H | 5-A-57 |
| A-344 | H | 6-A-57 |
| A-345 | H | 7-A-57 |
| A-346 | H | 4-A-58 |
| A-347 | H | 5-A-58 |
| A-348 | H | 6-A-58 |
| A-349 | H | 7-A-58 |
| A-350 | H | 4-A-59 |
| A-351 | H | 5-A-59 |
| A-352 | H | 6-A-59 |
| A-353 | H | 7-A-59 |
| A-354 | H | 4-A-60 |
| A-355 | H | 5-A-60 |
| A-356 | H | 6-A-60 |
| A-357 | H | 7-A-60 |
| A-358 | H | 4-A-61 |
| A-359 | H | 5-A-61 |
| A-360 | H | 6-A-61 |
| A-361 | H | 7-A-61 |
| A-362 | H | 4-A-62 |
| A-363 | H | 5-A-62 |
| A-364 | H | 6-A-62 |
| A-365 | H | 7-A-62 |
| A-366 | H | 4-A-63 |
| A-367 | H | 5-A-63 |
| A-368 | H | 6-A-63 |
| A-369 | H | 7-A-63 |
| A-370 | H | 4-A-64 |
| A-371 | H | 5-A-64 |
| A-372 | H | 6-A-64 |
| A-373 | H | 7-A-64 |
| A-374 | H | 4-A-65 |
| A-375 | H | 5-A-65 |
| A-376 | H | 6-A-65 |
| A-377 | H | 7-A-65 |
| A-378 | H | 4-A-66 |
| A-379 | H | 5-A-66 |
| A-380 | H | 6-A-66 |
| A-381 | H | 7-A-66 |
| A-382 | H | 4-A-67 |
| A-383 | H | 5-A-67 |
| A-384 | H | 6-A-67 |
| A-385 | H | 7-A-67 |
| A-386 | H | 4-A-68 |
| A-387 | H | 5-A-68 |
| A-388 | H | 6-A-68 |
| A-389 | H | 7-A-68 |
| A-390 | H | 4-A-69 |
| A-391 | H | 5-A-69 |
| A-392 | H | 6-A-69 |
| A-393 | H | 7-A-69 |
| A-394 | H | 4-A-70 |
| A-395 | H | 5-A-70 |
| A-396 | H | 6-A-70 |
| A-397 | H | 7-A-70 |
| A-398 | H | 4-A-71 |
| A-399 | H | 5-A-71 |
| A-400 | H | 6-A-71 |
| A-401 | H | 7-A-71 |
| A-402 | H | 4-A-72 |

TABLE A-continued

| No. | R² | R¹ |
|---|---|---|
| A-403 | H | 5-A-72 |
| A-404 | H | 6-A-72 |
| A-405 | H | 7-A-72 |
| A-406 | H | 4-A-73 |
| A-407 | H | 5-A-73 |
| A-408 | H | 6-A-73 |
| A-409 | H | 7-A-73 |
| A-410 | H | 4-A-74 |
| A-411 | H | 5-A-74 |
| A-412 | H | 6-A-74 |
| A-413 | H | 7-A-74 |
| A-414 | H | 4-A-75 |
| A-415 | H | 5-A-75 |
| A-416 | H | 6-A-75 |
| A-417 | H | 7-A-75 |
| A-418 | H | 4-A-76 |
| A-419 | H | 5-A-76 |
| A-420 | H | 6-A-76 |
| A-421 | H | 7-A-76 |
| A-422 | H | 4-A-77 |
| A-423 | H | 5-A-77 |
| A-424 | H | 6-A-77 |
| A-425 | H | 7-A-77 |
| A-426 | H | 4-A-78 |
| A-427 | H | 5-A-78 |
| A-428 | H | 6-A-78 |
| A-429 | H | 7-A-78 |
| A-430 | H | 4-A-79 |
| A-431 | H | 5-A-79 |
| A-432 | H | 6-A-79 |
| A-433 | H | 7-A-79 |
| A-434 | H | 4-A-80 |
| A-435 | H | 5-A-80 |
| A-436 | H | 6-A-80 |
| A-437 | H | 7-A-80 |
| A-438 | H | 4-A-81 |
| A-439 | H | 5-A-81 |
| A-440 | H | 6-A-81 |
| A-441 | H | 7-A-81 |
| A-442 | H | 4-A-82 |
| A-443 | H | 5-A-82 |
| A-444 | H | 6-A-82 |
| A-445 | H | 7-A-82 |
| A-446 | H | 4-A-83 |
| A-447 | H | 5-A-83 |
| A-448 | H | 6-A-83 |
| A-449 | H | 7-A-83 |
| A-450 | H | 4-A-84 |
| A-451 | H | 5-A-84 |
| A-452 | H | 6-A-84 |
| A-453 | H | 7-A-84 |
| A-454 | H | 4-A-85 |
| A-455 | H | 5-A-85 |
| A-456 | H | 6-A-85 |
| A-457 | H | 7-A-85 |
| A-458 | H | 4-A-86 |
| A-459 | H | 5-A-86 |
| A-460 | H | 6-A-86 |
| A-461 | H | 7-A-86 |
| A-462 | H | 4-A-87 |
| A-463 | H | 5-A-87 |
| A-464 | H | 6-A-87 |
| A-465 | H | 7-A-87 |
| A-466 | H | 4-A-88 |
| A-467 | H | 5-A-88 |
| A-468 | H | 6-A-88 |
| A-469 | H | 7-A-88 |
| A-470 | H | 4-A-89 |
| A-471 | H | 5-A-89 |
| A-472 | H | 6-A-89 |
| A-473 | H | 7-A-89 |
| A-474 | H | 4-A-90 |
| A-475 | H | 5-A-90 |
| A-476 | H | 6-A-90 |
| A-477 | H | 7-A-90 |
| A-478 | H | 4-A-91 |
| A-479 | H | 5-A-91 |
| A-480 | H | 6-A-91 |
| A-481 | H | 7-A-91 |
| A-482 | H | 4-A-92 |
| A-483 | H | 5-A-92 |
| A-484 | H | 6-A-92 |
| A-485 | H | 7-A-92 |
| A-486 | H | 4-A-93 |
| A-487 | H | 5-A-93 |
| A-488 | H | 6-A-93 |
| A-489 | H | 7-A-93 |
| A-490 | H | 4-A-94 |
| A-491 | H | 5-A-94 |
| A-492 | H | 6-A-94 |
| A-493 | H | 7-A-94 |
| A-494 | H | 4-A-95 |
| A-495 | H | 5-A-95 |
| A-496 | H | 6-A-95 |
| A-497 | H | 7-A-95 |
| A-498 | H | 4-A-96 |
| A-499 | H | 5-A-96 |
| A-500 | H | 6-A-96 |
| A-501 | H | 7-A-96 |
| A-502 | H | 4-A-97 |
| A-503 | H | 5-A-97 |
| A-504 | H | 6-A-97 |
| A-505 | H | 7-A-97 |
| A-506 | H | 4-A-98 |
| A-507 | H | 5-A-98 |
| A-508 | H | 6-A-98 |
| A-509 | H | 7-A-98 |
| A-510 | H | 4-A-99 |
| A-511 | H | 5-A-99 |
| A-512 | H | 6-A-99 |
| A-513 | H | 7-A-99 |
| A-514 | H | 4-A-100 |
| A-515 | H | 5-A-100 |
| A-516 | H | 6-A-100 |
| A-517 | H | 7-A-100 |
| A-518 | H | 4-A-101 |
| A-519 | H | 5-A-101 |
| A-520 | H | 6-A-101 |
| A-521 | H | 7-A-101 |
| A-522 | H | 4-A-102 |
| A-523 | H | 5-A-102 |
| A-524 | H | 6-A-102 |
| A-525 | H | 7-A-102 |
| A-526 | H | 4-A-103 |
| A-527 | H | 5-A-103 |
| A-528 | H | 6-A-103 |
| A-529 | H | 7-A-103 |
| A-530 | H | 4-A-104 |
| A-531 | H | 5-A-104 |
| A-532 | H | 6-A-104 |
| A-533 | H | 7-A-104 |
| A-534 | H | 4-A-104 |
| A-535 | H | 5-A-104 |
| A-536 | H | 6-A-104 |
| A-537 | H | 7-A-104 |
| A-538 | H | 4-A-105 |
| A-539 | H | 5-A-105 |
| A-540 | H | 6-A-105 |
| A-541 | H | 7-A-105 |
| A-542 | H | 4-A-106 |
| A-543 | H | 5-A-106 |
| A-544 | H | 6-A-106 |
| A-545 | H | 7-A-106 |
| A-546 | H | 4-A-107 |
| A-547 | H | 5-A-107 |
| A-548 | H | 6-A-107 |
| A-549 | H | 7-A-107 |
| A-550 | H | 4-A-108 |
| A-551 | H | 5-A-108 |
| A-552 | H | 6-A-108 |
| A-553 | H | 7-A-108 |
| A-554 | H | 4-A-109 |
| A-555 | H | 5-A-109 |
| A-556 | H | 6-A-109 |
| A-557 | H | 7-A-109 |
| A-558 | H | 4-A-110 |

TABLE A-continued

| No. | R² | R¹ |
|---|---|---|
| A-559 | H | 5-A-110 |
| A-560 | H | 6-A-110 |
| A-561 | H | 7-A-110 |
| A-562 | H | 4-A-111 |
| A-563 | H | 5-A-111 |
| A-564 | H | 6-A-111 |
| A-565 | H | 7-A-111 |
| A-566 | F | H |
| A-567 | F | 4-Cl |
| A-568 | F | 5-Cl |
| A-569 | F | 6-Cl |
| A-570 | F | 7-Cl |
| A-571 | F | 4-Br |
| A-572 | F | 5-Br |
| A-573 | F | 6-Br |
| A-574 | F | 7-Br |
| A-575 | F | 4-CN |
| A-576 | F | 5-CN |
| A-577 | F | 6-CN |
| A-578 | F | 7-CN |
| A-579 | F | 4-OH |
| A-580 | F | 5-OH |
| A-581 | F | 6-OH |
| A-582 | F | 7-OH |
| A-583 | F | 4-methyl |
| A-584 | F | 5-methyl |
| A-585 | F | 6-methyl |
| A-586 | F | 7-methyl |
| A-587 | F | 4-ethyl |
| A-588 | F | 5-ethyl |
| A-589 | F | 6-ethyl |
| A-590 | F | 7-ethyl |
| A-591 | F | 4-propyl |
| A-592 | F | 5-propyl |
| A-593 | F | 6-propyl |
| A-594 | F | 7-propyl |
| A-595 | F | 4-isopropyl |
| A-596 | F | 5-isopropyl |
| A-597 | F | 6-isopropyl |
| A-598 | F | 7-isopropyl |
| A-599 | F | 4-hydroxymethyl |
| A-600 | F | 5-hydroxymethyl |
| A-601 | F | 6-hydroxymethyl |
| A-602 | F | 7-hydroxymethyl |
| A-603 | F | 4-(2-hydroxyethyl) |
| A-604 | F | 5-(2-hydroxyethyl) |
| A-605 | F | 6-(2-hydroxyethyl) |
| A-606 | F | 7-(2-hydroxyethyl) |
| A-607 | F | 4-(1-hydroxyethyl) |
| A-608 | F | 5-(1-hydroxyethyl) |
| A-609 | F | 6-(1-hydroxyethyl) |
| A-610 | F | 7-(1-hydroxyethyl) |
| A-611 | F | 4-(3-hydroxypropyl) |
| A-612 | F | 5-(3-hydroxypropyl) |
| A-613 | F | 6-(3-hydroxypropyl) |
| A-614 | F | 7-(3-hydroxypropyl) |
| A-615 | F | 4-(2-hydroxypropyl) |
| A-616 | F | 5-(2-hydroxypropyl) |
| A-617 | F | 6-(2-hydroxypropyl) |
| A-618 | F | 7-(2-hydroxypropyl) |
| A-619 | F | 4-(1-hydroxypropyl) |
| A-620 | F | 5-(1-hydroxypropyl) |
| A-621 | F | 6-(1-hydroxypropyl) |
| A-622 | F | 7-(1-hydroxypropyl) |
| A-623 | F | 4-aminomethyl |
| A-624 | F | 5-aminomethyl |
| A-625 | F | 6-aminomethyl |
| A-626 | F | 7-aminomethyl |
| A-627 | F | 4-(2-aminoethyl) |
| A-628 | F | 5-(2-aminoethyl) |
| A-629 | F | 6-(2-aminoethyl) |
| A-630 | F | 7-(2-aminoethyl) |
| A-631 | F | 4-(1-aminoethyl) |
| A-632 | F | 5-(1-aminoethyl) |
| A-633 | F | 6-(1-aminoethyl) |
| A-634 | F | 7-(1-aminoethyl) |
| A-635 | F | 4-(3-aminopropyl) |
| A-636 | F | 5-(3-aminopropyl) |
| A-637 | F | 6-(3-aminopropyl) |
| A-638 | F | 7-(3-aminopropyl) |
| A-639 | F | 4-(2-aminopropyl) |
| A-640 | F | 5-(2-aminopropyl) |
| A-641 | F | 6-(2-aminopropyl) |
| A-642 | F | 7-(2-aminopropyl) |
| A-643 | F | 4-(1-aminopropyl) |
| A-644 | F | 5-(1-aminopropyl) |
| A-645 | F | 6-(1-aminopropyl) |
| A-646 | F | 7-(1-aminopropyl) |
| A-647 | F | 4-COOH |
| A-648 | F | 5-COOH |
| A-649 | F | 6-COOH |
| A-650 | F | 7-COOH |
| A-651 | F | 4-COOCH₃ |
| A-652 | F | 5-COOCH₃ |
| A-653 | F | 6-COOCH₃ |
| A-654 | F | 7-COOCH₃ |
| A-655 | F | 4-COOCH₂CH₃ |
| A-656 | F | 5-COOCH₂CH₃ |
| A-657 | F | 6-COOCH₂CH₃ |
| A-658 | F | 7-COOCH₂CH₃ |
| A-659 | F | 4-COOCF₃ |
| A-660 | F | 5-COOCF₃ |
| A-661 | F | 6-COOCF₃ |
| A-662 | F | 7-COOCF₃ |
| A-663 | F | 4-CONH₂ |
| A-664 | F | 5-CONH₂ |
| A-665 | F | 6-CONH₂ |
| A-666 | F | 7-CONH₂ |
| A-667 | F | 4-CONHCH₃ |
| A-668 | F | 5-CONHCH₃ |
| A-669 | F | 6-CONHCH₃ |
| A-670 | F | 7-CONHCH₃ |
| A-671 | F | 4-CON(CH₃)₂ |
| A-672 | F | 5-CON(CH₃)₂ |
| A-673 | F | 6-CON(CH₃)₂ |
| A-674 | F | 7-CON(CH₃)₂ |
| A-675 | F | 4-CONHCH₂CH₃ |
| A-676 | F | 5-CONHCH₂CH₃ |
| A-677 | F | 6-CONHCH₂CH₃ |
| A-678 | F | 7-CONHCH₂CH₃ |
| A-679 | F | 4-CON(CH₂CH₃)₂ |
| A-680 | F | 5-CON(CH₂CH₃)₂ |
| A-681 | F | 6-CON(CH₂CH₃)₂ |
| A-682 | F | 7-CON(CH₂CH₃)₂ |
| A-683 | F | 4-A-1 |
| A-684 | F | 5-A-1 |
| A-685 | F | 6-A-1 |
| A-686 | F | 7-A-1 |
| A-687 | F | 4-A-2 |
| A-688 | F | 5-A-2 |
| A-689 | F | 6-A-2 |
| A-690 | F | 7-A-2 |
| A-691 | F | 4-A-3 |
| A-692 | F | 5-A-3 |
| A-693 | F | 6-A-3 |
| A-694 | F | 7-A-3 |
| A-695 | F | 4-A-4 |
| A-696 | F | 5-A-4 |
| A-697 | F | 6-A-4 |
| A-698 | F | 7-A-4 |
| A-699 | F | 4-A-5 |
| A-700 | F | 5-A-5 |
| A-701 | F | 6-A-5 |
| A-702 | F | 7-A-5 |
| A-703 | F | 4-A-6 |
| A-704 | F | 5-A-6 |
| A-705 | F | 6-A-6 |
| A-706 | F | 7-A-6 |
| A-707 | F | 4-A-7 |
| A-708 | F | 5-A-7 |
| A-709 | F | 6-A-7 |
| A-710 | F | 7-A-7 |
| A-711 | F | 4-A-8 |
| A-712 | F | 5-A-8 |
| A-713 | F | 6-A-8 |
| A-714 | F | 7-A-8 |

TABLE A-continued

| No. | R² | R¹ |
|---|---|---|
| A-715 | F | 4-A-9 |
| A-716 | F | 5-A-9 |
| A-717 | F | 6-A-9 |
| A-718 | F | 7-A-9 |
| A-719 | F | 4-A-10 |
| A-720 | F | 5-A-10 |
| A-721 | F | 6-A-10 |
| A-722 | F | 7-A-10 |
| A-723 | F | 4-A-11 |
| A-724 | F | 5-A-11 |
| A-725 | F | 6-A-11 |
| A-726 | F | 7-A-11 |
| A-727 | F | 4-A-12 |
| A-728 | F | 5-A-12 |
| A-729 | F | 6-A-12 |
| A-730 | F | 7-A-12 |
| A-731 | F | 4-A-13 |
| A-732 | F | 5-A-13 |
| A-733 | F | 6-A-13 |
| A-734 | F | 7-A-13 |
| A-735 | F | 4-A-14 |
| A-736 | F | 5-A-14 |
| A-737 | F | 6-A-14 |
| A-738 | F | 7-A-14 |
| A-739 | F | 4-A-15 |
| A-740 | F | 5-A-15 |
| A-741 | F | 6-A-15 |
| A-742 | F | 7-A-15 |
| A-743 | F | 4-A-16 |
| A-744 | F | 5-A-16 |
| A-745 | F | 6-A-16 |
| A-746 | F | 7-A-16 |
| A-747 | F | 4-A-17 |
| A-748 | F | 5-A-17 |
| A-749 | F | 6-A-17 |
| A-750 | F | 7-A-17 |
| A-751 | F | 4-A-18 |
| A-752 | F | 5-A-18 |
| A-753 | F | 6-A-18 |
| A-754 | F | 7-A-18 |
| A-755 | F | 4-A-19 |
| A-756 | F | 5-A-19 |
| A-757 | F | 6-A-19 |
| A-758 | F | 7-A-19 |
| A-759 | F | 4-A-20 |
| A-760 | F | 5-A-20 |
| A-761 | F | 6-A-20 |
| A-762 | F | 7-A-20 |
| A-763 | F | 4-A-21 |
| A-764 | F | 5-A-21 |
| A-765 | F | 6-A-21 |
| A-766 | F | 7-A-21 |
| A-767 | F | 4-A-22 |
| A-768 | F | 5-A-22 |
| A-769 | F | 6-A-22 |
| A-770 | F | 7-A-22 |
| A-771 | F | 4-A-23 |
| A-772 | F | 5-A-23 |
| A-773 | F | 6-A-23 |
| A-774 | F | 7-A-23 |
| A-775 | F | 4-A-24 |
| A-776 | F | 5-A-24 |
| A-777 | F | 6-A-24 |
| A-778 | F | 7-A-24 |
| A-779 | F | 4-A-25 |
| A-780 | F | 5-A-25 |
| A-781 | F | 6-A-25 |
| A-782 | F | 7-A-25 |
| A-783 | F | 4-A-26 |
| A-784 | F | 5-A-26 |
| A-785 | F | 6-A-26 |
| A-786 | F | 7-A-26 |
| A-787 | F | 4-A-27 |
| A-788 | F | 5-A-27 |
| A-789 | F | 6-A-27 |
| A-790 | F | 7-A-27 |
| A-791 | F | 4-A-28 |
| A-792 | F | 5-A-28 |
| A-793 | F | 6-A-28 |
| A-794 | F | 7-A-28 |
| A-795 | F | 4-A-29 |
| A-796 | F | 5-A-29 |
| A-797 | F | 6-A-29 |
| A-798 | F | 7-A-29 |
| A-799 | F | 4-A-30 |
| A-800 | F | 5-A-30 |
| A-801 | F | 6-A-30 |
| A-802 | F | 7-A-30 |
| A-803 | F | 4-A-31 |
| A-804 | F | 5-A-31 |
| A-805 | F | 6-A-31 |
| A-806 | F | 7-A-31 |
| A-807 | F | 4-A-32 |
| A-808 | F | 5-A-32 |
| A-809 | F | 6-A-32 |
| A-810 | F | 7-A-32 |
| A-811 | F | 4-A-33 |
| A-812 | F | 5-A-33 |
| A-813 | F | 6-A-33 |
| A-814 | F | 7-A-33 |
| A-815 | F | 4-A-34 |
| A-816 | F | 5-A-34 |
| A-817 | F | 6-A-34 |
| A-818 | F | 7-A-34 |
| A-819 | F | 4-A-35 |
| A-820 | F | 5-A-35 |
| A-821 | F | 6-A-35 |
| A-822 | F | 7-A-35 |
| A-823 | F | 4-A-36 |
| A-824 | F | 5-A-36 |
| A-825 | F | 6-A-36 |
| A-826 | F | 7-A-36 |
| A-827 | F | 4-A-37 |
| A-828 | F | 5-A-37 |
| A-829 | F | 6-A-37 |
| A-830 | F | 7-A-37 |
| A-831 | F | 4-A-38 |
| A-832 | F | 5-A-38 |
| A-833 | F | 6-A-38 |
| A-834 | F | 7-A-38 |
| A-835 | F | 4-A-39 |
| A-836 | F | 5-A-39 |
| A-837 | F | 6-A-39 |
| A-838 | F | 7-A-39 |
| A-839 | F | 4-A-40 |
| A-840 | F | 5-A-40 |
| A-841 | F | 6-A-40 |
| A-842 | F | 7-A-40 |
| A-843 | F | 4-A-41 |
| A-844 | F | 5-A-41 |
| A-845 | F | 6-A-41 |
| A-846 | F | 7-A-41 |
| A-847 | F | 4-A-42 |
| A-848 | F | 5-A-42 |
| A-849 | F | 6-A-42 |
| A-850 | F | 7-A-42 |
| A-851 | F | 4-A-43 |
| A-852 | F | 5-A-43 |
| A-853 | F | 6-A-43 |
| A-854 | F | 7-A-43 |
| A-855 | F | 4-A-44 |
| A-856 | F | 5-A-44 |
| A-857 | F | 6-A-44 |
| A-858 | F | 7-A-44 |
| A-859 | F | 4-A-45 |
| A-860 | F | 5-A-45 |
| A-861 | F | 6-A-45 |
| A-862 | F | 7-A-45 |
| A-863 | F | 4-A-46 |
| A-864 | F | 5-A-46 |
| A-865 | F | 6-A-46 |
| A-866 | F | 7-A-46 |
| A-867 | F | 4-A-47 |
| A-868 | F | 5-A-47 |
| A-869 | F | 6-A-47 |
| A-870 | F | 7-A-47 |

TABLE A-continued

| No. | R² | R¹ |
|---|---|---|
| A-871 | F | 4-A-48 |
| A-872 | F | 5-A-48 |
| A-873 | F | 6-A-48 |
| A-874 | F | 7-A-48 |
| A-875 | F | 4-A-49 |
| A-876 | F | 5-A-49 |
| A-877 | F | 6-A-49 |
| A-878 | F | 7-A-49 |
| A-879 | F | 4-A-50 |
| A-880 | F | 5-A-50 |
| A-881 | F | 6-A-50 |
| A-882 | F | 7-A-50 |
| A-883 | F | 4-A-51 |
| A-884 | F | 5-A-51 |
| A-885 | F | 6-A-51 |
| A-886 | F | 7-A-51 |
| A-887 | F | 4-A-52 |
| A-888 | F | 5-A-52 |
| A-889 | F | 6-A-52 |
| A-890 | F | 7-A-52 |
| A-891 | F | 4-A-53 |
| A-892 | F | 5-A-53 |
| A-893 | F | 6-A-53 |
| A-894 | F | 7-A-53 |
| A-895 | F | 4-A-54 |
| A-896 | F | 5-A-54 |
| A-897 | F | 6-A-54 |
| A-898 | F | 7-A-54 |
| A-899 | F | 4-A-55 |
| A-900 | F | 5-A-55 |
| A-901 | F | 6-A-55 |
| A-902 | F | 7-A-55 |
| A-903 | F | 4-A-56 |
| A-904 | F | 5-A-56 |
| A-905 | F | 6-A-56 |
| A-906 | F | 7-A-56 |
| A-907 | F | 4-A-57 |
| A-908 | F | 5-A-57 |
| A-909 | F | 6-A-57 |
| A-910 | F | 7-A-57 |
| A-911 | F | 4-A-58 |
| A-912 | F | 5-A-58 |
| A-913 | F | 6-A-58 |
| A-914 | F | 7-A-58 |
| A-915 | F | 4-A-59 |
| A-916 | F | 5-A-59 |
| A-917 | F | 6-A-59 |
| A-918 | F | 7-A-59 |
| A-919 | F | 4-A-60 |
| A-920 | F | 5-A-60 |
| A-921 | F | 6-A-60 |
| A-922 | F | 7-A-60 |
| A-923 | F | 4-A-61 |
| A-924 | F | 5-A-61 |
| A-925 | F | 6-A-61 |
| A-926 | F | 7-A-61 |
| A-927 | F | 4-A-62 |
| A-928 | F | 5-A-62 |
| A-929 | F | 6-A-62 |
| A-930 | F | 7-A-62 |
| A-931 | F | 4-A-63 |
| A-932 | F | 5-A-63 |
| A-933 | F | 6-A-63 |
| A-934 | F | 7-A-63 |
| A-935 | F | 4-A-64 |
| A-936 | F | 5-A-64 |
| A-937 | F | 6-A-64 |
| A-938 | F | 7-A-64 |
| A-939 | F | 4-A-65 |
| A-940 | F | 5-A-65 |
| A-941 | F | 6-A-65 |
| A-942 | F | 7-A-65 |
| A-943 | F | 4-A-66 |
| A-944 | F | 5-A-66 |
| A-945 | F | 6-A-66 |
| A-946 | F | 7-A-66 |
| A-947 | F | 4-A-67 |
| A-948 | F | 5-A-67 |
| A-949 | F | 6-A-67 |
| A-950 | F | 7-A-67 |
| A-951 | F | 4-A-68 |
| A-952 | F | 5-A-68 |
| A-953 | F | 6-A-68 |
| A-954 | F | 7-A-68 |
| A-955 | F | 4-A-69 |
| A-956 | F | 5-A-69 |
| A-957 | F | 6-A-69 |
| A-958 | F | 7-A-69 |
| A-959 | F | 4-A-70 |
| A-960 | F | 5-A-70 |
| A-961 | F | 6-A-70 |
| A-962 | F | 7-A-70 |
| A-963 | F | 4-A-71 |
| A-964 | F | 5-A-71 |
| A-965 | F | 6-A-71 |
| A-966 | F | 7-A-71 |
| A-967 | F | 4-A-72 |
| A-968 | F | 5-A-72 |
| A-969 | F | 6-A-72 |
| A-970 | F | 7-A-72 |
| A-971 | F | 4-A-73 |
| A-972 | F | 5-A-73 |
| A-973 | F | 6-A-73 |
| A-974 | F | 7-A-73 |
| A-975 | F | 4-A-74 |
| A-976 | F | 5-A-74 |
| A-977 | F | 6-A-74 |
| A-978 | F | 7-A-74 |
| A-979 | F | 4-A-75 |
| A-980 | F | 5-A-75 |
| A-981 | F | 6-A-75 |
| A-982 | F | 7-A-75 |
| A-983 | F | 4-A-76 |
| A-984 | F | 5-A-76 |
| A-985 | F | 6-A-76 |
| A-986 | F | 7-A-76 |
| A-987 | F | 4-A-77 |
| A-988 | F | 5-A-77 |
| A-989 | F | 6-A-77 |
| A-990 | F | 7-A-77 |
| A-991 | F | 4-A-78 |
| A-992 | F | 5-A-78 |
| A-993 | F | 6-A-78 |
| A-994 | F | 7-A-78 |
| A-995 | F | 4-A-79 |
| A-996 | F | 5-A-79 |
| A-997 | F | 6-A-79 |
| A-998 | F | 7-A-79 |
| A-999 | F | 4-A-80 |
| A-1000 | F | 5-A-80 |
| A-1001 | F | 6-A-80 |
| A-1002 | F | 7-A-80 |
| A-1003 | F | 4-A-81 |
| A-1004 | F | 5-A-81 |
| A-1005 | F | 6-A-81 |
| A-1006 | F | 7-A-81 |
| A-1007 | F | 4-A-82 |
| A-1008 | F | 5-A-82 |
| A-1009 | F | 6-A-82 |
| A-1010 | F | 7-A-82 |
| A-1011 | F | 4-A-83 |
| A-1012 | F | 5-A-83 |
| A-1013 | F | 6-A-83 |
| A-1014 | F | 7-A-83 |
| A-1015 | F | 4-A-84 |
| A-1016 | F | 5-A-84 |
| A-1017 | F | 6-A-84 |
| A-1018 | F | 7-A-84 |
| A-1019 | F | 4-A-85 |
| A-1020 | F | 5-A-85 |
| A-1021 | F | 6-A-85 |
| A-1022 | F | 7-A-85 |
| A-1023 | F | 4-A-86 |
| A-1024 | F | 5-A-86 |
| A-1025 | F | 6-A-86 |
| A-1026 | F | 7-A-86 |

TABLE A-continued

| No. | R² | R¹ |
|---|---|---|
| A-1027 | F | 4-A-87 |
| A-1028 | F | 5-A-87 |
| A-1029 | F | 6-A-87 |
| A-1030 | F | 7-A-87 |
| A-1031 | F | 4-A-88 |
| A-1032 | F | 5-A-88 |
| A-1033 | F | 6-A-88 |
| A-1034 | F | 7-A-88 |
| A-1035 | F | 4-A-89 |
| A-1036 | F | 5-A-89 |
| A-1037 | F | 6-A-89 |
| A-1038 | F | 7-A-89 |
| A-1039 | F | 4-A-90 |
| A-1040 | F | 5-A-90 |
| A-1041 | F | 6-A-90 |
| A-1042 | F | 7-A-90 |
| A-1043 | F | 4-A-91 |
| A-1044 | F | 5-A-91 |
| A-1045 | F | 6-A-91 |
| A-1046 | F | 7-A-91 |
| A-1047 | F | 4-A-92 |
| A-1048 | F | 5-A-92 |
| A-1049 | F | 6-A-92 |
| A-1050 | F | 7-A-92 |
| A-1051 | F | 4-A-93 |
| A-1052 | F | 5-A-93 |
| A-1053 | F | 6-A-93 |
| A-1054 | F | 7-A-93 |
| A-1055 | F | 4-A-94 |
| A-1056 | F | 5-A-94 |
| A-1057 | F | 6-A-94 |
| A-1058 | F | 7-A-94 |
| A-1059 | F | 4-A-95 |
| A-1060 | F | 5-A-95 |
| A-1061 | F | 6-A-95 |
| A-1062 | F | 7-A-95 |
| A-1063 | F | 4-A-96 |
| A-1064 | F | 5-A-96 |
| A-1065 | F | 6-A-96 |
| A-1066 | F | 7-A-96 |
| A-1067 | F | 4-A-97 |
| A-1068 | F | 5-A-97 |
| A-1069 | F | 6-A-97 |
| A-1070 | F | 7-A-97 |
| A-1071 | F | 4-A-98 |
| A-1072 | F | 5-A-98 |
| A-1073 | F | 6-A-98 |
| A-1074 | F | 7-A-98 |
| A-1075 | F | 4-A-99 |
| A-1076 | F | 5-A-99 |
| A-1077 | F | 6-A-99 |
| A-1078 | F | 7-A-99 |
| A-1079 | F | 4-A-100 |
| A-1080 | F | 5-A-100 |
| A-1081 | F | 6-A-100 |
| A-1082 | F | 7-A-100 |
| A-1083 | F | 4-A-101 |
| A-1084 | F | 5-A-101 |
| A-1085 | F | 6-A-101 |
| A-1086 | F | 7-A-101 |
| A-1087 | F | 4-A-102 |
| A-1088 | F | 5-A-102 |
| A-1089 | F | 6-A-102 |
| A-1090 | F | 7-A-102 |
| A-1091 | F | 4-A-103 |
| A-1092 | F | 5-A-103 |
| A-1093 | F | 6-A-103 |
| A-1094 | F | 7-A-103 |
| A-1095 | F | 4-A-104 |
| A-1096 | F | 5-A-104 |
| A-1097 | F | 6-A-104 |
| A-1098 | F | 7-A-104 |
| A-1099 | F | 4-A-104 |
| A-1100 | F | 5-A-104 |
| A-1101 | F | 6-A-104 |
| A-1102 | F | 7-A-104 |
| A-1103 | F | 4-A-105 |
| A-1104 | F | 5-A-105 |
| A-1105 | F | 6-A-105 |
| A-1106 | F | 7-A-105 |
| A-1107 | F | 4-A-106 |
| A-1108 | F | 5-A-106 |
| A-1109 | F | 6-A-106 |
| A-1110 | F | 7-A-106 |
| A-1111 | F | 4-A-107 |
| A-1112 | F | 5-A-107 |
| A-1113 | F | 6-A-107 |
| A-1114 | F | 7-A-107 |
| A-1115 | F | 4-A-108 |
| A-1116 | F | 5-A-108 |
| A-1117 | F | 6-A-108 |
| A-1118 | F | 7-A-108 |
| A-1119 | F | 4-A-109 |
| A-1120 | F | 5-A-109 |
| A-1121 | F | 6-A-109 |
| A-1122 | F | 7-A-109 |
| A-1123 | F | 4-A-110 |
| A-1124 | F | 5-A-110 |
| A-1125 | F | 6-A-110 |
| A-1126 | F | 7-A-110 |
| A-1127 | F | 4-A-111 |
| A-1128 | F | 5-A-111 |
| A-1129 | F | 6-A-111 |
| A-1130 | F | 7-A-111 |
| A-1131 | allyl | H |
| A-1132 | allyl | 4-Cl |
| A-1133 | allyl | 5-Cl |
| A-1134 | allyl | 6-Cl |
| A-1135 | allyl | 7-Cl |
| A-1136 | allyl | 4-Br |
| A-1137 | allyl | 5-Br |
| A-1138 | allyl | 6-Br |
| A-1139 | allyl | 7-Br |
| A-1140 | allyl | 4-CN |
| A-1141 | allyl | 5-CN |
| A-1142 | allyl | 6-CN |
| A-1143 | allyl | 7-CN |
| A-1144 | allyl | 4-OH |
| A-1145 | allyl | 5-OH |
| A-1146 | allyl | 6-OH |
| A-1147 | allyl | 7-OH |
| A-1148 | allyl | 4-methyl |
| A-1149 | allyl | 5-methyl |
| A-1150 | allyl | 6-methyl |
| A-1151 | allyl | 7-methyl |
| A-1152 | allyl | 4-ethyl |
| A-1153 | allyl | 5-ethyl |
| A-1154 | allyl | 6-ethyl |
| A-1155 | allyl | 7-ethyl |
| A-1156 | allyl | 4-propyl |
| A-1157 | allyl | 5-propyl |
| A-1158 | allyl | 6-propyl |
| A-1159 | allyl | 7-propyl |
| A-1160 | allyl | 4-isopropyl |
| A-1161 | allyl | 5-isopropyl |
| A-1162 | allyl | 6-isopropyl |
| A-1163 | allyl | 7-isopropyl |
| A-1164 | allyl | 4-hydroxymethyl |
| A-1165 | allyl | 5-hydroxymethyl |
| A-1166 | allyl | 6-hydroxymethyl |
| A-1167 | allyl | 7-hydroxymethyl |
| A-1168 | allyl | 4-(2-hydroxyethyl) |
| A-1169 | allyl | 5-(2-hydroxyethyl) |
| A-1170 | allyl | 6-(2-hydroxyethyl) |
| A-1171 | allyl | 7-(2-hydroxyethyl) |
| A-1172 | allyl | 4-(1-hydroxyethyl) |
| A-1173 | allyl | 5-(1-hydroxyethyl) |
| A-1174 | allyl | 6-(1-hydroxyethyl) |
| A-1175 | allyl | 7-(1-hydroxyethyl) |
| A-1176 | allyl | 4-(3-hydroxypropyl) |
| A-1177 | allyl | 5-(3-hydroxypropyl) |
| A-1178 | allyl | 6-(3-hydroxypropyl) |
| A-1179 | allyl | 7-(3-hydroxypropyl) |
| A-1180 | allyl | 4-(2-hydroxypropyl) |
| A-1181 | allyl | 5-(2-hydroxypropyl) |
| A-1182 | allyl | 6-(2-hydroxypropyl) |

TABLE A-continued

| No. | R² | R¹ |
|---|---|---|
| A-1183 | allyl | 7-(2-hydroxypropyl) |
| A-1184 | allyl | 4-(1-hydroxypropyl) |
| A-1185 | allyl | 5-(1-hydroxypropyl) |
| A-1186 | allyl | 6-(1-hydroxypropyl) |
| A-1187 | allyl | 7-(1-hydroxypropyl) |
| A-1188 | allyl | 4-aminomethyl |
| A-1189 | allyl | 5-aminomethyl |
| A-1190 | allyl | 6-aminomethyl |
| A-1191 | allyl | 7-aminomethyl |
| A-1192 | allyl | 4-(2-aminoethyl) |
| A-1193 | allyl | 5-(2-aminoethyl) |
| A-1194 | allyl | 6-(2-aminoethyl) |
| A-1195 | allyl | 7-(2-aminoethyl) |
| A-1196 | allyl | 4-(1-aminoethyl) |
| A-1197 | allyl | 5-(1-aminoethyl) |
| A-1198 | allyl | 6-(1-aminoethyl) |
| A-1199 | allyl | 7-(1-aminoethyl) |
| A-1200 | allyl | 4-(3-aminopropyl) |
| A-1201 | allyl | 5-(3-aminopropyl) |
| A-1202 | allyl | 6-(3-aminopropyl) |
| A-1203 | allyl | 7-(3-aminopropyl) |
| A-1204 | allyl | 4-(2-aminopropyl) |
| A-1205 | allyl | 5-(2-aminopropyl) |
| A-1206 | allyl | 6-(2-aminopropyl) |
| A-1207 | allyl | 7-(2-aminopropyl) |
| A-1208 | allyl | 4-(1-aminopropyl) |
| A-1209 | allyl | 5-(1-aminopropyl) |
| A-1210 | allyl | 6-(1-aminopropyl) |
| A-1211 | allyl | 7-(1-aminopropyl) |
| A-1212 | allyl | 4-COOH |
| A-1213 | allyl | 5-COOH |
| A-1214 | allyl | 6-COOH |
| A-1215 | allyl | 7-COOH |
| A-1216 | allyl | 4-COOCH₃ |
| A-1217 | allyl | 5-COOCH₃ |
| A-1218 | allyl | 6-COOCH₃ |
| A-1219 | allyl | 7-COOCH₃ |
| A-1220 | allyl | 4-COOCH₂CH₃ |
| A-1221 | allyl | 5-COOCH₂CH₃ |
| A-1222 | allyl | 6-COOCH₂CH₃ |
| A-1223 | allyl | 7-COOCH₂CH₃ |
| A-1224 | allyl | 4-COOCF₃ |
| A-1225 | allyl | 5-COOCF₃ |
| A-1226 | allyl | 6-COOCF₃ |
| A-1227 | allyl | 7-COOCF₃ |
| A-1228 | allyl | 4-CONH₂ |
| A-1229 | allyl | 5-CONH₂ |
| A-1230 | allyl | 6-CONH₂ |
| A-1231 | allyl | 7-CONH₂ |
| A-1232 | allyl | 4-CONHCH₃ |
| A-1233 | allyl | 5-CONHCH₃ |
| A-1234 | allyl | 6-CONHCH₃ |
| A-1235 | allyl | 7-CONHCH₃ |
| A-1236 | allyl | 4-CON(CH₃)₂ |
| A-1237 | allyl | 5-CON(CH₃)₂ |
| A-1238 | allyl | 6-CON(CH₃)₂ |
| A-1239 | allyl | 7-CON(CH₃)₂ |
| A-1240 | allyl | 4-CONHCH₂CH₃ |
| A-1241 | allyl | 5-CONHCH₂CH₃ |
| A-1242 | allyl | 6-CONHCH₂CH₃ |
| A-1243 | allyl | 7-CONHCH₂CH₃ |
| A-1244 | allyl | 4-CON(CH₂CH₃)₂ |
| A-1245 | allyl | 5-CON(CH₂CH₃)₂ |
| A-1246 | allyl | 6-CON(CH₂CH₃)₂ |
| A-1247 | allyl | 7-CON(CH₂CH₃)₂ |
| A-1248 | allyl | 4-A-1 |
| A-1249 | allyl | 5-A-1 |
| A-1250 | allyl | 6-A-1 |
| A-1251 | allyl | 7-A-1 |
| A-1252 | allyl | 4-A-2 |
| A-1253 | allyl | 5-A-2 |
| A-1254 | allyl | 6-A-2 |
| A-1255 | allyl | 7-A-2 |
| A-1256 | allyl | 4-A-3 |
| A-1257 | allyl | 5-A-3 |
| A-1258 | allyl | 6-A-3 |
| A-1259 | allyl | 7-A-3 |
| A-1260 | allyl | 4-A-4 |
| A-1261 | allyl | 5-A-4 |
| A-1262 | allyl | 6-A-4 |
| A-1263 | allyl | 7-A-4 |
| A-1264 | allyl | 4-A-5 |
| A-1265 | allyl | 5-A-5 |
| A-1266 | allyl | 6-A-5 |
| A-1267 | allyl | 7-A-5 |
| A-1268 | allyl | 4-A-6 |
| A-1269 | allyl | 5-A-6 |
| A-1270 | allyl | 6-A-6 |
| A-1271 | allyl | 7-A-6 |
| A-1272 | allyl | 4-A-7 |
| A-1273 | allyl | 5-A-7 |
| A-1274 | allyl | 6-A-7 |
| A-1275 | allyl | 7-A-7 |
| A-1276 | allyl | 4-A-8 |
| A-1277 | allyl | 5-A-8 |
| A-1278 | allyl | 6-A-8 |
| A-1279 | allyl | 7-A-8 |
| A-1280 | allyl | 4-A-9 |
| A-1281 | allyl | 5-A-9 |
| A-1282 | allyl | 6-A-9 |
| A-1283 | allyl | 7-A-9 |
| A-1284 | allyl | 4-A-10 |
| A-1285 | allyl | 5-A-10 |
| A-1286 | allyl | 6-A-10 |
| A-1287 | allyl | 7-A-10 |
| A-1288 | allyl | 4-A-11 |
| A-1289 | allyl | 5-A-11 |
| A-1290 | allyl | 6-A-11 |
| A-1291 | allyl | 7-A-11 |
| A-1292 | allyl | 4-A-12 |
| A-1293 | allyl | 5-A-12 |
| A-1294 | allyl | 6-A-12 |
| A-1295 | allyl | 7-A-12 |
| A-1296 | allyl | 4-A-13 |
| A-1297 | allyl | 5-A-13 |
| A-1298 | allyl | 6-A-13 |
| A-1299 | allyl | 7-A-13 |
| A-1300 | allyl | 4-A-14 |
| A-1301 | allyl | 5-A-14 |
| A-1302 | allyl | 6-A-14 |
| A-1303 | allyl | 7-A-14 |
| A-1304 | allyl | 4-A-15 |
| A-1305 | allyl | 5-A-15 |
| A-1306 | allyl | 6-A-15 |
| A-1307 | allyl | 7-A-15 |
| A-1308 | allyl | 4-A-16 |
| A-1309 | allyl | 5-A-16 |
| A-1310 | allyl | 6-A-16 |
| A-1311 | allyl | 7-A-16 |
| A-1312 | allyl | 4-A-17 |
| A-1313 | allyl | 5-A-17 |
| A-1314 | allyl | 6-A-17 |
| A-1315 | allyl | 7-A-17 |
| A-1316 | allyl | 4-A-18 |
| A-1317 | allyl | 5-A-18 |
| A-1318 | allyl | 6-A-18 |
| A-1319 | allyl | 7-A-18 |
| A-1320 | allyl | 4-A-19 |
| A-1321 | allyl | 5-A-19 |
| A-1322 | allyl | 6-A-19 |
| A-1323 | allyl | 7-A-19 |
| A-1324 | allyl | 4-A-20 |
| A-1325 | allyl | 5-A-20 |
| A-1326 | allyl | 6-A-20 |
| A-1327 | allyl | 7-A-20 |
| A-1328 | allyl | 4-A-21 |
| A-1329 | allyl | 5-A-21 |
| A-1330 | allyl | 6-A-21 |
| A-1331 | allyl | 7-A-21 |
| A-1332 | allyl | 4-A-22 |
| A-1333 | allyl | 5-A-22 |
| A-1334 | allyl | 6-A-22 |
| A-1335 | allyl | 7-A-22 |
| A-1336 | allyl | 4-A-23 |
| A-1337 | allyl | 5-A-23 |
| A-1338 | allyl | 6-A-23 |

TABLE A-continued

| No. | R² | R¹ |
|---|---|---|
| A-1339 | allyl | 7-A-23 |
| A-1340 | allyl | 4-A-24 |
| A-1341 | allyl | 5-A-24 |
| A-1342 | allyl | 6-A-24 |
| A-1343 | allyl | 7-A-24 |
| A-1344 | allyl | 4-A-25 |
| A-1345 | allyl | 5-A-25 |
| A-1346 | allyl | 6-A-25 |
| A-1347 | allyl | 7-A-25 |
| A-1348 | allyl | 4-A-26 |
| A-1349 | allyl | 5-A-26 |
| A-1350 | allyl | 6-A-26 |
| A-1351 | allyl | 7-A-26 |
| A-1352 | allyl | 4-A-27 |
| A-1353 | allyl | 5-A-27 |
| A-1354 | allyl | 6-A-27 |
| A-1355 | allyl | 7-A-27 |
| A-1356 | allyl | 4-A-28 |
| A-1357 | allyl | 5-A-28 |
| A-1358 | allyl | 6-A-28 |
| A-1359 | allyl | 7-A-28 |
| A-1360 | allyl | 4-A-29 |
| A-1361 | allyl | 5-A-29 |
| A-1362 | allyl | 6-A-29 |
| A-1363 | allyl | 7-A-29 |
| A-1364 | allyl | 4-A-30 |
| A-1365 | allyl | 5-A-30 |
| A-1366 | allyl | 6-A-30 |
| A-1367 | allyl | 7-A-30 |
| A-1368 | allyl | 4-A-31 |
| A-1369 | allyl | 5-A-31 |
| A-1370 | allyl | 6-A-31 |
| A-1371 | allyl | 7-A-31 |
| A-1372 | allyl | 4-A-32 |
| A-1373 | allyl | 5-A-32 |
| A-1374 | allyl | 6-A-32 |
| A-1375 | allyl | 7-A-32 |
| A-1376 | allyl | 4-A-33 |
| A-1377 | allyl | 5-A-33 |
| A-1378 | allyl | 6-A-33 |
| A-1379 | allyl | 7-A-33 |
| A-1380 | allyl | 4-A-34 |
| A-1381 | allyl | 5-A-34 |
| A-1382 | allyl | 6-A-34 |
| A-1383 | allyl | 7-A-34 |
| A-1384 | allyl | 4-A-35 |
| A-1385 | allyl | 5-A-35 |
| A-1386 | allyl | 6-A-35 |
| A-1387 | allyl | 7-A-35 |
| A-1388 | allyl | 4-A-36 |
| A-1389 | allyl | 5-A-36 |
| A-1390 | allyl | 6-A-36 |
| A-1391 | allyl | 7-A-36 |
| A-1392 | allyl | 4-A-37 |
| A-1393 | allyl | 5-A-37 |
| A-1394 | allyl | 6-A-37 |
| A-1395 | allyl | 7-A-37 |
| A-1396 | allyl | 4-A-38 |
| A-1397 | allyl | 5-A-38 |
| A-1398 | allyl | 6-A-38 |
| A-1399 | allyl | 7-A-38 |
| A-1400 | allyl | 4-A-39 |
| A-1401 | allyl | 5-A-39 |
| A-1402 | allyl | 6-A-39 |
| A-1403 | allyl | 7-A-39 |
| A-1404 | allyl | 4-A-40 |
| A-1405 | allyl | 5-A-40 |
| A-1406 | allyl | 6-A-40 |
| A-1407 | allyl | 7-A-40 |
| A-1408 | allyl | 4-A-41 |
| A-1409 | allyl | 5-A-41 |
| A-1410 | allyl | 6-A-41 |
| A-1411 | allyl | 7-A-41 |
| A-1412 | allyl | 4-A-42 |
| A-1413 | allyl | 5-A-42 |
| A-1414 | allyl | 6-A-42 |
| A-1415 | allyl | 7-A-42 |
| A-1416 | allyl | 4-A-43 |
| A-1417 | allyl | 5-A-43 |
| A-1418 | allyl | 6-A-43 |
| A-1419 | allyl | 7-A-43 |
| A-1420 | allyl | 4-A-44 |
| A-1421 | allyl | 5-A-44 |
| A-1422 | allyl | 6-A-44 |
| A-1423 | allyl | 7-A-44 |
| A-1424 | allyl | 4-A-45 |
| A-1425 | allyl | 5-A-45 |
| A-1426 | allyl | 6-A-45 |
| A-1427 | allyl | 7-A-45 |
| A-1428 | allyl | 4-A-46 |
| A-1429 | allyl | 5-A-46 |
| A-1430 | allyl | 6-A-46 |
| A-1431 | allyl | 7-A-46 |
| A-1432 | allyl | 4-A-47 |
| A-1433 | allyl | 5-A-47 |
| A-1434 | allyl | 6-A-47 |
| A-1435 | allyl | 7-A-47 |
| A-1436 | allyl | 4-A-48 |
| A-1437 | allyl | 5-A-48 |
| A-1438 | allyl | 6-A-48 |
| A-1439 | allyl | 7-A-48 |
| A-1440 | allyl | 4-A-49 |
| A-1441 | allyl | 5-A-49 |
| A-1442 | allyl | 6-A-49 |
| A-1443 | allyl | 7-A-49 |
| A-1444 | allyl | 4-A-50 |
| A-1445 | allyl | 5-A-50 |
| A-1446 | allyl | 6-A-50 |
| A-1447 | allyl | 7-A-50 |
| A-1448 | allyl | 4-A-51 |
| A-1449 | allyl | 5-A-51 |
| A-1450 | allyl | 6-A-51 |
| A-1451 | allyl | 7-A-51 |
| A-1452 | allyl | 4-A-52 |
| A-1453 | allyl | 5-A-52 |
| A-1454 | allyl | 6-A-52 |
| A-1455 | allyl | 7-A-52 |
| A-1456 | allyl | 4-A-53 |
| A-1457 | allyl | 5-A-53 |
| A-1458 | allyl | 6-A-53 |
| A-1459 | allyl | 7-A-53 |
| A-1460 | allyl | 4-A-54 |
| A-1461 | allyl | 5-A-54 |
| A-1462 | allyl | 6-A-54 |
| A-1463 | allyl | 7-A-54 |
| A-1464 | allyl | 4-A-55 |
| A-1465 | allyl | 5-A-55 |
| A-1466 | allyl | 6-A-55 |
| A-1467 | allyl | 7-A-55 |
| A-1468 | allyl | 4-A-56 |
| A-1469 | allyl | 5-A-56 |
| A-1470 | allyl | 6-A-56 |
| A-1471 | allyl | 7-A-56 |
| A-1472 | allyl | 4-A-57 |
| A-1473 | allyl | 5-A-57 |
| A-1474 | allyl | 6-A-57 |
| A-1475 | allyl | 7-A-57 |
| A-1476 | allyl | 4-A-58 |
| A-1477 | allyl | 5-A-58 |
| A-1478 | allyl | 6-A-58 |
| A-1479 | allyl | 7-A-58 |
| A-1480 | allyl | 4-A-59 |
| A-1481 | allyl | 5-A-59 |
| A-1482 | allyl | 6-A-59 |
| A-1483 | allyl | 7-A-59 |
| A-1484 | allyl | 4-A-60 |
| A-1485 | allyl | 5-A-60 |
| A-1486 | allyl | 6-A-60 |
| A-1487 | allyl | 7-A-60 |
| A-1488 | allyl | 4-A-61 |
| A-1489 | allyl | 5-A-61 |
| A-1490 | allyl | 6-A-61 |
| A-1491 | allyl | 7-A-61 |
| A-1492 | allyl | 4-A-62 |
| A-1493 | allyl | 5-A-62 |
| A-1494 | allyl | 6-A-62 |

TABLE A-continued

| No. | R² | R¹ |
|---|---|---|
| A-1495 | allyl | 7-A-62 |
| A-1496 | allyl | 4-A-63 |
| A-1497 | allyl | 5-A-63 |
| A-1498 | allyl | 6-A-63 |
| A-1499 | allyl | 7-A-63 |
| A-1500 | allyl | 4-A-64 |
| A-1501 | allyl | 5-A-64 |
| A-1502 | allyl | 6-A-64 |
| A-1503 | allyl | 7-A-64 |
| A-1504 | allyl | 4-A-65 |
| A-1505 | allyl | 5-A-65 |
| A-1506 | allyl | 6-A-65 |
| A-1507 | allyl | 7-A-65 |
| A-1508 | allyl | 4-A-66 |
| A-1509 | allyl | 5-A-66 |
| A-1510 | allyl | 6-A-66 |
| A-1511 | allyl | 7-A-66 |
| A-1512 | allyl | 4-A-67 |
| A-1513 | allyl | 5-A-67 |
| A-1514 | allyl | 6-A-67 |
| A-1515 | allyl | 7-A-67 |
| A-1516 | allyl | 4-A-68 |
| A-1517 | allyl | 5-A-68 |
| A-1518 | allyl | 6-A-68 |
| A-1519 | allyl | 7-A-68 |
| A-1520 | allyl | 4-A-69 |
| A-1521 | allyl | 5-A-69 |
| A-1522 | allyl | 6-A-69 |
| A-1523 | allyl | 7-A-69 |
| A-1524 | allyl | 4-A-70 |
| A-1525 | allyl | 5-A-70 |
| A-1526 | allyl | 6-A-70 |
| A-1527 | allyl | 7-A-70 |
| A-1528 | allyl | 4-A-71 |
| A-1529 | allyl | 5-A-71 |
| A-1530 | allyl | 6-A-71 |
| A-1531 | allyl | 7-A-71 |
| A-1532 | allyl | 4-A-72 |
| A-1533 | allyl | 5-A-72 |
| A-1534 | allyl | 6-A-72 |
| A-1535 | allyl | 7-A-72 |
| A-1536 | allyl | 4-A-73 |
| A-1537 | allyl | 5-A-73 |
| A-1538 | allyl | 6-A-73 |
| A-1539 | allyl | 7-A-73 |
| A-1540 | allyl | 4-A-74 |
| A-1541 | allyl | 5-A-74 |
| A-1542 | allyl | 6-A-74 |
| A-1543 | allyl | 7-A-74 |
| A-1544 | allyl | 4-A-75 |
| A-1545 | allyl | 5-A-75 |
| A-1546 | allyl | 6-A-75 |
| A-1547 | allyl | 7-A-75 |
| A-1548 | allyl | 4-A-76 |
| A-1549 | allyl | 5-A-76 |
| A-1550 | allyl | 6-A-76 |
| A-1551 | allyl | 7-A-76 |
| A-1552 | allyl | 4-A-77 |
| A-1553 | allyl | 5-A-77 |
| A-1554 | allyl | 6-A-77 |
| A-1555 | allyl | 7-A-77 |
| A-1556 | allyl | 4-A-78 |
| A-1557 | allyl | 5-A-78 |
| A-1558 | allyl | 6-A-78 |
| A-1559 | allyl | 7-A-78 |
| A-1560 | allyl | 4-A-79 |
| A-1561 | allyl | 5-A-79 |
| A-1562 | allyl | 6-A-79 |
| A-1563 | allyl | 7-A-79 |
| A-1564 | allyl | 4-A-80 |
| A-1565 | allyl | 5-A-80 |
| A-1566 | allyl | 6-A-80 |
| A-1567 | allyl | 7-A-80 |
| A-1568 | allyl | 4-A-81 |
| A-1569 | allyl | 5-A-81 |
| A-1570 | allyl | 6-A-81 |
| A-1571 | allyl | 7-A-81 |
| A-1572 | allyl | 4-A-82 |
| A-1573 | allyl | 5-A-82 |
| A-1574 | allyl | 6-A-82 |
| A-1575 | allyl | 7-A-82 |
| A-1576 | allyl | 4-A-83 |
| A-1577 | allyl | 5-A-83 |
| A-1578 | allyl | 6-A-83 |
| A-1579 | allyl | 7-A-83 |
| A-1580 | allyl | 4-A-84 |
| A-1581 | allyl | 5-A-84 |
| A-1582 | allyl | 6-A-84 |
| A-1583 | allyl | 7-A-84 |
| A-1584 | allyl | 4-A-85 |
| A-1585 | allyl | 5-A-85 |
| A-1586 | allyl | 6-A-85 |
| A-1587 | allyl | 7-A-85 |
| A-1588 | allyl | 4-A-86 |
| A-1589 | allyl | 5-A-86 |
| A-1590 | allyl | 6-A-86 |
| A-1591 | allyl | 7-A-86 |
| A-1592 | allyl | 4-A-87 |
| A-1593 | allyl | 5-A-87 |
| A-1594 | allyl | 6-A-87 |
| A-1595 | allyl | 7-A-87 |
| A-1596 | allyl | 4-A-88 |
| A-1597 | allyl | 5-A-88 |
| A-1598 | allyl | 6-A-88 |
| A-1599 | allyl | 7-A-88 |
| A-1600 | allyl | 4-A-89 |
| A-1601 | allyl | 5-A-89 |
| A-1602 | allyl | 6-A-89 |
| A-1603 | allyl | 7-A-89 |
| A-1604 | allyl | 4-A-90 |
| A-1605 | allyl | 5-A-90 |
| A-1606 | allyl | 6-A-90 |
| A-1607 | allyl | 7-A-90 |
| A-1608 | allyl | 4-A-91 |
| A-1609 | allyl | 5-A-91 |
| A-1610 | allyl | 6-A-91 |
| A-1611 | allyl | 7-A-91 |
| A-1612 | allyl | 4-A-92 |
| A-1613 | allyl | 5-A-92 |
| A-1614 | allyl | 6-A-92 |
| A-1615 | allyl | 7-A-92 |
| A-1616 | allyl | 4-A-93 |
| A-1617 | allyl | 5-A-93 |
| A-1618 | allyl | 6-A-93 |
| A-1619 | allyl | 7-A-93 |
| A-1620 | allyl | 4-A-94 |
| A-1621 | allyl | 5-A-94 |
| A-1622 | allyl | 6-A-94 |
| A-1623 | allyl | 7-A-94 |
| A-1624 | allyl | 4-A-95 |
| A-1625 | allyl | 5-A-95 |
| A-1626 | allyl | 6-A-95 |
| A-1627 | allyl | 7-A-95 |
| A-1628 | allyl | 4-A-96 |
| A-1629 | allyl | 5-A-96 |
| A-1630 | allyl | 6-A-96 |
| A-1631 | allyl | 7-A-96 |
| A-1632 | allyl | 4-A-97 |
| A-1633 | allyl | 5-A-97 |
| A-1634 | allyl | 6-A-97 |
| A-1635 | allyl | 7-A-97 |
| A-1636 | allyl | 4-A-98 |
| A-1637 | allyl | 5-A-98 |
| A-1638 | allyl | 6-A-98 |
| A-1639 | allyl | 7-A-98 |
| A-1640 | allyl | 4-A-99 |
| A-1641 | allyl | 5-A-99 |
| A-1642 | allyl | 6-A-99 |
| A-1643 | allyl | 7-A-99 |
| A-1644 | allyl | 4-A-100 |
| A-1645 | allyl | 5-A-100 |
| A-1646 | allyl | 6-A-100 |
| A-1647 | allyl | 7-A-100 |
| A-1648 | allyl | 4-A-101 |
| A-1649 | allyl | 5-A-101 |
| A-1650 | allyl | 6-A-101 |

TABLE A-continued

| No. | R² | R¹ |
|---|---|---|
| A-1651 | allyl | 7-A-101 |
| A-1652 | allyl | 4-A-102 |
| A-1653 | allyl | 5-A-102 |
| A-1654 | allyl | 6-A-102 |
| A-1655 | allyl | 7-A-102 |
| A-1656 | allyl | 4-A-103 |
| A-1657 | allyl | 5-A-103 |
| A-1658 | allyl | 6-A-103 |
| A-1659 | allyl | 7-A-103 |
| A-1660 | allyl | 4-A-104 |
| A-1661 | allyl | 5-A-104 |
| A-1662 | allyl | 6-A-104 |
| A-1663 | allyl | 7-A-104 |
| A-1664 | allyl | 4-A-104 |
| A-1665 | allyl | 5-A-104 |
| A-1666 | allyl | 6-A-104 |
| A-1667 | allyl | 7-A-104 |
| A-1668 | allyl | 4-A-105 |
| A-1669 | allyl | 5-A-105 |
| A-1670 | allyl | 6-A-105 |
| A-1671 | allyl | 7-A-105 |
| A-1672 | allyl | 4-A-106 |
| A-1673 | allyl | 5-A-106 |
| A-1674 | allyl | 6-A-106 |
| A-1675 | allyl | 7-A-106 |
| A-1676 | allyl | 4-A-107 |
| A-1677 | allyl | 5-A-107 |
| A-1678 | allyl | 6-A-107 |
| A-1679 | allyl | 7-A-107 |
| A-1680 | allyl | 4-A-108 |
| A-1681 | allyl | 5-A-108 |
| A-1682 | allyl | 6-A-108 |
| A-1683 | allyl | 7-A-108 |
| A-1684 | allyl | 4-A-109 |
| A-1685 | allyl | 5-A-109 |
| A-1686 | allyl | 6-A-109 |
| A-1687 | allyl | 7-A-109 |
| A-1688 | allyl | 4-A-110 |
| A-1689 | allyl | 5-A-110 |
| A-1690 | allyl | 6-A-110 |
| A-1691 | allyl | 7-A-110 |
| A-1692 | allyl | 4-A-111 |
| A-1693 | allyl | 5-A-111 |
| A-1694 | allyl | 6-A-111 |
| A-1695 | allyl | 7-A-111 |
| A-1696 | $CH_2CHF_2$ | H |
| A-1697 | $CH_2CHF_2$ | 4-Cl |
| A-1698 | $CH_2CHF_2$ | 5-Cl |
| A-1699 | $CH_2CHF_2$ | 6-Cl |
| A-1700 | $CH_2CHF_2$ | 7-Cl |
| A-1701 | $CH_2CHF_2$ | 4-Br |
| A-1702 | $CH_2CHF_2$ | 5-Br |
| A-1703 | $CH_2CHF_2$ | 6-Br |
| A-1704 | $CH_2CHF_2$ | 7-Br |
| A-1705 | $CH_2CHF_2$ | 4-CN |
| A-1706 | $CH_2CHF_2$ | 5-CN |
| A-1707 | $CH_2CHF_2$ | 6-CN |
| A-1708 | $CH_2CHF_2$ | 7-CN |
| A-1709 | $CH_2CHF_2$ | 4-OH |
| A-1710 | $CH_2CHF_2$ | 5-OH |
| A-1711 | $CH_2CHF_2$ | 6-OH |
| A-1712 | $CH_2CHF_2$ | 7-OH |
| A-1713 | $CH_2CHF_2$ | 4-methyl |
| A-1714 | $CH_2CHF_2$ | 5-methyl |
| A-1715 | $CH_2CHF_2$ | 6-methyl |
| A-1716 | $CH_2CHF_2$ | 7-methyl |
| A-1717 | $CH_2CHF_2$ | 4-ethyl |
| A-1718 | $CH_2CHF_2$ | 5-ethyl |
| A-1719 | $CH_2CHF_2$ | 6-ethyl |
| A-1720 | $CH_2CHF_2$ | 7-ethyl |
| A-1721 | $CH_2CHF_2$ | 4-propyl |
| A-1722 | $CH_2CHF_2$ | 5-propyl |
| A-1723 | $CH_2CHF_2$ | 6-propyl |
| A-1724 | $CH_2CHF_2$ | 7-propyl |
| A-1725 | $CH_2CHF_2$ | 4-isopropyl |
| A-1726 | $CH_2CHF_2$ | 5-isopropyl |
| A-1727 | $CH_2CHF_2$ | 6-isopropyl |
| A-1728 | $CH_2CHF_2$ | 7-isopropyl |
| A-1729 | $CH_2CHF_2$ | 4-hydroxymethyl |
| A-1730 | $CH_2CHF_2$ | 5-hydroxymethyl |
| A-1731 | $CH_2CHF_2$ | 6-hydroxymethyl |
| A-1732 | $CH_2CHF_2$ | 7-hydroxymethyl |
| A-1733 | $CH_2CHF_2$ | 4-(2-hydroxyethyl) |
| A-1734 | $CH_2CHF_2$ | 5-(2-hydroxyethyl) |
| A-1735 | $CH_2CHF_2$ | 6-(2-hydroxyethyl) |
| A-1736 | $CH_2CHF_2$ | 7-(2-hydroxyethyl) |
| A-1737 | $CH_2CHF_2$ | 4-(1-hydroxyethyl) |
| A-1738 | $CH_2CHF_2$ | 5-(1-hydroxyethyl) |
| A-1739 | $CH_2CHF_2$ | 6-(1-hydroxyethyl) |
| A-1740 | $CH_2CHF_2$ | 7-(1-hydroxyethyl) |
| A-1741 | $CH_2CHF_2$ | 4-(3-hydroxypropyl) |
| A-1742 | $CH_2CHF_2$ | 5-(3-hydroxypropyl) |
| A-1743 | $CH_2CHF_2$ | 6-(3-hydroxypropyl) |
| A-1744 | $CH_2CHF_2$ | 7-(3-hydroxypropyl) |
| A-1745 | $CH_2CHF_2$ | 4-(2-hydroxypropyl) |
| A-1746 | $CH_2CHF_2$ | 5-(2-hydroxypropyl) |
| A-1747 | $CH_2CHF_2$ | 6-(2-hydroxypropyl) |
| A-1748 | $CH_2CHF_2$ | 7-(2-hydroxypropyl) |
| A-1749 | $CH_2CHF_2$ | 4-(1-hydroxypropyl) |
| A-1750 | $CH_2CHF_2$ | 5-(1-hydroxypropyl) |
| A-1751 | $CH_2CHF_2$ | 6-(1-hydroxypropyl) |
| A-1752 | $CH_2CHF_2$ | 7-(1-hydroxypropyl) |
| A-1753 | $CH_2CHF_2$ | 4-aminomethyl |
| A-1754 | $CH_2CHF_2$ | 5-aminomethyl |
| A-1755 | $CH_2CHF_2$ | 6-aminomethyl |
| A-1756 | $CH_2CHF_2$ | 7-aminomethyl |
| A-1757 | $CH_2CHF_2$ | 4-(2-aminoethyl) |
| A-1758 | $CH_2CHF_2$ | 5-(2-aminoethyl) |
| A-1759 | $CH_2CHF_2$ | 6-(2-aminoethyl) |
| A-1760 | $CH_2CHF_2$ | 7-(2-aminoethyl) |
| A-1761 | $CH_2CHF_2$ | 4-(1-aminoethyl) |
| A-1762 | $CH_2CHF_2$ | 5-(1-aminoethyl) |
| A-1763 | $CH_2CHF_2$ | 6-(1-aminoethyl) |
| A-1764 | $CH_2CHF_2$ | 7-(1-aminoethyl) |
| A-1765 | $CH_2CHF_2$ | 4-(3-aminopropyl) |
| A-1766 | $CH_2CHF_2$ | 5-(3-aminopropyl) |
| A-1767 | $CH_2CHF_2$ | 6-(3-aminopropyl) |
| A-1768 | $CH_2CHF_2$ | 7-(3-aminopropyl) |
| A-1769 | $CH_2CHF_2$ | 4-(2-aminopropyl) |
| A-1770 | $CH_2CHF_2$ | 5-(2-aminopropyl) |
| A-1771 | $CH_2CHF_2$ | 6-(2-aminopropyl) |
| A-1772 | $CH_2CHF_2$ | 7-(2-aminopropyl) |
| A-1773 | $CH_2CHF_2$ | 4-(1-aminopropyl) |
| A-1774 | $CH_2CHF_2$ | 5-(1-aminopropyl) |
| A-1775 | $CH_2CHF_2$ | 6-(1-aminopropyl) |
| A-1776 | $CH_2CHF_2$ | 7-(1-aminopropyl) |
| A-1777 | $CH_2CHF_2$ | 4-COOH |
| A-1778 | $CH_2CHF_2$ | 5-COOH |
| A-1779 | $CH_2CHF_2$ | 6-COOH |
| A-1780 | $CH_2CHF_2$ | 7-COOH |
| A-1781 | $CH_2CHF_2$ | 4-COOCH$_3$ |
| A-1782 | $CH_2CHF_2$ | 5-COOCH$_3$ |
| A-1783 | $CH_2CHF_2$ | 6-COOCH$_3$ |
| A-1784 | $CH_2CHF_2$ | 7-COOCH$_3$ |
| A-1785 | $CH_2CHF_2$ | 4-COOCH$_2$CH$_3$ |
| A-1786 | $CH_2CHF_2$ | 5-COOCH$_2$CH$_3$ |
| A-1787 | $CH_2CHF_2$ | 6-COOCH$_2$CH$_3$ |
| A-1788 | $CH_2CHF_2$ | 7-COOCH$_2$CH$_3$ |
| A-1789 | $CH_2CHF_2$ | 4-COOCF$_3$ |
| A-1790 | $CH_2CHF_2$ | 5-COOCF$_3$ |
| A-1791 | $CH_2CHF_2$ | 6-COOCF$_3$ |
| A-1792 | $CH_2CHF_2$ | 7-COOCF$_3$ |
| A-1793 | $CH_2CHF_2$ | 4-CONH$_2$ |
| A-1794 | $CH_2CHF_2$ | 5-CONH$_2$ |
| A-1795 | $CH_2CHF_2$ | 6-CONH$_2$ |
| A-1796 | $CH_2CHF_2$ | 7-CONH$_2$ |
| A-1797 | $CH_2CHF_2$ | 4-CONHCH$_3$ |
| A-1798 | $CH_2CHF_2$ | 5-CONHCH$_3$ |
| A-1799 | $CH_2CHF_2$ | 6-CONHCH$_3$ |
| A-1800 | $CH_2CHF_2$ | 7-CONHCH$_3$ |
| A-1801 | $CH_2CHF_2$ | 4-CON(CH$_3$)$_2$ |
| A-1802 | $CH_2CHF_2$ | 5-CON(CH$_3$)$_2$ |
| A-1803 | $CH_2CHF_2$ | 6-CON(CH$_3$)$_2$ |
| A-1804 | $CH_2CHF_2$ | 7-CON(CH$_3$)$_2$ |
| A-1805 | $CH_2CHF_2$ | 4-CONHCH$_2$CH$_3$ |
| A-1806 | $CH_2CHF_2$ | 5-CONHCH$_2$CH$_3$ |

TABLE A-continued

| No. | R² | R¹ |
|---|---|---|
| A-1807 | CH₂CHF₂ | 6-CONHCH₂CH₃ |
| A-1808 | CH₂CHF₂ | 7-CONHCH₂CH₃ |
| A-1809 | CH₂CHF₂ | 4-CON(CH₂CH₃)₂ |
| A-1810 | CH₂CHF₂ | 5-CON(CH₂CH₃)₂ |
| A-1811 | CH₂CHF₂ | 6-CON(CH₂CH₃)₂ |
| A-1812 | CH₂CHF₂ | 7-CON(CH₂CH₃)₂ |
| A-1813 | CH₂CHF₂ | 4-A-1 |
| A-1814 | CH₂CHF₂ | 5-A-1 |
| A-1815 | CH₂CHF₂ | 6-A-1 |
| A-1816 | CH₂CHF₂ | 7-A-1 |
| A-1817 | CH₂CHF₂ | 4-A-2 |
| A-1818 | CH₂CHF₂ | 5-A-2 |
| A-1819 | CH₂CHF₂ | 6-A-2 |
| A-1820 | CH₂CHF₂ | 7-A-2 |
| A-1821 | CH₂CHF₂ | 4-A-3 |
| A-1822 | CH₂CHF₂ | 5-A-3 |
| A-1823 | CH₂CHF₂ | 6-A-3 |
| A-1824 | CH₂CHF₂ | 7-A-3 |
| A-1825 | CH₂CHF₂ | 4-A-4 |
| A-1826 | CH₂CHF₂ | 5-A-4 |
| A-1827 | CH₂CHF₂ | 6-A-4 |
| A-1828 | CH₂CHF₂ | 7-A-4 |
| A-1829 | CH₂CHF₂ | 4-A-5 |
| A-1830 | CH₂CHF₂ | 5-A-5 |
| A-1831 | CH₂CHF₂ | 6-A-5 |
| A-1832 | CH₂CHF₂ | 7-A-5 |
| A-1833 | CH₂CHF₂ | 4-A-6 |
| A-1834 | CH₂CHF₂ | 5-A-6 |
| A-1835 | CH₂CHF₂ | 6-A-6 |
| A-1836 | CH₂CHF₂ | 7-A-6 |
| A-1837 | CH₂CHF₂ | 4-A-7 |
| A-1838 | CH₂CHF₂ | 5-A-7 |
| A-1839 | CH₂CHF₂ | 6-A-7 |
| A-1840 | CH₂CHF₂ | 7-A-7 |
| A-1841 | CH₂CHF₂ | 4-A-8 |
| A-1842 | CH₂CHF₂ | 5-A-8 |
| A-1843 | CH₂CHF₂ | 6-A-8 |
| A-1844 | CH₂CHF₂ | 7-A-8 |
| A-1845 | CH₂CHF₂ | 4-A-9 |
| A-1846 | CH₂CHF₂ | 5-A-9 |
| A-1847 | CH₂CHF₂ | 6-A-9 |
| A-1848 | CH₂CHF₂ | 7-A-9 |
| A-1849 | CH₂CHF₂ | 4-A-10 |
| A-1850 | CH₂CHF₂ | 5-A-10 |
| A-1851 | CH₂CHF₂ | 6-A-10 |
| A-1852 | CH₂CHF₂ | 7-A-10 |
| A-1853 | CH₂CHF₂ | 4-A-11 |
| A-1854 | CH₂CHF₂ | 5-A-11 |
| A-1855 | CH₂CHF₂ | 6-A-11 |
| A-1856 | CH₂CHF₂ | 7-A-11 |
| A-1857 | CH₂CHF₂ | 4-A-12 |
| A-1858 | CH₂CHF₂ | 5-A-12 |
| A-1859 | CH₂CHF₂ | 6-A-12 |
| A-1860 | CH₂CHF₂ | 7-A-12 |
| A-1861 | CH₂CHF₂ | 4-A-13 |
| A-1862 | CH₂CHF₂ | 5-A-13 |
| A-1863 | CH₂CHF₂ | 6-A-13 |
| A-1864 | CH₂CHF₂ | 7-A-13 |
| A-1865 | CH₂CHF₂ | 4-A-14 |
| A-1866 | CH₂CHF₂ | 5-A-14 |
| A-1867 | CH₂CHF₂ | 6-A-14 |
| A-1868 | CH₂CHF₂ | 7-A-14 |
| A-1869 | CH₂CHF₂ | 4-A-15 |
| A-1870 | CH₂CHF₂ | 5-A-15 |
| A-1871 | CH₂CHF₂ | 6-A-15 |
| A-1872 | CH₂CHF₂ | 7-A-15 |
| A-1873 | CH₂CHF₂ | 4-A-16 |
| A-1874 | CH₂CHF₂ | 5-A-16 |
| A-1875 | CH₂CHF₂ | 6-A-16 |
| A-1876 | CH₂CHF₂ | 7-A-16 |
| A-1877 | CH₂CHF₂ | 4-A-17 |
| A-1878 | CH₂CHF₂ | 5-A-17 |
| A-1879 | CH₂CHF₂ | 6-A-17 |
| A-1880 | CH₂CHF₂ | 7-A-17 |
| A-1881 | CH₂CHF₂ | 4-A-18 |
| A-1882 | CH₂CHF₂ | 5-A-18 |
| A-1883 | CH₂CHF₂ | 6-A-18 |
| A-1884 | CH₂CHF₂ | 7-A-18 |
| A-1885 | CH₂CHF₂ | 4-A-19 |
| A-1886 | CH₂CHF₂ | 5-A-19 |
| A-1887 | CH₂CHF₂ | 6-A-19 |
| A-1888 | CH₂CHF₂ | 7-A-19 |
| A-1889 | CH₂CHF₂ | 4-A-20 |
| A-1890 | CH₂CHF₂ | 5-A-20 |
| A-1891 | CH₂CHF₂ | 6-A-20 |
| A-1892 | CH₂CHF₂ | 7-A-20 |
| A-1893 | CH₂CHF₂ | 4-A-21 |
| A-1894 | CH₂CHF₂ | 5-A-21 |
| A-1895 | CH₂CHF₂ | 6-A-21 |
| A-1896 | CH₂CHF₂ | 7-A-21 |
| A-1897 | CH₂CHF₂ | 4-A-22 |
| A-1898 | CH₂CHF₂ | 5-A-22 |
| A-1899 | CH₂CHF₂ | 6-A-22 |
| A-1900 | CH₂CHF₂ | 7-A-22 |
| A-1901 | CH₂CHF₂ | 4-A-23 |
| A-1902 | CH₂CHF₂ | 5-A-23 |
| A-1903 | CH₂CHF₂ | 6-A-23 |
| A-1904 | CH₂CHF₂ | 7-A-23 |
| A-1905 | CH₂CHF₂ | 4-A-24 |
| A-1906 | CH₂CHF₂ | 5-A-24 |
| A-1907 | CH₂CHF₂ | 6-A-24 |
| A-1908 | CH₂CHF₂ | 7-A-24 |
| A-1909 | CH₂CHF₂ | 4-A-25 |
| A-1910 | CH₂CHF₂ | 5-A-25 |
| A-1911 | CH₂CHF₂ | 6-A-25 |
| A-1912 | CH₂CHF₂ | 7-A-25 |
| A-1913 | CH₂CHF₂ | 4-A-26 |
| A-1914 | CH₂CHF₂ | 5-A-26 |
| A-1915 | CH₂CHF₂ | 6-A-26 |
| A-1916 | CH₂CHF₂ | 7-A-26 |
| A-1917 | CH₂CHF₂ | 4-A-27 |
| A-1918 | CH₂CHF₂ | 5-A-27 |
| A-1919 | CH₂CHF₂ | 6-A-27 |
| A-1920 | CH₂CHF₂ | 7-A-27 |
| A-1921 | CH₂CHF₂ | 4-A-28 |
| A-1922 | CH₂CHF₂ | 5-A-28 |
| A-1923 | CH₂CHF₂ | 6-A-28 |
| A-1924 | CH₂CHF₂ | 7-A-28 |
| A-1925 | CH₂CHF₂ | 4-A-29 |
| A-1926 | CH₂CHF₂ | 5-A-29 |
| A-1927 | CH₂CHF₂ | 6-A-29 |
| A-1928 | CH₂CHF₂ | 7-A-29 |
| A-1929 | CH₂CHF₂ | 4-A-30 |
| A-1930 | CH₂CHF₂ | 5-A-30 |
| A-1931 | CH₂CHF₂ | 6-A-30 |
| A-1932 | CH₂CHF₂ | 7-A-30 |
| A-1933 | CH₂CHF₂ | 4-A-31 |
| A-1934 | CH₂CHF₂ | 5-A-31 |
| A-1935 | CH₂CHF₂ | 6-A-31 |
| A-1936 | CH₂CHF₂ | 7-A-31 |
| A-1937 | CH₂CHF₂ | 4-A-32 |
| A-1938 | CH₂CHF₂ | 5-A-32 |
| A-1939 | CH₂CHF₂ | 6-A-32 |
| A-1940 | CH₂CHF₂ | 7-A-32 |
| A-1941 | CH₂CHF₂ | 4-A-33 |
| A-1942 | CH₂CHF₂ | 5-A-33 |
| A-1943 | CH₂CHF₂ | 6-A-33 |
| A-1944 | CH₂CHF₂ | 7-A-33 |
| A-1945 | CH₂CHF₂ | 4-A-34 |
| A-1946 | CH₂CHF₂ | 5-A-34 |
| A-1947 | CH₂CHF₂ | 6-A-34 |
| A-1948 | CH₂CHF₂ | 7-A-34 |
| A-1949 | CH₂CHF₂ | 4-A-35 |
| A-1950 | CH₂CHF₂ | 5-A-35 |
| A-1951 | CH₂CHF₂ | 6-A-35 |
| A-1952 | CH₂CHF₂ | 7-A-35 |
| A-1953 | CH₂CHF₂ | 4-A-36 |
| A-1954 | CH₂CHF₂ | 5-A-36 |
| A-1955 | CH₂CHF₂ | 6-A-36 |
| A-1956 | CH₂CHF₂ | 7-A-36 |
| A-1957 | CH₂CHF₂ | 4-A-37 |
| A-1958 | CH₂CHF₂ | 5-A-37 |
| A-1959 | CH₂CHF₂ | 6-A-37 |
| A-1960 | CH₂CHF₂ | 7-A-37 |
| A-1961 | CH₂CHF₂ | 4-A-38 |
| A-1962 | CH₂CHF₂ | 5-A-38 |

TABLE A-continued

| No. | R² | R¹ |
|---|---|---|
| A-1963 | CH$_2$CHF$_2$ | 6-A-38 |
| A-1964 | CH$_2$CHF$_2$ | 7-A-38 |
| A-1965 | CH$_2$CHF$_2$ | 4-A-39 |
| A-1966 | CH$_2$CHF$_2$ | 5-A-39 |
| A-1967 | CH$_2$CHF$_2$ | 6-A-39 |
| A-1968 | CH$_2$CHF$_2$ | 7-A-39 |
| A-1969 | CH$_2$CHF$_2$ | 4-A-40 |
| A-1970 | CH$_2$CHF$_2$ | 5-A-40 |
| A-1971 | CH$_2$CHF$_2$ | 6-A-40 |
| A-1972 | CH$_2$CHF$_2$ | 7-A-40 |
| A-1973 | CH$_2$CHF$_2$ | 4-A-41 |
| A-1974 | CH$_2$CHF$_2$ | 5-A-41 |
| A-1975 | CH$_2$CHF$_2$ | 6-A-41 |
| A-1976 | CH$_2$CHF$_2$ | 7-A-41 |
| A-1977 | CH$_2$CHF$_2$ | 4-A-42 |
| A-1978 | CH$_2$CHF$_2$ | 5-A-42 |
| A-1979 | CH$_2$CHF$_2$ | 6-A-42 |
| A-1980 | CH$_2$CHF$_2$ | 7-A-42 |
| A-1981 | CH$_2$CHF$_2$ | 4-A-43 |
| A-1982 | CH$_2$CHF$_2$ | 5-A-43 |
| A-1983 | CH$_2$CHF$_2$ | 6-A-43 |
| A-1984 | CH$_2$CHF$_2$ | 7-A-43 |
| A-1985 | CH$_2$CHF$_2$ | 4-A-44 |
| A-1986 | CH$_2$CHF$_2$ | 5-A-44 |
| A-1987 | CH$_2$CHF$_2$ | 6-A-44 |
| A-1988 | CH$_2$CHF$_2$ | 7-A-44 |
| A-1989 | CH$_2$CHF$_2$ | 4-A-45 |
| A-1990 | CH$_2$CHF$_2$ | 5-A-45 |
| A-1991 | CH$_2$CHF$_2$ | 6-A-45 |
| A-1992 | CH$_2$CHF$_2$ | 7-A-45 |
| A-1993 | CH$_2$CHF$_2$ | 4-A-46 |
| A-1994 | CH$_2$CHF$_2$ | 5-A-46 |
| A-1995 | CH$_2$CHF$_2$ | 6-A-46 |
| A-1996 | CH$_2$CHF$_2$ | 7-A-46 |
| A-1997 | CH$_2$CHF$_2$ | 4-A-47 |
| A-1998 | CH$_2$CHF$_2$ | 5-A-47 |
| A-1999 | CH$_2$CHF$_2$ | 6-A-47 |
| A-2000 | CH$_2$CHF$_2$ | 7-A-47 |
| A-2001 | CH$_2$CHF$_2$ | 4-A-48 |
| A-2002 | CH$_2$CHF$_2$ | 5-A-48 |
| A-2003 | CH$_2$CHF$_2$ | 6-A-48 |
| A-2004 | CH$_2$CHF$_2$ | 7-A-48 |
| A-2005 | CH$_2$CHF$_2$ | 4-A-49 |
| A-2006 | CH$_2$CHF$_2$ | 5-A-49 |
| A-2007 | CH$_2$CHF$_2$ | 6-A-49 |
| A-2008 | CH$_2$CHF$_2$ | 7-A-49 |
| A-2009 | CH$_2$CHF$_2$ | 4-A-50 |
| A-2010 | CH$_2$CHF$_2$ | 5-A-50 |
| A-2011 | CH$_2$CHF$_2$ | 6-A-50 |
| A-2012 | CH$_2$CHF$_2$ | 7-A-50 |
| A-2013 | CH$_2$CHF$_2$ | 4-A-51 |
| A-2014 | CH$_2$CHF$_2$ | 5-A-51 |
| A-2015 | CH$_2$CHF$_2$ | 6-A-51 |
| A-2016 | CH$_2$CHF$_2$ | 7-A-51 |
| A-2017 | CH$_2$CHF$_2$ | 4-A-52 |
| A-2018 | CH$_2$CHF$_2$ | 5-A-52 |
| A-2019 | CH$_2$CHF$_2$ | 6-A-52 |
| A-2020 | CH$_2$CHF$_2$ | 7-A-52 |
| A-2021 | CH$_2$CHF$_2$ | 4-A-53 |
| A-2022 | CH$_2$CHF$_2$ | 5-A-53 |
| A-2023 | CH$_2$CHF$_2$ | 6-A-53 |
| A-2024 | CH$_2$CHF$_2$ | 7-A-53 |
| A-2025 | CH$_2$CHF$_2$ | 4-A-54 |
| A-2026 | CH$_2$CHF$_2$ | 5-A-54 |
| A-2027 | CH$_2$CHF$_2$ | 6-A-54 |
| A-2028 | CH$_2$CHF$_2$ | 7-A-54 |
| A-2029 | CH$_2$CHF$_2$ | 4-A-55 |
| A-2030 | CH$_2$CHF$_2$ | 5-A-55 |
| A-2031 | CH$_2$CHF$_2$ | 6-A-55 |
| A-2032 | CH$_2$CHF$_2$ | 7-A-55 |
| A-2033 | CH$_2$CHF$_2$ | 4-A-56 |
| A-2034 | CH$_2$CHF$_2$ | 5-A-56 |
| A-2035 | CH$_2$CHF$_2$ | 6-A-56 |
| A-2036 | CH$_2$CHF$_2$ | 7-A-56 |
| A-2037 | CH$_2$CHF$_2$ | 4-A-57 |
| A-2038 | CH$_2$CHF$_2$ | 5-A-57 |
| A-2039 | CH$_2$CHF$_2$ | 6-A-57 |
| A-2040 | CH$_2$CHF$_2$ | 7-A-57 |
| A-2041 | CH$_2$CHF$_2$ | 4-A-58 |
| A-2042 | CH$_2$CHF$_2$ | 5-A-58 |
| A-2043 | CH$_2$CHF$_2$ | 6-A-58 |
| A-2044 | CH$_2$CHF$_2$ | 7-A-58 |
| A-2045 | CH$_2$CHF$_2$ | 4-A-59 |
| A-2046 | CH$_2$CHF$_2$ | 5-A-59 |
| A-2047 | CH$_2$CHF$_2$ | 6-A-59 |
| A-2048 | CH$_2$CHF$_2$ | 7-A-59 |
| A-2049 | CH$_2$CHF$_2$ | 4-A-60 |
| A-2050 | CH$_2$CHF$_2$ | 5-A-60 |
| A-2051 | CH$_2$CHF$_2$ | 6-A-60 |
| A-2052 | CH$_2$CHF$_2$ | 7-A-60 |
| A-2053 | CH$_2$CHF$_2$ | 4-A-61 |
| A-2054 | CH$_2$CHF$_2$ | 5-A-61 |
| A-2055 | CH$_2$CHF$_2$ | 6-A-61 |
| A-2056 | CH$_2$CHF$_2$ | 7-A-61 |
| A-2057 | CH$_2$CHF$_2$ | 4-A-62 |
| A-2058 | CH$_2$CHF$_2$ | 5-A-62 |
| A-2059 | CH$_2$CHF$_2$ | 6-A-62 |
| A-2060 | CH$_2$CHF$_2$ | 7-A-62 |
| A-2061 | CH$_2$CHF$_2$ | 4-A-63 |
| A-2062 | CH$_2$CHF$_2$ | 5-A-63 |
| A-2063 | CH$_2$CHF$_2$ | 6-A-63 |
| A-2064 | CH$_2$CHF$_2$ | 7-A-63 |
| A-2065 | CH$_2$CHF$_2$ | 4-A-64 |
| A-2066 | CH$_2$CHF$_2$ | 5-A-64 |
| A-2067 | CH$_2$CHF$_2$ | 6-A-64 |
| A-2068 | CH$_2$CHF$_2$ | 7-A-64 |
| A-2069 | CH$_2$CHF$_2$ | 4-A-65 |
| A-2070 | CH$_2$CHF$_2$ | 5-A-65 |
| A-2071 | CH$_2$CHF$_2$ | 6-A-65 |
| A-2072 | CH$_2$CHF$_2$ | 7-A-65 |
| A-2073 | CH$_2$CHF$_2$ | 4-A-66 |
| A-2074 | CH$_2$CHF$_2$ | 5-A-66 |
| A-2075 | CH$_2$CHF$_2$ | 6-A-66 |
| A-2076 | CH$_2$CHF$_2$ | 7-A-66 |
| A-2077 | CH$_2$CHF$_2$ | 4-A-67 |
| A-2078 | CH$_2$CHF$_2$ | 5-A-67 |
| A-2079 | CH$_2$CHF$_2$ | 6-A-67 |
| A-2080 | CH$_2$CHF$_2$ | 7-A-67 |
| A-2081 | CH$_2$CHF$_2$ | 4-A-68 |
| A-2082 | CH$_2$CHF$_2$ | 5-A-68 |
| A-2083 | CH$_2$CHF$_2$ | 6-A-68 |
| A-2084 | CH$_2$CHF$_2$ | 7-A-68 |
| A-2085 | CH$_2$CHF$_2$ | 4-A-69 |
| A-2086 | CH$_2$CHF$_2$ | 5-A-69 |
| A-2087 | CH$_2$CHF$_2$ | 6-A-69 |
| A-2088 | CH$_2$CHF$_2$ | 7-A-69 |
| A-2089 | CH$_2$CHF$_2$ | 4-A-70 |
| A-2090 | CH$_2$CHF$_2$ | 5-A-70 |
| A-2091 | CH$_2$CHF$_2$ | 6-A-70 |
| A-2092 | CH$_2$CHF$_2$ | 7-A-70 |
| A-2093 | CH$_2$CHF$_2$ | 4-A-71 |
| A-2094 | CH$_2$CHF$_2$ | 5-A-71 |
| A-2095 | CH$_2$CHF$_2$ | 6-A-71 |
| A-2096 | CH$_2$CHF$_2$ | 7-A-71 |
| A-2097 | CH$_2$CHF$_2$ | 4-A-72 |
| A-2098 | CH$_2$CHF$_2$ | 5-A-72 |
| A-2099 | CH$_2$CHF$_2$ | 6-A-72 |
| A-2100 | CH$_2$CHF$_2$ | 7-A-72 |
| A-2101 | CH$_2$CHF$_2$ | 4-A-73 |
| A-2102 | CH$_2$CHF$_2$ | 5-A-73 |
| A-2103 | CH$_2$CHF$_2$ | 6-A-73 |
| A-2104 | CH$_2$CHF$_2$ | 7-A-73 |
| A-2105 | CH$_2$CHF$_2$ | 4-A-74 |
| A-2106 | CH$_2$CHF$_2$ | 5-A-74 |
| A-2107 | CH$_2$CHF$_2$ | 6-A-74 |
| A-2108 | CH$_2$CHF$_2$ | 7-A-74 |
| A-2109 | CH$_2$CHF$_2$ | 4-A-75 |
| A-2110 | CH$_2$CHF$_2$ | 5-A-75 |
| A-2111 | CH$_2$CHF$_2$ | 6-A-75 |
| A-2112 | CH$_2$CHF$_2$ | 7-A-75 |
| A-2113 | CH$_2$CHF$_2$ | 4-A-76 |
| A-2114 | CH$_2$CHF$_2$ | 5-A-76 |
| A-2115 | CH$_2$CHF$_2$ | 6-A-76 |
| A-2116 | CH$_2$CHF$_2$ | 7-A-76 |
| A-2117 | CH$_2$CHF$_2$ | 4-A-77 |
| A-2118 | CH$_2$CHF$_2$ | 5-A-77 |

TABLE A-continued

| No. | R² | R¹ |
|---|---|---|
| A-2119 | CH₂CHF₂ | 6-A-77 |
| A-2120 | CH₂CHF₂ | 7-A-77 |
| A-2121 | CH₂CHF₂ | 4-A-78 |
| A-2122 | CH₂CHF₂ | 5-A-78 |
| A-2123 | CH₂CHF₂ | 6-A-78 |
| A-2124 | CH₂CHF₂ | 7-A-78 |
| A-2125 | CH₂CHF₂ | 4-A-79 |
| A-2126 | CH₂CHF₂ | 5-A-79 |
| A-2127 | CH₂CHF₂ | 6-A-79 |
| A-2128 | CH₂CHF₂ | 7-A-79 |
| A-2129 | CH₂CHF₂ | 4-A-80 |
| A-2130 | CH₂CHF₂ | 5-A-80 |
| A-2131 | CH₂CHF₂ | 6-A-80 |
| A-2132 | CH₂CHF₂ | 7-A-80 |
| A-2133 | CH₂CHF₂ | 4-A-81 |
| A-2134 | CH₂CHF₂ | 5-A-81 |
| A-2135 | CH₂CHF₂ | 6-A-81 |
| A-2136 | CH₂CHF₂ | 7-A-81 |
| A-2137 | CH₂CHF₂ | 4-A-82 |
| A-2138 | CH₂CHF₂ | 5-A-82 |
| A-2139 | CH₂CHF₂ | 6-A-82 |
| A-2140 | CH₂CHF₂ | 7-A-82 |
| A-2141 | CH₂CHF₂ | 4-A-83 |
| A-2142 | CH₂CHF₂ | 5-A-83 |
| A-2143 | CH₂CHF₂ | 6-A-83 |
| A-2144 | CH₂CHF₂ | 7-A-83 |
| A-2145 | CH₂CHF₂ | 4-A-84 |
| A-2146 | CH₂CHF₂ | 5-A-84 |
| A-2147 | CH₂CHF₂ | 6-A-84 |
| A-2148 | CH₂CHF₂ | 7-A-84 |
| A-2149 | CH₂CHF₂ | 4-A-85 |
| A-2150 | CH₂CHF₂ | 5-A-85 |
| A-2151 | CH₂CHF₂ | 6-A-85 |
| A-2152 | CH₂CHF₂ | 7-A-85 |
| A-2153 | CH₂CHF₂ | 4-A-86 |
| A-2154 | CH₂CHF₂ | 5-A-86 |
| A-2155 | CH₂CHF₂ | 6-A-86 |
| A-2156 | CH₂CHF₂ | 7-A-86 |
| A-2157 | CH₂CHF₂ | 4-A-87 |
| A-2158 | CH₂CHF₂ | 5-A-87 |
| A-2159 | CH₂CHF₂ | 6-A-87 |
| A-2160 | CH₂CHF₂ | 7-A-87 |
| A-2161 | CH₂CHF₂ | 4-A-88 |
| A-2162 | CH₂CHF₂ | 5-A-88 |
| A-2163 | CH₂CHF₂ | 6-A-88 |
| A-2164 | CH₂CHF₂ | 7-A-88 |
| A-2165 | CH₂CHF₂ | 4-A-89 |
| A-2166 | CH₂CHF₂ | 5-A-89 |
| A-2167 | CH₂CHF₂ | 6-A-89 |
| A-2168 | CH₂CHF₂ | 7-A-89 |
| A-2169 | CH₂CHF₂ | 4-A-90 |
| A-2170 | CH₂CHF₂ | 5-A-90 |
| A-2171 | CH₂CHF₂ | 6-A-90 |
| A-2172 | CH₂CHF₂ | 7-A-90 |
| A-2173 | CH₂CHF₂ | 4-A-91 |
| A-2174 | CH₂CHF₂ | 5-A-91 |
| A-2175 | CH₂CHF₂ | 6-A-91 |
| A-2176 | CH₂CHF₂ | 7-A-91 |
| A-2177 | CH₂CHF₂ | 4-A-92 |
| A-2178 | CH₂CHF₂ | 5-A-92 |
| A-2179 | CH₂CHF₂ | 6-A-92 |
| A-2180 | CH₂CHF₂ | 7-A-92 |
| A-2181 | CH₂CHF₂ | 4-A-93 |
| A-2182 | CH₂CHF₂ | 5-A-93 |
| A-2183 | CH₂CHF₂ | 6-A-93 |
| A-2184 | CH₂CHF₂ | 7-A-93 |
| A-2185 | CH₂CHF₂ | 4-A-94 |
| A-2186 | CH₂CHF₂ | 5-A-94 |
| A-2187 | CH₂CHF₂ | 6-A-94 |
| A-2188 | CH₂CHF₂ | 7-A-94 |
| A-2189 | CH₂CHF₂ | 4-A-95 |
| A-2190 | CH₂CHF₂ | 5-A-95 |
| A-2191 | CH₂CHF₂ | 6-A-95 |
| A-2192 | CH₂CHF₂ | 7-A-95 |
| A-2193 | CH₂CHF₂ | 4-A-96 |
| A-2194 | CH₂CHF₂ | 5-A-96 |
| A-2195 | CH₂CHF₂ | 6-A-96 |
| A-2196 | CH₂CHF₂ | 7-A-96 |
| A-2197 | CH₂CHF₂ | 4-A-97 |
| A-2198 | CH₂CHF₂ | 5-A-97 |
| A-2199 | CH₂CHF₂ | 6-A-97 |
| A-2200 | CH₂CHF₂ | 7-A-97 |
| A-2201 | CH₂CHF₂ | 4-A-98 |
| A-2202 | CH₂CHF₂ | 5-A-98 |
| A-2203 | CH₂CHF₂ | 6-A-98 |
| A-2204 | CH₂CHF₂ | 7-A-98 |
| A-2205 | CH₂CHF₂ | 4-A-99 |
| A-2206 | CH₂CHF₂ | 5-A-99 |
| A-2207 | CH₂CHF₂ | 6-A-99 |
| A-2208 | CH₂CHF₂ | 7-A-99 |
| A-2209 | CH₂CHF₂ | 4-A-100 |
| A-2210 | CH₂CHF₂ | 5-A-100 |
| A-2211 | CH₂CHF₂ | 6-A-100 |
| A-2212 | CH₂CHF₂ | 7-A-100 |
| A-2213 | CH₂CHF₂ | 4-A-101 |
| A-2214 | CH₂CHF₂ | 5-A-101 |
| A-2215 | CH₂CHF₂ | 6-A-101 |
| A-2216 | CH₂CHF₂ | 7-A-101 |
| A-2217 | CH₂CHF₂ | 4-A-102 |
| A-2218 | CH₂CHF₂ | 5-A-102 |
| A-2219 | CH₂CHF₂ | 6-A-102 |
| A-2220 | CH₂CHF₂ | 7-A-102 |
| A-2221 | CH₂CHF₂ | 4-A-103 |
| A-2222 | CH₂CHF₂ | 5-A-103 |
| A-2223 | CH₂CHF₂ | 6-A-103 |
| A-2224 | CH₂CHF₂ | 7-A-103 |
| A-2225 | CH₂CHF₂ | 4-A-104 |
| A-2226 | CH₂CHF₂ | 5-A-104 |
| A-2227 | CH₂CHF₂ | 6-A-104 |
| A-2228 | CH₂CHF₂ | 7-A-104 |
| A-2229 | CH₂CHF₂ | 4-A-104 |
| A-2230 | CH₂CHF₂ | 5-A-104 |
| A-2231 | CH₂CHF₂ | 6-A-104 |
| A-2232 | CH₂CHF₂ | 7-A-104 |
| A-2233 | CH₂CHF₂ | 4-A-105 |
| A-2234 | CH₂CHF₂ | 5-A-105 |
| A-2235 | CH₂CHF₂ | 6-A-105 |
| A-2236 | CH₂CHF₂ | 7-A-105 |
| A-2237 | CH₂CHF₂ | 4-A-106 |
| A-2238 | CH₂CHF₂ | 5-A-106 |
| A-2239 | CH₂CHF₂ | 6-A-106 |
| A-2240 | CH₂CHF₂ | 7-A-106 |
| A-2241 | CH₂CHF₂ | 4-A-107 |
| A-2242 | CH₂CHF₂ | 5-A-107 |
| A-2243 | CH₂CHF₂ | 6-A-107 |
| A-2244 | CH₂CHF₂ | 7-A-107 |
| A-2245 | CH₂CHF₂ | 4-A-108 |
| A-2246 | CH₂CHF₂ | 5-A-108 |
| A-2247 | CH₂CHF₂ | 6-A-108 |
| A-2248 | CH₂CHF₂ | 7-A-108 |
| A-2249 | CH₂CHF₂ | 4-A-109 |
| A-2250 | CH₂CHF₂ | 5-A-109 |
| A-2251 | CH₂CHF₂ | 6-A-109 |
| A-2252 | CH₂CHF₂ | 7-A-109 |
| A-2253 | CH₂CHF₂ | 4-A-110 |
| A-2254 | CH₂CHF₂ | 5-A-110 |
| A-2255 | CH₂CHF₂ | 6-A-110 |
| A-2256 | CH₂CHF₂ | 7-A-110 |
| A-2257 | CH₂CHF₂ | 4-A-111 |
| A-2258 | CH₂CHF₂ | 5-A-111 |
| A-2259 | CH₂CHF₂ | 6-A-111 |
| A-2260 | CH₂CHF₂ | 7-A-111 |
| A-2261 | CH₃ | H |
| A-2262 | CH₃ | 4-Cl |
| A-2263 | CH₃ | 5-Cl |
| A-2264 | CH₃ | 6-Cl |
| A-2265 | CH₃ | 7-Cl |
| A-2266 | CH₃ | 4-Br |
| A-2267 | CH₃ | 5-Br |
| A-2268 | CH₃ | 6-Br |
| A-2269 | CH₃ | 7-Br |
| A-2270 | CH₃ | 4-CN |
| A-2271 | CH₃ | 5-CN |
| A-2272 | CH₃ | 6-CN |
| A-2273 | CH₃ | 7-CN |
| A-2274 | CH₃ | 4-OH |

TABLE A-continued

| No. | R² | R¹ |
|---|---|---|
| A-2275 | CH₃ | 5-OH |
| A-2276 | CH₃ | 6-OH |
| A-2277 | CH₃ | 7-OH |
| A-2278 | CH₃ | 4-methyl |
| A-2279 | CH₃ | 5-methyl |
| A-2280 | CH₃ | 6-methyl |
| A-2281 | CH₃ | 7-methyl |
| A-2282 | CH₃ | 4-ethyl |
| A-2283 | CH₃ | 5-ethyl |
| A-2284 | CH₃ | 6-ethyl |
| A-2285 | CH₃ | 7-ethyl |
| A-2286 | CH₃ | 4-propyl |
| A-2287 | CH₃ | 5-propyl |
| A-2288 | CH₃ | 6-propyl |
| A-2289 | CH₃ | 7-propyl |
| A-2290 | CH₃ | 4-isopropyl |
| A-2291 | CH₃ | 5-isopropyl |
| A-2292 | CH₃ | 6-isopropyl |
| A-2293 | CH₃ | 7-isopropyl |
| A-2294 | CH₃ | 4-hydroxymethyl |
| A-2295 | CH₃ | 5-hydroxymethyl |
| A-2296 | CH₃ | 6-hydroxymethyl |
| A-2297 | CH₃ | 7-hydroxymethyl |
| A-2298 | CH₃ | 4-(2-hydroxyethyl) |
| A-2299 | CH₃ | 5-(2-hydroxyethyl) |
| A-2300 | CH₃ | 6-(2-hydroxyethyl) |
| A-2301 | CH₃ | 7-(2-hydroxyethyl) |
| A-2302 | CH₃ | 4-(1-hydroxyethyl) |
| A-2303 | CH₃ | 5-(1-hydroxyethyl) |
| A-2304 | CH₃ | 6-(1-hydroxyethyl) |
| A-2305 | CH₃ | 7-(1-hydroxyethyl) |
| A-2306 | CH₃ | 4-(3-hydroxypropyl) |
| A-2307 | CH₃ | 5-(3-hydroxypropyl) |
| A-2308 | CH₃ | 6-(3-hydroxypropyl) |
| A-2309 | CH₃ | 7-(3-hydroxypropyl) |
| A-2310 | CH₃ | 4-(2-hydroxypropyl) |
| A-2311 | CH₃ | 5-(2-hydroxypropyl) |
| A-2312 | CH₃ | 6-(2-hydroxypropyl) |
| A-2313 | CH₃ | 7-(2-hydroxypropyl) |
| A-2314 | CH₃ | 4-(1-hydroxypropyl) |
| A-2315 | CH₃ | 5-(1-hydroxypropyl) |
| A-2316 | CH₃ | 6-(1-hydroxypropyl) |
| A-2317 | CH₃ | 7-(1-hydroxypropyl) |
| A-2318 | CH₃ | 4-aminomethyl |
| A-2319 | CH₃ | 5-aminomethyl |
| A-2320 | CH₃ | 6-aminomethyl |
| A-2321 | CH₃ | 7-aminomethyl |
| A-2322 | CH₃ | 4-(2-aminoethyl) |
| A-2323 | CH₃ | 5-(2-aminoethyl) |
| A-2324 | CH₃ | 6-(2-aminoethyl) |
| A-2325 | CH₃ | 7-(2-aminoethyl) |
| A-2326 | CH₃ | 4-(1-aminoethyl) |
| A-2327 | CH₃ | 5-(1-aminoethyl) |
| A-2328 | CH₃ | 6-(1-aminoethyl) |
| A-2329 | CH₃ | 7-(1-aminoethyl) |
| A-2330 | CH₃ | 4-(3-aminopropyl) |
| A-2331 | CH₃ | 5-(3-aminopropyl) |
| A-2332 | CH₃ | 6-(3-aminopropyl) |
| A-2333 | CH₃ | 7-(3-aminopropyl) |
| A-2334 | CH₃ | 4-(2-aminopropyl) |
| A-2335 | CH₃ | 5-(2-aminopropyl) |
| A-2336 | CH₃ | 6-(2-aminopropyl) |
| A-2337 | CH₃ | 7-(2-aminopropyl) |
| A-2338 | CH₃ | 4-(1-aminopropyl) |
| A-2339 | CH₃ | 5-(1-aminopropyl) |
| A-2340 | CH₃ | 6-(1-aminopropyl) |
| A-2341 | CH₃ | 7-(1-aminopropyl) |
| A-2342 | CH₃ | 4-COOH |
| A-2343 | CH₃ | 5-COOH |
| A-2344 | CH₃ | 6-COOH |
| A-2345 | CH₃ | 7-COOH |
| A-2346 | CH₃ | 4-COOCH₃ |
| A-2347 | CH₃ | 5-COOCH₃ |
| A-2348 | CH₃ | 6-COOCH₃ |
| A-2349 | CH₃ | 7-COOCH₃ |
| A-2350 | CH₃ | 4-COOCH₂CH₃ |
| A-2351 | CH₃ | 5-COOCH₂CH₃ |
| A-2352 | CH₃ | 6-COOCH₂CH₃ |
| A-2353 | CH₃ | 7-COOCH₂CH₃ |
| A-2354 | CH₃ | 4-COOCF₃ |
| A-2355 | CH₃ | 5-COOCF₃ |
| A-2356 | CH₃ | 6-COOCF₃ |
| A-2357 | CH₃ | 7-COOCF₃ |
| A-2358 | CH₃ | 4-CONH₂ |
| A-2359 | CH₃ | 5-CONH₂ |
| A-2360 | CH₃ | 6-CONH₂ |
| A-2361 | CH₃ | 7-CONH₂ |
| A-2362 | CH₃ | 4-CONHCH₃ |
| A-2363 | CH₃ | 5-CONHCH₃ |
| A-2364 | CH₃ | 6-CONHCH₃ |
| A-2365 | CH₃ | 7-CONHCH₃ |
| A-2366 | CH₃ | 4-CON(CH₃)₂ |
| A-2367 | CH₃ | 5-CON(CH₃)₂ |
| A-2368 | CH₃ | 6-CON(CH₃)₂ |
| A-2369 | CH₃ | 7-CON(CH₃)₂ |
| A-2370 | CH₃ | 4-CONHCH₂CH₃ |
| A-2371 | CH₃ | 5-CONHCH₂CH₃ |
| A-2372 | CH₃ | 6-CONHCH₂CH₃ |
| A-2373 | CH₃ | 7-CONHCH₂CH₃ |
| A-2374 | CH₃ | 4-CON(CH₂CH₃)₂ |
| A-2375 | CH₃ | 5-CON(CH₂CH₃)₂ |
| A-2376 | CH₃ | 6-CON(CH₂CH₃)₂ |
| A-2377 | CH₃ | 7-CON(CH₂CH₃)₂ |
| A-2378 | CH₃ | 4-A-1 |
| A-2379 | CH₃ | 5-A-1 |
| A-2380 | CH₃ | 6-A-1 |
| A-2381 | CH₃ | 7-A-1 |
| A-2382 | CH₃ | 4-A-2 |
| A-2383 | CH₃ | 5-A-2 |
| A-2384 | CH₃ | 6-A-2 |
| A-2385 | CH₃ | 7-A-2 |
| A-2386 | CH₃ | 4-A-3 |
| A-2387 | CH₃ | 5-A-3 |
| A-2388 | CH₃ | 6-A-3 |
| A-2389 | CH₃ | 7-A-3 |
| A-2390 | CH₃ | 4-A-4 |
| A-2391 | CH₃ | 5-A-4 |
| A-2392 | CH₃ | 6-A-4 |
| A-2393 | CH₃ | 7-A-4 |
| A-2394 | CH₃ | 4-A-5 |
| A-2395 | CH₃ | 5-A-5 |
| A-2396 | CH₃ | 6-A-5 |
| A-2397 | CH₃ | 7-A-5 |
| A-2398 | CH₃ | 4-A-6 |
| A-2399 | CH₃ | 5-A-6 |
| A-2400 | CH₃ | 6-A-6 |
| A-2401 | CH₃ | 7-A-6 |
| A-2402 | CH₃ | 4-A-7 |
| A-2403 | CH₃ | 5-A-7 |
| A-2404 | CH₃ | 6-A-7 |
| A-2405 | CH₃ | 7-A-7 |
| A-2406 | CH₃ | 4-A-8 |
| A-2407 | CH₃ | 5-A-8 |
| A-2408 | CH₃ | 6-A-8 |
| A-2409 | CH₃ | 7-A-8 |
| A-2410 | CH₃ | 4-A-9 |
| A-2411 | CH₃ | 5-A-9 |
| A-2412 | CH₃ | 6-A-9 |
| A-2413 | CH₃ | 7-A-9 |
| A-2414 | CH₃ | 4-A-10 |
| A-2415 | CH₃ | 5-A-10 |
| A-2416 | CH₃ | 6-A-10 |
| A-2417 | CH₃ | 7-A-10 |
| A-2418 | CH₃ | 4-A-11 |
| A-2419 | CH₃ | 5-A-11 |
| A-2420 | CH₃ | 6-A-11 |
| A-2421 | CH₃ | 7-A-11 |
| A-2422 | CH₃ | 4-A-12 |
| A-2423 | CH₃ | 5-A-12 |
| A-2424 | CH₃ | 6-A-12 |
| A-2425 | CH₃ | 7-A-12 |
| A-2426 | CH₃ | 4-A-13 |
| A-2427 | CH₃ | 5-A-13 |
| A-2428 | CH₃ | 6-A-13 |
| A-2429 | CH₃ | 7-A-13 |
| A-2430 | CH₃ | 4-A-14 |

TABLE A-continued

| No. | R² | R¹ |
|---|---|---|
| A-2431 | CH₃ | 5-A-14 |
| A-2432 | CH₃ | 6-A-14 |
| A-2433 | CH₃ | 7-A-14 |
| A-2434 | CH₃ | 4-A-15 |
| A-2435 | CH₃ | 5-A-15 |
| A-2436 | CH₃ | 6-A-15 |
| A-2437 | CH₃ | 7-A-15 |
| A-2438 | CH₃ | 4-A-16 |
| A-2439 | CH₃ | 5-A-16 |
| A-2440 | CH₃ | 6-A-16 |
| A-2441 | CH₃ | 7-A-16 |
| A-2442 | CH₃ | 4-A-17 |
| A-2443 | CH₃ | 5-A-17 |
| A-2444 | CH₃ | 6-A-17 |
| A-2445 | CH₃ | 7-A-17 |
| A-2446 | CH₃ | 4-A-18 |
| A-2447 | CH₃ | 5-A-18 |
| A-2448 | CH₃ | 6-A-18 |
| A-2449 | CH₃ | 7-A-18 |
| A-2450 | CH₃ | 4-A-19 |
| A-2451 | CH₃ | 5-A-19 |
| A-2452 | CH₃ | 6-A-19 |
| A-2453 | CH₃ | 7-A-19 |
| A-2454 | CH₃ | 4-A-20 |
| A-2455 | CH₃ | 5-A-20 |
| A-2456 | CH₃ | 6-A-20 |
| A-2457 | CH₃ | 7-A-20 |
| A-2458 | CH₃ | 4-A-21 |
| A-2459 | CH₃ | 5-A-21 |
| A-2460 | CH₃ | 6-A-21 |
| A-2461 | CH₃ | 7-A-21 |
| A-2462 | CH₃ | 4-A-22 |
| A-2463 | CH₃ | 5-A-22 |
| A-2464 | CH₃ | 6-A-22 |
| A-2465 | CH₃ | 7-A-22 |
| A-2466 | CH₃ | 4-A-23 |
| A-2467 | CH₃ | 5-A-23 |
| A-2468 | CH₃ | 6-A-23 |
| A-2469 | CH₃ | 7-A-23 |
| A-2470 | CH₃ | 4-A-24 |
| A-2471 | CH₃ | 5-A-24 |
| A-2472 | CH₃ | 6-A-24 |
| A-2473 | CH₃ | 7-A-24 |
| A-2474 | CH₃ | 4-A-25 |
| A-2475 | CH₃ | 5-A-25 |
| A-2476 | CH₃ | 6-A-25 |
| A-2477 | CH₃ | 7-A-25 |
| A-2478 | CH₃ | 4-A-26 |
| A-2479 | CH₃ | 5-A-26 |
| A-2480 | CH₃ | 6-A-26 |
| A-2481 | CH₃ | 7-A-26 |
| A-2482 | CH₃ | 4-A-27 |
| A-2483 | CH₃ | 5-A-27 |
| A-2484 | CH₃ | 6-A-27 |
| A-2485 | CH₃ | 7-A-27 |
| A-2486 | CH₃ | 4-A-28 |
| A-2487 | CH₃ | 5-A-28 |
| A-2488 | CH₃ | 6-A-28 |
| A-2489 | CH₃ | 7-A-28 |
| A-2490 | CH₃ | 4-A-29 |
| A-2491 | CH₃ | 5-A-29 |
| A-2492 | CH₃ | 6-A-29 |
| A-2493 | CH₃ | 7-A-29 |
| A-2494 | CH₃ | 4-A-30 |
| A-2495 | CH₃ | 5-A-30 |
| A-2496 | CH₃ | 6-A-30 |
| A-2497 | CH₃ | 7-A-30 |
| A-2498 | CH₃ | 4-A-31 |
| A-2499 | CH₃ | 5-A-31 |
| A-2500 | CH₃ | 6-A-31 |
| A-2501 | CH₃ | 7-A-31 |
| A-2502 | CH₃ | 4-A-32 |
| A-2503 | CH₃ | 5-A-32 |
| A-2504 | CH₃ | 6-A-32 |
| A-2505 | CH₃ | 7-A-32 |
| A-2506 | CH₃ | 4-A-33 |
| A-2507 | CH₃ | 5-A-33 |
| A-2508 | CH₃ | 6-A-33 |
| A-2509 | CH₃ | 7-A-33 |
| A-2510 | CH₃ | 4-A-34 |
| A-2511 | CH₃ | 5-A-34 |
| A-2512 | CH₃ | 6-A-34 |
| A-2513 | CH₃ | 7-A-34 |
| A-2514 | CH₃ | 4-A-35 |
| A-2515 | CH₃ | 5-A-35 |
| A-2516 | CH₃ | 6-A-35 |
| A-2517 | CH₃ | 7-A-35 |
| A-2518 | CH₃ | 4-A-36 |
| A-2519 | CH₃ | 5-A-36 |
| A-2520 | CH₃ | 6-A-36 |
| A-2521 | CH₃ | 7-A-36 |
| A-2522 | CH₃ | 4-A-37 |
| A-2523 | CH₃ | 5-A-37 |
| A-2524 | CH₃ | 6-A-37 |
| A-2525 | CH₃ | 7-A-37 |
| A-2526 | CH₃ | 4-A-38 |
| A-2527 | CH₃ | 5-A-38 |
| A-2528 | CH₃ | 6-A-38 |
| A-2529 | CH₃ | 7-A-38 |
| A-2530 | CH₃ | 4-A-39 |
| A-2531 | CH₃ | 5-A-39 |
| A-2532 | CH₃ | 6-A-39 |
| A-2533 | CH₃ | 7-A-39 |
| A-2534 | CH₃ | 4-A-40 |
| A-2535 | CH₃ | 5-A-40 |
| A-2536 | CH₃ | 6-A-40 |
| A-2537 | CH₃ | 7-A-40 |
| A-2538 | CH₃ | 4-A-41 |
| A-2539 | CH₃ | 5-A-41 |
| A-2540 | CH₃ | 6-A-41 |
| A-2541 | CH₃ | 7-A-41 |
| A-2542 | CH₃ | 4-A-42 |
| A-2543 | CH₃ | 5-A-42 |
| A-2544 | CH₃ | 6-A-42 |
| A-2545 | CH₃ | 7-A-42 |
| A-2546 | CH₃ | 4-A-43 |
| A-2547 | CH₃ | 5-A-43 |
| A-2548 | CH₃ | 6-A-43 |
| A-2549 | CH₃ | 7-A-43 |
| A-2550 | CH₃ | 4-A-44 |
| A-2551 | CH₃ | 5-A-44 |
| A-2552 | CH₃ | 6-A-44 |
| A-2553 | CH₃ | 7-A-44 |
| A-2554 | CH₃ | 4-A-45 |
| A-2555 | CH₃ | 5-A-45 |
| A-2556 | CH₃ | 6-A-45 |
| A-2557 | CH₃ | 7-A-45 |
| A-2558 | CH₃ | 4-A-46 |
| A-2559 | CH₃ | 5-A-46 |
| A-2560 | CH₃ | 6-A-46 |
| A-2561 | CH₃ | 7-A-46 |
| A-2562 | CH₃ | 4-A-47 |
| A-2563 | CH₃ | 5-A-47 |
| A-2564 | CH₃ | 6-A-47 |
| A-2565 | CH₃ | 7-A-47 |
| A-2566 | CH₃ | 4-A-48 |
| A-2567 | CH₃ | 5-A-48 |
| A-2568 | CH₃ | 6-A-48 |
| A-2569 | CH₃ | 7-A-48 |
| A-2570 | CH₃ | 4-A-49 |
| A-2571 | CH₃ | 5-A-49 |
| A-2572 | CH₃ | 6-A-49 |
| A-2573 | CH₃ | 7-A-49 |
| A-2574 | CH₃ | 4-A-50 |
| A-2575 | CH₃ | 5-A-50 |
| A-2576 | CH₃ | 6-A-50 |
| A-2577 | CH₃ | 7-A-50 |
| A-2578 | CH₃ | 4-A-51 |
| A-2579 | CH₃ | 5-A-51 |
| A-2580 | CH₃ | 6-A-51 |
| A-2581 | CH₃ | 7-A-51 |
| A-2582 | CH₃ | 4-A-52 |
| A-2583 | CH₃ | 5-A-52 |
| A-2584 | CH₃ | 6-A-52 |
| A-2585 | CH₃ | 7-A-52 |
| A-2586 | CH₃ | 4-A-53 |

TABLE A-continued

| No. | R² | R¹ |
|---|---|---|
| A-2587 | CH₃ | 5-A-53 |
| A-2588 | CH₃ | 6-A-53 |
| A-2589 | CH₃ | 7-A-53 |
| A-2590 | CH₃ | 4-A-54 |
| A-2591 | CH₃ | 5-A-54 |
| A-2592 | CH₃ | 6-A-54 |
| A-2593 | CH₃ | 7-A-54 |
| A-2594 | CH₃ | 4-A-55 |
| A-2595 | CH₃ | 5-A-55 |
| A-2596 | CH₃ | 6-A-55 |
| A-2597 | CH₃ | 7-A-55 |
| A-2598 | CH₃ | 4-A-56 |
| A-2599 | CH₃ | 5-A-56 |
| A-2600 | CH₃ | 6-A-56 |
| A-2601 | CH₃ | 7-A-56 |
| A-2602 | CH₃ | 4-A-57 |
| A-2603 | CH₃ | 5-A-57 |
| A-2604 | CH₃ | 6-A-57 |
| A-2605 | CH₃ | 7-A-57 |
| A-2606 | CH₃ | 4-A-58 |
| A-2607 | CH₃ | 5-A-58 |
| A-2608 | CH₃ | 6-A-58 |
| A-2609 | CH₃ | 7-A-58 |
| A-2610 | CH₃ | 4-A-59 |
| A-2611 | CH₃ | 5-A-59 |
| A-2612 | CH₃ | 6-A-59 |
| A-2613 | CH₃ | 7-A-59 |
| A-2614 | CH₃ | 4-A-60 |
| A-2615 | CH₃ | 5-A-60 |
| A-2616 | CH₃ | 6-A-60 |
| A-2617 | CH₃ | 7-A-60 |
| A-2618 | CH₃ | 4-A-61 |
| A-2619 | CH₃ | 5-A-61 |
| A-2620 | CH₃ | 6-A-61 |
| A-2621 | CH₃ | 7-A-61 |
| A-2622 | CH₃ | 4-A-62 |
| A-2623 | CH₃ | 5-A-62 |
| A-2624 | CH₃ | 6-A-62 |
| A-2625 | CH₃ | 7-A-62 |
| A-2626 | CH₃ | 4-A-63 |
| A-2627 | CH₃ | 5-A-63 |
| A-2628 | CH₃ | 6-A-63 |
| A-2629 | CH₃ | 7-A-63 |
| A-2630 | CH₃ | 4-A-64 |
| A-2631 | CH₃ | 5-A-64 |
| A-2632 | CH₃ | 6-A-64 |
| A-2633 | CH₃ | 7-A-64 |
| A-2634 | CH₃ | 4-A-65 |
| A-2635 | CH₃ | 5-A-65 |
| A-2636 | CH₃ | 6-A-65 |
| A-2637 | CH₃ | 7-A-65 |
| A-2638 | CH₃ | 4-A-66 |
| A-2639 | CH₃ | 5-A-66 |
| A-2640 | CH₃ | 6-A-66 |
| A-2641 | CH₃ | 7-A-66 |
| A-2642 | CH₃ | 4-A-67 |
| A-2643 | CH₃ | 5-A-67 |
| A-2644 | CH₃ | 6-A-67 |
| A-2645 | CH₃ | 7-A-67 |
| A-2646 | CH₃ | 4-A-68 |
| A-2647 | CH₃ | 5-A-68 |
| A-2648 | CH₃ | 6-A-68 |
| A-2649 | CH₃ | 7-A-68 |
| A-2650 | CH₃ | 4-A-69 |
| A-2651 | CH₃ | 5-A-69 |
| A-2652 | CH₃ | 6-A-69 |
| A-2653 | CH₃ | 7-A-69 |
| A-2654 | CH₃ | 4-A-70 |
| A-2655 | CH₃ | 5-A-70 |
| A-2656 | CH₃ | 6-A-70 |
| A-2657 | CH₃ | 7-A-70 |
| A-2658 | CH₃ | 4-A-71 |
| A-2659 | CH₃ | 5-A-71 |
| A-2660 | CH₃ | 6-A-71 |
| A-2661 | CH₃ | 7-A-71 |
| A-2662 | CH₃ | 4-A-72 |
| A-2663 | CH₃ | 5-A-72 |
| A-2664 | CH₃ | 6-A-72 |
| A-2665 | CH₃ | 7-A-72 |
| A-2666 | CH₃ | 4-A-73 |
| A-2667 | CH₃ | 5-A-73 |
| A-2668 | CH₃ | 6-A-73 |
| A-2669 | CH₃ | 7-A-73 |
| A-2670 | CH₃ | 4-A-74 |
| A-2671 | CH₃ | 5-A-74 |
| A-2672 | CH₃ | 6-A-74 |
| A-2673 | CH₃ | 7-A-74 |
| A-2674 | CH₃ | 4-A-75 |
| A-2675 | CH₃ | 5-A-75 |
| A-2676 | CH₃ | 6-A-75 |
| A-2677 | CH₃ | 7-A-75 |
| A-2678 | CH₃ | 4-A-76 |
| A-2679 | CH₃ | 5-A-76 |
| A-2680 | CH₃ | 6-A-76 |
| A-2681 | CH₃ | 7-A-76 |
| A-2682 | CH₃ | 4-A-77 |
| A-2683 | CH₃ | 5-A-77 |
| A-2684 | CH₃ | 6-A-77 |
| A-2685 | CH₃ | 7-A-77 |
| A-2686 | CH₃ | 4-A-78 |
| A-2687 | CH₃ | 5-A-78 |
| A-2688 | CH₃ | 6-A-78 |
| A-2689 | CH₃ | 7-A-78 |
| A-2690 | CH₃ | 4-A-79 |
| A-2691 | CH₃ | 5-A-79 |
| A-2692 | CH₃ | 6-A-79 |
| A-2693 | CH₃ | 7-A-79 |
| A-2694 | CH₃ | 4-A-80 |
| A-2695 | CH₃ | 5-A-80 |
| A-2696 | CH₃ | 6-A-80 |
| A-2697 | CH₃ | 7-A-80 |
| A-2698 | CH₃ | 4-A-81 |
| A-2699 | CH₃ | 5-A-81 |
| A-2700 | CH₃ | 6-A-81 |
| A-2701 | CH₃ | 7-A-81 |
| A-2702 | CH₃ | 4-A-82 |
| A-2703 | CH₃ | 5-A-82 |
| A-2704 | CH₃ | 6-A-82 |
| A-2705 | CH₃ | 7-A-82 |
| A-2706 | CH₃ | 4-A-83 |
| A-2707 | CH₃ | 5-A-83 |
| A-2708 | CH₃ | 6-A-83 |
| A-2709 | CH₃ | 7-A-83 |
| A-2710 | CH₃ | 4-A-84 |
| A-2711 | CH₃ | 5-A-84 |
| A-2712 | CH₃ | 6-A-84 |
| A-2713 | CH₃ | 7-A-84 |
| A-2714 | CH₃ | 4-A-85 |
| A-2715 | CH₃ | 5-A-85 |
| A-2716 | CH₃ | 6-A-85 |
| A-2717 | CH₃ | 7-A-85 |
| A-2718 | CH₃ | 4-A-86 |
| A-2719 | CH₃ | 5-A-86 |
| A-2720 | CH₃ | 6-A-86 |
| A-2721 | CH₃ | 7-A-86 |
| A-2722 | CH₃ | 4-A-87 |
| A-2723 | CH₃ | 5-A-87 |
| A-2724 | CH₃ | 6-A-87 |
| A-2725 | CH₃ | 7-A-87 |
| A-2726 | CH₃ | 4-A-88 |
| A-2727 | CH₃ | 5-A-88 |
| A-2728 | CH₃ | 6-A-88 |
| A-2729 | CH₃ | 7-A-88 |
| A-2730 | CH₃ | 4-A-89 |
| A-2731 | CH₃ | 5-A-89 |
| A-2732 | CH₃ | 6-A-89 |
| A-2733 | CH₃ | 7-A-89 |
| A-2734 | CH₃ | 4-A-90 |
| A-2735 | CH₃ | 5-A-90 |
| A-2736 | CH₃ | 6-A-90 |
| A-2737 | CH₃ | 7-A-90 |
| A-2738 | CH₃ | 4-A-91 |
| A-2739 | CH₃ | 5-A-91 |
| A-2740 | CH₃ | 6-A-91 |
| A-2741 | CH₃ | 7-A-91 |
| A-2742 | CH₃ | 4-A-92 |

TABLE A-continued

| No. | R² | R¹ |
|---|---|---|
| A-2743 | CH₃ | 5-A-92 |
| A-2744 | CH₃ | 6-A-92 |
| A-2745 | CH₃ | 7-A-92 |
| A-2746 | CH₃ | 4-A-93 |
| A-2747 | CH₃ | 5-A-93 |
| A-2748 | CH₃ | 6-A-93 |
| A-2749 | CH₃ | 7-A-93 |
| A-2750 | CH₃ | 4-A-94 |
| A-2751 | CH₃ | 5-A-94 |
| A-2752 | CH₃ | 6-A-94 |
| A-2753 | CH₃ | 7-A-94 |
| A-2754 | CH₃ | 4-A-95 |
| A-2755 | CH₃ | 5-A-95 |
| A-2756 | CH₃ | 6-A-95 |
| A-2757 | CH₃ | 7-A-95 |
| A-2758 | CH₃ | 4-A-96 |
| A-2759 | CH₃ | 5-A-96 |
| A-2760 | CH₃ | 6-A-96 |
| A-2761 | CH₃ | 7-A-96 |
| A-2762 | CH₃ | 4-A-97 |
| A-2763 | CH₃ | 5-A-97 |
| A-2764 | CH₃ | 6-A-97 |
| A-2765 | CH₃ | 7-A-97 |
| A-2766 | CH₃ | 4-A-98 |
| A-2767 | CH₃ | 5-A-98 |
| A-2768 | CH₃ | 6-A-98 |
| A-2769 | CH₃ | 7-A-98 |
| A-2770 | CH₃ | 4-A-99 |
| A-2771 | CH₃ | 5-A-99 |
| A-2772 | CH₃ | 6-A-99 |
| A-2773 | CH₃ | 7-A-99 |
| A-2774 | CH₃ | 4-A-100 |
| A-2775 | CH₃ | 5-A-100 |
| A-2776 | CH₃ | 6-A-100 |
| A-2777 | CH₃ | 7-A-100 |
| A-2778 | CH₃ | 4-A-101 |
| A-2779 | CH₃ | 5-A-101 |
| A-2780 | CH₃ | 6-A-101 |
| A-2781 | CH₃ | 7-A-101 |
| A-2782 | CH₃ | 4-A-102 |
| A-2783 | CH₃ | 5-A-102 |
| A-2784 | CH₃ | 6-A-102 |
| A-2785 | CH₃ | 7-A-102 |
| A-2786 | CH₃ | 4-A-103 |
| A-2787 | CH₃ | 5-A-103 |
| A-2788 | CH₃ | 6-A-103 |
| A-2789 | CH₃ | 7-A-103 |
| A-2790 | CH₃ | 4-A-104 |
| A-2791 | CH₃ | 5-A-104 |
| A-2792 | CH₃ | 6-A-104 |
| A-2793 | CH₃ | 7-A-104 |
| A-2794 | CH₃ | 4-A-104 |
| A-2795 | CH₃ | 5-A-104 |
| A-2796 | CH₃ | 6-A-104 |
| A-2797 | CH₃ | 7-A-104 |
| A-2798 | CH₃ | 4-A-105 |
| A-2799 | CH₃ | 5-A-105 |
| A-2800 | CH₃ | 6-A-105 |
| A-2801 | CH₃ | 7-A-105 |
| A-2802 | CH₃ | 4-A-106 |
| A-2803 | CH₃ | 5-A-106 |
| A-2804 | CH₃ | 6-A-106 |
| A-2805 | CH₃ | 7-A-106 |
| A-2806 | CH₃ | 4-A-107 |
| A-2807 | CH₃ | 5-A-107 |
| A-2808 | CH₃ | 6-A-107 |
| A-2809 | CH₃ | 7-A-107 |
| A-2810 | CH₃ | 4-A-108 |
| A-2811 | CH₃ | 5-A-108 |
| A-2812 | CH₃ | 6-A-108 |
| A-2813 | CH₃ | 7-A-108 |
| A-2814 | CH₃ | 4-A-109 |
| A-2815 | CH₃ | 5-A-109 |
| A-2816 | CH₃ | 6-A-109 |
| A-2817 | CH₃ | 7-A-109 |
| A-2818 | CH₃ | 4-A-110 |
| A-2819 | CH₃ | 5-A-110 |
| A-2820 | CH₃ | 6-A-110 |
| A-2821 | CH₃ | 7-A-110 |
| A-2822 | CH₃ | 4-A-111 |
| A-2823 | CH₃ | 5-A-111 |
| A-2824 | CH₃ | 6-A-111 |
| A-2825 | CH₃ | 7-A-111 |
| A-2826 | OH | H |
| A-2827 | OH | 4-Cl |
| A-2828 | OH | 5-Cl |
| A-2829 | OH | 6-Cl |
| A-2830 | OH | 7-Cl |
| A-2831 | OH | 4-Br |
| A-2832 | OH | 5-Br |
| A-2833 | OH | 6-Br |
| A-2834 | OH | 7-Br |
| A-2835 | OH | 4-CN |
| A-2836 | OH | 5-CN |
| A-2837 | OH | 6-CN |
| A-2838 | OH | 7-CN |
| A-2839 | OH | 4-OH |
| A-2840 | OH | 5-OH |
| A-2841 | OH | 6-OH |
| A-2842 | OH | 7-OH |
| A-2843 | OH | 4-methyl |
| A-2844 | OH | 5-methyl |
| A-2845 | OH | 6-methyl |
| A-2846 | OH | 7-methyl |
| A-2847 | OH | 4-ethyl |
| A-2848 | OH | 5-ethyl |
| A-2849 | OH | 6-ethyl |
| A-2850 | OH | 7-ethyl |
| A-2851 | OH | 4-propyl |
| A-2852 | OH | 5-propyl |
| A-2853 | OH | 6-propyl |
| A-2854 | OH | 7-propyl |
| A-2855 | OH | 4-isopropyl |
| A-2856 | OH | 5-isopropyl |
| A-2857 | OH | 6-isopropyl |
| A-2858 | OH | 7-isopropyl |
| A-2859 | OH | 4-hydroxymethyl |
| A-2860 | OH | 5-hydroxymethyl |
| A-2861 | OH | 6-hydroxymethyl |
| A-2862 | OH | 7-hydroxymethyl |
| A-2863 | OH | 4-(2-hydroxyethyl) |
| A-2864 | OH | 5-(2-hydroxyethyl) |
| A-2865 | OH | 6-(2-hydroxyethyl) |
| A-2866 | OH | 7-(2-hydroxyethyl) |
| A-2867 | OH | 4-(1-hydroxyethyl) |
| A-2868 | OH | 5-(1-hydroxyethyl) |
| A-2869 | OH | 6-(1-hydroxyethyl) |
| A-2870 | OH | 7-(1-hydroxyethyl) |
| A-2871 | OH | 4-(3-hydroxypropyl) |
| A-2872 | OH | 5-(3-hydroxypropyl) |
| A-2873 | OH | 6-(3-hydroxypropyl) |
| A-2874 | OH | 7-(3-hydroxypropyl) |
| A-2875 | OH | 4-(2-hydroxypropyl) |
| A-2876 | OH | 5-(2-hydroxypropyl) |
| A-2877 | OH | 6-(2-hydroxypropyl) |
| A-2878 | OH | 7-(2-hydroxypropyl) |
| A-2879 | OH | 4-(1-hydroxypropyl) |
| A-2880 | OH | 5-(1-hydroxypropyl) |
| A-2881 | OH | 6-(1-hydroxypropyl) |
| A-2882 | OH | 7-(1-hydroxypropyl) |
| A-2883 | OH | 4-aminomethyl |
| A-2884 | OH | 5-aminomethyl |
| A-2885 | OH | 6-aminomethyl |
| A-2886 | OH | 7-aminomethyl |
| A-2887 | OH | 4-(2-aminoethyl) |
| A-2888 | OH | 5-(2-aminoethyl) |
| A-2889 | OH | 6-(2-aminoethyl) |
| A-2890 | OH | 7-(2-aminoethyl) |
| A-2891 | OH | 4-(1-aminoethyl) |
| A-2892 | OH | 5-(1-aminoethyl) |
| A-2893 | OH | 6-(1-aminoethyl) |
| A-2894 | OH | 7-(1-aminoethyl) |
| A-2895 | OH | 4-(3-aminopropyl) |
| A-2896 | OH | 5-(3-aminopropyl) |
| A-2897 | OH | 6-(3-aminopropyl) |
| A-2898 | OH | 7-(3-aminopropyl) |

TABLE A-continued

| No. | R² | R¹ |
|---|---|---|
| A-2899 | OH | 4-(2-aminopropyl) |
| A-2900 | OH | 5-(2-aminopropyl) |
| A-2901 | OH | 6-(2-aminopropyl) |
| A-2902 | OH | 7-(2-aminopropyl) |
| A-2903 | OH | 4-(1-aminopropyl) |
| A-2904 | OH | 5-(1-aminopropyl) |
| A-2905 | OH | 6-(1-aminopropyl) |
| A-2906 | OH | 7-(1-aminopropyl) |
| A-2907 | OH | 4-COOH |
| A-2908 | OH | 5-COOH |
| A-2909 | OH | 6-COOH |
| A-2910 | OH | 7-COOH |
| A-2911 | OH | 4-COOCH₃ |
| A-2912 | OH | 5-COOCH₃ |
| A-2913 | OH | 6-COOCH₃ |
| A-2914 | OH | 7-COOCH₃ |
| A-2915 | OH | 4-COOCH₂CH₃ |
| A-2916 | OH | 5-COOCH₂CH₃ |
| A-2917 | OH | 6-COOCH₂CH₃ |
| A-2918 | OH | 7-COOCH₂CH₃ |
| A-2919 | OH | 4-COOCF₃ |
| A-2920 | OH | 5-COOCF₃ |
| A-2921 | OH | 6-COOCF₃ |
| A-2922 | OH | 7-COOCF₃ |
| A-2923 | OH | 4-CONH₂ |
| A-2924 | OH | 5-CONH₂ |
| A-2925 | OH | 6-CONH₂ |
| A-2926 | OH | 7-CONH₂ |
| A-2927 | OH | 4-CONHCH₃ |
| A-2928 | OH | 5-CONHCH₃ |
| A-2929 | OH | 6-CONHCH₃ |
| A-2930 | OH | 7-CONHCH₃ |
| A-2931 | OH | 4-CON(CH₃)₂ |
| A-2932 | OH | 5-CON(CH₃)₂ |
| A-2933 | OH | 6-CON(CH₃)₂ |
| A-2934 | OH | 7-CON(CH₃)₂ |
| A-2935 | OH | 4-CONHCH₂CH₃ |
| A-2936 | OH | 5-CONHCH₂CH₃ |
| A-2937 | OH | 6-CONHCH₂CH₃ |
| A-2938 | OH | 7-CONHCH₂CH₃ |
| A-2939 | OH | 4-CON(CH₂CH₃)₂ |
| A-2940 | OH | 5-CON(CH₂CH₃)₂ |
| A-2941 | OH | 6-CON(CH₂CH₃)₂ |
| A-2942 | OH | 7-CON(CH₂CH₃)₂ |
| A-2943 | OH | 4-A-1 |
| A-2944 | OH | 5-A-1 |
| A-2945 | OH | 6-A-1 |
| A-2946 | OH | 7-A-1 |
| A-2947 | OH | 4-A-2 |
| A-2948 | OH | 5-A-2 |
| A-2949 | OH | 6-A-2 |
| A-2950 | OH | 7-A-2 |
| A-2951 | OH | 4-A-3 |
| A-2952 | OH | 5-A-3 |
| A-2953 | OH | 6-A-3 |
| A-2954 | OH | 7-A-3 |
| A-2955 | OH | 4-A-4 |
| A-2956 | OH | 5-A-4 |
| A-2957 | OH | 6-A-4 |
| A-2958 | OH | 7-A-4 |
| A-2959 | OH | 4-A-5 |
| A-2960 | OH | 5-A-5 |
| A-2961 | OH | 6-A-5 |
| A-2962 | OH | 7-A-5 |
| A-2963 | OH | 4-A-6 |
| A-2964 | OH | 5-A-6 |
| A-2965 | OH | 6-A-6 |
| A-2966 | OH | 7-A-6 |
| A-2967 | OH | 4-A-7 |
| A-2968 | OH | 5-A-7 |
| A-2969 | OH | 6-A-7 |
| A-2970 | OH | 7-A-7 |
| A-2971 | OH | 4-A-8 |
| A-2972 | OH | 5-A-8 |
| A-2973 | OH | 6-A-8 |
| A-2974 | OH | 7-A-8 |
| A-2975 | OH | 4-A-9 |
| A-2976 | OH | 5-A-9 |
| A-2977 | OH | 6-A-9 |
| A-2978 | OH | 7-A-9 |
| A-2979 | OH | 4-A-10 |
| A-2980 | OH | 5-A-10 |
| A-2981 | OH | 6-A-10 |
| A-2982 | OH | 7-A-10 |
| A-2983 | OH | 4-A-11 |
| A-2984 | OH | 5-A-11 |
| A-2985 | OH | 6-A-11 |
| A-2986 | OH | 7-A-11 |
| A-2987 | OH | 4-A-12 |
| A-2988 | OH | 5-A-12 |
| A-2989 | OH | 6-A-12 |
| A-2990 | OH | 7-A-12 |
| A-2991 | OH | 4-A-13 |
| A-2992 | OH | 5-A-13 |
| A-2993 | OH | 6-A-13 |
| A-2994 | OH | 7-A-13 |
| A-2995 | OH | 4-A-14 |
| A-2996 | OH | 5-A-14 |
| A-2997 | OH | 6-A-14 |
| A-2998 | OH | 7-A-14 |
| A-2999 | OH | 4-A-15 |
| A-3000 | OH | 5-A-15 |
| A-3001 | OH | 6-A-15 |
| A-3002 | OH | 7-A-15 |
| A-3003 | OH | 4-A-16 |
| A-3004 | OH | 5-A-16 |
| A-3005 | OH | 6-A-16 |
| A-3006 | OH | 7-A-16 |
| A-3007 | OH | 4-A-17 |
| A-3008 | OH | 5-A-17 |
| A-3009 | OH | 6-A-17 |
| A-3010 | OH | 7-A-17 |
| A-3011 | OH | 4-A-18 |
| A-3012 | OH | 5-A-18 |
| A-3013 | OH | 6-A-18 |
| A-3014 | OH | 7-A-18 |
| A-3015 | OH | 4-A-19 |
| A-3016 | OH | 5-A-19 |
| A-3017 | OH | 6-A-19 |
| A-3018 | OH | 7-A-19 |
| A-3019 | OH | 4-A-20 |
| A-3020 | OH | 5-A-20 |
| A-3021 | OH | 6-A-20 |
| A-3022 | OH | 7-A-20 |
| A-3023 | OH | 4-A-21 |
| A-3024 | OH | 5-A-21 |
| A-3025 | OH | 6-A-21 |
| A-3026 | OH | 7-A-21 |
| A-3027 | OH | 4-A-22 |
| A-3028 | OH | 5-A-22 |
| A-3029 | OH | 6-A-22 |
| A-3030 | OH | 7-A-22 |
| A-3031 | OH | 4-A-23 |
| A-3032 | OH | 5-A-23 |
| A-3033 | OH | 6-A-23 |
| A-3034 | OH | 7-A-23 |
| A-3035 | OH | 4-A-24 |
| A-3036 | OH | 5-A-24 |
| A-3037 | OH | 6-A-24 |
| A-3038 | OH | 7-A-24 |
| A-3039 | OH | 4-A-25 |
| A-3040 | OH | 5-A-25 |
| A-3041 | OH | 6-A-25 |
| A-3042 | OH | 7-A-25 |
| A-3043 | OH | 4-A-26 |
| A-3044 | OH | 5-A-26 |
| A-3045 | OH | 6-A-26 |
| A-3046 | OH | 7-A-26 |
| A-3047 | OH | 4-A-27 |
| A-3048 | OH | 5-A-27 |
| A-3049 | OH | 6-A-27 |
| A-3050 | OH | 7-A-27 |
| A-3051 | OH | 4-A-28 |
| A-3052 | OH | 5-A-28 |
| A-3053 | OH | 6-A-28 |
| A-3054 | OH | 7-A-28 |

TABLE A-continued

| No. | R² | R¹ |
|---|---|---|
| A-3055 | OH | 4-A-29 |
| A-3056 | OH | 5-A-29 |
| A-3057 | OH | 6-A-29 |
| A-3058 | OH | 7-A-29 |
| A-3059 | OH | 4-A-30 |
| A-3060 | OH | 5-A-30 |
| A-3061 | OH | 6-A-30 |
| A-3062 | OH | 7-A-30 |
| A-3063 | OH | 4-A-31 |
| A-3064 | OH | 5-A-31 |
| A-3065 | OH | 6-A-31 |
| A-3066 | OH | 7-A-31 |
| A-3067 | OH | 4-A-32 |
| A-3068 | OH | 5-A-32 |
| A-3069 | OH | 6-A-32 |
| A-3070 | OH | 7-A-32 |
| A-3071 | OH | 4-A-33 |
| A-3072 | OH | 5-A-33 |
| A-3073 | OH | 6-A-33 |
| A-3074 | OH | 7-A-33 |
| A-3075 | OH | 4-A-34 |
| A-3076 | OH | 5-A-34 |
| A-3077 | OH | 6-A-34 |
| A-3078 | OH | 7-A-34 |
| A-3079 | OH | 4-A-35 |
| A-3080 | OH | 5-A-35 |
| A-3081 | OH | 6-A-35 |
| A-3082 | OH | 7-A-35 |
| A-3083 | OH | 4-A-36 |
| A-3084 | OH | 5-A-36 |
| A-3085 | OH | 6-A-36 |
| A-3086 | OH | 7-A-36 |
| A-3087 | OH | 4-A-37 |
| A-3088 | OH | 5-A-37 |
| A-3089 | OH | 6-A-37 |
| A-3090 | OH | 7-A-37 |
| A-3091 | OH | 4-A-38 |
| A-3092 | OH | 5-A-38 |
| A-3093 | OH | 6-A-38 |
| A-3094 | OH | 7-A-38 |
| A-3095 | OH | 4-A-39 |
| A-3096 | OH | 5-A-39 |
| A-3097 | OH | 6-A-39 |
| A-3098 | OH | 7-A-39 |
| A-3099 | OH | 4-A-40 |
| A-3100 | OH | 5-A-40 |
| A-3101 | OH | 6-A-40 |
| A-3102 | OH | 7-A-40 |
| A-3103 | OH | 4-A-41 |
| A-3104 | OH | 5-A-41 |
| A-3105 | OH | 6-A-41 |
| A-3106 | OH | 7-A-41 |
| A-3107 | OH | 4-A-42 |
| A-3108 | OH | 5-A-42 |
| A-3109 | OH | 6-A-42 |
| A-3110 | OH | 7-A-42 |
| A-3111 | OH | 4-A-43 |
| A-3112 | OH | 5-A-43 |
| A-3113 | OH | 6-A-43 |
| A-3114 | OH | 7-A-43 |
| A-3115 | OH | 4-A-44 |
| A-3116 | OH | 5-A-44 |
| A-3117 | OH | 6-A-44 |
| A-3118 | OH | 7-A-44 |
| A-3119 | OH | 4-A-45 |
| A-3120 | OH | 5-A-45 |
| A-3121 | OH | 6-A-45 |
| A-3122 | OH | 7-A-45 |
| A-3123 | OH | 4-A-46 |
| A-3124 | OH | 5-A-46 |
| A-3125 | OH | 6-A-46 |
| A-3126 | OH | 7-A-46 |
| A-3127 | OH | 4-A-47 |
| A-3128 | OH | 5-A-47 |
| A-3129 | OH | 6-A-47 |
| A-3130 | OH | 7-A-47 |
| A-3131 | OH | 4-A-48 |
| A-3132 | OH | 5-A-48 |
| A-3133 | OH | 6-A-48 |
| A-3134 | OH | 7-A-48 |
| A-3135 | OH | 4-A-49 |
| A-3136 | OH | 5-A-49 |
| A-3137 | OH | 6-A-49 |
| A-3138 | OH | 7-A-49 |
| A-3139 | OH | 4-A-50 |
| A-3140 | OH | 5-A-50 |
| A-3141 | OH | 6-A-50 |
| A-3142 | OH | 7-A-50 |
| A-3143 | OH | 4-A-51 |
| A-3144 | OH | 5-A-51 |
| A-3145 | OH | 6-A-51 |
| A-3146 | OH | 7-A-51 |
| A-3147 | OH | 4-A-52 |
| A-3148 | OH | 5-A-52 |
| A-3149 | OH | 6-A-52 |
| A-3150 | OH | 7-A-52 |
| A-3151 | OH | 4-A-53 |
| A-3152 | OH | 5-A-53 |
| A-3153 | OH | 6-A-53 |
| A-3154 | OH | 7-A-53 |
| A-3155 | OH | 4-A-54 |
| A-3156 | OH | 5-A-54 |
| A-3157 | OH | 6-A-54 |
| A-3158 | OH | 7-A-54 |
| A-3159 | OH | 4-A-55 |
| A-3160 | OH | 5-A-55 |
| A-3161 | OH | 6-A-55 |
| A-3162 | OH | 7-A-55 |
| A-3163 | OH | 4-A-56 |
| A-3164 | OH | 5-A-56 |
| A-3165 | OH | 6-A-56 |
| A-3166 | OH | 7-A-56 |
| A-3167 | OH | 4-A-57 |
| A-3168 | OH | 5-A-57 |
| A-3169 | OH | 6-A-57 |
| A-3170 | OH | 7-A-57 |
| A-3171 | OH | 4-A-58 |
| A-3172 | OH | 5-A-58 |
| A-3173 | OH | 6-A-58 |
| A-3174 | OH | 7-A-58 |
| A-3175 | OH | 4-A-59 |
| A-3176 | OH | 5-A-59 |
| A-3177 | OH | 6-A-59 |
| A-3178 | OH | 7-A-59 |
| A-3179 | OH | 4-A-60 |
| A-3180 | OH | 5-A-60 |
| A-3181 | OH | 6-A-60 |
| A-3182 | OH | 7-A-60 |
| A-3183 | OH | 4-A-61 |
| A-3184 | OH | 5-A-61 |
| A-3185 | OH | 6-A-61 |
| A-3186 | OH | 7-A-61 |
| A-3187 | OH | 4-A-62 |
| A-3188 | OH | 5-A-62 |
| A-3189 | OH | 6-A-62 |
| A-3190 | OH | 7-A-62 |
| A-3191 | OH | 4-A-63 |
| A-3192 | OH | 5-A-63 |
| A-3193 | OH | 6-A-63 |
| A-3194 | OH | 7-A-63 |
| A-3195 | OH | 4-A-64 |
| A-3196 | OH | 5-A-64 |
| A-3197 | OH | 6-A-64 |
| A-3198 | OH | 7-A-64 |
| A-3199 | OH | 4-A-65 |
| A-3200 | OH | 5-A-65 |
| A-3201 | OH | 6-A-65 |
| A-3202 | OH | 7-A-65 |
| A-3203 | OH | 4-A-66 |
| A-3204 | OH | 5-A-66 |
| A-3205 | OH | 6-A-66 |
| A-3206 | OH | 7-A-66 |
| A-3207 | OH | 4-A-67 |
| A-3208 | OH | 5-A-67 |
| A-3209 | OH | 6-A-67 |
| A-3210 | OH | 7-A-67 |

TABLE A-continued

| No. | R² | R¹ |
|---|---|---|
| A-3211 | OH | 4-A-68 |
| A-3212 | OH | 5-A-68 |
| A-3213 | OH | 6-A-68 |
| A-3214 | OH | 7-A-68 |
| A-3215 | OH | 4-A-69 |
| A-3216 | OH | 5-A-69 |
| A-3217 | OH | 6-A-69 |
| A-3218 | OH | 7-A-69 |
| A-3219 | OH | 4-A-70 |
| A-3220 | OH | 5-A-70 |
| A-3221 | OH | 6-A-70 |
| A-3222 | OH | 7-A-70 |
| A-3223 | OH | 4-A-71 |
| A-3224 | OH | 5-A-71 |
| A-3225 | OH | 6-A-71 |
| A-3226 | OH | 7-A-71 |
| A-3227 | OH | 4-A-72 |
| A-3228 | OH | 5-A-72 |
| A-3229 | OH | 6-A-72 |
| A-3230 | OH | 7-A-72 |
| A-3231 | OH | 4-A-73 |
| A-3232 | OH | 5-A-73 |
| A-3233 | OH | 6-A-73 |
| A-3234 | OH | 7-A-73 |
| A-3235 | OH | 4-A-74 |
| A-3236 | OH | 5-A-74 |
| A-3237 | OH | 6-A-74 |
| A-3238 | OH | 7-A-74 |
| A-3239 | OH | 4-A-75 |
| A-3240 | OH | 5-A-75 |
| A-3241 | OH | 6-A-75 |
| A-3242 | OH | 7-A-75 |
| A-3243 | OH | 4-A-76 |
| A-3244 | OH | 5-A-76 |
| A-3245 | OH | 6-A-76 |
| A-3246 | OH | 7-A-76 |
| A-3247 | OH | 4-A-77 |
| A-3248 | OH | 5-A-77 |
| A-3249 | OH | 6-A-77 |
| A-3250 | OH | 7-A-77 |
| A-3251 | OH | 4-A-78 |
| A-3252 | OH | 5-A-78 |
| A-3253 | OH | 6-A-78 |
| A-3254 | OH | 7-A-78 |
| A-3255 | OH | 4-A-79 |
| A-3256 | OH | 5-A-79 |
| A-3257 | OH | 6-A-79 |
| A-3258 | OH | 7-A-79 |
| A-3259 | OH | 4-A-80 |
| A-3260 | OH | 5-A-80 |
| A-3261 | OH | 6-A-80 |
| A-3262 | OH | 7-A-80 |
| A-3263 | OH | 4-A-81 |
| A-3264 | OH | 5-A-81 |
| A-3265 | OH | 6-A-81 |
| A-3266 | OH | 7-A-81 |
| A-3267 | OH | 4-A-82 |
| A-3268 | OH | 5-A-82 |
| A-3269 | OH | 6-A-82 |
| A-3270 | OH | 7-A-82 |
| A-3271 | OH | 4-A-83 |
| A-3272 | OH | 5-A-83 |
| A-3273 | OH | 6-A-83 |
| A-3274 | OH | 7-A-83 |
| A-3275 | OH | 4-A-84 |
| A-3276 | OH | 5-A-84 |
| A-3277 | OH | 6-A-84 |
| A-3278 | OH | 7-A-84 |
| A-3279 | OH | 4-A-85 |
| A-3280 | OH | 5-A-85 |
| A-3281 | OH | 6-A-85 |
| A-3282 | OH | 7-A-85 |
| A-3283 | OH | 4-A-86 |
| A-3284 | OH | 5-A-86 |
| A-3285 | OH | 6-A-86 |
| A-3286 | OH | 7-A-86 |
| A-3287 | OH | 4-A-87 |
| A-3288 | OH | 5-A-87 |
| A-3289 | OH | 6-A-87 |
| A-3290 | OH | 7-A-87 |
| A-3291 | OH | 4-A-88 |
| A-3292 | OH | 5-A-88 |
| A-3293 | OH | 6-A-88 |
| A-3294 | OH | 7-A-88 |
| A-3295 | OH | 4-A-89 |
| A-3296 | OH | 5-A-89 |
| A-3297 | OH | 6-A-89 |
| A-3298 | OH | 7-A-89 |
| A-3299 | OH | 4-A-90 |
| A-3300 | OH | 5-A-90 |
| A-3301 | OH | 6-A-90 |
| A-3302 | OH | 7-A-90 |
| A-3303 | OH | 4-A-91 |
| A-3304 | OH | 5-A-91 |
| A-3305 | OH | 6-A-91 |
| A-3306 | OH | 7-A-91 |
| A-3307 | OH | 4-A-92 |
| A-3308 | OH | 5-A-92 |
| A-3309 | OH | 6-A-92 |
| A-3310 | OH | 7-A-92 |
| A-3311 | OH | 4-A-93 |
| A-3312 | OH | 5-A-93 |
| A-3313 | OH | 6-A-93 |
| A-3314 | OH | 7-A-93 |
| A-3315 | OH | 4-A-94 |
| A-3316 | OH | 5-A-94 |
| A-3317 | OH | 6-A-94 |
| A-3318 | OH | 7-A-94 |
| A-3319 | OH | 4-A-95 |
| A-3320 | OH | 5-A-95 |
| A-3321 | OH | 6-A-95 |
| A-3322 | OH | 7-A-95 |
| A-3323 | OH | 4-A-96 |
| A-3324 | OH | 5-A-96 |
| A-3325 | OH | 6-A-96 |
| A-3326 | OH | 7-A-96 |
| A-3327 | OH | 4-A-97 |
| A-3328 | OH | 5-A-97 |
| A-3329 | OH | 6-A-97 |
| A-3330 | OH | 7-A-97 |
| A-3331 | OH | 4-A-98 |
| A-3332 | OH | 5-A-98 |
| A-3333 | OH | 6-A-98 |
| A-3334 | OH | 7-A-98 |
| A-3335 | OH | 4-A-99 |
| A-3336 | OH | 5-A-99 |
| A-3337 | OH | 6-A-99 |
| A-3338 | OH | 7-A-99 |
| A-3339 | OH | 4-A-100 |
| A-3340 | OH | 5-A-100 |
| A-3341 | OH | 6-A-100 |
| A-3342 | OH | 7-A-100 |
| A-3343 | OH | 4-A-101 |
| A-3344 | OH | 5-A-101 |
| A-3345 | OH | 6-A-101 |
| A-3346 | OH | 7-A-101 |
| A-3347 | OH | 4-A-102 |
| A-3348 | OH | 5-A-102 |
| A-3349 | OH | 6-A-102 |
| A-3350 | OH | 7-A-102 |
| A-3351 | OH | 4-A-103 |
| A-3352 | OH | 5-A-103 |
| A-3353 | OH | 6-A-103 |
| A-3354 | OH | 7-A-103 |
| A-3355 | OH | 4-A-104 |
| A-3356 | OH | 5-A-104 |
| A-3357 | OH | 6-A-104 |
| A-3358 | OH | 7-A-104 |
| A-3359 | OH | 4-A-104 |
| A-3360 | OH | 5-A-104 |
| A-3361 | OH | 6-A-104 |
| A-3362 | OH | 7-A-104 |
| A-3363 | OH | 4-A-105 |
| A-3364 | OH | 5-A-105 |
| A-3365 | OH | 6-A-105 |
| A-3366 | OH | 7-A-105 |

TABLE A-continued

| No. | R² | R¹ |
| --- | --- | --- |
| A-3367 | OH | 4-A-106 |
| A-3368 | OH | 5-A-106 |
| A-3369 | OH | 6-A-106 |
| A-3370 | OH | 7-A-106 |
| A-3371 | OH | 4-A-107 |
| A-3372 | OH | 5-A-107 |
| A-3373 | OH | 6-A-107 |
| A-3374 | OH | 7-A-107 |
| A-3375 | OH | 4-A-108 |
| A-3376 | OH | 5-A-108 |
| A-3377 | OH | 6-A-108 |
| A-3378 | OH | 7-A-108 |
| A-3379 | OH | 4-A-109 |
| A-3380 | OH | 5-A-109 |
| A-3381 | OH | 6-A-109 |
| A-3382 | OH | 7-A-109 |
| A-3383 | OH | 4-A-110 |
| A-3384 | OH | 5-A-110 |
| A-3385 | OH | 6-A-110 |
| A-3386 | OH | 7-A-110 |
| A-3387 | OH | 4-A-111 |
| A-3388 | OH | 5-A-111 |
| A-3389 | OH | 6-A-111 |
| A-3390 | OH | 7-A-111 |

Among the above compounds, preference is given to compounds of formulae I.1 to I.21, I.37 to I.57, I.73 to I.93 and I.109 to I.129. More preference is given to compounds I.1 to I.6, I.10 to I.17, I.37 to I.42, I.46 to I.53, I.73 to I.78, I.82 to I.89, I.109 to I.114 and I.118 to I.125. Even more preference is given to compounds of formulae I.1, I.2, I.3, I.10, I.11, I.12, I.13, I.14, I.15, I.16, I.17, I.37, I.38, I.39, I.46, I.47, I.48, I.49, I.50, I.51, I.52, I.53, I.74, I.77, I.83, I.84, I.87, I.88, I.109, I.110, I.111, I.113, I.118, I.119, I.120 and I.124. Particular preference is given to compounds of formulae I.10, I.11, I.12, I.13, I.46, I.47, I.48, I.49, I.110 and I.120. Specific preference is given to compounds of formulae I.13, I.46, I.49, I.110 and I.120.

The compounds of the present invention can be prepared by analogy to routine techniques a skilled person is familiar with. In particular, the compounds of the formula IA and IB can be prepared according to the following schemes, wherein the variables, if not stated otherwise, are as defined above. In the below schemes, compounds of formula IA are expressed as target molecules. However, the same reactions apply to the syntheses of compounds IB.

Compounds of formula IA can be prepared by reacting the indolol compound 1 with the the pyridyl derivative 2, where X is Cl or Br. The reaction can be carried out under the conditions of a Heck reaction, via Pd-catalysed cross coupling, generally in the presence of a base. Alternatively, 1 and 2 can be reacted in a nucleophilic aromatic substitution reaction in the presence of a strong, non-nucleophilic base, such as NaH, LDA or preferably sodium bis(trimethylsilyl) amide (NaHMDS). If suitable, the nucleophilic aromatic substitution reaction can also be carried out with the N-oxide of the pyridyl compound 2.

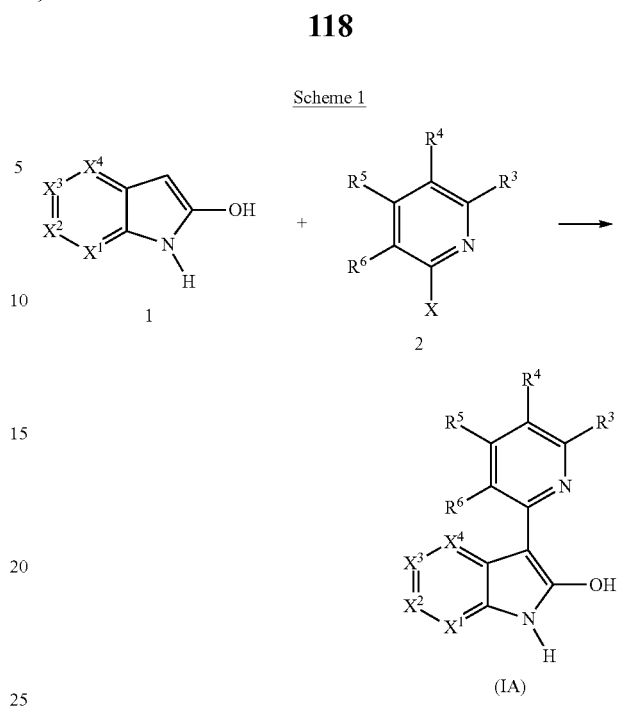

Compounds 1 are either commercially available or can be synthesized by procedures generally known in the art. For example, generally known substitution reactions for introducing different substituents $R^1$ (different from hydrogen) can be applied. For instance, a compound 1 wherein at least one substituent $R^1$ is hydrogen can be halogenated, for example by reaction with N-chlorosuccinimide, N-bromosuccinimide or N-iodosuccinimide, to give a compound 1 wherein this $R^1$ is Cl, Br or I. This in turn can be reacted with CuCN to give a compound 1 wherein this $R^1$ is CN. An exemplary reaction pattern using indolone as a scaffold for compound 1 is shown in scheme 2.

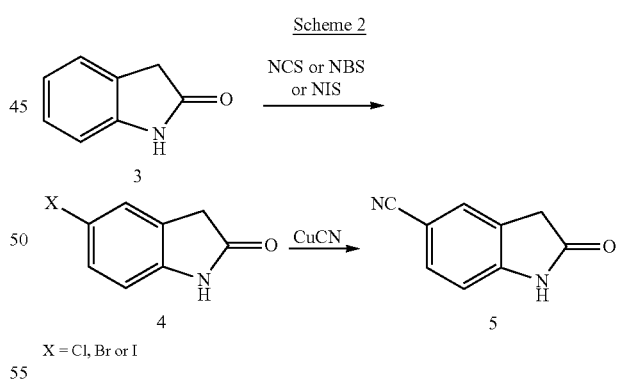

If $R^1$ is Ar, this substituent can be introduced via a Suzuki coupling reaction, as shown in schemes 3 and 4 exemplarily for indolone as a scaffold for compound 1. BRR' is a boronic acid residue [B(OH)₂] or a boronic ester group, such as B(O-t-butyl)₂, B(—O—C(CH₃)₂—C(CH₃)₂—O—) and the like. The reaction is carried in the presence of a palladium catalyst, especially a palladium phosphane catalyst, such as tetrakis(triphenylphosphine)palladium(0), and of a base, such as NaOH, Na₂CO₃, NaHCO₃, Na₃PO₄, sodium methanolate, sodium ethanolate and the like.

Scheme 3

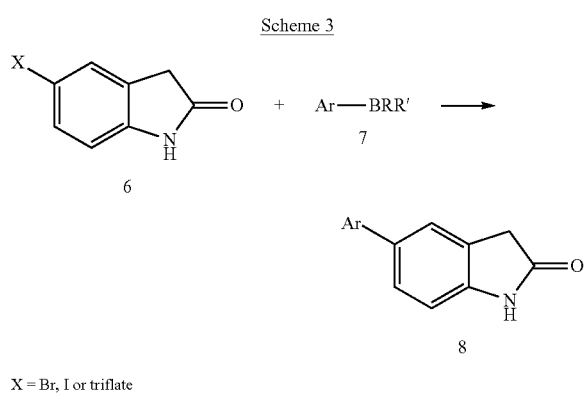

X = Br, I or triflate

Scheme 4

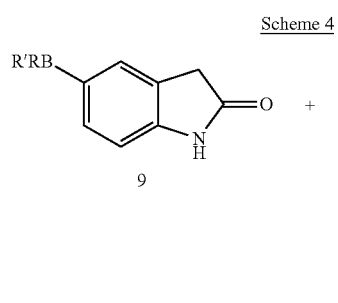

X = Br, I or triflate

Compounds 2 are either commercially available or can be synthesized by procedures generally known in the art.

Compounds 2, wherein $R^3$ and $R^4$ form together a group —$(CH_2)_3$—C(O)— (compound 2.1), can for example be prepared by reacting 3-aminocyclohex-2-enone 9 with an alkyl-propiolate, e.g. methylpropiolate 10, and subsequently halogenating the keto/enol group of 11 with a halogenating agent, such as $POCl_3$, as shown in scheme 5. The same reaction sequence can be applied for producing compounds, wherein $R^3$ and $R^4$ form together a group —$(CH_2)_2$—C(O)— by using 3-aminocyclopent-2-enone instead of 9, for producing compounds, wherein $R^3$ and $R^4$ form together a group —C(O)—$(CH_2)_3$— by using 2-aminocyclohex-2-enone instead of 9, for producing compounds, wherein $R^3$ and $R^4$ form together a group —C(O)—$(CH_2)_2$— by using 2-aminocyclopent-2-enone instead of 9, etc.

Scheme 5

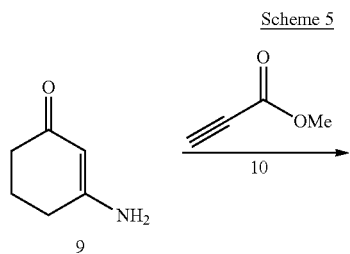

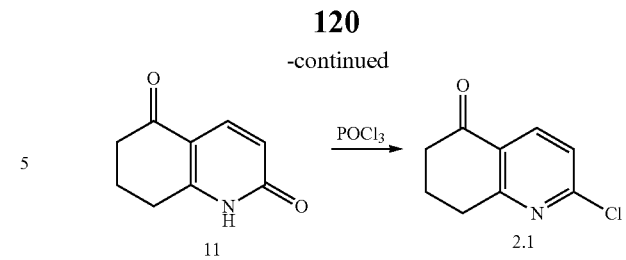

For producing compounds 2, wherein $R^4$ and $R^5$ form together a group —C(O)—O—$CH_2$— or —$CH_2$—$NR^c$—$CH_2$—, the reaction sequence shown in scheme 6 can be used. The carboxyl group of 12 is suitably first converted into its acid chloride, e.g. via reaction with thionyl chloride or oxalylchloride, and the acid chloride is then reacted with diisopropylamine to the amide 13. Deprotonation with LDA in the activated 4-position yields a carbanion which nucleophilicaly attacks dimethylformamide to give the amide-aldehyde 14. Reduction of the aldehyde group, e.g. with $NaBH_4$, and subsequent esterification leads to the furanone 15. If desired, this can be subjected to a reductive ring-opening reaction to the dimethylol 16, which is converted into the respective dimethylchloride 17. Reaction of 17 with a primary amine R—$NH_2$, where advantageously R is a group which can be easily removed, such as benzyl or PMB (PMB=para-methoxybenzyl), yields the pyrrolidinypyridine 18, which is deprotected to 19. Deprotection is carried out depending on the group R, e.g. with HCl or 1-chloroethyl-chloroformiate if R is benzyl or a substituted benzyl, such as PMB.

Scheme 6

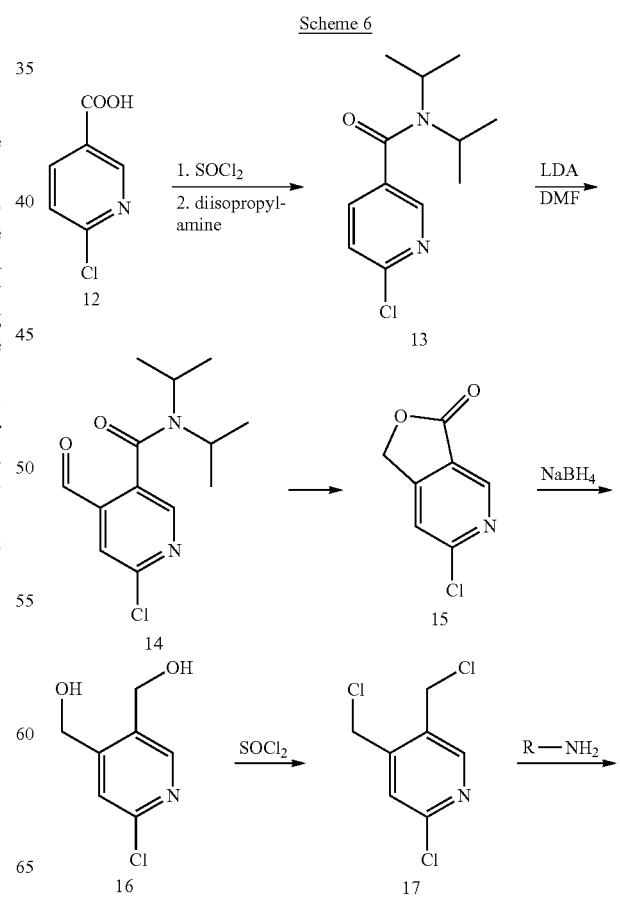

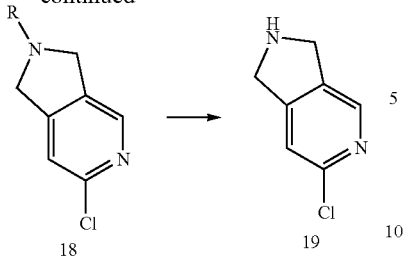

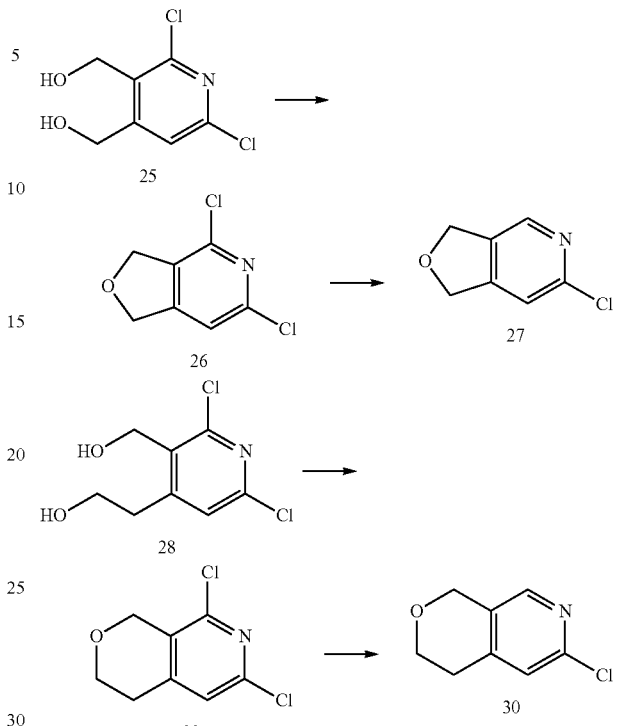

Scheme 8

Compounds 2, wherein $R^5$ and $R^6$ form together a group —C(O)—O—CH$_2$— or —CH$_2$—NR$^c$—CH$_2$—, can be prepared in an analogous reaction sequence, however starting from 2-chloro-nicotinic acid.

Compounds 2, wherein $R^4$ and $R^5$ form together a group —(CH$_2$)$_4$—, can be prepared by the reaction sequence shown in scheme 7. 20 is subjected to a ring-closing reaction with ammonium carbonate under heating (230° C.), as described in Chemische Berichte 1948, 81, 279-285. Alternatively, 21 is reacted according to the procedure described in J. Chem. Soc. 1932, 2426-2430 to 22. The diol 22 is then converted into the respective dichloride 23, e.g. with phosphoryl chloride. Reaction with zinc powder and aqueous HCl as described in Chemische Berichte 1948, 81, 279-285 finally yields 24.

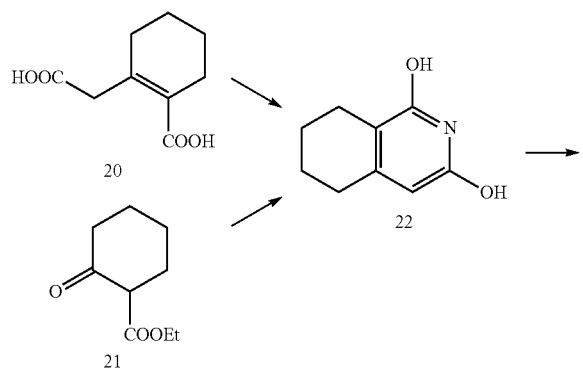

Scheme 7

Compounds 2, wherein $R^4$ and $R^5$ form together a group —CH$_2$—O—CH$_2$— or —CH$_2$—O—CH$_2$—CH$_2$—, can be prepared as shown in scheme 8. 25 or 28 are reacted with triethylsilane, Mn(IV) oxide and trifluoroacetic acid as described in Tetrahedron Lett. 2008, 49(47), 6701-6703. Removal of one chlorine atom is accomplished using zinc powder and aqueous HCl, as described in Chemische Berichte 1948, 81, 279-285.

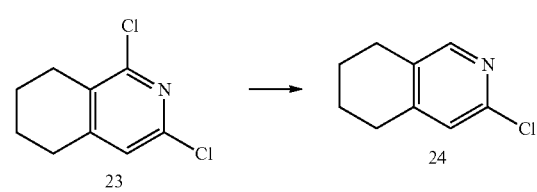

Compounds 2, wherein $R^4$ and $R^5$ form together a group —CH$_2$—CH$_2$—NR$^c$—C(O)— are known and described, for example, in EP-A-1180514. Compounds 2, wherein $R^4$ and $R^5$ form together a group —CH$_2$—CH$_2$—NR$^c$—CH$_2$—, can be prepared by reducing compound 31, as shown in scheme 9. Reduction can be carried out, for example, by using a borane reduction agent, such as 9-BBN. Compound 31 is known from EP-A-1180514.

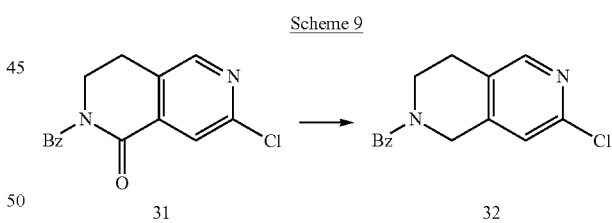

Scheme 9

Compounds IA can be converted into compounds IB, wherein $R^2$ is fluorine, by reaction of IA with a suitable fluorinating agent, such as 1-fluoro-2,4,6-trimethylpyridinium triflate in the presence of a suitable base, such as n-butyllithium or sodium bis(trimethylsilyl)-amide in a suitable solvent, such as tetrahydrofuran or dioxane at from −40° C. to 80° C.

If not indicated otherwise, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

The acid addition salts of compounds IA and IB are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The present invention moreover relates to compounds of formula I as defined above, wherein at least one of the atoms has been replaced by its stable, non-radioactive isotope (e.g., hydrogen by deuterium, $^{13}$C by $^{13}$C, $^{14}$N by $^{15}$N, $^{16}$O by $^{18}$O) and preferably wherein at least one hydrogen atom has been replaced by a deuterium atom.

Of course, the compounds according to the invention contain more of the respective isotope than this naturally occurs and thus is anyway present in the compounds I.

Stable isotopes (e.g., deuterium, $^{13}$C, $^{15}$N, $^{18}$O) are non-radioactive isotopes which contain one additional neutron than the normally abundant isotope of the respective atom. Deuterated compounds have been used in pharmaceutical research to investigate the in vivo metabolic fate of the compounds by evaluation of the mechanism of action and metabolic pathway of the non deuterated parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10): 927-932 (1995); Kushner et al., *Can. J. Physiol. Pharmacol.*, 77, 79-88 (1999).

Incorporation of a heavy atom particularly substitution of deuterium for hydrogen, can give rise to an isotope effect that could alter the pharmacokinetics of the drug. This effect is usually insignificant if the label is placed at a metabolically inert position of the molecule.

Stable isotope labeling of a drug can alter its physicochemical properties such as pKa and lipid solubility. These changes may influence the fate of the drug at different steps along its passage through the body. Absorption, distribution, metabolism or excretion can be changed. Absorption and distribution are processes that depend primarily on the molecular size and the lipophilicity of the substance. These effects and alterations can affect the pharmacodynamic response of the drug molecule if the isotopic substitution affects a region involved in a ligand-receptor interaction.

Drug metabolism can give rise to large isotopic effect if the breaking of a chemical bond to a deuterium atom is the rate limiting step in the process. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. In any reaction in which the breaking of this bond is the rate limiting step, the reaction will proceed slower for the molecule with the heavy isotope due to "kinetic isotope effect". A reaction involving breaking a C-D bond can be up to 700 percent slower than a similar reaction involving breaking a C—H bond. If the C-D bond is not involved in any of the steps leading to the metabolite, there may not be any effect to alter the behavior of the drug. If a deuterium is placed at a site involved in the metabolism of a drug, an isotope effect will be observed only if breaking of the C-D bond is the rate limiting step. There is evidence to suggest that whenever cleavage of an aliphatic C—H bond occurs, usually by oxidation catalyzed by a mixed-function oxidase, replacement of the hydrogen by deuterium will lead to observable isotope effect. It is also important to understand that the incorporation of deuterium at the site of metabolism slows its rate to the point where another metabolite produced by attack at a carbon atom not substituted by deuterium becomes the major pathway a process called "metabolic switching".

Deuterium tracers, such as deuterium-labeled drugs and doses, in some cases repeatedly, of thousands of milligrams of deuterated water, are also used in healthy humans of all ages, including neonates and pregnant women, without reported incident (e.g. Pons G and Rey E, Pediatrics 1999 104: 633; Coward W A et al., Lancet 1979 7: 13; Schwarcz H P, Control. Clin. Trials 1984 5(4 Suppl): 573; Rodewald L E et al., J. Pediatr. 1989 114: 885; Butte N F et al. Br. J. Nutr. 1991 65: 3; MacLennan A H et al. Am. J. Obstet Gynecol. 1981 139: 948). Thus, it is clear that any deuterium released, for instance, during the metabolism of compounds of this invention poses no health risk.

The weight percentage of hydrogen in a mammal (approximately 9%) and natural abundance of deuterium (approximately 0.015%) indicates that a 70 kg human normally contains nearly a gram of deuterium. Furthermore, replacement of up to about 15% of normal hydrogen with deuterium has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci 1960 84: 736; Czakja D M et al., Am. J. Physiol. 1961 201: 357). Higher deuterium concentrations, usually in excess of 20%, can be toxic in animals. However, acute replacement of as high as 15%-23% of the hydrogen in humans' fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Increasing the amount of deuterium present in a compound above its natural abundance is called enrichment or deuterium-enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %.

The hydrogens present on a particular organic compound have different capacities for exchange with deuterium. Certain hydrogen atoms are easily exchangeable under physiological conditions and, if replaced by deuterium atoms, it is expected that they will readily exchange for protons after administration to a patient. Certain hydrogen atoms may be exchanged for deuterium atoms by the action of a deuteric acid such as $D_2SO_4/D_2O$. Alternatively, deuterium atoms may be incorporated in various combinations during the synthesis of compounds of the invention. Certain hydrogen atoms are not easily exchangeable for deuterium atoms. However, deuterium atoms at the remaining positions may be incorporated by the use of deuterated starting materials or intermediates during the construction of compounds of the invention.

Deuterated and deuterium-enriched compounds of the invention can be prepared by using known methods described in the literature. Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure. Relevant procedures and intermediates are disclosed, for instance in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; 20090082471, the methods are hereby incorporated by reference.

The present invention further relates to a pharmaceutical composition comprising at least one compound of formulae IA or IB, a stereoisomer, prodrug, tautomer and/or physiologically tolerated acid addition salt thereof and optionally at least one physiologically acceptable carrier and/or auxiliary substance.

The invention also relates to the use of the compounds of formulae IA or IB or of a stereoisomer, prodrug, tautomer or physiologically tolerated acid addition salt thereof for the preparation of a medicament for the treatment of a disorder susceptible to the treatment with a compound that modulates, preferably inhibits, the activity of glycogen synthase kinase 3β.

Furthermore, the invention relates to a method for treating a medical disorder susceptible to treatment with a compound that modulates glycogen synthase kinase 3β activity, said method comprising administering an effective amount of at least one compound of formulae IA or IB or of a stereoisomer, prodrug, tautomer or physiologically tolerated acid addition salt thereof or of a pharmaceutical composition as defined above to a subject in need thereof.

The compounds of the of formulae IA or IB according to the present invention, as well as the stereoisomers, the tautomers, the prodrugs and physiologically tolerated acid addition salts thereof, are capable of modulating the activity on glycogen synthase kinase 3β. In particular, the compounds of the of formulae IA or IB, as well as the stereoisomers, the tautomers, the prodrugs and physiologically tolerated acid addition salts thereof, have an inhibitory activity on glycogen synthase kinase 3β. Amongst the compounds of formulae IA or IB those are preferred which achieve effective inhibition at low concentrations. In particular, compounds of the formulae IA and IB are preferred which inhibit glycogen synthase kinase 3β at a level of $IC_{50}<1$ μMol, more preferably at a level of $IC_{50}<0.5$ μMol, particularly preferably at a level of $IC_{50}<0.2$ μMol and most preferably at a level of $IC_{50}<0.1$ μMol.

Therefore the compounds of the of formulae IA or IB according to the present invention, their stereoisomers, tautomers, their prodrugs and their physiologically tolerated acid addition salts are useful for the treatment of a medical disorder susceptible to treatment with a compound that modulates glycogen synthase kinase 3β activity. As mentioned above, diseases caused by abnormal GSK-3β activity and which thus can be treated by supplying the compound of the formulae IA and IB, a steroisomer, tautomer, prodrug and/or a physiologically tolerated acid addition salt thereof, include in particular neurodegenerative diseases such as Alzheimer's disease. In addition, the compounds of the present invention are also useful for treatment of other neurodegenerative diseases such as Parkinson's disease, tauopathies (e.g. frontotemporoparietal dementia, corticobasal degeneration, Pick's disease, progressive supranuclear palsy, argyophilic brain disease) and other dementia including vascular dementia; acute stroke and others traumatic injuries; cerebrovascular accidents (e.g. age related macular degeneration); brain and spinal cord trauma; peripheral neuropathies; bipolar disorders, retinopathies and glaucoma. In addition, the compounds of the present invention are also useful for treatment of schizophrenia.

Diseases which can be treated by supplying the compound of the of formulae IA or IB, a steroisomer, tautomer, prodrug and/or a physiologically tolerated acid addition salt thereof, include furthermore inflammatory diseases, such as rheumatoid arthritis and osteoarthritis.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

Within the context of the treatment, the use according to the invention of the compounds of the formulae IA or IB involves a method. In this method, an effective quantity of one or more compounds IA or IB, a steroisomer, tautomer, prodrug or physiologically tolerable acid addition salt thereof, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to pharmaceutical compositions for treating an individual, preferably a mammal, in particular a human being, productive animal or domestic animal. Thus, the compounds according to the invention are customarily administered in the form of pharmaceutical compositions which comprise a pharmaceutically acceptable excipient together with at least one compound according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the pharmaceutical compositions, the compounds according to the invention are optionally mixed or diluted with one or more excipients. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik and angrenzende Gebiete [Encyclopedia of auxiliary substances for pharmacy, cosmetics and related fields], 4$^{th}$ edition, Aulendorf: ECV-Editio-Kantor-Verlag, 1996.

The following examples serve to explain the invention without limiting it.

EXAMPLES

The compounds were either characterized via proton-NMR in d$_6$-dimethylsulfoxide or d-chloroform on a 400 MHz or 500 MHz NMR instrument (Bruker AVANCE), or by mass spectrometry, generally recorded via HPLC-MS in a fast gradient on C18-material (electrospray-ionisation (ESI) mode), or melting point.

The magnetic nuclear resonance spectral properties (NMR) refer to the chemical shifts (δ) expressed in parts per million (ppm). The relative area of the shifts in the $^1$H-NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

Abbreviations:
DMSO dimethylsulfoxide
DCM dichloromethane
DMF dimethylformamide
MeOH methanol
EtOAc ethylacetate
THF tetrahydrofurane
TBDMS tert-butyldimethylsilyl
TBFA tert-butylammonium fluoride
RT room temperature
d days I. Preparation Examples Example 1

3-(5-Hydroxy-5,6,7,8-tetrahydroquinolin-2-yl)-2-oxoindoline-5-carbonitrile

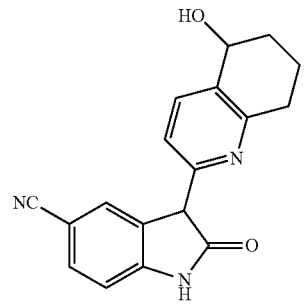 [SMILES: N#Cc1ccc2c(c1)C(c1ccc3c(n1)CCCC3O)C(=O)N2]

1.1 5-(tert-Butyldimethylsilyloxy)-2-chloro-5,6,7,8-tetrahydroquinoline

A solution of 2-chloro-5,6,7,8-tetrahydroquinolin-5-ol (500 mg, 2.72 mmol) in DMF (10 mL) was treated with imidazole (260 mg, 3.81 mmol). After complete dissolution TBDMS-Cl was added and the resulting mixture was stirred at RT for 16 h. The reaction mixture was diluted with EtOAc (40 mL) and was washed with brine (5×). The organic layer was collected, dried with Na$_2$SO$_4$, filtered, and the solvent was evaporated at reduced pressure yielding the titled compound as an oil. Amount 760 mg. Yield 94%.

$^1$H-NMR (DMSO-d$_6$, 400 MHz) δ 0.16 (d, 6H), 0.89 (s, 9H), 1.70 (m, 1H), 1.78 (m, 1H), 1.95 (m, 2H), 2.79 (m, 2H), 4.84 (dd, 1H), 7.31 (d, 1H), 7.66 (d, 1H);

MS (ES-API) m/z 298.1 (M+H$^+$, 100%).

1.2 3-(5-(tert-Butyldimethylsilyloxy)-5,6,7,8-tetrahydroquinolin-2-yl)-2-oxoindoline-5-carbonitrile To a suspension of 2-oxoindoline-5-carbonitrile (30 mg, 0.190 mmol) in THF placed in a microwave vial were added sequentially 5-(tert-butyldimethylsilyloxy)-2-chloro-5,6,7,8-tetrahydroquinoline (67.8 mg, 0.228 mmol), K$_2$CO$_3$ (52.4 mg, 0.379 mmol), X-PHOS (7.23 mg, 0.015 mmol), and Pd$_2$(dba)$_3$ (3.47 mg, 3.79 μmol). The vial was sealed and flushed with argon. The mixture was heated in a microwave oven at 80° C. for 95 min. The mixture was cooled to RT and diluted with water and ethyl acetate. The organic layer was separated and the remaining aqueous layer was extracted with dichloromethane. The combined dichloromethane extracts were dried over sodium sulfate, filtered, and evaporated to dryness. Amount 32 mg. Yield 40%.

$^1$H-NMR (DMSO-d$_6$, 400 MHz) δ 0.19 (d, 6H), 0.92 (s, 9H), 1.73 (m, 1H), 1.81 (m, 1H), 1.97 (m, 2H), 2.79 (m, 1H), 2.87 (m, 1H), 4.79 (m, 1H), 7.04 (dd, 1H), 7.29 (dd, 1H), 7.74 (m, 2H), 7.92 (s, 1H), 10.90 (s, 1H)

MS (ES-API) m/z 420.2 (M+H$^+$, 100%).

1.3 3-(5-Hydroxy-5,6,7,8-tetrahydroquinolin-2-yl)-2-oxoindoline-5-carbonitrile

A suspension of 3-(5-(tert-butyldimethylsilyloxy)-5,6,7,8-tetrahydroquinolin-2-yl)-2-oxoindoline-5-carbonitrile (26 mg, 0.062 mmol) in tetrahydrofuran (5 mL) was cooled to 0° C. To this mixture was added dropwise a 1.0M solution of TBAF in THF (0.124 ml, 0.124 mmol) resulting in a clear yellow solution. The reaction was stirred for 1 h at 0° C. and then warmed to RT. After 3 h another portion of TBAF (1.0M in THF, 0.124 ml, 0.124 mmol) was added and the reaction was stirred at RT for 16 h. The mixture was diluted with ethyl acetate and the organic layer was washed with water (2×) and brine (1×). The organic layer was dried over sodium sulfate, filtered, and evaporated to dryness. The crude was purified by flash chromatography (silica gel, DCM/MeOH) yielding a yellow solid. Amount 11 mg. Yield 59%.

$^1$H-NMR (DMSO-d$_6$, 400 MHz) δ 1.75 (m, 2H), 1.93 (m, 2H), 2.78 (m, 2H), 4.54 (bs, 1H), 5.38 (bs, 1H), 7.02 (d, 1H), 7.28 (dd, 1H), 7.68 (d, 1H), 7.84 (d, 1H), 7.89 (s, 1H), 10.88 (s, 1H), 14.90 (bs, 1H)

MS (ES-API) m/z 306.1 (M+H$^+$, 100%).

Example 2

2-Oxo-3-(5,6,7,8-tetrahydro-1,6-naphthyridin-2-yl)indoline-5-carbonitrile

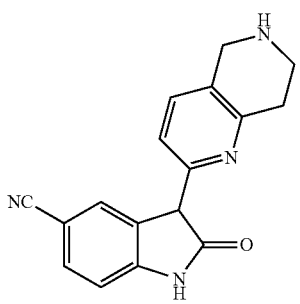 [SMILES: N#Cc1ccc2c(c1)C(c1ccc3c(n1)CCNC3)C(=O)N2]

2.1 tert-Butyl 2-chloro-7,8-dihydro-1,6-naphthyridine-6(5H)-carboxylate

To a solution of 2-chloro-5,6,7,8-tetrahydro-1,6-naphthyridine (500 mg, 2.97 mmol) in dioxane (7.4 mL) and water (7.4 mL) was added sodium bicarbonate in as a solid in one portion (498 mg, 5.93 mmol). After stirring the resulting suspension for 10 min at RT Boc$_2$O (777 mg, 3.56 mmol) was added and the mixture was stirred for 16 h. The mixture was diluted with ethyl acetate and the organic layer was washed with water and brine. The organic phase was dried over sodium sulfate, filtered, and evaporated to dryness. Amount 693 mg. Yield 87%.

$^1$H-NMR (CDCl$_3$, 400 MHz) δ 1.52 (s, 9H), 2.99 (t, 2H), 3.75 (t, 2H), 4.58 (s, 2H), 7.17 (d, 1H), 7.39 (d, 1H)

MS (ES-API) m/z 369.1 (M+H$^+$, 100%).

2.2 tert-Butyl 2-(5-cyano-2-oxoindolin-3-yl)-7,8-dihydro-1,6-naphthyridine-6(5H)-carboxylate

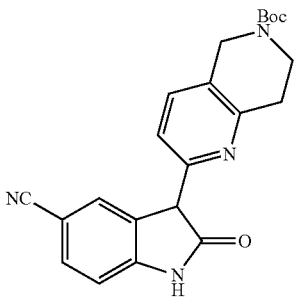 [SMILES: CC(C)(C)OC(=O)N1CCc2nc(C3C(=O)Nc4ccc(C#N)cc43)ccc2C1]

The title compound was prepared as described for Example 1.2 using 2-oxoindoline-5-carbonitrile (59 mg, 0.373 mmol), X-PHOS (14.23 mg, 0.030 mmol), K$_2$CO$_3$ (103 mg, 0.746 mmol), tert-butyl 2-chloro-7,8-dihydro-1,6-naphthyridine-6(5H)-carboxylate (120 mg, 0.448 mmol), and Pd$_2$(dba)$_3$ (6.83 mg, 7.46 µmol). The mixture was heated in a microwave oven at 100° C. for 2 h min. The mixture was cooled to RT and the resulting precipitate was removed by filtration. The remaining residue was dissolved in a mixture of dichloromethane and 2-propanol and the solution was washed with water. The aqueous layer was re-extracted with dichloromethane/2-propanol (3/1, v/v). The combined organic layers were washed with brine, dried over sodium sulfate, filtered, and evaporated to dryness. Amount 86 mg. Yield 59%.

$^1$H-NMR (DMSO-d$_6$, 400 MHz) δ 1.47 (s, 9H), 2.91 (t, 2H), 3.69 (t, 2H), 4.45 (s, 2H), 7.02 (d, 1H), 7.28 (d, 1H), 7.72 (s, 1H), 7.93 (s, 1H), 10.92 (bs, 1H), 15.05 (bs, 1H)

MS (ES-API) m/z 391.2 (M+H$^+$, 100%).

2.3 2-Oxo-3-(5,6,7,8-tetrahydro-1,6-naphthyridin-2-yl)indoline-5-carbonitrile

A solution of tert-butyl 2-(5-cyano-2-oxoindolin-3-yl)-7,8-dihydro-1,6-naphthyridine-6(5H)-carboxylate (73 mg, 0.187 mmol) in 4N HCl in dioxane (5 mL) was stirred at RT for 3 h. After this period all volatiles were removed in vacuo. The residue was dissolved in water and washed with ethyl acetate. The aqueous layer was neutralized with saturated solution of sodium bicarbonate and extracted with ethyl acetate. The latter extracts were dried over sodium sulfate, filtered, and evaporated to dryness. Quant. yield.

$^1$H-NMR (DMSO-d$_6$, 400 MHz) δ 2.76 (t, 2H), 3.04 (m, 2H), 3.76 (s, 2H), 7.00 (m, 1H), 7.19 (m, 1H), 7.54 (m, 1H), 7.66 (m, 1H), 7.87 (bs, 1H), 10.59 (bs, 1H)

MS (ES-API) m/z 291.0 (M+H$^+$, 100%).

Example 3

2-Hydroxy-3-(5-oxo-5,6,7,8-tetrahydroquinolin-2-yl)-1H-indole-5-carbonitrile

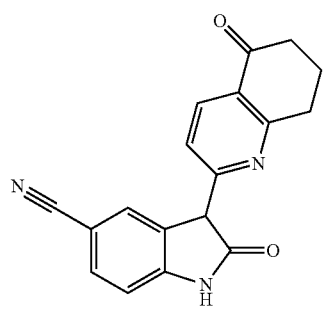 [SMILES: N#Cc1ccc2c(c1)C(c1ccc3c(n1)CCCC3=O)C(=O)N2]

3.1 7,8-Dihydroquinoline-2,5(1H,6H)-dione

Methyl propiolate (5.03 ml, 56.2 mmol) was added to finely ground 3-aminocyclohex-2-enone (5 g, 45.0 mmol). The resulting mixture was heated to 105° C. resulting in a dark brown solution and stirred under reflux for 60 min. Then the reflux condenser was removed and the excess methyl propiolate was distilled off by raising the temperature to 170° C. The reaction mixture was cooled to RT and the resulting solid was triturated with dichloromethane (10 mL) and heated to 40° C. for 25 min. The hot mixture was filtered and the yellow residue was washed with dichloromethane (10 mL). The solid was dried under reduced pressure. Amount 2.07 g. Yield 28%.

$^1$H-NMR (DMSO-d$_6$, 400 MHz) δ 2.03 (m, 2H), 2.45 (m, 2H), 2.81 (t, 2H), 6.25 (d, 1H), 7.78 (d, 1H), 12.05 (bs, 1H)

MS (ES-API) m/z 164.1 (M+H$^+$, 100%).

3.2 2-Chloro-7,8-dihydroquinolin-5(6H)-one

To a suspension of 7,8-dihydroquinoline-2,5(1H,6H)-dione (1.5 g, 9.19 mmol) in acetonitrile (22 mL) was added dropwise phosphorous oxychloride (1.714 mL, 18.39 mmol). The resulting solution was heated to 100° C. and stirred for 2 h. The reaction was cooled to RT and poured into ice-cold water. After basifying the mixture with 2 M sodium hydroxide solution it was extracted with ethyl acetate (3×). After each extraction the pH of the aqueous phase was checked and if necessary adjusted by adding 1 M sodium hydroxide solution. The combined organic layers were dried over sodium sulfate, filtered, and evaporated to dryness. The crude was purified by flash chromatography (silica gel, cyclohexane/ethyl acetate) yielding a colourless solid. Amount 1.23 g. Yield 74%.

$^1$H-NMR (DMSO-d$_6$, 400 MHz) δ 2.13 (m, 2H), 2.68 (m, 2H), 3.08 (t, 2H), 7.53 (d, 1H), 8.20 (d, 1H)

MS (ES-API) m/z 182.0 (M+H$^+$, 100%).

3.3 2-Hydroxy-3-(5-oxo-5,6,7,8-tetrahydroquinolin-2-yl)-1H-indole-5-carbonitrile To a suspension of 2-chloro-7,8-dihydroquinolin-5(6H)-one (50 mg, 0.275 mmol) and 2-oxoindoline-5-carbonitrile (45.7 mg, 0.289 mmol) in tetrahydrofuran (1.4 mL) was added a 1.0 M solution of sodium bis(trimethylsilyl)amide (641 µL, 0.641 mmol). The mixture was stirred for 3 min at RT and then heated in a microwave oven to 110° C. for 10 min. After cooling to RT the reaction was quenched by addition of methanol (1 mL). The resulting solution was evaporated to dryness. The crude was purified by flash chromatography (silica gel, dichloromethane/methanol) yielding an orange solid. Amount 17 mg. Yield 20%.

$^1$H-NMR (DMSO-d$_6$, 400 MHz) δ 2.17 (m, 2H), 2.59 (t, 2H), 3.08 (t, 2H), 7.06 (d, 1H), 7.38 (dd, 1H), 7.68 (d, 1H), 7.98 (m, 2H), 11.11 (s, 1H), 14.78 (bs, 1H)

MS (ES-API) m/z 304 (M+H$^+$, 100%).

Example 4

2-Hydroxy-3-(8-hydroxy-5,6,7,8-tetrahydroquinolin-2-yl)-1H-indole-5-carbonitrile

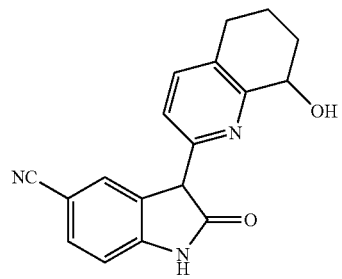 [SMILES: N#Cc1ccc2c(c1)C(c1ccc3c(n1)C(O)CCC3)C(=O)N2]

4.1 2-Chloro-8-hydroxy-5,6,7,8-tetrahydroquinoline 1-oxide

To an ice-cold solution of 2-chloro-5,6,7,8-tetrahydroquinolin-8-ol (300 mg, 1.634 mmol) in dichloromethane (5 mL) was added 3-chloroperbenzoic acid (604 mg, 2.451 mmol) in small portions over a period of 5 min. The reaction mixture was slowly warmed to RT and stirred for 20 h. The reaction was quenched by the addition of water. The aqueous phase was removed and the organic layer was washed with a 10% aqueous sodium thiosulfate solution (2×), with a 2M sodium carbonate solution (2×), and with brine (1×). The organic layer was dried over sodium sulfate, filtered, and evaporated to dryness furnishing a beige solid. Amount 320 mg. Yield 98%.

$^1$H-NMR (CDCl$_3$, 400 MHz) δ 1.80 (m, 1H), 1.93 (m, 1H), 2.13 (m, 2H), 2.72 (m, 1H), 2.84 (m, 1H), 5.13 (t, 1H), 7.09 (d, 1H), 7.40 (d, 1H)

MS (ES-API) m/z 200.1 (M+H$^+$, 100%).

4.2 2-(5-Cyano-2-oxoindolin-3-yl)-8-hydroxy-5,6,7,8-tetrahydroquinoline 1-oxide The title compound was prepared as described for Example 3.3 using 2-chloro-8-hydroxy-5,6,7,8-tetrahydroquinoline 1-oxide (100 mg, 0.501 mmol), 2-oxoindoline-5-carbonitrile (83 mg, 0,526 mmol), tetrahydrofuran (2.5 mL), and a 1.0 M solution of sodium bis(trimethylsilyl)amide (1.668 µL, 1.668 mmol). The reaction was quenched by addition of methanol (2.5 mL). The resulting solution was evaporated to dryness. The crude was used in the following reaction step without further purification.

MS (ES-API) m/z 322.1 (M+H$^+$, 100%).

4.3 2-Hydroxy-3-(8-hydroxy-5,6,7,8-tetrahydroquinolin-2-yl)-1H-indole-5-carbonitrile To a suspension of crude 2-(5-cyano-2-oxoindolin-3-yl)-8-hydroxy-5,6,7,8-tetrahydroquinoline 1-oxide (263 mg, 0.819 mmol) in ethyl acetate (12 mL) and acetonitrile (12 mL) was added dropwise a solution of phosphorous trichloride (0.644 mL, 7.37 mmol) in ethyl acetate (4 mL). The resulting suspension was stirred at RT. After 24 h the mixture was diluted with ethyl acetate and washed with a saturated sodium bicarbonate solution (2×). The aqueous phase was re-extracted with ethyl acetate (1×) and the combined organic extracts were dried over sodium sulfate, filtered, and evaporated to dryness (52 mg). The crude was dissolved in a mixture of water (2 mL) and dimethylformamide (3 mL) and the solution was heated in a microwave oven at 120° C. for 5 min. After cooling to RT the reaction mixture was diluted with ethyl acetate was washed with brine (5×). The organic layer was dried over sodium sulfate, filtered, and evaporated to dryness. The crude was purified by flash chromatography (silica gel, dichloromethane/methanol) yielding yellow solid. Amount 8.6 mg. Yield 18%.

$^1$H-NMR (DMSO-$d_6$, 400 MHz) δ 1.70 (m, 2H), 1.90 (m, 1H), 2.10 (m, 1H), 2.63 (m, 2H), 4.66 (m, 1H), 6.04 (d, 1H), 6.98 (d, 1H), 7.24 (d, 1H), 7.61 (d, 1H), 7.70 (d, 1H), 7.88 (s, 1H), 10.81 (s, 1H), 15.05 (bs, 1H)

MS (ES-API) m/z 306.0 (M+H$^+$, 100%).

Example 5

3-(6,7-Dihydro-5H-pyrrolo[3,4-b]pyridin-2-yl)-2-oxoindoline-5-carbonitrile hydrochloride

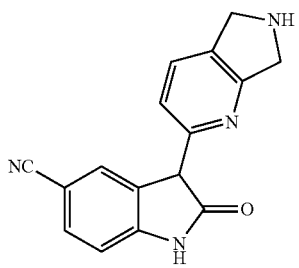 [SMILES: N#Cc1ccc2c(c1)C(c1ccc3c(n1)CNC3)C(=O)N2]

5.1 tert-Butyl 2-chloro-5H-pyrrolo[3,4-b]pyridine-6(7H)-carboxylate

The title compound was prepared as described for Example 2.1 using 2-chloro-6,7-dihydro-5H-pyrrolo[3,4-b]pyridine (500 mg, 3.23 mmol), sodium bicarbonate (543 mg, 6.47 mmol), and Boc2O (870 mg, 3.987 mmol) in a mixture of dioxane (7.4 mL) and water (7.4 mL). After work up as described in Example 4 the titled compound was obtained as a beige solid. Amount 814 mg. Yield 99%.

$^1$H-NMR (CDCl$_3$, 400 MHz) δ 1.55 (s, 9H), 4.69 (m, 4H), 7.26 (d, 1H), 7.54 (m, 1H); MS (ES-API) m/z 255.1 (M+H$^+$, 10%).

5.2 tert-Butyl 2-(5-cyano-2-oxoindolin-3-yl)-5H-pyrrolo[3,4-b]pyridine-6(7H)-carboxylate

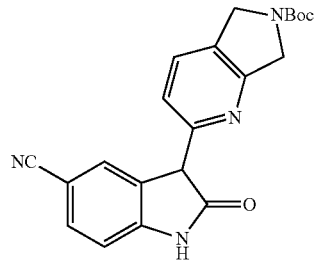 [SMILES: CC(C)(C)OC(=O)N1Cc2ccc(C3C(=O)Nc4ccc(C#N)cc43)nc2C1]

The title compound was prepared as described for Example 1.2 using 2-oxoindoline-5-carbonitrile (200 mg, 1.265 mmol), tert-butyl 2-chloro-5H-pyrrolo[3,4-b]pyridine-6(7H)-carboxylate (387 mg, 1.517 mmol), K$_2$CO$_3$ (350 mg, 2.53 mmol), X-PHOS (48.2 mg, 0.101 mmol), Pd$_2$(dba)$_3$ (23.16 mg, 0.025 mmol), and tetrahydrofuran (4 mL). The reaction mixture was heated in a microwave oven at 100° C. for 90 min. After cooling to RT the mixture was filtered and the yellow residue was washed with tetrahydrofuran (10 mL) and water (10 mL). The solid was dried under reduced pressure. Amount 193 mg. Yield 40%.

$^1$H-NMR (DMSO-$d_6$, 400 MHz) δ 1.47 (s, 9H), 4.52 (m, 2H), 4.72 (d, 2H), 7.04 (d, 1H), 7.28 (d, 1H), 7.80 (m, 2H), 7.98 (s, 1H), 11.05 (s, 1H)

MS (ES-API) m/z 377.1 (M+H$^+$, 10%).

5.3 3-(6,7-Dihydro-5H-pyrrolo[3,4-b]pyridin-2-yl)-2-oxoindoline-5-carbonitrile hydrochloride To a suspension of tert-butyl 2-(5-cyano-2-oxoindolin-3-yl)-5H-pyrrolo[3,4-b]pyridine-6(7H)-carboxylate (70 mg, 0.186 mmol) in dioxane (2 mL) was added dropwise 4N HCl in dioxane (2.5 mL). After stirring the resulting mixture at RT for 3d all volatiles were removed under reduced pressure. The residue was suspended in diethylether and stirred at RT for 2 h. The suspension was filtered, the remaining solid was washed with diethylether and dried under reduced pressure. Amount 55 mg. Yield 95%.

$^1$H-NMR (DMSO-$d_6$, 400 MHz) δ 4.48 (m, 2H), 4.67 (s, 2H), 7.09 (m, 1H), 7.40 (m, 1H), 7.85 (m, 2H), 8.12 (s, 1H), 9.87 (m, 2H), 11.18 (m, 1H)

MS (ES-API) m/z 277.1 (M+H$^+$, 100%).

Example 6

3-(5-Methoxy-5,6,7,8-tetrahydroquinolin-2-yl)-2-oxoindoline-5-carbonitrile

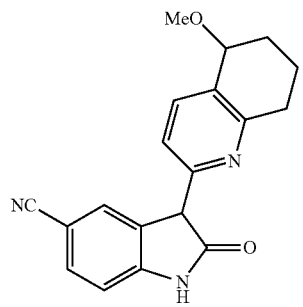 [SMILES: COC1CCCc2nc(C3C(=O)Nc4ccc(C#N)cc43)ccc21]

6.1 2-Chloro-5-methoxy-5,6,7,8-tetrahydroquinoline

To a solution of 2-chloro-5,6,7,8-tetrahydroquinolin-5-ol (319 mg, 1,737 mmol) in tetrahydrofuran (8 mL) was added in small portions sodium hydride (83 mg, 2,085 mmol; 60 on mineral oil). After stirring the resulting suspension for 20 min at RT methyl iodide (0.119 ml, 1.911 mmol) was added dropwise. The reaction mixture was stirred at RT for 20 h. The reaction was quenched by addition of a saturated ammonium chloride solution. The layers were separated and the aqueous layer was extracted with ethyl acetate (3×). The combined organic layers were washed with brine and dried over sodium sulfate, filtered, and evaporated to dryness. The crude was purified by flash chromatography (silica gel, cyclohexane/ethylacetate) yielding a slightly yellow oil. Amount 210 mg. Yield 61%.

$^1$H-NMR (DMSO-$d_6$, 400 MHz) δ 1.77 (m, 1H), 1.90 (m, 3H), 2.79 (m, 2H), 3.37 (s, 3H), 4.37 (m, 1H), 7.32 (d, 1H), 7.77 (d, 1H)

MS (ES-API) m/z 198.1 (M+H$^+$, 100%).

6.2 3-(5-Methoxy-5,6,7,8-tetrahydroquinolin-2-yl)-2-oxoindoline-5-carbonitrile The title compound was prepared as described for Example 1.2 using 2-oxoindoline-5-carbonitrile (60 mg, 0.379 mmol), 2-chloro-5-methoxy-5,6,7,8-tetrahydroquinoline (90 mg, 0,455 mmol), K$_2$CO$_3$ (105 mg, 0.76 mmol), X-PHOS (14.47 mg, 0.030 mmol), Pd$_2$(dba)$_3$ (6.95 mg, 7.59 μmol), and tetrahydrofuran (1.9 mL). The reaction mixture was heated in a microwave oven at 100° C. for 120 min. After cooling to RT the mixture was diluted with ethyl acetate. The organic layer was separated and the aqueous layer was extracted with ethyl acetate (2×). The combined organic layers were dried over sodium sulfate, filtered, and evaporated to dryness. The crude was purified by flash chromatography (silica gel, dichloromethane/methanol). The product containing fractions were combined, evaporated to dryness, and the resulting solid was triturated with diethylether. Amount 27 mg. Yield 22%.

$^1$H-NMR (DMSO-$d_6$, 400 MHz) δ 1.87 (m, 4H), 2.81 (m, 2H), 3.40 (s, 3H), 4.28 (s, 1H), 7.04 (d, 1H), 7.31 (d, 1H), 7.68 (d, 1H), 7.77 (d, 1H), 7.91 (s, 1H), 10.96 (s, 1H), 14.93 (bs, 1H)

MS (ES-API) m/z 320.1 (M+H$^+$, 100%).

II. Biological Tests

The compounds according to the invention exhibit very good affinities for GSK-3 (<1 μM, frequently <100 nM) and exhibited good selectivity against multiple kinase targets.

Methods—Biochemical hGSK-3Beta Assay

Compounds were tested for their ability to inhibit human Glycogen Synthase Kinase-3 beta (hGSK-3β) to phosphorylate biotin-YRRAAVPPSPSLSRHSSPHQ(pS)EDEEE. Compounds were incubated with 0.5 μCi 33P-ATP, 10 μM ATP, 0.0125 U hGSK-3β (Upstate cell signaling solutions) and 1 μM substrate (biotin-YRRAAVPPSPSLSRHSSPHQ (pS)EDEEE) in 50 mM HEPES, 10 mM MgCl$_2$, 100 mM Na$_3$VO$_4$, 1 mM DTT, 0.0075% Triton, 2% DMSO (total volume 50 μL) for 30 minutes at room temperature. The incubation was stopped by addition of an equal volume of 100 mM EDTA, 4M NaCl. 80 μL of this mixture was added to streptavidin-coated Flash-plates (PerkinElmer). Following a wash step, 33P incorporation was quantified on a MicroBeta microplate liquid scintillation counter (Perkin Elmer). IC$_{50}$s were determined by fitting a sigmoidal dose-response curve to the counts obtained at the different concentrations in GraphPad Prism.

The results of the binding tests are given in the table below.

| Example # | GSK-3β IC$_{50}$ (nM) |
|---|---|
| 1 | +++ |
| 2.2 | +++ |
| 2 | +++ |
| 3 | +++ |
| 4 | +++ |
| 5 | +++ |
| 6 | +++ | n.d. not determined
GSK-3β IC$_{50}$ (nM):
Ranges:
+ >10 μM
++ from 100 nM to 10 μM
+++ <100 nM

We claim:

1. A method for treating a neurodegenerative disorder or inflammatory disorder selected from the group consisting of schizophrenia, Alzheimer's disease, Parkinson's disease, tauopathies, vascular dementia, acute stroke and bipolar disorders, retinopathies, glaucoma, rheumatoid arthritis and osteoarthritis, said method comprising administering an effective amount of at least one heterocyclic compound of the general formulae (IA) or (IB)

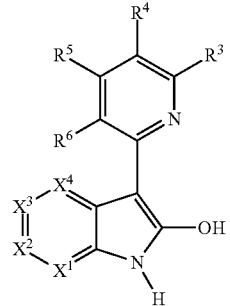

(IA)

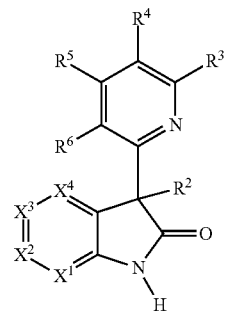

(IB)

a stereoisomer, N-oxide, tautomer, or physiologically tolerated acid addition salt thereof; or at least one heterocyclic compound of the general formulae (IA) and (IB), wherein at least one of the atoms has been replaced by its stable, non-radioactive isotope, wherein X$^1$, X$^2$, X$^3$ and X$^4$ are independently of each other selected from the group consisting of CR$^1$ and N;

each R$^1$ is independently selected from the group consisting of hydrogen, cyano, NR$^a$R$^b$, OH, halogen, C$_1$-C$_6$-alkyl, C$_1$-C$_6$-haloalkyl, C$_3$-C$_7$-cycloalkyl, C$_3$-C$_7$-halocycloalkyl, C$_2$-C$_4$-alkenyl, C$_2$-C$_4$-haloalkoxy, C$_1$-C$_6$- alkoxy, $C_1$-$C_6$-haloalkoxy, formyl, $C_1$-$C_6$-alkylcarbonyl, $C_1$-$C_6$-haloalkylcarbonyl, COOH, $C_1$-$C_6$-alkoxycarbonyl, $C_1$-$C_6$-haloalkoxycarbonyl, $C_1$-$C_6$-alkyl-$NR^aR^b$, CO—$NR^aR^b$, an aromatic radical Ar, which is selected from the group consisting of phenyl and a 5- or 6-membered N—or C—bound heteroaromatic radical comprising 1, 2 or 3 heteroatoms independently selected from the group consisting of O, S and N as ring members, wherein Ar is unsubstituted or carries one or two radicals $R^7$ and wherein Ar may also be bonded via a $CH_2$ group, and saturated or partially unsaturated 3-, 4-, 5-, 6- or 7-membered heterocyclic radical comprising 1, 2 or 3 heteroatoms selected from the group consisting of O, S and N as ring members, wherein the heterocyclic radical is unsubstituted or substituted by 1, 2, 3 or 4 radicals independently selected from the group consisting of halogen, cyano, $C_1$-$C_4$-alkyl, $C_1$-$C_4$-haloalkyl, $C_1$-$C_4$-alkoxy and $C_1$-$C_4$-haloalkoxy;

$R^2$ is hydrogen, $C_1$-$C_4$-alkyl, $C_1$-$C_4$-haloalkyl, $C_2$-$C_4$-alkenyl, $C_2$-$C_4$-haloalkenyl, OH or F;

$R^3$ and $R^4$; or $R^4$ and $R^5$; or $R^5$ and $R^6$ form together a bridging group —$(CH_2)_m$—, wherein m is 3, 4 or 5, where 1, 2 or 3 of the $CH_2$ groups may be replaced by a group or a heteroatom selected from the group consisting of CO, O, S, SO, $SO_2$, $NR^c$ and NO, and where 1, 2 or 3 hydrogen atoms of the bridging group may be replaced by a radical $R^8$;

where the radicals $R^3$, $R^4$, $R^5$ and $R^6$, which are not part of the bridging group, are independently selected from the group consisting of hydrogen, halogen, cyano, $C_1$-$C_4$-alkyl, $C_1$-$C_4$-haloalkyl, $C_1$-$C_4$-alkoxy, $C_1$-$C_4$-haloalkoxy and $NR^aR^b$;

each $R^7$ is independently selected from the group consisting of halogen, OH, CN, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $NR^aR^b$, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, CO—$NR^aR^b$, a phenyl group and a saturated, partially unsaturated or aromatic 5- or 6-membered heterocyclic radical comprising 1, 2 or 3 heteroatoms selected from the group consisting of O, S and N as ring members, wherein phenyl and the heterocyclic radical are, independently of each other, unsubstituted or substituted by 1, 2, 3 or 4 radicals independently selected from the group consisting of halogen, cyano, $C_1$-$C_4$-alkyl, $C_1$-$C_4$-haloalkyl, $C_1$-$C_4$-alkoxy and $C_1$-$C_4$-haloalkoxy, or in the heterocyclic ring two geminally bound radicals may together form a group =O;

each $R^8$ is independently selected from the group consisting of halogen, OH, CN, $C_1$-$C_6$-alkyl, $C_1$-$C_6$-haloalkyl, $C_3$-$C_6$-cycloalkyl, $C_3$-$C_6$-halocycloalkyl, $C_1$-$C_6$-alkoxy, $C_1$-$C_6$-haloalkoxy, $NR^a$, $R^b$, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, CO—$NR^aR^b$, a phenyl group and a saturated, partially unsaturated or aromatic 3-, 4-, 5-, 6- or 7-membered heterocyclic radical comprising 1, 2 or 3 heteroatoms selected from the group consisting of O, S and N as ring members, wherein phenyl and the heterocyclic radical are, independently of each other, unsubstituted or substituted by 1, 2, 3 or 4 radicals independently selected from the group consisting of halogen, cyano, $C_1$-$C_4$-alkyl, $C_1$-$C_4$-haloalkyl, $C_1$-$C_4$-alkoxy and $C_1$-$C_4$-haloalkoxy;

$R^a$ and $R^b$ are independently of each other selected from the group consisting of hydrogen, $C_1$-$C_6$-alkyl, $C_1$-$C_4$-haloalkyl, $C_1$-$C_4$-alkoxy, $C_1$-$C_4$-haloalkyl, $C_1$-$C_4$-alkylcarbonyl, $C_1$-$C_4$-haloalkylcarbonyl, $C_1$-$C_6$-alkoxycarbonyl and $C_1$-$C_6$-haloalkoxycarbonyl; or $R^a$ and $R^b$ form, together with the nitrogen atom to which they are bonded, a 3-, 4-, 5-, 6- or 7-membered saturated or unsaturated aromatic or non-aromatic N-heterocyclic ring, which may contain 1 further heteroatom or heteroatom-containing group selected from the group consisting of N, O, S, SO and $SO_2$ as a ring member, where the N-heterocyclic ring may carry 1 or 2 radicals selected from the group consisting of halogen, cyano, $C_1$-$C_4$-alkyl and $C_1$-$C_4$-haloalkyl, $C_1$-$C_4$-alkoxy and $C_1$-$C_4$-haloalkoxy; and each $R^c$ is independently selected from the group consisting of hydrogen, $C_1$-$C_6$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkoxycarbonyl and $C_1$-$C_6$-haloalkoxycarbonyl.

2. The method of claim 1, wherein $R^3$ and $R^4$; or $R^4$ and $R^5$; or $R^5$ and $R^6$ form together a bridging group —$(CH_2)_m$—, wherein m is 3, 4 or 5, where 1, 2 or 3 of the $CH_2$ groups may be replaced by a group or a heteroatom selected from the group consisting of CO, O, S, SO, $SO_2$, $NR^c$ and NO, and where 1, 2 or 3 hydrogen atoms of the bridging group may be replaced by a radical $R^8$; wherein if $R^3$ and $R^4$ form a bridging group $(CH_2)_m$—, the $CH_2$ unit bound in the position of $R^3$ is not replaced by a $NR^c$ group; wherein the radicals $R^3$, $R^4$, $R^5$ and $R^6$, which are not part of the bridging group, are independently selected from the group consisting of hydrogen, halogen, cyano, $C_1$-$C_4$-alkyl, $C_1$-$C_4$-haloalkyl, $C_1$-$C_4$-alkoxy and $C_1$-$C_4$-haloalkoxy, and wherein $R^4$, $R^5$ and $R^6$ may independently also be selected from $NR^aR^b$.

3. The method of claim 1, wherein $R^3$ and $R^4$; or $R^4$ and $R^5$; or $R^5$ and $R^6$ form together a bridging group —$(CH_2)_m$—, wherein m is 3, 4 or 5, wherein 1 or 2 of the $CH_2$ groups may be replaced by a group or a heteroatom selected from the group consisting of CO, O and $NR^c$, and wherein 1 or 2 or 3 hydrogen atoms of the bridging group may be replaced by a radical $R^8$.

4. The method of claim 1, wherein m is 3 or 4.

5. The method of claim 3, wherein the bridging group is selected from the group consisting of $CH_2CH_2CH_2$—, —$OCH_2CH_2$, $CH_2CH_2O$—, —$CH_2OCH_2$—, —$NR^cCH_2CH_2$—, —$CH_2CH_2NR^c$—, —$CH_2NR^cCH_2$—, —$CH_2CH_2CH_2CH_2$—, —$OCH_2CH_2CH_2$—, —$CH_2OCH_2CH_2$—, —$CH_2CH_2OCH_2$—, —$CH_2CH_2CH_2O$—, —$NR^cCH_2CH_2CH_2$—, —$CH_2NR^cCH_2CH_2$—, —$CH_2CH_2NR^cCH_2$—, —$CH_2CH_2CH_2NR^c$—, —C(=O)$CH_2CH_2CH_2$—, —$CH_2C$(=O)$CH_2$—, —$CH_2CH_2C$(=O)$CH_2$— and —$CH_2CH_2CH_2C$(=O)—, wherein the hydrogen atoms of the above groups may be replaced by 1 or 2 radicals $R^8$.

6. The method of claim 5; wherein the bridging group is selected from the group consisting of —$CH_2CH_2CH_2$—, —$OCH_2CH_2$—, —$CH_2CH_2$, O—, —$CH_2OCH_2$—, —$CH_2NR^cCH_2$—, —$CH_2CH_2CH_2CH_2$—, —$OCH_2CH_2CH_2$—, —$CH_2OCH_2CH_2$—, —$CH_2CH_2OCH_2$—, —$CH_2CH_2CH_2O$—, —$CH_2NR^cCH_2CH_2$—, —$CH_2CH_2NR^cCH_2$—, —C(=O)$CH_2CH_2CH_2$—, —$CH_2C$(=O)$CH_2CH_2$—, —$CH_2CH_2C$(=O)$CH_2$— and —$CH_2CH_2CH_2C$(=O)—, wherein the hydrogen atoms of the above groups may be replaced by 1 or 2 radicals $R^8$.

7. The method of claim 6, wherein the bridging group is selected from the group consisting of —$CH_2CH_2CH_2$—, —$CH_2NR^cCH_2$—, —$CH_2CH_2CH_2$—, —$CH_2NR^cCH_2CH_2$—, —$CH_2CH_2NR^cCH_2$—, —C(=O)

$CH_2CH_2CH_2$—, —$CH_2C(\!=\!O)CH_2CH_2$—, —$CH_2CH_2C(\!=\!O)CH_2$— and —$CH_2CH_2CH_2C(\!=\!O)$—, wherein the hydrogen atoms of the above groups may be replaced by 1 or 2 radicals $R^8$.

8. The method of claim 1, wherein the radicals $R^3$, $R^4$, $R^5$ and $R^6$, which are not part of the bridging group, are hydrogen.

9. The method of claim 1, wherein $R^3$ and $R^4$; or $R^4$ and $R^5$ form together a bridging group —$(CH_2)_m$—, wherein m is 3, 4 or 5, where 1, 2 or 3 of the $CH_2$ groups may be replaced by a group or a heteroatom selected from the group consisting of CO, O, S, SO, $SO_2$, $NR^c$ and NO, and where 1, 2 or 3 hydrogen atoms of the bridging group may be replaced by a radical $R^8$.

10. The method of claim 9, wherein $R^3$ and $R^4$ form together a bridging group —$(CH_2)_m$—, wherein m is 3, 4 or 5, where 1, 2 or 3 of the $CH_2$ groups may be replaced by a group or a heteroatom selected from the group consisting of CO, O, S, SO, $SO_2$, $NR^c$ and NO, and where 1, 2 or 3 hydrogen atoms of the bridging group may be replaced by a radical $R^8$.

11. The method of claim 1, wherein each $R^8$ is independently selected from the group consisting of halogen, OH, $C_1$-$C_4$-alkyl, $C_1$-$C_4$-haloalkyl, $C_1$-$C_4$-alkoxy, $C_1$-$C_4$-haloalkoxy, $NR^aR^b$, $C_1$-$C_6$-alkylcarbonyl, $C_1$-$C_6$-haloalkylcarbonyl, $C_1$-$C_6$-alkoxycarbonyl and $C_1$-$C_6$-haloalkoxycarbonyl.

12. The method of claim 11, wherein each $R^8$ is independently selected from the group consisting of OH, $C_1$-$C_4$-alkoxy and $C_1$-$C_4$-haloalkoxy.

13. The method of claim 1, wherein $R^c$ is hydrogen or $C_1$-$C_6$-alkoxycarbonyl.

14. The method of claim 1, wherein all of $X^1$, $X^2$, $X^3$ and $X^4$ are $CR^1$ or one of $X^1$, $X^2$, $X^3$ and $X^4$ is N and the others are $CR^1$.

15. The method of claim 14, wherein all of $X^1$, $X^2$, $X^3$ and $X^4$ are $CR^1$.

16. The method of claim 15, where $X^1$, $X^2$ and $X^4$ are CH and $X^3$ is $CR^1$.

17. The method of claim 16, wherein $X^3$ is $CR^1$, and wherein $R^1$ is H, CN or COOH.

18. The method of claim 1, wherein $R^2$ is hydrogen.

19. The method of claim 1, wherein $R^2$ is $C_1$-$C_4$-alkyl, $C_1$-$C_4$-fluoroalkyl, $C_2$-$C_4$-alkenyl or fluorine.

20. The method of claim 1, wherein the heterocyclic compounds are of the formulae (IA-1) and (IB-1)

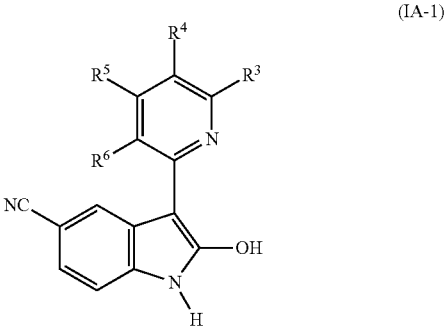
(IA-1)

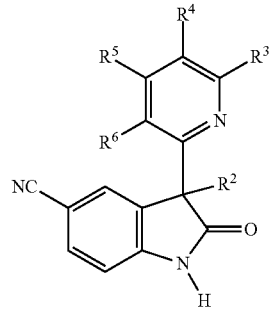
(IB-1)

21. The method of claim 1, wherein at least one hydrogen atom of the heterocyclic compound has been replaced by a deuterium atom.

22. The method of claim 1, wherein the heterocyclic compound is selected from the group consisting of:

- 3-(5-hydroxy-5,6,7,8-tetrahydro-quinolin-2-yl)-2-oxoindoline-5-carbonitrile;
- tert-butyl 2-(5-cyano-2-oxoindolin-3-yl)-7,8-dihydro-1,6-naphthyridine-6(5H)-carboxylate;
- 2-oxo-3-(5,6,7,8-tetrahydro-1,6-naphthyridin-2-yl)indoline-5-carbonitrile,
- 2-hydroxy-3-(5-oxo-5,6,7,8-tetra-hydroquinolin-2-yl)-IH-indole-5-carbonitrile;
- 2-hydroxy-3-(8-hydroxy-5,6,7,8-tetrahydroquinolin-2-yl)- 1H-indole-5-carbonitrile;
- 3-(6,7-dihydro-5H-pyrrolo[3,4-b]pyridin-2-yl)-2-oxoindoline-5-carbonitrile; and
- 3-(5-methoxy-5,6,7,8-tetrahydro-quinolin-2-yl)-2-oxoindoline-5-carbonitrile;

or a stereoisomer, N-oxide, tautomer, or physiologically tolerated acid addition salt thereof.

23. The method of claim 1, wherein the heterocyclic compound is 3-(5-hydroxy-5,6,7,8-tetrahydro-quinolin-2-yl)-2-oxoindoline-5-carbonitrile or a stereoisomer, N-oxide, tautomer, or physiologically tolerated acid addition salt thereof.

24. The method of claim 1, wherein the heterocyclic compound is 3-(6,7-dihydro-5H-pyrrolo[3,4-b ]pyridin-2-yl)-2-oxoindoline-5-carbonitrile or a stereoisomer, N-oxide, tautomer, or physiologically tolerated acid addition salt thereof.

25. The method of claim 1, wherein the heterocyclic compound is 3-(5-methoxy-5,6,7,8-tetrahydro-quinolin-2-yl)-2-oxoindoline-5-carbonitrile or a stereoisomer, N-oxide, tautomer, or physiologically tolerated acid addition salt thereof.

* * * * *